US008183361B2

(12) United States Patent
Dale et al.

(10) Patent No.: US 8,183,361 B2
(45) Date of Patent: *May 22, 2012

(54) OLIGONUCLEOTIDE-CONTAINING PHARMACOLOGICAL COMPOSITIONS AND THEIR USE

(75) Inventors: Roderic M. K. Dale, Wilsonville, OR (US); Amy Arrow, Bethel, ME (US); Terry Thompson, Wilsonville, OR (US)

(73) Assignee: Lakewood-Amedex, Inc., Lakewood Ranch, FL (US)

( * ) Notice: Subject to any disclaimer, the term of this patent is extended or adjusted under 35 U.S.C. 154(b) by 228 days.

This patent is subject to a terminal disclaimer.

(21) Appl. No.: 11/673,509

(22) Filed: Feb. 9, 2007

(65) Prior Publication Data

US 2008/0167257 A1 Jul. 10, 2008

Related U.S. Application Data

(63) Continuation of application No. 10/191,997, filed on Jul. 10, 2002, now abandoned.

(60) Provisional application No. 60/303,820, filed on Jul. 10, 2001.

(51) Int. Cl.
*C07H 21/04* (2006.01)

(52) U.S. Cl. .................................................. 536/24.5

(58) Field of Classification Search ............... 536/24.5
See application file for complete search history.

(56) References Cited

U.S. PATENT DOCUMENTS

| | | | |
|---|---|---|---|
| 4,897,355 A | 1/1990 | Eppstein et al. | |
| 5,217,866 A | 6/1993 | Summerton et al. | |
| 5,256,649 A | 10/1993 | Le Fur et al. | |
| 5,474,796 A * | 12/1995 | Brennan | 427/2.13 |
| 5,514,788 A | 5/1996 | Bennett et al. | |
| 5,576,208 A | 11/1996 | Monia et al. | |
| 5,591,840 A | 1/1997 | Narayanan et al. | |
| 5,603,915 A | 2/1997 | Nelson et al. | |
| 5,652,131 A * | 7/1997 | Beavo et al. | 435/196 |
| 5,734,039 A | 3/1998 | Calabretta et al. | |
| 5,776,905 A | 7/1998 | Gibbons et al. | |
| 5,821,234 A | 10/1998 | Dzau | |
| 5,830,140 A | 11/1998 | Dillinger et al. | |
| 5,834,443 A | 11/1998 | Masiello | |
| 5,849,902 A | 12/1998 | Arrow et al. | |
| 5,948,768 A | 9/1999 | McMichael et al. | |
| 5,951,455 A | 9/1999 | Cowsert | |
| 5,989,912 A | 11/1999 | Arrow et al. | |
| 5,998,203 A | 12/1999 | Matulic-Adamic et al. | |
| 6,008,048 A | 12/1999 | Monia et al. | |
| 6,015,886 A | 1/2000 | Dale et al. | |
| 6,087,112 A * | 7/2000 | Dale | 435/6 |
| 6,211,162 B1 | 4/2001 | Dale et al. | |
| 6,211,349 B1 | 4/2001 | Dale et al. | |
| 6,344,323 B1 | 2/2002 | Seifert | |
| 6,440,723 B1 | 8/2002 | Dale | |
| 6,562,569 B1 | 5/2003 | Dale | |
| 6,582,908 B2 * | 6/2003 | Fodor et al. | 506/9 |
| 6,627,215 B1 | 9/2003 | Dale et al. | |
| 6,656,717 B1 | 12/2003 | Xin et al. | |
| 6,844,151 B1 | 1/2005 | Dale | |
| 2002/0032164 A1 | 3/2002 | Dale et al. | |
| 2002/0142980 A1 * | 10/2002 | Thompson et al. | 514/44 |
| 2003/0045490 A1 | 3/2003 | Dale et al. | |
| 2003/0083477 A1 | 5/2003 | Arrow et al. | |
| 2003/0180789 A1 | 9/2003 | Dale | |
| 2003/0207834 A1 | 11/2003 | Dale et al. | |
| 2004/0121352 A1 | 6/2004 | Dale | |
| 2005/0025815 A1 | 2/2005 | Dale et al. | |
| 2005/0107344 A1 | 5/2005 | Dale et al. | |
| 2005/0118618 A1 | 6/2005 | Dale | |
| 2008/0161257 A1 | 7/2008 | Dale et al. | |
| 2008/0167257 A1 | 7/2008 | Dale et al. | |
| 2008/0234214 A1 | 9/2008 | Dale et al. | |

FOREIGN PATENT DOCUMENTS

| | | |
|---|---|---|
| WO | WO 90/14074 A1 | 11/1990 |
| WO | WO 91/16024 A1 | 10/1991 |
| WO | WO 91/17424 A1 | 11/1991 |
| WO | WO 92/03568 | 3/1992 |
| WO | WO-94/15619 A1 | 7/1994 |
| WO | WO 94/28144 A1 | 12/1994 |
| WO | WO 95/10938 | 4/1995 |
| WO | WO 95/15761 A1 | 6/1995 |
| WO | WO-97/47325 A1 | 12/1997 |
| WO | WO 98/03533 A1 | 1/1998 |
| WO | WO 98/13526 A1 | 4/1998 |
| WO | WO 98/49348 A1 | 11/1998 |
| WO | WO 99/14346 | 3/1999 |
| WO | WO-99/53101 A1 | 10/1999 |
| WO | WO 00/40525 A2 | 7/2000 |
| WO | WO 00/40591 A1 | 7/2000 |
| WO | WO 00/40592 A1 | 7/2000 |
| WO | WO 00/40714 A2 | 7/2000 |
| WO | WO 00/57890 A1 | 10/2000 |
| WO | WO 00/70093 A1 | 11/2000 |

(Continued)

OTHER PUBLICATIONS

Galym, et al., "Complex Host Cell Responses to Antisense Suppression of ACHE Gene Expression", Antisese & Nucleic Acid Drug Development, 11:51-57 (2001).
Rubenstein, et al., "A Review of Various Antisense Oligonucleotide Therapeutic Approaches for Prostate Cancer" *Prostate Journal*, 2(4):179-188 (2000).
Shohami, et al., "Antisense Prevention of Neuronal Damages Following a Head Injury in Mice" *J. Mol. Med.*, 78:228-236 (2000).
Bost et al., "The jun kinase 2 isoform is preferentially required for epidermal growth factor-induced transformation of human A549 lung carcinoma cells", *Mol. Cell. Biol*, 19(3):1938-1949 (1999).
Lisziewicz et al., "Specific inhibition of human immunodeficiency virus type 1 replication by antisense oligonucleotides: an in vitro model for treatment", *Proc. Natl. Acad. Sci. USA*, 89:11209-11213 (1992).
Normanno et al., "Growth inhibition of human colon carcinoma cells by combinations of anti-epidermal growth factor-related growth factor antisense oligonucleotides", *Clin. Cancer Res.*, 2:601-609 (1996).

(Continued)

*Primary Examiner* — Brian Whiteman
(74) *Attorney, Agent, or Firm* — Mintz Levin Cohn Ferris Glovsky and Popeo, P.C.; Ingrid A. Beattie

(57) ABSTRACT

The present invention relates to methods and compositions containing oligonucleotides suitable for administration to humans and other mammals.

12 Claims, No Drawings

FOREIGN PATENT DOCUMENTS

| | | |
|---|---|---|
| WO | WO-00/70093 A1 | 11/2000 |
| WO | WO 01/23620 A2 | 4/2001 |
| WO | WO 02/000854 A1 | 11/2002 |
| WO | WO 02/089581 A1 | 11/2002 |
| WO | WO 03/006478 A1 | 11/2003 |

OTHER PUBLICATIONS

Agrawal et al., "Absorption, Tissue Distribution and In Vivo Stability in Rats of a Hybrid Antisense Oligonucleotide Following Oral Administration", Biochemical Pharmacology, v50 n4, pp. 571-576 (1995).
Agrawal et al., "Modified Oligonucleotides As Therapeutic and Diagnostic Agents", Current Opinion in Biotechnology, v 6 n1, pp. 12-19 (1995).
Agrawal et al., "Antisense Therapeutics: Is It As Simple As Simple As Complementary Base Recognition", Molecular Medicine Today, v 6 n2, pp. 72-81 (2000).
Altschul et al., "Issues in Searching Molecular Sequence Databases", Nature Genetics, v6, pp. 119-129 (1994).
Altschul et al., "Gapped BLAST and PSI-BLAST: A New Generation of Protein Database Search Programs", Nucleic Acid Research, v25 n17, pp. 3389-3402 (1997).
Belikova et al., Synthesis of Rebonucleosides and Diribonucleoside Phosphates Containing 2-Chloro-Ethylamine and Nitrogen Mustard Residues, Tetrahedron Letters, v37, pp. 3557-3562 (1967).
Bennett et al., "Parmacology of Antisense Therapeutic Agents", Methods in Molecular Medicine: Antisense Therapeutics, pp. 13-46 (1996).
Branch., "A Good Antisense Molecule Is Hard to Find", Trends in Biochemical Sciences, v23, pp. 45-50 (1998).
Chen et al., "In Vivo Expression of Single-Stranded DNA in Mammalian Cells With DNA Enzyme Sequences Targeted to C-raf", Antisense & Nucleic Acid Drug Development, v10. pp. 415-422 (2000).
Cohen et al., "Phosphorothioate Oligodeoxynucleotide Analogues", CRC Press:Boca Raton, FL, pp. 82-92, 97-117 (1989).
Dagle et al., "Oligonucleotide-Based Strategies to Reduce Gene Expression", Differentiation v69, pp. 75-82 (2001).
Egholm et al., "Peptide Nucleic Acids (PNA) Oligonucleotide Analogues With an Achiral Peptide Backbone", Journal American Chemical Society, v114, pp. 1895-1897 (1992).
Flanagan et al., "Cellular Penetration and Antisense Activity by a Phenoxazine-Substituted Heptanucleotide", Nature Biotechnology, v17 n1, pp. 48-52 (1999).
Froehler et al., "Phosporamidate Analogues of DNA: Synthesis and Thermal Stability of Heteroduplexes", Nucleic Acids Research, v16 n11, pp. 4831-4839 (1988).
Ghosh et al., "Evaluation of Some Properties of a Phosphorodithioate Oligodeoxyribonucleotide for Antisense Application", Nucleic Acids Research, v21 n24, pp. 5761-5765 (1993).
Green et al., "Antisense Oligonucleotides: An Evolving Technology for the Modulation of Gene Expression in Human Disease", Journal American College of Surgeons, v191 n1, pp. 93-105 (2000).
Henikoff et al., "Amino Acid Substitution Matrices From Protein Blocks", Proceedings of the National Academy of Sciences USA, v89, pp. 10915-10919 (1992).
Huang et al., "Acyclic Nucleic Acid Analogues: Synthesis and Oligomerization of Gamma, 4-Diamino-2oxo-1(2H)-pyrimidinepentanoic Acid and Delta, 4-Diamino-2-oxo-1(2H)-pyrimidinehexanoic Acid", Journal Organic Chemistry, v56, pp. 6007-6017 (1991).
Jen et al., "Suppression of Gene Expression by Targeted Disruption of Messenger RNA: Available Options and Current Strategies", Stem Cells, v18 n5, pp. 307-319 (2000).
Karlin et al., "Methods for Assessing the Statistical Significance of Molecular Sequence Features by Using General Scoring Schemes", Proceedings of the National Academy of Sciences USA, v 87:2264-2268 (1990).
Kushner et al., "Antisense Cancer Therapy: The State of the Science", Current Oncology Reports, v2, pp. 23-30 (2000).

Lesnick et al., "Ologiodeoxynucleotides Containing 2'-O-Modified Adeosine: Synthesis and Effects on Stability of DNA:RNA Duplexes", Biochemistry, v32 n30, pp. 7832-7838 (1993).
Ma et al., "Synthetic Oligonucleotides As Therapeutics: The Coming of Age", Biotechnology Annual Review, v5, pp. 155-196 (2000).
Marcus-Sekura et al., "Comparative Inhibition of Chloramphenicol Acetyltransferase Gene Expression by Antisense Oligonucleotide Analogus Having Alkyl Phospotriester, Methylphosphonate and Phosphothioate Linkages", Nucleic Acids Research, v15 n14, pp. 5749-5763 (1987).
Matthews et al., "Expanded Sequence Dependence of Thermodynamic Parameters Improves Prediction of RNA Secondary Structure", Journal Molecular Biology, v288, pp. 911-940 (1999).
Matthews et al., "Predicting Oligonucleotide Affinity to Nucleic Acid Targets", RNA, v5, pp. 1458-1469 (1999).
Micklefield., "Backbone Modification of Nucleic Acids: Synthesis, Structure and Therapeutic Applications", Current Medicinal Chemistry, v8 n10, pp. 1157-1179 (2001).
Milligan et al., "Current concepts in Antisense Drug Design", Journal of Medicinal Chemistry, v36 n14, pp. 1923-1937 (1993).
Miraglia et al., "Variations in mRNA Context Have No Effect on the Potency of Antisense Oligonucleotides", Antisense & Nucleic Acid Drug Development, v10, pp. 453-461 (2000).
Neurath et al., "Cytokine Gene Transcription by NF-Kappa B Family Members in Patients With Inflammatory Bowel Disease", Annals of the New York Academy of Sciences, v859, pp. 149-159 (1998).
Neurath et al., "Local Administration of Antisense Phosphorothioate Oligonucleotides to the p65 Subunit of NF-Kappa B Abrogates Established Experimental Colitis in Mice", Nature Medicine, v2 n9, pp. 998-1004 (1996).
Rudin et al., "Phase I Trial of ISIS 5132, An Antisense Oligonucleotide Inhibitor of c-raf-1, Administered by 24-Hour Weekly Infusion to Patients With Advance Cancer", Clinical Cancer Research, v7, pp. 1214-1220 (2001).
Sambrook et al., "Molecular Cloning: A Laboratory Manual", Cold Spring Harbor Laboratory Press (1989).
Shibahara et al., "Inhibition of Human Immunodeficiency Virus (HIV-1) Replication by Synthetic Oligo-RNA Derivatives", Nucleic Acids Research, v17 n1, pp. 239-252 (1989).
Summerton., "Intracellular Inactivation of Specific Nucleotide Sequences: A General Approach to the Treatment of Viral Diseases and Virally-Mediated Cancers", Journal of Theoretical Biology, v78, pp. 77-99 (1979).
Summerton et al., "Sequence-specific Crosslinking Agents for Nucleic Acids", Journal of Molecular Biology, v122, pp. 145-162 (1978).
Vlassov et al., "Penetration of Oligonucleotides Into Mouse Organism Through Mucosa and Skin", Federation of European Biochemical Societies, v327 n3, pp. 271-274 (1993).
Weller et al., "Molecular Modeling of Acyclic Polyamide Oligonucleotide Analogues", Journal Organic Chemistry, v56 n21, pp. 6000-6006 (1991).
Zamecnik et al., "Inhibition of Rous Sarcoma Virus Replication and Cell Transformation by a Specific Oligodeoxynucleotide", Proceedings of the National Academy of Science USA, v75 n1, pp. 280-284 (1978).
Zhu et al., "Inhibition of the expression of Phosphodiesterase 5 by Antisense Inhibits the Growth of Human colon Carcinoma (HT-29) Cells in Culture", Journal for the Federation of American Societies for Experimental Biology, v15 n5, p. A924 (2001).
Zhu et al., "Stable Expression of Phospodiesterase (PDE) 5 Antisense in Human Colon Turmor HT29 Cell Is Associated With Delayed G2/M Cell Cycle Progression", Proceedings of the American Association for Cancer Research Annual Meeting, v43, p. 64 (2002).
Francischi, et al., "Anti-inflammatory and analgesic effects of the phosphodiesterase 4 inhibitor rolipram in a rat model of arthritis", *Eur J. Pharmacol.*, 2000, vol. 399, No. 2-3, pp. 243-249.
Higashi, et al., "Enhanced Expression of Cyclooxygenase (COX)-2 in Human Skin Epidermal Cancer Cells: Evidence for Growth Suppression by Inhibiting COX-2 Expression", *Int. J. Cancer*, vol. 86, pp. 667-671, 2000, ISSN: 0020-7136.

Khan, et al., "In Vivo Inhibition of Cyclooxygenase-2 by a Selective Phosphorothioated Oligonucleotide", *Antisense & Nucleic Acid Drug Development*, vol. 11, pp. 199-207, 2001, ISSN: 1087-2906.

Lazzeri, et al., "Effects of Prostaglandin $E_2$ and cAMP Elevating Drugs on GM-CSF Release by Cultured Human Airway Smooth Muscle Cells", *Am. J. Respir. Cell Mol. Biol.*, vol. 24, pp. 44-48 2001, XP001180092ISSN: 1044-1549.

Mardini, et al., "Selective Inhibitors of Cyclooxygenase-2: A Growing Class of Anti-Inflammatory Drugs," *Mol. Interv.*, 2001, vol. 1, No. 1, pp. 30-38.

Sano, H. Journal of Clinical and Experimental Medicine (IGAKU NO AYUMI), 2000, vol. 195, No. 7, pp. 463-468.

Seibert, et al., "Pharmacological and biochemical demonstration of the role of cyclooxygenase 2 in inflammation and pain", *Proc. Natl. Acad. Sci. USA*, vol. 91, pp. 12013-12017, 1994, ISSN: 0027-8424.

Sumitani, et al., "Specific inhibition of cyclooxygenase-2 results in inhibition of proliferation of oral cancer cell lines via suppression of prostaglandin $E_2$ production", *J. Oral Pathol. Med.*, vol. 30, pp. 41-47, 2001, ISSN: 0904-2512.

Yamada, et al., "Selective Inhibition of Cyclooxygenase-2 with Antisense Oligodeoxynucleotide Restricts Induction of Rat Adjuvant-Induced Arthritis", *Biochemical and Biophysical Research Communications*, vol. 269, pp. 415-421, 2000, ISSN: 0006-291X.

Dobashi et al. "Simultaneous Suppression of cdc2 and cdk2 Activities Induces Neuronal Differentiation of PC12 Cells." *J. Biol. Chem.* 275.17(Apr. 2000):12572-12580.

Miyake et al. "Inhibition of Progression to Androgen-Independence by Combined Adjuvant Treatment with Antisense BCL-XL and Antisense BCL-2 Oligonucleotides plus Taxol After Castration in the Shionogi Tumor Model." *Int. J. Cancer.* 86.6(Jun. 2000):855-862.

Agrawal et al. "Antisense Therapeutics." *Curr. Opin. Chem. Biol.* 2.4(1998):519-528.

Hughes et al. "The Cellular Delivery of Antisense Oligonucleotides and Ribozymes." *Drug Disc. Today.* 6.6(2001):303-315.

Okamoto et al. "Attempt for Liver-Targeted Delivery of Antisense Oligonucleotides by Cholesterol Modification and Oral Adminstration."*Heptaol. Res.* 13.3(1999):252-258.

Tortora et al. "Oral Antisense That Targets Protein Kinase A Cooperates With Taxol and Inhibits Tumor Growth, Antiogenesis and Growth Factor Production." *Clin. Cancer Res.* 6.1(2000):2506-2512.

Wang. "Antitumor Activity and Pharmacokineticc of a Mixed-Backbone Antisense Oligonucleotide Targeted to the RIα Subunit of Protein Kinase A After Oral Administration." *PNAS.* 96.24(1999):13989-13994.

\* cited by examiner

SEQUENCE LISTING

```
<160> NUMBER OF SEQ ID NOS: 132

<210> SEQ ID NO 1
<211> LENGTH: 14
<212> TYPE: DNA
<213> ORGANISM: Artificial sequence
<220> FEATURE:
<223> OTHER INFORMATION: ASM oligonucleotide

<400> SEQUENCE: 1
cgtgtcagga gaac                                                        14

<210> SEQ ID NO 2
<211> LENGTH: 14
<212> TYPE: DNA
<213> ORGANISM: Artificial sequence
<220> FEATURE:
<223> OTHER INFORMATION: Ace1 oligonucleotide

<400> SEQUENCE: 2
catgacgcgg tgcg                                                        14

<210> SEQ ID NO 3
<211> LENGTH: 16
<212> TYPE: DNA
<213> ORGANISM: Artificial sequence
<220> FEATURE:
<223> OTHER INFORMATION: Acid-2 oligonucleotide

<400> SEQUENCE: 3
ggcagtcgtc cctcta                                                      16
```

```
<210> SEQ ID NO 4
<211> LENGTH: 16
<212> TYPE: DNA
<213> ORGANISM: Artificial sequence
<220> FEATURE:
<223> OTHER INFORMATION: Acid B2 oligonucleotide

<400> SEQUENCE: 4
aacgtttcac ttctca                                                   16

<210> SEQ ID NO 5
<211> LENGTH: 13
<212> TYPE: DNA
<213> ORGANISM: Artificial sequence
<220> FEATURE:
<223> OTHER INFORMATION: cd18-1 oligonucleotide

<400> SEQUENCE: 5
ttgctaccag tct                                                      13

<210> SEQ ID NO 6
<211> LENGTH: 16
<212> TYPE: DNA
<213> ORGANISM: Artificial sequence
<220> FEATURE:
<223> OTHER INFORMATION: CX2 (X2) oligonucleotide

<400> SEQUENCE: 6
tctacagttc agtcga                                                   16

<210> SEQ ID NO 7
<211> LENGTH: 18
<212> TYPE: DNA
<213> ORGANISM: Artificial sequence
<220> FEATURE:
<223> OTHER INFORMATION: Mg44 oligonucleotide

<400> SEQUENCE: 7
tgacaacatt gtagctac                                                 18

<210> SEQ ID NO 8
<211> LENGTH: 18
<212> TYPE: DNA
<213> ORGANISM: Artificial sequence
<220> FEATURE:
<223> OTHER INFORMATION: Mg44 oligonucleotide

<400> SEQUENCE: 8
agctacagaa tccttgga                                                 18

<210> SEQ ID NO 9
<211> LENGTH: 16
<212> TYPE: DNA
<213> ORGANISM: Artificial sequence
<220> FEATURE:
<223> OTHER INFORMATION: Mg44 oligonucleotide

<400> SEQUENCE: 9
gtcgggctat tcaggc                                                   16

<210> SEQ ID NO 10
<211> LENGTH: 16
<212> TYPE: DNA
<213> ORGANISM: Artificial sequence
<220> FEATURE:
<223> OTHER INFORMATION: P65-2M (65) oligonucleotide

<400> SEQUENCE: 10
```

```
gaacagttcg tccatg                                                    16

<210> SEQ ID NO 11
<211> LENGTH: 15
<212> TYPE: DNA
<213> ORGANISM: Artificial sequence
<220> FEATURE:
<223> OTHER INFORMATION: IL-501 oligonucleotide

<400> SEQUENCE: 11
cctcatggct ctgaa                                                     15

<210> SEQ ID NO 12
<211> LENGTH: 16
<212> TYPE: DNA
<213> ORGANISM: Artificial sequence
<220> FEATURE:
<223> OTHER INFORMATION: LO5-38 oligonucleotide

<400> SEQUENCE: 12
ggagggcatg gcgcgg                                                    16

<210> SEQ ID NO 13
<211> LENGTH: 16
<212> TYPE: DNA
<213> ORGANISM: Artificial sequence
<220> FEATURE:
<223> OTHER INFORMATION: MPB-19 oligonucleotide

<400> SEQUENCE: 13
cctgcatcgc gccgtg                                                    16

<210> SEQ ID NO 14
<211> LENGTH: 16
<212> TYPE: DNA
<213> ORGANISM: Artificial sequence
<220> FEATURE:
<223> OTHER INFORMATION: NEP-1 (CALLA) oligonucleotide

<400> SEQUENCE: 14
gacttgccca tcacct                                                    16

<210> SEQ ID NO 15
<211> LENGTH: 16
<212> TYPE: DNA
<213> ORGANISM: Artificial sequence
<220> FEATURE:
<223> OTHER INFORMATION: NPY-1 oligonucleotide

<400> SEQUENCE: 15
acctagcatg gtggct                                                    16

<210> SEQ ID NO 16
<211> LENGTH: 15
<212> TYPE: DNA
<213> ORGANISM: Artificial sequence
<220> FEATURE:
<223> OTHER INFORMATION: D5 (PDE5.1) oligonucleotide

<400> SEQUENCE: 16
cgctccatgg ttggc                                                     15

<210> SEQ ID NO 17
<211> LENGTH: 16
<212> TYPE: DNA
<213> ORGANISM: Artificial sequence
```

```
<220> FEATURE:
<223> OTHER INFORMATION: D7 oligonucleotide

<400> SEQUENCE: 17
cttccattga atacgc                                                    16

<210> SEQ ID NO 18
<211> LENGTH: 16
<212> TYPE: DNA
<213> ORGANISM: Artificial sequence
<220> FEATURE:
<223> OTHER INFORMATION: Per oligonucleotide

<400> SEQUENCE: 18
actgccatcc tcgctc                                                    16

<210> SEQ ID NO 19
<211> LENGTH: 16
<212> TYPE: DNA
<213> ORGANISM: Artificial sequence
<220> FEATURE:
<223> OTHER INFORMATION: TTP (TTPII) oligonucleotide

<400> SEQUENCE: 19
cggtggccat ggacgc                                                    16

<210> SEQ ID NO 20
<211> LENGTH: 17
<212> TYPE: DNA
<213> ORGANISM: Artificial sequence
<220> FEATURE:
<223> OTHER INFORMATION: TTPII oligonucleotide

<400> SEQUENCE: 20
aagttcatgg tttcgga                                                   17

<210> SEQ ID NO 21
<211> LENGTH: 19
<212> TYPE: DNA
<213> ORGANISM: Artificial sequence
<220> FEATURE:
<223> OTHER INFORMATION: MTP oligonucleotide

<400> SEQUENCE: 21
gaatcatatt tgaccagca                                                 19

<210> SEQ ID NO 22
<211> LENGTH: 16
<212> TYPE: DNA
<213> ORGANISM: Artificial sequence
<220> FEATURE:
<223> OTHER INFORMATION: HisR1 oligonucleotide

<400> SEQUENCE: 22
ggctcattgg cgcaag                                                    16

<210> SEQ ID NO 23
<211> LENGTH: 16
<212> TYPE: DNA
<213> ORGANISM: Artificial sequence
<220> FEATURE:
<223> OTHER INFORMATION: HisR1 oligonucleotide

<400> SEQUENCE: 23
agagcctccc ttagga                                                    16
```

```
<210> SEQ ID NO 24
<211> LENGTH: 16
<212> TYPE: DNA
<213> ORGANISM: Artificial sequence
<220> FEATURE:
<223> OTHER INFORMATION: CRP oligonucleotide

<400> SEQUENCE: 24
catggtcacg tcctgc                                                    16

<210> SEQ ID NO 25
<211> LENGTH: 18
<212> TYPE: DNA
<213> ORGANISM: Artificial sequence
<220> FEATURE:
<223> OTHER INFORMATION: CETP oligonucleotide

<400> SEQUENCE: 25
atggttatca ggcagtgg                                                  18

<210> SEQ ID NO 26
<211> LENGTH: 19
<212> TYPE: DNA
<213> ORGANISM: Artificial sequence
<220> FEATURE:
<223> OTHER INFORMATION: CETP oligonucleotide

<400> SEQUENCE: 26
catggttatc aggcagtgg                                                 19

<210> SEQ ID NO 27
<211> LENGTH: 16
<212> TYPE: DNA
<213> ORGANISM: Artificial sequence
<220> FEATURE:
<223> OTHER INFORMATION: CETP oligonucleotide

<400> SEQUENCE: 27
ctgaagaatt gaccac                                                    16

<210> SEQ ID NO 28
<211> LENGTH: 16
<212> TYPE: DNA
<213> ORGANISM: Artificial sequence
<220> FEATURE:
<223> OTHER INFORMATION: ICAM oligonucleotide

<400> SEQUENCE: 28
catagcgagg ctgagg                                                    16

<210> SEQ ID NO 29
<211> LENGTH: 15
<212> TYPE: DNA
<213> ORGANISM: Artificial sequence
<220> FEATURE:
<223> OTHER INFORMATION: TNF-alpha oligonucleotide

<400> SEQUENCE: 29
gtgctcatgg tgtcc                                                     15

<210> SEQ ID NO 30
<211> LENGTH: 15
<212> TYPE: DNA
<213> ORGANISM: Artificial sequence
<220> FEATURE:
<223> OTHER INFORMATION: Bone morphgenic protein-4 oligonucleotide

<400> SEQUENCE: 30
```

```
cgaccatcag cattc                                                    15

<210> SEQ ID NO 31
<211> LENGTH: 16
<212> TYPE: DNA
<213> ORGANISM: Artificial sequence
<220> FEATURE:
<223> OTHER INFORMATION: Beta adrenergic receptor-1 oligonucleotide

<400> SEQUENCE: 31
gcccatgccg agctgc                                                   16

<210> SEQ ID NO 32
<211> LENGTH: 16
<212> TYPE: DNA
<213> ORGANISM: Artificial sequence
<220> FEATURE:
<223> OTHER INFORMATION: IL-6 oligonucleotide

<400> SEQUENCE: 32
aggagttcat agctgg                                                   16

<210> SEQ ID NO 33
<211> LENGTH: 16
<212> TYPE: DNA
<213> ORGANISM: Artificial sequence
<220> FEATURE:
<223> OTHER INFORMATION: FAAH oligonucleotide

<400> SEQUENCE: 33
gcaccatgat cccttc                                                   16

<210> SEQ ID NO 34
<211> LENGTH: 16
<212> TYPE: DNA
<213> ORGANISM: Artificial sequence
<220> FEATURE:
<223> OTHER INFORMATION: ACAT oligonucleotide

<400> SEQUENCE: 34
cttcacccac cattgt                                                   16

<210> SEQ ID NO 35
<211> LENGTH: 18
<212> TYPE: DNA
<213> ORGANISM: Artificial sequence
<220> FEATURE:
<223> OTHER INFORMATION: IBAT oligonucleotide

<400> SEQUENCE: 35
cattcattgc tgggtctg                                                 18

<210> SEQ ID NO 36
<211> LENGTH: 15
<212> TYPE: DNA
<213> ORGANISM: Artificial sequence
<220> FEATURE:
<223> OTHER INFORMATION: HMGIC oligonucleotide

<400> SEQUENCE: 36
cgtgcgctca tcctg                                                    15

<210> SEQ ID NO 37
<211> LENGTH: 16
<212> TYPE: DNA
<213> ORGANISM: Artificial sequence
```

```
<220> FEATURE:
<223> OTHER INFORMATION: HMGIC oligonucleotide

<400> SEQUENCE: 37
aacgttgcgc ccccta                                                    16

<210> SEQ ID NO 38
<211> LENGTH: 16
<212> TYPE: DNA
<213> ORGANISM: Artificial sequence
<220> FEATURE:
<223> OTHER INFORMATION: Ghre oligonucleotide

<400> SEQUENCE: 38
tgcagacagg tgggcc                                                    16

<210> SEQ ID NO 39
<211> LENGTH: 17
<212> TYPE: DNA
<213> ORGANISM: Artificial sequence
<220> FEATURE:
<223> OTHER INFORMATION: Ghre oligonucleotide

<400> SEQUENCE: 39
gcatggcctc agctggg                                                   17

<210> SEQ ID NO 40
<211> LENGTH: 16
<212> TYPE: DNA
<213> ORGANISM: Artificial sequence
<220> FEATURE:
<223> OTHER INFORMATION: Ghre oligonucleotide

<400> SEQUENCE: 40
tgggcgatca cttgtc                                                    16

<210> SEQ ID NO 41
<211> LENGTH: 18
<212> TYPE: DNA
<213> ORGANISM: Artificial sequence
<220> FEATURE:
<223> OTHER INFORMATION: AAT1R oligonucleotide

<400> SEQUENCE: 41
cattttgatc acctgggt                                                  18

<210> SEQ ID NO 42
<211> LENGTH: 16
<212> TYPE: DNA
<213> ORGANISM: Artificial sequence
<220> FEATURE:
<223> OTHER INFORMATION: AAT1R oligonucleotide

<400> SEQUENCE: 42
cgaacatgtc actcaa                                                    16

<210> SEQ ID NO 43
<211> LENGTH: 17
<212> TYPE: DNA
<213> ORGANISM: Artificial sequence
<220> FEATURE:
<223> OTHER INFORMATION: VEGF oligonucleotide

<400> SEQUENCE: 43
aagttcatgg tttcgga                                                   17
```

-continued

```
<210> SEQ ID NO 44
<211> LENGTH: 17
<212> TYPE: DNA
<213> ORGANISM: Artificial sequence
<220> FEATURE:
<223> OTHER INFORMATION: VEGF oligonucleotide

<400> SEQUENCE: 44
tcaccgcctc ggcttgt                                                  17

<210> SEQ ID NO 45
<211> LENGTH: 15
<212> TYPE: DNA
<213> ORGANISM: Artificial sequence
<220> FEATURE:
<223> OTHER INFORMATION: FAS oligonucleotide

<400> SEQUENCE: 45
cctcctccat ggctg                                                    15

<210> SEQ ID NO 46
<211> LENGTH: 15
<212> TYPE: DNA
<213> ORGANISM: Artificial sequence
<220> FEATURE:
<223> OTHER INFORMATION: FAS oligonucleotide

<400> SEQUENCE: 46
gcctagccct cccgc                                                    15

<210> SEQ ID NO 47
<211> LENGTH: 16
<212> TYPE: DNA
<213> ORGANISM: Artificial sequence
<220> FEATURE:
<223> OTHER INFORMATION: AmP oligonucleotide

<400> SEQUENCE: 47
gcagcggctt gttcat                                                   16

<210> SEQ ID NO 48
<211> LENGTH: 15
<212> TYPE: DNA
<213> ORGANISM: Artificial sequence
<220> FEATURE:
<223> OTHER INFORMATION: AmP oligonucleotide

<400> SEQUENCE: 48
gagtcaagac ctcag                                                    15

<210> SEQ ID NO 49
<211> LENGTH: 16
<212> TYPE: DNA
<213> ORGANISM: Artificial sequence
<220> FEATURE:
<223> OTHER INFORMATION: PanLip oligonucleotide

<400> SEQUENCE: 49
gtggcagcat cgtggc                                                   16

<210> SEQ ID NO 50
<211> LENGTH: 16
<212> TYPE: DNA
<213> ORGANISM: Artificial sequence
<220> FEATURE:
<223> OTHER INFORMATION: PanLip oligonucleotide

<400> SEQUENCE: 50
```

```
cctaacacgg tgtgag                                                     16

<210> SEQ ID NO 51
<211> LENGTH: 17
<212> TYPE: DNA
<213> ORGANISM: Artificial sequence
<220> FEATURE:
<223> OTHER INFORMATION: ACC2 oligonucleotide

<400> SEQUENCE: 51
gaagcaagac cattcag                                                    17

<210> SEQ ID NO 52
<211> LENGTH: 17
<212> TYPE: DNA
<213> ORGANISM: Artificial sequence
<220> FEATURE:
<223> OTHER INFORMATION: ACC2 oligonucleotide

<400> SEQUENCE: 52
tcaggtggag gccgggc                                                    17

<210> SEQ ID NO 53
<211> LENGTH: 16
<212> TYPE: DNA
<213> ORGANISM: Artificial sequence
<220> FEATURE:
<223> OTHER INFORMATION: PKARIIbeta oligonucleotide

<400> SEQUENCE: 53
tgctcatcct gcctcc                                                     16

<210> SEQ ID NO 54
<211> LENGTH: 16
<212> TYPE: DNA
<213> ORGANISM: Artificial sequence
<220> FEATURE:
<223> OTHER INFORMATION: PKARIIbeta oligonucleotide

<400> SEQUENCE: 54
gcttcatgca gtgggt                                                     16

<210> SEQ ID NO 55
<211> LENGTH: 16
<212> TYPE: DNA
<213> ORGANISM: Artificial sequence
<220> FEATURE:
<223> OTHER INFORMATION: VR1R oligonucleotide

<400> SEQUENCE: 55
tcttcatcct tgctgg                                                     16

<210> SEQ ID NO 56
<211> LENGTH: 16
<212> TYPE: DNA
<213> ORGANISM: Artificial sequence
<220> FEATURE:
<223> OTHER INFORMATION: VR1R oligonucleotide

<400> SEQUENCE: 56
ctcacttctc cccgga                                                     16

<210> SEQ ID NO 57
<211> LENGTH: 16
<212> TYPE: DNA
<213> ORGANISM: Artificial sequence
```

-continued

```
<220> FEATURE:
<223> OTHER INFORMATION: ADAMTS oligonucleotide

<400> SEQUENCE: 57
gggacatggc actggt                                                      16

<210> SEQ ID NO 58
<211> LENGTH: 16
<212> TYPE: DNA
<213> ORGANISM: Artificial sequence
<220> FEATURE:
<223> OTHER INFORMATION: ADAMTS oligonucleotide

<400> SEQUENCE: 58
ttatttcctg cccgcc                                                      16

<210> SEQ ID NO 59
<211> LENGTH: 16
<212> TYPE: DNA
<213> ORGANISM: Artificial sequence
<220> FEATURE:
<223> OTHER INFORMATION: NPY-Y5R oligonucleotide

<400> SEQUENCE: 59
tgtggcaggt cagttg                                                      16

<210> SEQ ID NO 60
<211> LENGTH: 16
<212> TYPE: DNA
<213> ORGANISM: Artificial sequence
<220> FEATURE:
<223> OTHER INFORMATION: NPY-Y5R oligonucleotide

<400> SEQUENCE: 60
atccatatta tagtct                                                      16

<210> SEQ ID NO 61
<211> LENGTH: 16
<212> TYPE: DNA
<213> ORGANISM: Artificial sequence
<220> FEATURE:
<223> OTHER INFORMATION: NPY-Y5R oligonucleotide

<400> SEQUENCE: 61
tattacatat gaagac                                                      16

<210> SEQ ID NO 62
<211> LENGTH: 16
<212> TYPE: DNA
<213> ORGANISM: Artificial sequence
<220> FEATURE:
<223> OTHER INFORMATION: GNTV oligonucleotide

<400> SEQUENCE: 62
agccattgct ctctgg                                                      16

<210> SEQ ID NO 63
<211> LENGTH: 16
<212> TYPE: DNA
<213> ORGANISM: Artificial sequence
<220> FEATURE:
<223> OTHER INFORMATION: GNTV oligonucleotide

<400> SEQUENCE: 63
tgctataggc agtctt                                                      16
```

```
<210> SEQ ID NO 64
<211> LENGTH: 16
<212> TYPE: DNA
<213> ORGANISM: Artificial sequence
<220> FEATURE:
<223> OTHER INFORMATION: FCRG3 oligonucleotide

<400> SEQUENCE: 64
tgccacatga tgccac                                              16

<210> SEQ ID NO 65
<211> LENGTH: 16
<212> TYPE: DNA
<213> ORGANISM: Artificial sequence
<220> FEATURE:
<223> OTHER INFORMATION: FCRG3 oligonucleotide

<400> SEQUENCE: 65
gttgagcttc aaatgt                                              16

<210> SEQ ID NO 66
<211> LENGTH: 16
<212> TYPE: DNA
<213> ORGANISM: Artificial sequence
<220> FEATURE:
<223> OTHER INFORMATION: CD40L oligonucleotide

<400> SEQUENCE: 66
tcgatcatgc tgtgtt                                              16

<210> SEQ ID NO 67
<211> LENGTH: 16
<212> TYPE: DNA
<213> ORGANISM: Artificial sequence
<220> FEATURE:
<223> OTHER INFORMATION: CD40L oligonucleotide

<400> SEQUENCE: 67
aggtgacact gttcag                                              16

<210> SEQ ID NO 68
<211> LENGTH: 16
<212> TYPE: DNA
<213> ORGANISM: Artificial sequence
<220> FEATURE:
<223> OTHER INFORMATION: ETS-1 oligonucleotide

<400> SEQUENCE: 68
acggccgcct tcatgg                                              16

<210> SEQ ID NO 69
<211> LENGTH: 16
<212> TYPE: DNA
<213> ORGANISM: Artificial sequence
<220> FEATURE:
<223> OTHER INFORMATION: ETS-1 oligonucleotide

<400> SEQUENCE: 69
gccatcactc gtcggc                                              16

<210> SEQ ID NO 70
<211> LENGTH: 16
<212> TYPE: DNA
<213> ORGANISM: Artificial sequence
<220> FEATURE:
<223> OTHER INFORMATION: ADAMTS-5 oligonucleotide

<400> SEQUENCE: 70
```

-continued ccgagcagca tagtgc                                                        16

<210> SEQ ID NO 71
<211> LENGTH: 16
<212> TYPE: DNA
<213> ORGANISM: Artificial sequence
<220> FEATURE:
<223> OTHER INFORMATION: ADAMTS-5 oligonucleotide

<400> SEQUENCE: 71
tcataaccac aggcta                                                        16

<210> SEQ ID NO 72
<211> LENGTH: 16
<212> TYPE: DNA
<213> ORGANISM: Artificial sequence
<220> FEATURE:
<223> OTHER INFORMATION: PTP-1B oligonucleotide

<400> SEQUENCE: 72
catgacgggc cagggc                                                        16

<210> SEQ ID NO 73
<211> LENGTH: 16
<212> TYPE: DNA
<213> ORGANISM: Artificial sequence
<220> FEATURE:
<223> OTHER INFORMATION: PTP-1B oligonucleotide

<400> SEQUENCE: 73
gggtcaggct atgtgt                                                        16

<210> SEQ ID NO 74
<211> LENGTH: 17
<212> TYPE: DNA
<213> ORGANISM: Artificial sequence
<220> FEATURE:
<223> OTHER INFORMATION: MMP-1 oligonucleotide

<400> SEQUENCE: 74
gcatactggc ctttgtc                                                       17

<210> SEQ ID NO 75
<211> LENGTH: 17
<212> TYPE: DNA
<213> ORGANISM: Artificial sequence
<220> FEATURE:
<223> OTHER INFORMATION: MMP-1 oligonucleotide

<400> SEQUENCE: 75
tcaatttttc ctgcagt                                                       17

<210> SEQ ID NO 76
<211> LENGTH: 16
<212> TYPE: DNA
<213> ORGANISM: Artificial sequence
<220> FEATURE:
<223> OTHER INFORMATION: Cat oligonucleotide

<400> SEQUENCE: 76
gccatagcgt gcggtt                                                        16

<210> SEQ ID NO 77
<211> LENGTH: 16
<212> TYPE: DNA
<213> ORGANISM: Artificial sequence

```
<220> FEATURE:
<223> OTHER INFORMATION: Cat oligonucleotide

<400> SEQUENCE: 77
cccggcctca cagatt                                                    16

<210> SEQ ID NO 78
<211> LENGTH: 17
<212> TYPE: DNA
<213> ORGANISM: Artificial sequence
<220> FEATURE:
<223> OTHER INFORMATION: MMP-17 oligonucleotide

<400> SEQUENCE: 78
catggcgctc acatggg                                                   17

<210> SEQ ID NO 79
<211> LENGTH: 17
<212> TYPE: DNA
<213> ORGANISM: Artificial sequence
<220> FEATURE:
<223> OTHER INFORMATION: MMP-17 oligonucleotide

<400> SEQUENCE: 79
tgtcatagcg tcagggc                                                   17

<210> SEQ ID NO 80
<211> LENGTH: 16
<212> TYPE: DNA
<213> ORGANISM: Artificial sequence
<220> FEATURE:
<223> OTHER INFORMATION: OPG oligonucleotide

<400> SEQUENCE: 80
tcattgtggt ccccgg                                                    16

<210> SEQ ID NO 81
<211> LENGTH: 16
<212> TYPE: DNA
<213> ORGANISM: Artificial sequence
<220> FEATURE:
<223> OTHER INFORMATION: OPG oligonucleotide

<400> SEQUENCE: 81
tccagttata agcagc                                                    16

<210> SEQ ID NO 82
<211> LENGTH: 1684
<212> TYPE: DNA
<213> ORGANISM: Homo sapiens
<220> FEATURE:
<221> NAME/KEY: misc_feature
<223> OTHER INFORMATION: Pde4:  Acc. No. U50158

<400> SEQUENCE: 82
aatatgaagg agcagccctc atgtgccggc accgggcatc cgagcatggc gggaggaggc      60
ctaccagaaa ctggccagcg agaccctgga ggagctggac tggtgtctgg accagctaga     120
gaccctacag accaggcact ccgtcagtga gatggcctcc aacaagttta aaaggatgct     180
taatcgggag ctcacccatc tctctgaaat gagtcggtct ggaaatcaag tgtcagagtt     240
tatatcaaac acattcttag ataagcaaca tgaagtggaa attccttctc caactcagaa     300
ggaaaaggag aaaagaaaa gaccaatgtc tcagatcagt ggagtcaaga aattgatgca     360
cagctctagt ctgactaatt caagtatccc aaggtttgga gttaaaactg aacaagaaga     420
```

| | |
|---|---|
| tgtccttgcc aaggaactag aagatgtgaa caaatggggt cttcatgttt tcagaatagc | 480 |
| agagttgtct ggtaaccggc ccttgactgt tatcatgcac accattttc aggaacggga | 540 |
| tttattaaaa acatttaaaa ttccagtaga tactttaatt acatatctta tgactctcga | 600 |
| agaccattac catgctgatg tggcctatca acaatatc catgctgcag atgttgtcca | 660 |
| gtctactcat gtgctattat ctacacctgc tttggaggct gtgtttacag atttggagat | 720 |
| tcttgcagca atttttgcca gtgcaataca tgatgtagat catcctggtg tgtccaatca | 780 |
| atttctgatc aatacaaact ctgaacttgc cttgatgtac aatgattcct cagtcttaga | 840 |
| gaaccatcat ttggctgtgg gctttaaatt gcttcaggaa gaaaactgtg acattttcca | 900 |
| gaatttgacc aaaaaacaaa gacaatcttt aaggaaaatg gtcattgaca tcgtacttgc | 960 |
| aacagatatg tcaaaacaca tgaatctact ggctgatttg aagactatgg ttgaaactaa | 1020 |
| gaaagtgaca agctctggag ttcttcttct tgataattat tccgatagga ttcaggttct | 1080 |
| tcagaatatg gtgcactgtg cagatctgag caacccaaca aagcctctcc agctgtaccg | 1140 |
| ccagtggacg gaccggataa tggaggagtt cttccgccaa ggagaccgag agagggaacg | 1200 |
| tggcatggag ataagcccca tgtgtgacaa gcacaatgct tccgtggaaa atcacaggt | 1260 |
| gggcttcata gactatattg ttcatcccct ctgggagaca tgggcagacc tcgtccaccc | 1320 |
| tgacgcccag gatattttgg acactttgga ggacaatcgt gaatggtacc agagcacaat | 1380 |
| ccctcagagc ccctctcctg cacctgatga cccagaggag ggccggcagg gtcaaactga | 1440 |
| gaaattccag tttgaactaa ctttagagga agatggtgag tcagacacgg aaaaggacag | 1500 |
| tggcagtcaa gtggaagaag acactagctg cagtgactcc aagactcttc gtactcaaga | 1560 |
| ctcagagtct actgaaattc cccttgatga acaggttgaa gaggaggcag taggggaaga | 1620 |
| agaggaaagc caacctgaag cctgtgtcat agatgatcgt tctcctgaca cgtaacagtg | 1680 |
| caaa | 1684 |

<210> SEQ ID NO 83
<211> LENGTH: 4020
<212> TYPE: DNA
<213> ORGANISM: Homo sapiens
<220> FEATURE:
<221> NAME/KEY: misc_feature
<223> OTHER INFORMATION: ACE-1: Acc. No. J04144.1

<400> SEQUENCE: 83

| | |
|---|---|
| gccgagcacc gcgcaccgcg tcatgggggc cgcctcgggc cgccggggc cggggctgct | 60 |
| gctgccgctg ccgctgctgt tgctgctgcc gccgcagccc gccctggcgt tggaccccgg | 120 |
| gctgcagccc ggcaactttt ctgctgacga ggcggggcg cagctcttcg cgcagagcta | 180 |
| caactccagc gccgaacagg tgctgttcca gagcgtggcc gccagctggg cgcacgacac | 240 |
| caacatcacc gcggagaatg caaggcgcca ggaggaagca gccctgctca gccaggagtt | 300 |
| tgcggaggcc tggggccaga aggccaagga gctgtatgaa ccgatctggc agaacttcac | 360 |
| ggacccgcag ctgcgcagga tcatcggagc tgtgcgaacc ctgggctctg ccaacctgcc | 420 |
| cctggctaag cggcagcagt acaacgccct gctaagcaac atgagcagga tctactccac | 480 |
| cgccaaggtc tgcctcccca caagactgc cacctgctgg tccctggacc cagatctcac | 540 |
| caacatcctg gcttcctcgc gaagctacg catgctcctg tttgcctggg agggctggca | 600 |
| caacgctgcg ggcatcccgc tgaaccgct gtacgaggat ttcactgccc tcagcaatga | 660 |
| agcctacaag caggacggct tcacagacac ggggggctac tggcgctcct ggtacaactc | 720 |
| ccccaccttc gaggacgatc tggaacacct ctaccaacag ctagagcccc tctacctgaa | 780 |

| | |
|---|---|
| cctccatgcc ttcgtccgcc gcgcactgca tcgccgatac ggagacagat acatcaacct | 840 |
| caggggaccc atccctgctc atctgctggg agacatgtgg gcccagagct gggaaaacat | 900 |
| ctacgacatg gtggtgcctt tcccagacaa gcccaacctc gatgtcacca gtactatgct | 960 |
| gcagcagggc tggaacgcca cgcacatgtt ccgggtggca gaggagttct tcacctccct | 1020 |
| ggagctctcc cccatgcctc ccgagttctg gaagggtcg atgctggaga agccggccga | 1080 |
| cgggcgggaa gtggtgtgcc acgcctcggc ttgggacttc tacaacagga aagacttcag | 1140 |
| gatcaagcag tgcacacggg tcacgatgga ccagctctcc acagtgcacc atgagatggg | 1200 |
| ccatatacag tactacctgc agtacaagga tctgcccgtc tccctgcgtc gggggggccaa | 1260 |
| ccccggcttc catgaggcca ttggggacgt gctggcgctc tcggtctcca ctcctgaaca | 1320 |
| tctgcacaaa atcggcctgc tggaccgtgt caccaatgac acggaaagtg acatcaatta | 1380 |
| cttgctaaaa atggcactgg aaaaaattgc cttcctgccc tttggctact ggtggacca | 1440 |
| gtggcgctgg ggggtcttta gtgggcgtac ccccccttcc cgctcaaact cgactggtg | 1500 |
| gtatcttcga accaagtatc aggggatctg tcctcctgtt acccgaaacg aaacccactt | 1560 |
| tgatgctgga gctaagtttc atgttccaaa tgtgacacca tacatcaggt actttgtgag | 1620 |
| ttttgtcctg cagttccagt tccatgaagc cctgtgcaag gaggcaggct atgagggccc | 1680 |
| actgcaccag tgtgacatct accggtccac caaggcaggg gccaagctcc ggaaggtgct | 1740 |
| gcaggctggc tcctccaggc cctggcagga ggtgctgaag acatggtcg gcttagatgc | 1800 |
| cctggatgcc cagccgctgc tcaagtactt ccagccagtc acccagtggc tgcaggagca | 1860 |
| gaaccagcag aacggcgagg tcctgggctg gcccgagtac cagtggcacc gccgttgcc | 1920 |
| tgacaactac ccggagggca tagacctggt gactgatgag gctgaggcca gcaagtttgt | 1980 |
| ggaggaatat gaccggacat cccaggtggt gtggaacgag tatgccgagg ccaactggaa | 2040 |
| ctacaacacc aacatcacca cagagaccag caagattctg ctgcagaaga acatgcaaat | 2100 |
| agccaaccac accctgaagt acggcaccca ggccaggaag tttgatgtga accagttgca | 2160 |
| gaacaccact atcaagcgga tcataaagaa ggttcaggac ctagaacggg cagcgctgcc | 2220 |
| tgcccaggag ctggaggagt acaacaagat cctgttggat atggaaacca cctacagcgt | 2280 |
| ggccactgtg tgccacccga atggcagctg cctgcagctc gagccagatc tgacgaatgt | 2340 |
| gatggccaca tcccggaaat atgaagacct gttatgggca tgggagggct ggcgagacaa | 2400 |
| ggcggggaga gccatcctcc agttttaccc gaaatacgtg gaactcatca accaggctgc | 2460 |
| ccggctcaat ggctatgtag atgcagggga ctcgtggagg tctatgtacg agacaccatc | 2520 |
| cctggagcaa gacctggagc ggctcttcca ggagctgcag ccactctacc tcaacctgca | 2580 |
| tgcctacgtg cgccgggccc tgcaccgtca ctacgggccc cagcacatca acctggaggg | 2640 |
| gcccattcct gctcacctgc tgggaacat gtgggcgcag acctggtcca acatctatga | 2700 |
| cttggtggtg cccttcccctt cagcccctc gatggacacc acagaggcta tgctaaagca | 2760 |
| gggctggacg cccaggagga tgtttaagga ggctgatgat ttcttcacct ccctgggct | 2820 |
| gctgcccgtg cctcctgagt tctggaacaa gtcgatgctg gagaagccaa ccgacgggcg | 2880 |
| ggaggtggtc tgccacgcct cggcctggga cttctacaac ggcaaggact tccggatcaa | 2940 |
| gcagtgcacc accgtgaact tggaggacct ggtggtggcc caccacgaaa tgggccacat | 3000 |
| ccagtatttc atgcagtaca aagacttacc tgtggccttg agggagggtg ccaaccccgg | 3060 |
| cttccatgag gccattgggg acgtgctagc cctctcagtg tctacgccca agcacctgca | 3120 |
| cagtctcaac ctgctgagca gtgagggtgg cagcgacgag catgacatca actttctgat | 3180 |

```
gaagatggcc cttgacaaga tcgcctttat ccccttcagc tacctcgtcg atcagtggcg    3240
ctggagggta tttgatggaa gcatcaccaa ggagaactat aaccaggagt ggtggagcct    3300
caggctgaag taccagggcc tctgccccc  agtgcccagg actcaaggtg actttgaccc    3360
aggggccaag ttccacattc cttctagcgt gccttacatc aggtactttg tcagcttcat    3420
catccagttc cagttccacg aggcactgtg ccaggcagct ggccacacgg gcccctgca     3480 caagtgtgac atctaccagt ccaaggaggc cgggcagcgc ctggcgaccg ccatgaagct    3540
gggcttcagt aggccgtggc cggaagccat gcagctgatc acgggccagc caacatgag     3600 cgcctcggcc atgttgagct acttcaagcc gctgctggac tggctccgca cggagaacga    3660
gctgcatggg gagaagctgg gctggccgca gtacaactgg acgccgaact ccgctcgctc    3720
agaagggccc ctcccagaca gcggccgcgt cagcttcctg ggcctggacc tggatgcgca    3780
gcaggcccgc gtgggccagt ggctgctgct cttcctgggc atcgccctgc tggtagccac    3840
cctgggcctc agccagcggc tcttcagcat ccgccaccgc agcctccacc ggcactccca    3900
cgggccccag ttcggctccg aggtggagct gagacactcc tgaggtgacc cggctgggtc    3960
ggccctgccc aagggcctcc caccagagac tgggatggga cactggtgg  gcagctgagg    4020

<210> SEQ ID NO 84
<211> LENGTH: 3556
<212> TYPE: DNA
<213> ORGANISM: Homo sapiens
<220> FEATURE:
<221> NAME/KEY: misc_feature
<223> OTHER INFORMATION: Acid2: Acc. No. NM_000704

<400> SEQUENCE: 84
tgttgggtgg gagcacaggc accgggcacc atggggaagg ccgagaacta tgagctctac      60
tcggtggagc tgggtcctgg ccctggcggg gacatggctg ccaagatgag caagaagaag     120
aaggcgggtg gcggggggtgg caagaggaag gagaagctgg agaacatgaa gaaggagatg    180
gagattaacg accaccagct gtcagtggcg gagctggaac agaaatacca gaccagtgcc     240
accaagggcc tctctgcgag cctggctgct gagctgctgc tgcgggatgg gcccaacgca     300
ctgcggccac cacggggcac cccagagtac gtcaagttcg cgaggcagct ggccgggggc     360
ctgcagtgcc tcatgtgggt tgccgccgcc atctgcctca tcgcctttgc catccaggct     420
agtgaggggg acctcaccac cgacgacaat ctgtacctgg caatcgctct cattgctgtg     480
gttgtcgtca ccgctgcttt tggctactac caggaattca gagcaccaa  catcatcgcc     540 agctttaaga accttgtgcc acagcaagcc actgtcatcc gcgatggaga caaattccag     600
atcaacgctg accaactggt ggtgggcgac ctggtggaga tgaaaggtgg ggacagagtg     660
cccgccgaca tccgcatcct ggcggcccag ggctgcaagg tggacaactc ctcgctgaca     720
ggggagtctg agccacaaac ccgctcaccc gagtgcacgc acgagagccc tctggagacc     780
cgcaacatcg ccttcttctc caccatgtgc cttgagggca ccgcgcaggg cctggtggtg    840
aacacgggcg accgcaccat cattgggcgc atcgcatcgc tggcgtcggg ggtggaaaac     900
gagaagacac ccatcgctat cgagatcgag catttgtgg  acatcatcgc gggcctggcc    960
attctcttcg gtgccacatt ttttattgtg gccatgtgca ttggctacac cttcctgcgg    1020
gccatggtct tcttcatggc catcgtggtg gcctatgtgc ctgaggggct gctggccact    1080
gtcacagtct gcctgtccct gacagccaag cgcctggcca gtaagaactg cgtggtcaag    1140
aacctggagg cggtggagac attgggctcc acttcggtga tctgctcgga caagacaggg    1200
```

```
actctcactc agaaccgcat gactgtgtcc catctgtggt ttgacaacca catccacaca   1260
gctgacacca cggaagacca gtcagggcag acgtttgacc agtcctcgga gacgtggcgg   1320
gcgctgtgcc gggtgctcac cctgtgcaac cgcgccgcct tcaagtccgg ccaggatgca   1380
gtgcctgtgc ccaagcgcat cgtgattgga gacgcatcgg agacggcgct gctcaagttc   1440
tcggagctga cgctgggcaa cgccatgggc taccgggacc gcttcccaaa agtctgcgag   1500
ataccctta actccaccaa caagttccag ctgtccatcc atacgctgga ggacccgcgg   1560
gacccgcgac acttgctggt gatgaagggc gcccccgagc gcgtgctgga gcgctgcagc   1620
tccatcctta tcaagggcca ggagctgccg ctggacgagc agtggcgcga ggccttccag   1680
accgcctacc tcagcctggg aggcctgggc gaacgcgtgc tcggcttctg ccagctctac   1740
ctgaatgaga aggactaccc cgcctggcta tgccttcgacg tagaggccat gaactttcca   1800
tctagcggcc tctgctttgc gggacttgta tccatgattg acccaccccg ggccaccgtc   1860
cctgatgctg tgctcaagtg tcgcaccgca ggcatccggg tgatcatggt aacgggtgac   1920
caccccatca ccgccaaggc cattgcagcc agtgtgggca tcatctcgga aggcagcgag   1980
acagtggagg acatcgctgc ccgcctccgt gtgcccgtag accaggttaa tcgcaaggat   2040
gcccgtgcct gtgtgatcaa tggcatgcag ctgaaggaca tggacccatc ggaactggtc   2100
gaggccctgc gcacccaccc cgagatggtg tttgcgcgca ccagccccca gcagaagctg   2160
gtgatcgtgg agagctgcca gcggctgggt gcgattgtgg ccgtcacggg ggatggtgtg   2220
aatgactccc cagctctgaa gaaggcagac atcggagtag ccatgggcat cgctggctca   2280
gatgctgcca aaaatgcagc tgacatgatc ctgctggatg acaactttgc ctccattgtg   2340
acaggcgtgg agcagggtcg actgatcttc gacaacctga agaagtctat tgcctacaca   2400
ttgaccaaga acatcccaga gctgacaccc tacctcatct acatcaccgt cagcgtgccc   2460
ctgcccctcg ggtgcatcac catcctcttc atcgaactct gcactgacat tttcccatct   2520
gtgtccctgg catatgaaaa ggccgagagt gacatcatgc acctgcgtcc acgcaaccca   2580
aagcgtgaca gattggtcaa cgagcccctg gctgcctact cctacttcca gattggtgcc   2640
attcagtcct ttgctggctt cactgactac ttcacggcaa tggcccagga gggctggttc   2700
ccactgctgt gcgtgggggct gcgggcgcag tgggaggacc accacctaca agatctgcag   2760
gacagctacg gccaggagtg gacattcggg cagcgcctgt accagcagta cacctgctac   2820
accgtgttct tcatcagcat tgaggtgtgc cagatcgccg atgtcctcat ccgcaagacg   2880
cgccgtctct ctgccttcca gcaaggcttc ttcaggaata agatcctggt gatcgccatc   2940
gtgttccagg tctgcatcgg ctgcttcctg tgctactgcc ccggcatgcc caacatcttc   3000
aacttcatgc ccattcggtt ccagtggtgg ctggtccccc tgcccctacgg catcctcatc   3060
ttcgtctatg atgagatccg gaagcttgga gttcgctgtt gcccagggag ctggtgggac   3120
caggaactct actattagag ggacgactgc cttcaagcat ccctgcaact gccacagcag   3180
gtgggggcag ggcacgtggg accctctgga cagccaccaa gatatctgag caaccaagag   3240
tcccagcccc accagtatct gcttctgtag cccacggcac cccaaacttg gagggacctg   3300
cccactcccc tccccattc caaggttcg cacctcctgg agcagcagcg cctgggcagt   3360
cctctgggct ggcctcggga aagccgccac ctgtggtggc ggtggggctc tgacagggag   3420
tacagctgac cgcttctgga gggtgttct gttcttagga ctccagtcca ggctggacgg   3480
ctgcctgagg gcccttcgtt aaagacacgc ttgtgtcctg ggcgatggta ataaaaccag   3540
ctcatgctga ctgtgc                                                   3556
```

<210> SEQ ID NO 85
<211> LENGTH: 1444
<212> TYPE: DNA
<213> ORGANISM: Homo sapiens
<220> FEATURE:
<221> NAME/KEY: misc_feature
<223> OTHER INFORMATION: AcidB2: Acc. No. NM_000705

<400> SEQUENCE: 85

| | | | | | | |
|---|---|---|---|---|---|---|
| agtctgggcg | tagagggtgc | agggagcaga | cgggaggatc | tcaggccagg | gacgatggcg | 60 |
| gctctgcagg | agaagaagac | gtgtggccag | cgcatggagg | agttccagcg | ttactgctgg | 120 |
| aacccggaca | cggggcagat | gctgggccgc | accctgtccc | ggtgggtgtg | gatcagcctg | 180 |
| tactacgtgg | ccttctacgt | ggtgatgact | gggctcttcg | ccctgtgcct | ctatgtgctg | 240 |
| atgcagacag | tggacccgta | cacaccggac | taccaagacc | agctacggtc | accagggta | 300 |
| accttaaggc | cggatgttta | cggggagaaa | ggcctggaaa | ttgtctacaa | cgtctctgat | 360 |
| aacagaacct | gggcagacct | cacacagact | ctccacgcct | tcctagcagg | ctactctcca | 420 |
| gcagcccagg | aggacagcat | caactgcacc | tccgagcagt | acttcttcca | ggagagtttc | 480 |
| cgcgctccca | accacaccaa | gttctcctgc | aagttcacgg | cagatatgct | gcagaactgc | 540 |
| tcaggcctgg | cggatcccaa | cttcggcttt | gaagaaggaa | agccatgttt | tattattaaa | 600 |
| atgaacagga | tcgtcaagtt | cctccccagc | aacggctcgg | ccccagagt | ggactgcgcc | 660 |
| ttcctggacc | agccccgcga | gctcggccag | ccgctgcagg | tcaagtacta | ccctcccaac | 720 |
| ggcaccttca | gtctgcacta | cttcccttat | acgggaaga | aagcccagcc | ccactacagc | 780 |
| aaccccctgg | tggcagcgaa | gctcctcaac | atccccagga | acgctgaggt | cgccatcgtg | 840 |
| tgcaaggtca | tggcagagca | cgtgaccttc | aacaatcccc | cgacccgta | tgaagggaaa | 900 |
| gtggagttca | aactcaagat | tgagaagtga | aacgtttgcg | caggggtcct | gggcacgcct | 960 |
| gcggggtcgc | tcaaggacac | cctcctggtt | gggcttacct | tgcccgtcag | ttccctgcca | 1020 |
| aatcatcccc | aaagtggttt | ggagcaacgg | tgttgtcagt | gtgcgaactc | cagagaagcg | 1080 |
| cccacatctg | aaggacctgc | tcgcgagtat | cagttcttcc | ttgttgaatt | cttacagttt | 1140 |
| ttagatggaa | tttgctgcta | taagaatgtc | cagctaccat | gggaacgcaa | ggcagcaact | 1200 |
| ctctaattaa | ccaggtcata | aaacgattc | gtcttctatg | tagacatcac | tttcttacta | 1260 |
| taatttattt | ttctacactt | caatatgaac | tgccccccc | acattaatat | aaaaactact | 1320 |
| aatgcactga | tatgaaacac | ggcttacact | aatgacattc | tgaattcttg | cttttaaaat | 1380 |
| tgcaattcct | aagttgtaaa | cataaaatat | attaaagtta | ctcttattgt | atgtaaaaaa | 1440 |
| aaaa | | | | | | 1444 |

<210> SEQ ID NO 86
<211> LENGTH: 2776
<212> TYPE: DNA
<213> ORGANISM: Homo sapiens
<220> FEATURE:
<221> NAME/KEY: misc_feature
<223> OTHER INFORMATION: Cd-18: Acc. No. M15395

<400> SEQUENCE: 86

| | | | | | | |
|---|---|---|---|---|---|---|
| cagggcagac | tggtagcaaa | gccccacgc | ccagccagga | gcaccgccgc | ggactccagc | 60 |
| acaccgaggg | acatgctggg | cctgcgcccc | ccactgctcg | ccctggtggg | gctgctctcc | 120 |
| ctcgggtgcg | tcctctctca | ggagtgcacg | aagttcaagg | tcagcagctg | ccgggaatgc | 180 |
| atcgagtcgg | ggcccggctg | cacctggtgc | cagaagctga | acttcacagg | gccggggat | 240 |

```
cctgactcca ttcgctgcga cacccggcca cagctgctca tgaggggctg tgcggctgac    300
gacatcatgg accccacaag cctcgctgaa acccaggaag accacaatgg gggccagaag    360
cagctgtccc cacaaaaagt gacgctttac ctgcgaccag gccaggcagc agcgttcaac    420
gtgaccttcc ggcgggccaa gggctacccc atcgacctgt actatctgat ggacctctcc    480
tactccatgc ttgatgacct caggaatgtc aagaagctag gtggcgacct gctccgggcc    540
ctcaacgaga tcaccgagtc cggccgcatt ggcttcgggt ccttcgtgga caagaccgtg    600
ctgccgttcg tgaacacgca ccctgataag ctgcgaaacc catgccccaa caaggagaaa    660
gagtgccagc cccgtttgc cttcaggcac gtgctgaagc tgaccaacaa ctccaaccag    720
tttcagaccg aggtcgggaa gcagctgatt ccggaaacc tggatgcacc cgagggtggg    780
ctggacgcca tgatgcaggt cgccgcctgc cggaggaaa tcggctggcg caacgtcacg    840
cggctgctgg tgtttgccac tgatgacggc ttccatttcg cgggcgacgg aaagctgggc    900
gccatcctga cccccaacga cggccgctgt cacctggagg acaacttgta caagaggagc    960
aacgaattcg actacccatc ggtgggccag ctggcgcaca agctggctga aaacaacatc   1020
cagcccatct tcgcggtgac cagtaggatg gtgaagacct acgagaaact caccgagatc   1080
atccccaagt cagccgtggg ggagctgtct gaggactcca gcaatgtggt ccatctcatt   1140
aagaatgctt acaataaact ctcctccagg gtcttcctgg atcacaacgc cctccccgac   1200
accctgaaag tcacctacga ctccttctgc agcaatggag tgacgcacag gaaccagccc   1260
agaggtgact gtgatggcgt gcagatcaat gtcccgatca ccttccaggt gaaggtcacg   1320
gccacagagt gcatccagga gcagtcgttt gtcatccggg cgctgggctt cacggacata   1380
gtgaccgtgc aggttcttcc ccagtgtgag tgccggtgcc gggaccagag cagagaccgc   1440
agcctctgcc atggcaaggg cttcttggag tgcggcatct gcaggtgtga cactggctac   1500
attgggaaaa actgtgagtg ccagacacag ggccggagca gccaggagct ggaaggaagc   1560
tgccggaagg acaacaactc catcatctgc tcagggctgg gggactgtgt ctgcgggcag   1620
tgcctgtgcc acaccagcga cgtccccggc aagctgatat acgggcagta ctgcgagtgt   1680
gacaccatca actgtgagcg ctacaacggc caggtctgcg gcggcccggg gaggggggctc   1740
tgcttctgcg ggaagtgccg ctgccacccg ggctttgagg gctcagcgtg ccagtgcgag   1800
aggaccactg agggctgcct gaacccgcgg cgtgttgagt gtagtggtcg tggccggtgc   1860
cgctgcaacg tatgcgagtg ccattcaggc taccagctgc ctctgtgcca ggagtgcccc   1920
ggctgccccct cacccctgtgg caagtacatc tcctgcgccg agtgcctgaa gttcgaaaag   1980
ggccccttg ggagaactg cagcgcggcg tgtccggggcc tgcagctgtc gaacaacccc   2040
gtgaagggca ggacctgcaa ggagagggac tcagagggct gctgggtggc ctacacgctg   2100
gagcagcagg acgggatgga ccgctacctc atctatgtgg atgagagccg agagtgtgtg   2160
gcaggccccca acatcgccgc catcgtcggg ggcaccgtgg caggcatcgt gctgatcggc   2220
attctcctgc tggtcatctg gaaggctctg atccacctga gcgacctccg ggagtacagg   2280
cgctttgaga aggagaagct caagtcccag tggaacaatg ataatcccct ttttcaagagc   2340
gccaccacga cggtcatgaa ccccaagttt gctgagagtt aggagcactt ggtgaagaca   2400
aggccgtcag gacccaccat gtctgcccca tcacgcggcc gagacatggc ttggccacag   2460
ctcttgagga tgtcaccaat taaccagaaa tccagttatt ttccgccctc aaaatgacag   2520
ccatggccgg ccggtgcttc tggggggctcg tcgggggggac agctccactc tgactggcac   2580
agtctttgca tggagacttg aggagggctt gaggttggtg aggttaggtg cgtgtttcct   2640
```

```
gtgcaagtca ggacatcagt ctgattaaag gtggtgccaa tttatttaca tttaaacttg      2700
tcagggtata aaatgacatc ccattaatta tattgttaat caatcacgtg tatagaaaaa      2760
aaaataaaac ttcaat                                                      2776

<210> SEQ ID NO 87
<211> LENGTH: 3387
<212> TYPE: DNA
<213> ORGANISM: Homo sapiens
<220> FEATURE:
<221> NAME/KEY: misc_feature
<223> OTHER INFORMATION: Cox2:  Acc. No. M90100

<400> SEQUENCE: 87
gtccaggaac tcctcagcag cgcctccttc agctccacag ccagacgccc tcagacagca        60
aagcctaccc ccgcgccgcg ccctgcccgc cgctgcgatg ctcgcccgcg ccctgctgct       120
gtgcgcggtc ctggcgctca gccatacagc aaatccttgc tgttcccacc catgtcaaaa       180
ccgaggtgta tgtatgagtg tgggatttga ccagtataag tgcgattgta cccggacagg       240
attctatgga gaaaactgct caacaccgga ttttttgaca agaataaaat tatttctgaa       300
acccactcca aacacagtgc actacatact tacccacttc aagggatttt ggaacgttgt       360
gaataacatt cccttccttc gaaatgcaat tatgagttat gtgttgacat ccagatcaca       420
tttgattgac agtccaccaa cttacaatgc tgactatggc tacaaaagct gggaagcctt       480
ctctaacctc tcctattata ctagagccct tcctcctgtg cctgatgatt gcccgactcc       540
cttgggtgtc aaaggtaaaa agcagcttcc tgattcaaat gagattgtgg aaaattgct       600 tctaagaaga aagttcatcc ctgatcccca gggctcaaac atgatgtttg cattctttgc       660
ccagcacttc acgcatcagt ttttcaagac agatcataag cgagggccag ctttcaccaa       720
cgggctgggc catggggtgg acttaaatca tatttacggt gaaactctgg ctagacagcg       780
taaactgcgc cttttcaagg atggaaaaat gaaatatcag ataattgatg gagagatgta       840
tcctcccaca gtcaaagata tcaggcagag atgatctac cctcctcaag tccctgagca       900
tctacggttt gctgtggggc aggaggtctt tggtctggtg cctggtctga tgatgtatgc       960
cacaatctgg ctgagggaac acaacagagt atgcgatgtg cttaaacagg agcatcctga      1020
atggggtgat gagcagttgt tccagacaag caggctaata ctgataggag agactattaa      1080
gattgtgatt gaagattatg tgcaacactt gagtggctat cacttcaaac tgaaatttga      1140
cccagaacta cttttcaaca aacaattcca gtaccaaaat cgtattgctg ctgaatttaa      1200
caccctctat cactggcatc cccttctgcc tgacaccttt caaattcatg accagaaata      1260
caactatcaa cagtttatct acaacaactc tatattgctg aacatggaa ttacccagtt      1320 tgttgaatca ttcaccaggc aaattgctgg cagggttgct ggtggtagga atgttccacc      1380
cgcagtacag aaagtatcac aggcttccat tgaccagagc aggcagatga ataccagtc      1440 ttttaatgag taccgcaaac gctttatgct gaagccctat gaatcatttg aagaacttac      1500
aggagaaaag gaaatgtctg cagagttgga agcactctat ggtgacatcg atgctgtgga      1560
gctgtatcct gcccttctgg tagaaaagcc tcggccagat gccatctttg gtgaaaccat      1620
ggtagaagtt ggagcaccat ctccccttgaa aggacttatg ggtaatgtta tatgttctcc      1680
tgcctactgg aagccaagca ttttggtgg agaagtgggt tttcaaatca tcaacactgc      1740
ctcaattcag tctctcatct gcaataacgt gaagggctgt cccttactt cattcagtgt      1800 tccagatcca gagctcatta aaacagtcac catcaatgca agttcttccc gctccggact      1860
agatgatatc aatcccacag tactactaaa agaacgttcg actgaactgt agaagtctaa      1920
```

```
tgatcatatt tatttattta tatgaaccat gtctattaat ttaattattt aataatattt    1980
atattaaact ccttatgtta cttaacatct tctgtaacag aagtcagtac tcctgttgcg    2040
gagaaaggag tcatacttgt gaagactttt atgtcactac tctaaagatt ttgctgttgc    2100
tgttaagttt ggaaaacagt ttttattctg ttttataaac cagagagaaa tgagttttga    2160
cgtcttttta cttgaatttc aacttatatt ataaggacga aagtaaagat gtttgaatac    2220
ttaaacacta tcacaagatg ccaaaatgct gaaagttttt acactgtcga tgtttccaat    2280
gcatcttcca tgatgcatta gaagtaacta atgtttgaaa ttttaaagta cttttgggta    2340
tttttctgtc atcaaacaaa acaggtatca gtgcattatt aaatgaatat ttaaattaga    2400
cattaccagt aatttcatgt ctactttta  aaatcagcaa tgaaacaata atttgaaatt    2460
tctaaattca tagggtagaa tcacctgtaa aagcttgttt gatttcttaa agttattaaa    2520
cttgtacata taccaaaaag aagctgtctt ggatttaaat ctgtaaaatc agatgaaatt    2580
ttactacaat tgcttgttaa aatattttat aagtgatgtt cctttttcac caagagtata    2640 aacctttta  gtgtgactgt taaaacttcc ttttaaatca aaatgccaaa tttattaagg    2700
tggtggagcc actgcagtgt tatctcaaaa taagaatatc ctgttgagat attccagaat    2760
ctgtttatat ggctggtaac atgtaaaaac cccataaccc cgccaaaagg ggtcctaccc    2820
ttgaacataa agcaataacc aaaggagaaa agcccaaatt attggttcca aatttagggt    2880 ttaaacttt  tgaagcaaac ttttttttag ccttgtgcac tgcagacctg gtactcagat    2940
tttgctatga ggttaatgaa gtaccaagct gtgcttgaat aacgatatgt tttctcagat    3000
tttctgttgt acagtttaat ttagcagtcc atatcacatt gcaaaagtag caatgacctc    3060
ataaaatacc tcttcaaaat gcttaaattc atttcacaca ttaattttat ctcagtcttg    3120
aagccaattc agtaggtgca ttggaatcaa gcctggctac ctgcatgctg ttccttttct    3180
tttcttcttt tagccatttt gctaagagac acagtcttct caaacacttc gtttctccta    3240
ttttgtttta ctagttttaa gatcagagtt cactttcttt ggactctgcc tatattttct    3300
tacctgaact tttgcaagtt ttcaggtaaa cctcagctca ggactgctat ttagctcctc    3360
ttaagaagat taaaaaaaaa aaaaaag                                         3387
```

<210> SEQ ID NO 88  
<211> LENGTH: 4471  
<212> TYPE: DNA  
<213> ORGANISM: Homo sapiens  
<220> FEATURE:  
<221> NAME/KEY: misc_feature  
<223> OTHER INFORMATION: HMG Co-A:  Acc. No. NM_000859

<400> SEQUENCE: 88

```
ttcggtggcc tctagtgaga tctggaggat ccaaggattc tgtagctaca atgttgtcaa      60
gactttttcg aatgcatggc ctctttgtgg cctcccatcc ctgggaagtc atagtgggga     120
cagtgacact gaccatctgc atgatgtcca tgaacatgtt tactggtaac aataagatct     180
gtggttggaa ttatgaatgt ccaaagtttg aagaggatgt tttgagcagt gacattataa     240
ttctgacaat aacacgatgc atagccatcc tgtatattta cttccagttc cagaatttac     300
gtcaacttgg atcaaaatat attttgggta ttgctggcct tttcacaatt ttctcaagtt     360
ttgtattcag tacagttgtc attcacttct tagacaaaga attgacaggc ttgaatgaag     420
ctttgccctt tttcctactt ttgattgacc tttccagagc aagcacatta gcaaagtttg     480
ccctcagttc caactcacag gatgaagtaa gggaaaatat tgctcgtgga atggcaattt     540
```

```
taggtcctac gtttaccctc gatgctcttg ttgaatgtct tgtgattgga gttggtacca      600
tgtcagggt acgtcagctt gaaattatgt gctgctttgg ctgcatgtca gttcttgcca       660
actacttcgt gttcatgact ttcttcccag cttgtgtgtc cttggtatta gagctttctc      720
gggaaagccg cgagggtcgt ccaatttggc agctcagcca ttttgcccga gttttagaag      780
aagaagaaaa taagccgaat cctgtaactc agagggtcaa gatgattatg tctctaggct      840
tggttcttgt tcatgctcac agtcgctgga tagctgatcc ttctcctcaa aacagtacag      900
cagatacttc taaggtttca ttaggactgg atgaaaatgt gtccaagaga attgaaccaa      960
gtgtttccct ctggcagttt tatctctcta aaatgatcag catggatatt gaacaagtta     1020
ttaccctaag tttagctctc cttctggctg tcaagtacat cttctttgaa caaacagaga     1080
cagaatctac actctcatta aaaaaccta tcacatctcc tgtagtgaca caaaagaaag      1140
tcccagacaa ttgttgtaga cgtgaaccta tgctggtcag aaataaccag aaatgtgatt     1200
cagtagagga agagacaggg ataaaccgag aagaaaagt tgaggttata aaacccttag      1260
tggctgaaac agataccca acagagcta catttgtggt tggtaactcc tccttactcg       1320
atacttcatc agtactggtg acacaggaac ctgaaattga acttcccagg gaacctcggc     1380
ctaatgaaga atgtctacag atacttggga atgcagagaa aggtgcaaaa ttccttagtg     1440
atgctgagat catccagtta gtcaatgcta agcatatccc agcctacaag ttggaaactc     1500
tgatggaaac tcatgagcgt ggtgtatcta ttcgccgaca gttactttcc aagaagcttt     1560
cagaaccttc ttctctccag tacctaccttt acagggatta taattactcc ttggtgatgg    1620
gagcttgttg tgagaatgtt attggatata tgcccatccc tgttggagtg gcaggacccc     1680
tttgcttaga tgaaaagaa tttcaggttc aatggcaac aacagaaggt tgtcttgtgg       1740
ccagcaccaa tagaggctgc agagcaatag gtcttggtgg aggtgccagc agccgagtcc     1800
ttgcagatgg gatgactcgt ggcccagttg tgcgtcttcc acgtgcttgt gactctgcag     1860
aagtgaaagc ctggctcgaa acatctgaag ggttcgcagt gataaaggag gcatttgaca     1920
gcactagcag atttgcacgt ctacagaaac ttcatacaag tatagctgga cgcaacctttt   1980
atatccgttt ccagtccagg tcaggggatg ccatgggat gaacatgatt tcaaagggta     2040
cagagaaagc actttcaaaa cttcacgagt atttccctga aatgcagatt ctagccgtta     2100
gtggtaacta ttgtactgac aagaaacctg ctgctataaa ttggatagag ggaagaggaa     2160
aatctgttgt ttgtgaagct gtcattccag ccaaggttgt cagagaagta ttaaagacta     2220
ccacagaggc tatgattgag gtcaacatta acaagaattt agtgggctct gccatggctg     2280
ggagcatagg aggctacaac gcccatgcag caaacattgt caccgccatc tacattgcct     2340
gtggacagga tgcagcacag aatgttggta gttcaaactg tattacttta atggaagcaa     2400
gtggtcccac aaatgaagat ttatatatca gctgcaccat gccatctata gagataggaa     2460
cggtgggtgg tgggaccaac ctactacctc agcaagcctg tttgcagatg ctaggtgttc     2520
aaggagcatg caaagataat cctggggaaa atgcccggca gcttgcccga attgtgtgtg     2580
ggaccgtaat ggctggggaa ttgtcactta tggcagcatt ggcagcagga catcttgtca     2640
aaagtcacat gattcacaac aggtcgaaga tcaatttaca agacctccaa ggagcttgca     2700
ccaagaagac agcctgaata gcccgacagt tctgaactgg aacatgggca ttgggttcta     2760
aaggactaac ataaaatctg tgaattaaaa aagctcaatg cattgtcttg tggaggatga     2820
ataaatgtga tcactgagac agccacttgg ttttggctc tttcagagag gtctcaggtt     2880
cttttccatgc agactcctca gatctgaaca cagtttagtg ctttacatgc tgtgctcttt    2940
```

-continued

```
gaagagattt caacaagaat attgtatgtt aaagcatcag agatggtaat ctacagctca    3000
cctctgaaag caaatataag ctgggaaaaa agttttgatg aaattcttga agttcatggt    3060
gatcagtgca attgaccttc tccctcactc ctgccagttg aaaatggatt tttaaattat    3120
actgtagctg atgaaactcc tgattttgta gttaatttat taagtctggg atgtagaact    3180
tcaagaagta agagctaagt tctaagttca tgtttgtaaa ttaatacttc atttggtgct    3240
ggtctatttt gattttgggg ggtaatcagc attattcttc agaaggggac ctgttttctt    3300
caagggaaga aacactctta ttcccaaact acagaataat gtgttaaaca tgctaaatag    3360
ttctatcagg aaaacaaatc actgtattta tctccgcagg ctatttgttc agagaggcct    3420
tttgtttaaa tataaatgtt taaatataaa tgtttgtctg gattggctat aacatgtctt    3480
tcagcattag gcttttaaga aacacagggt tttgtattct ttactaaaga tatcagagct    3540
cttaatgttg cttagatgag ggtgactgtc aagtacaagc aagactggga ccttagaaat    3600
cattgtagaa acacagtttt gaaagatttt taccatgtct ctaagccaac tttaattgct    3660
taaaagacat ttttatttag ttgaaaaatc tagttttttt tgtaaactgt accaaatctg    3720
tatatgttgt aataaaactt atgctagttt attggaagtg ttcaagaaat aaaaatcaac    3780
ttgtgtactg ataaaatact ctagcctggg ccagagaaga taatgttctt taatgttgtc    3840
aggaaaccct ggcttgcttg ccgagcctaa tgaaagggaa agtcagcttt cagagccagt    3900
gaaggagcca cgtgaatggc cctagaactg tgcctagttc ctgtggccag gaggttggtg    3960
actgaaacat tcacacaggg ctcttggatg gacccacgaa cgctcttagc tttctcaggg    4020
ggtcagcaga gttattgaat cttaattttt tttaatgtac aagttttgta taaataataa    4080
agaactcctt attttgtatt acatctaatg cttaagtgtt gctcttggaa agctgatgat    4140
gtctcttgta gagatgactc tgaaaaacat tccaggaaac catggcagca tggagagcct    4200
cttagtgatt gtgtctgcat tgttattgtg gaagatttac cttttctgtt gtacgtaaag    4260
cttaaattac ttttgttgtg acttttttagc cagtgacttt ttctgagctt tcatggaag    4320 tggcagtgaa aaatatgttg agtgttcaaa aaagtgactg taattaatat cttgctggat    4380
taatgttttg tacaattact aaaattgtata cattttgtta tagaatactt ttttctagtt    4440
tcagtaaata atgaaaagga agttaatacc a                                   4471
```

<210> SEQ ID NO 89
<211> LENGTH: 2444
<212> TYPE: DNA
<213> ORGANISM: Homo sapiens
<220> FEATURE:
<221> NAME/KEY: misc_feature
<223> OTHER INFORMATION: NM_021975

<400> SEQUENCE: 89

```
ggcacgaggc ggggccgggt cgcagctggg cccgcggcat ggacgaactg ttcccctca      60 tcttcccggc agagcagccc aagcagcggg gcatgcgctt ccgctacaag tgcgaggggc    120
gctccgcggg cagcatccca ggcgagagga gcacagatac caccaagacc cacccccacca   180 tcaagatcaa tggctacaca ggaccaggga cagtgcgcat ctccctggtc accaaggacc    240
ctcctcaccg gcctcacccc cacgagcttt taggaaagga ctgccgggat ggcttctatg    300
aggctgagct ctgcccggac cgctgcatcc acagtttcca gaacctggga atccagtgtg    360
tgaagaagcg ggacctggag caggctatca gtcagcgcat ccagaccaac aacaacccct    420
tccaagttcc tatagaagag cagcgtgggg actacgacct gaatgctgtg cggctctgct    480
tccaggtgac agtgcgggac ccatcaggca ggcccctccg cctgccgcct gtccttttctc   540
```

```
atcccatctt tgacaatcgt gcccccaaca ctgccgagct caagatctgc cgagtgaacc    600
gaaactctgg cagctgcctc ggtggggatg agatcttcct actgtgtgac aaggtgcaga    660
aagaggacat tgaggtgtat ttcacgggac caggctggga ggcccgaggc tccttttcgc    720
aagctgatgt gcaccgacaa gtggccattg tgttccggac ccctccctac gcagacccca    780
gcctgcaggc tcctgtgcgt gtctccatgc agctgcggcg gccttccgac cgggagctca    840
gtgagcccat ggaattccag tacctgccag atacagacga tcgtcaccgg attgaggaga    900
aacgtaaaag gacatatgag accttcaaga gcatcatgaa gaagagtcct ttcagcggac    960
ccaccgaccc ccggcctcca cctcgacgca ttgctgtgcc ttcccgcagc tcagcttctg   1020
tccccaagcc agcaccccag ccctatccct ttacgtcatc cctgagcacc atcaactatg   1080
atgagtttcc caccatggtg tttccttctg ggcagatcag ccaggcctcg gccttggccc   1140
cggcccctcc ccaagtcctg ccccaggctc cagcccctgc ccctgctcca gccatggtat   1200
cagctctggc ccaggcccca gcccctgtcc cagtcctagc cccaggccct cctcaggctg   1260
tggccccacc tgcccccaag cccacccagg ctggggaagg aacgctgtca gaggccctgc   1320
tgcagctgca gtttgatgat gaagacctgg gggccttgct tggcaacagc acagacccag   1380
ctgtgttcac agacctggca tccgtcgaca actccgagtt tcagcagctg ctgaaccagg   1440
gcatacctgt ggcccccac  acaactgagc ccatgctgat ggagtaccct gaggctataa   1500
ctcgcctagt gacagcccag aggcccccg  acccagctcc tgctccactg ggggccccgg   1560
ggctccccaa tggcctcctt tcaggagatg aagacttctc ctccattgcg gacatggact   1620
tctcagccct gctgagtcag atcagctcct aagggggtga cgcctgccct ccccagagca   1680
ctggttgcag gggattgaag ccctccaaaa gcacttacgg attctggtgg ggtgtgttcc   1740
aactgccccc aactttgtgg atgtcttcct tggagggggg agccatattt tattctttta   1800
ttgtcagtat ctgtatctct ctctcttttt ggaggtgctt aagcagaagc attaacttct   1860
ctggaaaggg gggagctggg gaaactcaaa cttttcccct gtcctgatgg tcagctccct   1920
tctctgtagg gaactgtggg gtcccccatc cccatcctcc agcttctggt actctcctag   1980
agacagaagc aggctggagg taaggccttt gagcccacaa agccttatca agtgtcttcc   2040
atcatggatt cattacagct taatcaaaat aacgccccag ataccagccc ctgtatggca   2100
ctggcattgt ccctgtgcct aacaccagcg tttgaggggc tgccttcctg ccctacagag   2160
gtctctgccg gctctttcct tgctcaacca tggctgaagg aaacagtgca acagcactgg   2220
ctctctccag gatccagaag gggtttggtc tggacttcct tgctctcccc tcttctcaag   2280
tgccttaata gtagggtaag ttgttaagag tgggggagag caggctggca gctctccagt   2340
caggaggcat agttttagt  gaacaatcaa agcacttgga ctcttgctct ttctactctg   2400
aactaataaa gctgttgcca agctggacgg cacgagctcg tgcc                    2444

<210> SEQ ID NO 90
<211> LENGTH: 816
<212> TYPE: DNA
<213> ORGANISM: Homo sapiens

<400> SEQUENCE: 90
atgcactttc tttgccaaag gcaaacgcag aacgtttcag agccatgagg atgcttctgc     60
atttgagttt gctagctctt ggagctgcct acgtgtatgc catccccaca gaaattccca    120
caagtgcatt ggtgaaagag accttggcac tgctttctac tcatcgaact ctgctgatag    180
ccaatgagac tctgaggatt cctgttcctg tacataaaaa tcaccaactg tgcactgaag    240
```

```
aaatctttca gggaataggc acactggaga gtcaaactgt gcaagggggt actgtggaaa      300
gactattcaa aaacttgtcc ttaataaaga aatacattga cggccaaaaa aaaaagtgtg      360
gagaagaaag acgagagta aaccaattcc tagactacct gcaagagttt cttggtgtaa      420
tgaacaccga gtggataata gaaagttgag actaaactgg tttgttgcag ccaaagattt      480
tggaggagaa ggacatttta ctgcagtgag aatgagggcc aagaaagagt caggccttaa      540
ttttcaatat aatttaactt cagagggaaa gtaaatattt caggcatact gacactttgc      600
cagaaagcat aaaattctta aaatatattt cagatatcag aatcattgaa gtattttcct      660
ccaggcaaaa ttgatatact tttttcttat ttaacttaac attctgtaaa atgtctgtta      720
acttaatagt atttatgaaa tggttaagaa tttggtaaat tagtatttat ttaatgttat      780
gttgtgttct aataaaacaa aaatagacaa ctgttc                                816

<210> SEQ ID NO 91
<211> LENGTH: 2484
<212> TYPE: DNA
<213> ORGANISM: Homo sapiens
<220> FEATURE:
<221> NAME/KEY: misc_feature
<223> OTHER INFORMATION: L05:  Acc. No. J03571

<400> SEQUENCE: 91
gggcccggcg ctcgctgctc ccgcggcccg cgccatgccc tcctacacgg tcaccgtggc       60
cactggcagc cagtggttcg ccggcactga cgactacatc tacctcagcc tcgtgggctc      120
ggcgggctgc agcgagaagc acctgctgga caagcccttc tacaacgact tcgagcgtgg      180
cgcggtggat tcatacgacg tgactgtgga cgaggaactg ggcgagatcc agctggtcag      240
aatcgagaag cgcaagtact ggctgaatga cgactggtac ctgaagtaca tcacgctgaa      300
gacgccccac ggggactaca tcgagttccc ctgctaccgc tggatcaccg gcgatgtcga      360
ggttgtcctg agggatggac gcgcaaagtt ggcccgagat gaccaaattc acattctcaa      420
gcaacaccga cgtaaagaac tggaaacacg gcaaaaacaa tatcgatgga tggagtggaa      480
ccctggcttc cccttgagca tcgatgccaa atgccacaag gatttacccc gtgatatcca      540
gtttgatagt gaaaaaggag tggactttgt tctgaattac tccaaagcga tggagaacct      600
gttcatcaac cgcttcatgc acatgttcca gtcttcttgg aatgacttcg ccgactttga      660
gaaaatcttt gtcaagatca gcaacactat ttctgagcgg gtcatgaatc actggcagga      720
agacctgatg tttggctacc agttcctgaa tggctgcaac cctgtgttga tccggcgctg      780
cacagagctg cccgagaagc tcccggtgac cacggagatg gtagagtgca gcctggagcg      840
gcagctcagc ttggagcagg aggtccagca agggaacatt ttcatcgtgg actttgagct      900
gctggatggc atcgatgcca acaaaacaga cccctgcaca ctccagttcc tggccgctcc      960
catctgcttg ctgtataaga acctggccaa caagattgtc cccattgcca tccagctcaa     1020
ccaaatcccg ggagatgaga accctatttt cctcccttcg gatgcaaaat acgactggct     1080
tttggccaaa atctgggtgc gttccagtga cttccacgtc caccagacca tcacccacct     1140
tctgcgaaca catctggtgt ctgaggtttt tggcattgca atgtaccgcc agctgcctgc     1200
tgtgcacccc attttcaagc tgctggtggc acacgtgaga ttcaccattg caatcaacac     1260
caaggcccgt gagcagctca tctgcgagtg tggcctcttt gacaaggcca acgccacagg     1320
gggcggtggg cacgtgcaga tggtgcagag ggccatgaag gacctgacct atgcctccct     1380
gtgctttccc gaggccatca aggcccgggg catggagagc aaagaagaca tcccctacta     1440
```

| | |
|---|---|
| cttctaccgg gacgacgggc tcctggtgtg ggaagccatc aggacgttca cggccgaggt | 1500 |
| ggtagacatc tactacgagg gcgaccaggt ggtggaggag gacccggagc tgcaggactt | 1560 |
| cgtgaacgat gtctacgtgt acggcatgcg gggccgcaag tcctcaggct tccccaagtc | 1620 |
| ggtcaagagc cgggagcagc tgtcggagta cctgaccgtg gtgatcttca ccgcctccgc | 1680 |
| ccagcacgcc gcggtcaact tcggccagta cgactggtgc tcctggatcc ccaatgcgcc | 1740 |
| cccaaccatg cgagccccgc caccgactgc caagggcgtg gtgaccattg agcagatcgt | 1800 |
| ggacacgctg cccgaccgcg gccgctcctg ctggcatctg ggtgcagtgt gggcgctgag | 1860 |
| ccagttccag gaaaacgagc tgttcctggg catgtaccca gaagagcatt ttatcgagaa | 1920 |
| gcctgtgaag gaagccatgg cccgattccg caagaacctc gaggccattg tcagcgtgat | 1980 |
| tgctgagcgc aacaagaaga agcagctgcc atattactac ttgtcccccag accggattcc | 2040 |
| gaacagtgtg gccatctgag cacactgcca gtctcactgt gggaaggcca gctgcccag | 2100 |
| ccagatggac tccagcctgc ctggcaggtg tctggccagg cctcttggca gtcacatctc | 2160 |
| ttcctccgag gccagtacct ttccatttat tctttgatct tcagggaact gcatagattg | 2220 |
| atcaaagtgt aaacaccata gggacccatt ctacacagag caggactgca cagcgtcctg | 2280 |
| tccacaccca gctcagcatt tccacaccaa gcagcaacag caaatcacga ccactgatag | 2340 |
| atgtctattc ttgttggaga catgggatga ttattttctg ttctatttgt gcttagtcca | 2400 |
| attccttgca catagtaggt acccaattca attactattg aatgaattaa gaattggttg | 2460 |
| ccataaaaat aaatcagttc attt | 2484 |

<210> SEQ ID NO 92
<211> LENGTH: 2437
<212> TYPE: DNA
<213> ORGANISM: Homo sapiens
<220> FEATURE:
<221> NAME/KEY: misc_feature
<223> OTHER INFORMATION: MPB:  Acc. No.: M74047

<400> SEQUENCE: 92

| | |
|---|---|
| gcggccaccg gcgaggaaca cggcgcgatg caggttcagt gccagcagag cccagtgctg | 60 |
| gcaggcagcg ccactttggt cgcccttggg gcactggcct tgtacgtcgc gaagccctcc | 120 |
| ggctacggga agcacacgga gagcctgaag ccggcggcta cccgcctgcc agcccgcgcc | 180 |
| gcctggttcc tgcaggagct gccttccttc gcggtgcccg cggggatcct cgcccggcag | 240 |
| cccctctccc tcttcgggcc acctgggacg gtacttctgg gcctcttctg cgtacattac | 300 |
| ttccacagga catttgtgta ctcactgctc aatcgaggga ggccttatcc agctatactc | 360 |
| attctcagag gcactgcctt ctgcactgga atggagtcc ttcaaggcta ctatctgatt | 420 |
| tactgtgctg aataccctga tgggtggtac acagacatac ggtttagctt gggtgtcttc | 480 |
| ttatttattt tgggaatggg aataaacatt catagtgact atatattgcg ccagctcagg | 540 |
| aagcctggag aaatcagcta caggattcca caaggtggct tgtttacgta tgtttctgga | 600 |
| gccaatttcc tcggtgagat cattgaatgg atcggctatg ccctggccac ttggtccctc | 660 |
| ccagcacttg catttgcatt tttctcactt tgtttccttg gctgcgagc ttttcaccac | 720 |
| cataggttct acctcaagat gtttgaggac taccccaaat ctcggaaagc ccttattcca | 780 |
| ttcatctttt aaaggaacca aattaaaaag gagcagagct cccacaatgc tgatgaaaac | 840 |
| tgtcaagctg ctgaaactgt aattttcatg atataatagt catatatata tatatatata | 900 |
| tatatatata tatatatatg tatatatgta atagtaggtc tcctggcgtt ctgccagctg | 960 |
| gcctggggat tctgagtggt gtctgcttag agtttactcc taccccttcca gggacccta | 1020 |

```
tcctgatccc caactgaagc ttcaaaaagc cacttttcca aatggcgaca gttgcttctt    1080
agctattgct ctgagaaagt acaaacttct cctatgtctt tcaccgggca atccaagtac    1140
atgtggcttc atacccactc cctgtcaatg caggacaact ctgtaatcaa gaatttttg     1200 acttgaaggc agtacttata gaccttatta aaggtatgca ttttatacat gtaacagagt    1260
agcagaaatt taaactctga agccacaaag acccagagca aacccactcc caaatgaaaa    1320
ccccagtcat ggcttccttt ttcttggtta attaggaaag atgagaaatt attaggtaga    1380
ccttgaatac aggagccctc tcctcatagt gctgaaaaga tactgatgca ttgacctcat    1440
ttcaaatttg tgcagtgtct tagttgatga gtgcctctgt tttccagaag atttcacaat    1500
ccccggaaaa ctggtatggc tattcttgaa ggccaggttt taataaccac aaacaaaaag    1560
gcatgaacct gggtggctta tgagagagta gagaacaaca tgaccctgga tggctactaa    1620
gaggatagag aacagtttta caatagacat tgcaaactct catgtttttg gaaactggtg    1680
gcaatatcca aataatgagt agtgtaaaac aaagagaatt aatgatgagg ttacatgctg    1740
cttgcctcca ccagatgtcc acaacaatat gaagtacagc agaagcccca agcaactttc    1800 cttcctgga gcttcttcct tgtagttctc aggacctgtt caagaaggtg tctcctaggg      1860
gcagcctgaa tgcctccctc aaaggacctg caggcagaga ctgaaaattg cagacagagg    1920
ggcacgtctg ggcagaaaac ctgttttgtt tggctcagac atatagtttt tttttttta     1980 caaagtttca aaacttaaaa atcaggaga ttccttcata aaactctagc attctagttt      2040
catttaaaaa gttggaggat ctgaacatac agagcccaca tttccacacc agaactggaa    2100
ctacgtagct agtaagcatt tgagtttgca aactcttgtg aaggggtcac cccagcatga    2160
gtgctgagat atggactctc taaggaaggg gccgaacgct tgtaattgga atacatggaa    2220
atatttgtct tctcaggcct atgtttgcgg aatgcattgt caatatttag caaactgttt    2280
tgacaaatga gcaccagtgg tactaagcac agaaactcac tatataagtc acataggaaa    2340
cttgaaaggt ctgaggatga tgtagattac tgaaaaatac aaattgcaat catataaata    2400
agtgtttttg ttgttcatta aatacctta aatcatg                              2437
```

<210> SEQ ID NO 93
<211> LENGTH: 5595
<212> TYPE: DNA
<213> ORGANISM: Homo sapiens
<220> FEATURE:
<221> NAME/KEY: misc_feature
<223> OTHER INFORMATION: NEP=CALLA:  Acc. No. NM_000902

<400> SEQUENCE: 93

```
gcggagatgt gcaagtggcg aagcttgacc gagagcaggc tggagcagcc gcccaactcc      60
tggcgcggga tctgctgagg ggtcacggat tttaggtgat gggcaagtca gaaagtcaga     120
tggatataac tgtatcaac actccaaagc caaagaagaa acagcgatgg actcgactgg      180
agatcagcct ctcggtcctt gtcctgctcc tcaccatcat agctgtgaga atgatcgcac     240
tctatgcaac ctacgatgat ggtatttgca agtcatcaga ctgcataaaa tcagctgctc     300
gactgatcca aaacatggat gccaccactg agccttgtag agacttttc aaatatgctt      360 gcggaggctg gttgaaacgt aatgtcattc ccgagaccag ctcccgttac ggcaactttg     420 acatttaag agatgaacta gaagtcgttt tgaaagatgt ccttcaagaa cccaaaactg      480
aagatatagt agcagtgcag aaagcaaaag cattgtacag gtcttgtata aatgaatctg     540
ctattgatag cagaggtgga gaacctctac tcaaactgtt accagacata tatgggtggc    600
```

```
cagtagcaac agaaaactgg gagcaaaaat atggtgcttc ttggacagct gaaaaagcta    660
ttgcacaact gaattctaaa tatgggaaaa aagtccttat taatttgttt gttggcactg    720
atgataagaa ttctgtgaat catgtaattc atattgacca acctcgactt ggcctcccctt   780 ctagagatta ctatgaatgc actggaatct ataaagaggc ttgtacagca tatgtggatt    840
ttatgatttc tgtggccaga ttgattcgtc aggaagaaag attgcccatc gatgaaaacc    900
agcttgcttt ggaaatgaat aaagttatgg aattggaaaa agaaattgcc aatgctacgg    960
ctaaacctga agatcgaaat gatccaatgc ttctgtataa caagatgaga ttggcccaga    1020
tccaaaataa cttttcacta gagatcaatg gaagccatt cagctggttg aatttcacaa     1080
atgaaatcat gtcaactgtg aatattagta ttacaaatga ggaagatgtg gttgtttatg    1140
ctccagaata tttaaccaaa cttaagccca ttcttaccaa atattctgcc agagatcttc    1200
aaaatttaat gtcctggaga ttcataatgg atcttgtaag cagcctcagc cgaacctaca    1260
aggagtccag aaatgctttc cgcaaggccc tttatggtac aacctcagaa acagcaactt    1320
ggagacgttg tgcaaactat gtcaatggga atatggaaaa tgctgtgggg aggctttatg    1380
tggaagcagc atttgctgga gagagtaaac atgtggtcga ggatttgatt gcacagatcc    1440
gagaagtttt tattcagact ttagatgacc tcacttggat ggatgccgag acaaaaaaga    1500
gagctgaaga aaaggcctta gcaattaaag aaaggatcgg ctatcctgat gacattgttt    1560
caaatgataa caaactgaat aatgagtacc tcgagttgaa ctacaaagaa gatgaatact    1620
tcgagaacat aattcaaaat ttgaaattca gccaaagtaa acaactgaag aagctccgag    1680
aaaaggtgga caaagatgag tggataagtg gagcagctgt agtcaatgca tttttactctt    1740 caggaagaaa tcagatagtc ttcccagccg gcattctgca gcccccttc tttagtgccc     1800 agcagtccaa ctcattgaac tatgggggca tcggcatggt cataggacac gaaatcaccc    1860
atggcttcga tgacaatggc agaaacttta caaagatgg agacctcgtt gactggtgga     1920
ctcaacagtc tgcaagtaac tttaaggagc aatcccagtg catggtgtat cagtatggaa    1980
acttttcctg ggacctggca ggtggacagc accttaatgg aattaataca ctgggagaaa    2040
acattgctga taatggaggt cttggtcaag catacagagc ctatcagaat tatattaaaa    2100
agaatggcga agaaaaatta cttcctggac ttgacctaaa tcacaaacaa ctattttctct    2160 tgaactttgc acaggtgtgg tgtggaacct ataggccaga gtatgcggtt aactccatta    2220
aaacagatgt gcacagtcca ggcaatttca ggattattgg gactttgcag aactctgcag    2280
agttttcaga agccttttcac tgccgcaaga attcatacat gaatccagaa aagaagtgcc    2340
gggtttggtg atcttcaaaa gaagcattgc agcccttggc tagacttgcc aacaccacag    2400 aaatgggaa ttctctaatc gaaagaaaat gggcctagg ggtcactgta ctgacttgag      2460
ggtgattaac agagagggca ccatcacaat acagataaca ttaggttgtc ctagaaaggg    2520
tgtggaggga ggaagggggt ctaaggtcta tcaagtcaat catttctcac tgtgtacata    2580
atgcttaatt tctaaagata atattactgt ttatttctgt ttctcatatg gtctaccagt    2640
ttgctgatgt ccctagaaaa caatgcaaaa cctttgaggt agaccaggat ttctaatcaa    2700
aagggaaaag aagatgttga agaatagagt taggcaccag aagaagagta ggtgacacta    2760
tagtttaaaa cacattgcct aactactagt ttttactttt atttgcaaca tttacagtcc    2820
ttcaaaatcc ttccaaagaa ttcttataca cattggggcc ttggagctta catagtttta    2880
aactcatttt tgccatacat cagttattca ttctgtgatc atttattta agcactctta     2940 aagcaaaaaa tgaatgtcta aaattgtttt ttgttgtacc tgctttgact gatgctgaga    3000
```

```
ttcttcaggc ttcctgcaat tttctaagca atttcttgct ctatctctca aaacttggta    3060
tttttcagag atttatataa atgtaaaaat aataattttt atatttaatt attaactaca    3120
tttatgagta actattatta taggtaatca atgaatattg aagtttcagc ttaaaataaa    3180
cagttgtgaa ccaagatcta taaagcgata tacagatgaa aatttgagac tatttaaact    3240
tataaatcat attgatgaaa agatttaagc acaaacttta gggtaaaaat tgcgattgga    3300
cagttgtcta gagatatata tacttgtggt tttcaaattg gactttcaaa attaaatctg    3360
tccctgagag tgtctctgat aaaagggcaa atctgcacct atgtagctct gcatctcctg    3420
tcttttcagg tttgtcatca gatggaaata ttttgataat aaattgaaat tgtgaactca    3480
ttgctcccta agactgtgac aactgtctaa ctttagaagt gcatttctga atagaaatgg    3540
gaggcctctg atggaccttc tagaattata agtcacaaag agttctggaa aagaactgtt    3600
tactgcttga taggaattca tcttttgagg cttctgttcc tctcttttcc tgttgtattg    3660
actattttcg ttcattactt gattaagatt ttacaaaaga ggagcacttc caaaattctt    3720 attttttccta acaaaagatg aaagcaggga atttctatct aaatgatgag tattagttcc    3780
ctgtctcttg aaaaatgccc atttgccttt aaaaaaaaaa gttacagaaa tactataaca    3840
tatgtacata aattgcataa agcataagta tacagttcaa taaacttaac tttaactgaa    3900
caatggccct gtagccagca cctgtaagaa acagagcagt accagcgctc taaaagcacc    3960
tccttgtcac tttattactc ccagaacaac aactatcctg acttctaata tcattcacta    4020
gctttgcctg gttttgtctt ttatgcagat agaatcaatc agtatgtatt cttttgtgcc    4080
tggcttcttt ctctcagcct tacatttgtg agattcctct gtattgtgct gattgtggat    4140
cttttcattc tcattgcaga ataatgttct attgtgggac ttattacaat ttgttcatcc    4200
tattgttgat gggcacttga gaactttcca ttttggcgct attacaaata gtgcaactat    4260
gaatgtactg catgttacca tcttacttga gcctttaatg gacttatttc ttcaaatcct    4320
tccaaaaatt attataagca ttgaaattat agtttcaagc caactgtgga taccttacc     4380 ctttcctcct ttatcacaac caccgttaca agtatactta tatttcccta aaatacattt    4440
aaaacttacc taagtgacat ttgtagttgg agtaatagga gcttccagct ctaataaaac    4500
agctgtctct aacttatttt atttccatca tgtcagagca ggtgaagagc cagaagtgaa    4560
gagtgactag tacaaattat aaaaagccac tagactcttc actgttagct ttttaaaaca    4620
ttaggctccc atccctatgg aggaacaact ctccagtgcc tggatcccct ctgtctacaa    4680
atataagatt ttctgggcct aaaggataga tcaaagtcaa aaatagcaat gcctccctat    4740
ccctcacaca tccagacatc atgaattta catggtactc ttgttgagtt ctatagagcc     4800
ttctgatgtc tctaaagcac taccgattct ttggagttgt cacatcagat aagacatatc    4860
tctaattcca tccataaatc cagttctact atggctgagt tctggtcaaa gaagaaagt     4920 ttagaagctg agacacaaag ggttgggagc tgatgaaact cacaaatgat ggtaggaaga    4980
agctctcgac aatacccgtt ggcaaggagt ctgcctccat gctgcagtgt tcgagtggat    5040
tgtaggtgca agatggaaag gattgtaggt gcaagctgtc cagagaaaag agtccttgtt    5100
ccagccctat tctgccactc ctgacagggt gaccttgggt atttgcaata ttcctttggg    5160
cctctgcttc tctcacctaa aaaaagagaa ttagattata ttggtggttc tcagcaagag    5220
aaggagtatg tgtccaatgc tgccttccca tgaatctgtc tcccagttat gaatcagtgg    5280
gcaggataaa ctgaaaactc ccatttaagt gtctgaatcg agtgagacaa aattttagtc    5340
caaataacaa gtaccaaagt tttatcaagt ttgggtctgt gctgctgtta ctgttaacca    5400
```

```
tttaagtggg gcaaaacctt gctaatttc tcaaaagcat ttatcattct tgttgccaca      5460
gctggagctc tcaaactaaa agacatttgt tattttggaa agaagaaaga ctctattctc      5520
aaagtttcct aatcagaaat ttttatcagt ttccagtctc aaaaatacaa aataaaaaca      5580
aacgttttta atact                                                      5595

<210> SEQ ID NO 94
<211> LENGTH: 551
<212> TYPE: DNA
<213> ORGANISM: Homo sapiens
<220> FEATURE:
<221> NAME/KEY: misc_feature
<223> OTHER INFORMATION: NPY: Acc. No. K01911

<400> SEQUENCE: 94
accccatccg ctggctctca cccctcggag acgctcgccc gacagcatag tacttgccgc        60
ccagccacgc ccgcgcgcca gccaccatgc taggtaacaa gcgactgggg ctgtccggac       120
tgaccctcgc cctgtccctg ctcgtgtgcc tgggtgcgct ggccgaggcg taccccctcca      180 agccggacaa cccgggcgag gacgcaccag cggaggacat ggccagatac tactcggcgc      240
tgcgacacta catcaacctc atcaccaggc agagatatgg aaaacgatcc agcccagaga      300
cactgatttc agacctcttg atgagagaaa gcacagaaaa tgttcccaga actcggcttg      360
aagaccctgc aatgtggtga tgggaaatga gacttgctct ctggcctttt cctatttca       420 gcccatattt catcgtgtaa aacgagaatc cacccatcct accaatgcat gcagccactg      480
tgctgaattc tgcaatgttt tcctttgtca tcattgtata tatgtgtgtt taaataaagt      540
atcatgcatt c                                                           551

<210> SEQ ID NO 95
<211> LENGTH: 4382
<212> TYPE: DNA
<213> ORGANISM: Homo sapiens
<220> FEATURE:
<221> NAME/KEY: misc_feature
<223> OTHER INFORMATION: SEG_AB00161S

<400> SEQUENCE: 95
aagcttgctg aatcacctct taattcttgt agttgctttg tgcattcctt tgggtattcc        60
tcatagatac tcatgtctgc aaatggagaa tgtttacttt tcatttta tgccttatat        120 ttcttttttg tgttttgct tgttgcatt tgttttttct atttgtatga ccaaaatctt        180
tagcagtaca ggtaggtaac aaccaaataa tgtagaaccc cataagccac gttacagagt      240
ttgaatttta ttttagcaca gtgggaatac attgaaggtc tttagttaag ctgttgctca      300
tgagcaacaa atgagcaatg acatatatgt atgtatatac acatatatat cattgatttt      360
atatatatat atatatatat atatatatat atatatatat atatctat cttagtccac        420 ttgtgttgca ataacaaaat accacagact gggtcattta caaaaattaa atatatat       480 acatatacac acatatatat atcatacata tacacataca tacatcattg ctcatttgtt      540
tgttataaat agcattaaca gcattttca agttatatcc tgggagtgtt tatgatttac      600
ttattcttca actaattcca taacaagatt tgaggtgctt agaacaattc atgccaagtt      660
aaaacaaaat aattgggcaa attgggataa agaataaaat ggagttgaaa acaagaggc       720 ccaggtaatg tcagttcaaa atatgcttac ctttaactac tttaaattta caggaggtat      780
agttacacat tttggctgaa tctcccagag actagaactg tttgagacac ttctgttccc      840
caatcccttg tgatatgttt ctcaggtaat aggccttcac agtaactccc aaactatcat      900
```

| | |
|---|---|
| atataccaca cagacttgag attcactatt gagagaatct atgtactgtt tttctttttt | 960 |
| tttctttttt gttatagagc cggggggtctt acactgtcac tgaggctgaa gtgcaatggc | 1020 |
| acgatcatgg ctcactgcag ccttgacctc ctgggctcaa tcctcttgcc tcagcctctc | 1080 |
| gaataactag gattacaggt gtgttccccc atgcctggct aattttttaaa aattttgtgt | 1140 |
| agagatgggg tcatgccatg tggcccaggc tggttcaaac tcctgagctc aagtatcctt | 1200 |
| ctacctctcc ctcccaaagt tctgagatta caggaatgag ccactgtgcc cagcctatag | 1260 |
| attgttttc ttgaagcaat ttttcagaaa ccttcctggt ttctgataat ttaacccttt | 1320 |
| caggttagga gagaaaaatg aacattttga tattacccac tgtcttagtc catttgtgtt | 1380 |
| gctgtaataa aatatcacag actgggatat ttataaacaa tagaaattaa tttctctcag | 1440 |
| ttctggaggc tggaaactcc aaaatcaaag tgccagcaga tttggcaact ggtgagggct | 1500 |
| gctctttgct tacaaaatgg caccttgttg ctgcatcctc agcaagggtc agtgctgtgt | 1560 |
| cttcacatag tggaaagaat agaaggggcc aactgtctcc tttgggcctt ttttaaaaa | 1620 |
| ggcactaatg cattcacaaa ggcagagccc taatggtcta atccaccactt aaaggcacct | 1680 |
| cctcttaata ctgttgaatt agggattaag tttcaacatg aattttggag ggaatacaaa | 1740 |
| cattgaaatg attatacgtg tttatttaat caagtatcca acaaaagcaa ataattcaag | 1800 |
| ccccaaattc actgcatctt tagtagataa gcagagtttt aaattacgat tgatctcctg | 1860 |
| ttaggaggaa tgcatggatt tccacaagaa aaaactgtac tgaggagaaa ctttccacag | 1920 |
| taatgtgcca cttttcagtc aacgacagac cacatatatg agtcccataa gataatacta | 1980 |
| tattttact gtaccttttc tatgtttaga tatgtttaga cacacaaata tcattgcatt | 2040 |
| acaattgcct acagtattca gtacagtaat atgctgtata gatttgtggt ctaggagcaa | 2100 |
| tagcctaagt gtgtagtagg ctgagccatc tattttgtgt tagtacactg tgatgttcag | 2160 |
| agaaggatga aattgcctaa ggatacattt ctcagaatgt atcctgttgt tcggtgacgc | 2220 |
| atgactgtat tccatgagca ctataatcac tatcatagta acacattagg agagaattct | 2280 |
| catttctaaa tccaatataa tttatcaccc attagttcat actctactgc tttgattgct | 2340 |
| tttctttggt tgtggctacc tgcatacagc agtaaagttt cagaaaaact gaagtcgcaa | 2400 |
| aaggtcaatt actcaatgaa ggaaagataa accattgcat tgggggacta gaagatactt | 2460 |
| ttaaaagttc tcagattatc aatttaatga tgtgtttcta tgtagtgaat aatgccttaa | 2520 |
| attcttgcca agagtattta gaaggaagtt gtcagaagta tatcagctaa ctcatttttt | 2580 |
| tttatatcac tgctaatggt gtcattcaca cattgtgcaa cccataattc cagatttaat | 2640 |
| tctaccaaaa aatataggtc attgcaaaat gccatattaa aactgccaat gcatgacagg | 2700 |
| aagatgggga tgcagacaaa gcaaaggatg acaccaattc cttttttaaa gaagcaagat | 2760 |
| agggattgga caaaaaggct gagccatttt taatggatac ttttgaggga gtgttaattc | 2820 |
| caattttaatt aaaatgatgc attaatttaa aattgggata actggttgcc ctcgactgca | 2880 |
| cctgggttgc gccagtgctc tcggattaac ctaattgtac agaggtgccc ttgttttcta | 2940 |
| acttcatgca caaagcattg gaaattattt gtttgctttt tcttttccaa gtaaatcttt | 3000 |
| ttccagttat gcaaaaggga agtttgaggc aatggttaaa ggcacttaag ttataattat | 3060 |
| tgctgttatc attaacatta agcacgggta tggctttgtt gcaagttacc cacctacacc | 3120 |
| tgcaaatctc tcttgctagc acacgcccca gctctctcca cccgcagtgg tccgtggctg | 3180 |
| gaccgcttta agtcactgag cgggctgggc tctgaaggag gtcggtcccg ctcctcccag | 3240 |
| acccaagcgt agggctaggg aaaagctagg cgggaaggtc attgcactcc caggccccag | 3300 |

-continued

```
gaaaagggcc cagggtctca tcatctctta ctttcgggca aaacttccca catcgcgacc    3360
ttccctccct ggggcactct gagaacacac ccagtcacct agcgcgctcc ccagaagtcg    3420
gcttggcaca cagcgcaccc cagcggccgc gcggcctcct tccagccgcc gccacttggc    3480
ttccggagag ctcgccgggc gctgccgccg ccgccgccgc cgccgccgcc tcctgggaac    3540
caggggactg aagagcctgc gagagcggaa cactgccgga ccccgggtgg gggggcgcag    3600
cagctgcgcc tggcccccgcc caccacacct gggcgcccgt agaaccgcgc ggggcggggc    3660
ggggcaggag gctggcctgg cgctccggcc gctttgtcga agccggcccc gactggagca    3720
ggacgaaggg ggagggtctc gaggccgagt cctgttcttc tgagggacgg accccagctg    3780
gggtggaaaa gcagtaccag agagcctccg aggcgcgcgg tgccaaccat ggagcgggcc    3840
ggccccagct tcgggcagca gcgacagcag cagcagcccc agcagcagaa gcagcagcag    3900
agggatcagg actcggtcga agcatggctg gacgatcact gggactttac cttctcatac    3960
tttgttagaa aagccaccag gtaagaagag gacccacgga agacccgggg ctgatttctc    4020 tccctgttg aattgtgccc ttcgttcacc cctgttccca ggccctttgc ttttgaagta    4080
ggtcctcggt cctgttacga ggtagaaacc tcaactctaa gcgagcacag tcgaaaaact    4140
caagtgtcgg atttgataca acttgctcac aaagttcaaa tacaaaaatg tacttggttc    4200
aaatacaaaa atgtacttgc cgacctccca ccctcacccc cgccctctt ggtattcccc    4260 gggaacatga ttattttcat acatccgtgc tcacgggcct tcccctagcc cctctctagc    4320
cctctggttc cccaaaatcc aatcagcaaa acccaaacag tttctgagcc ccttccctgc    4380
ag                                                                   4382
```

<210> SEQ ID NO 96
<211> LENGTH: 3979
<212> TYPE: DNA
<213> ORGANISM: Homo sapiens
<220> FEATURE:
<221> NAME/KEY: misc_feature
<223> OTHER INFORMATION: Pde7a1: Acc. No. L12052

<400> SEQUENCE: 96

```
ggcggccgcg gcagggcggg cgccgcgcgg aggcagggcg ggcgtattca atggaagtgt      60
gttaccagct gccggtactg cccctggaca ggcggtcccc ccagcacgtc ctcagccgcc     120
gaggagccat cagcttcagc tccagctccg ctctcttcgg ctgccccaat ccccggcagc     180
tctctcagag gcgtggagct atttcctatg acagttctga tcagactgca ttatacattc     240
gtatgctagg agatgtacgt gtaaggagcc gagcaggatt tgaatcagaa agaagaggtt     300
ctcacccata tattgatttt cgtatttttcc actctcaatc tgaaattgaa gtgtctgtct     360
ctgcaaggaa tatcagaagg ctactaagtt tccagcgata tcttagatct tcacgctttt     420
ttcgtggtac tgcggtttca aattcctaa acatttagaa tgatgattat aatggacaag     480
ccaagtgtat gctgaaaaa gttggaaatt ggaatttga tatctttcta tttgatagac     540
taacaaatgg aaatagtcta gtaagcttaa cctttcattt atttagtctt catggattaa     600
ttgagtactt ccatttagat atgatgaaac ttcgtagatt tttagttatg attcaagaag     660
attaccacag tcaaaatcct taccataacg cagtccacgc tgcggatgtt actcaggcca     720
tgcactgtta cttaaaggaa cctaagcttg ccaattctgt aactccttgg gatatccttgc    780 tgagcttaat tgcagctgcc actcatgatc tggatcatca aggtgttaat caacctttcc     840
ttattaaaac taaccattac ttggcaactt tatacaagaa tacctcagta ctggaaaatc     900
accactggag atctgcagtg ggcttattga gagaatcagg cttattctca catctgccat     960
```

```
tagaaagcag gcaacaaatg gagacacaga taggtgctct gatactagcc acagacatca    1020
gtcgccagaa tgagtatctg tctttgttta ggtcccattt ggatagaggt gatttatgcc    1080
tagaagacac cagacacaga catttggttt tacagatggc tttgaaatgt gctgatattt    1140
gtaacccatg tcggacgtgg gaattaagca agcagtggag tgaaaaagta acggaggaat    1200
tcttccatca aggagatata gaaaaaaaat atcatttggg tgtgagtcca ctttgcgatc    1260
gtcacactga atctattgcc aacatccaga ttggttttat gacttaccta gtggagcctt    1320
tatttacaga atgggccagg ttttccaata caaggctatc ccagacaatg cttggacacg    1380
tggggctgaa taaagccagc tggaagggac tgcagagaga acagtcgagc agtgaggaca    1440
ctgatgctgc atttgagttg aactcacagt tattacctca ggaaaatcgg ttatcataac    1500
ccccagaacc agtgggacaa actgcctcct ggaggttttt agaaatgtga atgggtct     1560 tgaggtgaga gaacttaact cttgactgcc aaggtttcca agtgagtgat gccagccagc    1620
attatttatt tccaagattt cctctgttgg atcatttgaa cccacttgtt aattgcaaga    1680
cccgaacata cagcaatatg aatttggctt tcatgtgaaa ccttgaatat aaagcccagc    1740
aggagagaat ccgaaaggag taacaaagga agttttgata tgtgccacga cttttttcaaa   1800 gcatctaatc ttcaaaacgt caaacttgaa ttgttcagca acaatctctt ggaatttaac    1860
cagtctgatg caacaatgtg tatccttgtac cttccactaa gttctctctg agaaaatgga   1920
aatgtgaagt gcccagcctc tgctgcctct ggcaagacaa tgtttacaaa tcaactctga   1980
aaatattggt tctaaattgc cttggagcat gattgtgaag gaaccactca aacaaattta   2040
aagatcaaac tttagactgc agctctttcc ccctggtttg cctttttctt ctttggatgc   2100
caccaaagcc tcccatttgc tatagtttta tttcatgcac tggaaactga gcatttatcg   2160
tagagtaccg ccaagctttc actccagtgc cgtttggcaa tgcaatttttt tttagcaatt   2220 agtttttaat ttggggtggg aggggaagaa caccaatgtc ctagctgtat tatgattctg   2280
cactcaagac attgcatgtt gttttcacta ctgtacactt gacctgcaca tgcgagaaaa   2340
aggtggaatg ttttaaaacac cataatcagc tcaggtattt gccaatctga ataaaagtg    2400 ggatgggaga gcgtgtcctt cagatcaagg gtactaaagt cccttttcgct gcagtgagtg   2460 agaggtatgt tgtgtgtgaa tgtacggatg tgtgtttggt gatgtttgtg catgtgtgac   2520
gtgcatgtta tgtttctcca tgtgggcaaa gatttgaaag taagcttta tttattattt     2580 tagaatgtga cataatgagc agccacactc gggggagggg aaggttggta ggtaagctgt   2640
aacagattgc tccagttgcc ttaaactatg cacatagcta agtgaccaaa cttcttgttt   2700
tgatttgaaa aaagtgcatt gttttcttgt ccctcccttt gatgaaacgt taccctttga   2760
cgggcctttt gatgtgaaca gatgtttttct aggacaaact ataaggacta atttttaaact 2820 tcaaacattc cacttttgta atttgtttta aattgtttta tgtatagtaa gcacaactgt   2880
aatctagttt taagagaaac cggtgctttc ttttagttca tttgtatttc ccttgttact   2940
gtaaaagact gtttattaat tgtttacagt ttgttgcaac agccatttttc ttgggagaaa  3000 gcttgagtgt aaagccattt gtaaaaggct ttgccatact catttttaata tgtgcctgtt  3060 gctgttaact tttgatgaat aaaaacctat cttttcatga aacttctctc tatacaaatt   3120
gaaatacata atgctttctg gttcttcttc aaaccaaaac ttgtcaaatt catagacaag   3180
ataacagtaa aactgatgaa agtgttccat tgttggtata ccaggaacaa ggttatagag   3240
atgaaacttc aaagcttcac tcttcagtaa gctataagcc atctctgtaa gattgattcc   3300
aactattgca taagaatacc ctaatttttgg atgatttgaa cgggaaagaa tctgatgagc   3360
```

| | | |
|---|---|---|
| ttcactagtg taatttttcac tgaaatacac aagattgatt aacccaagta tgcccatgcc | 3420 | |
| tctgaagtct gtcttgggat catcaccctg aaaaccaatt tcagcccact gcttggagat | 3480 | |
| tctagcgttt aacttcttcg tgggcattag aagattccaa agcttcatga gtagctcttc | 3540 | |
| atgctgtagg ttatcagaat catatggcct tttcctcaca ctttctacat ccaaatacag | 3600 | |
| ctgtttataa ccagttatct gcagtaagca catcttcatg catattttaa aactggcatc | 3660 | |
| cttctcaggg ttaatattct tttccttcat aatatcatct acatatttgt ccacttcact | 3720 | |
| ctgaacaaca tgtgtcgcct tctgtaaaac cttattcttg gagtatgtca aggaattttc | 3780 | |
| tatcctgtgt gtcctttgtg cacctacata ggtatcaaat attcgctgca attcacactt | 3840 | |
| cccagtcatc tgtcgtaata gccatttcat ccaaaatcga aaaagtgcc catagaagaa | 3900 | |
| ctcccacaaa gaaataaaca ttttttttc ctcacaggag cggaagaact aggggagca | 3960 | |
| ggagctgcaa tgcggccgc | 3979 | |

<210> SEQ ID NO 97
<211> LENGTH: 2904
<212> TYPE: DNA
<213> ORGANISM: Homo sapiens
<220> FEATURE:
<221> NAME/KEY: misc_feature
<223> OTHER INFORMATION: Per-1: Acc. No. AB005293

<400> SEQUENCE: 97

| | | |
|---|---|---|
| ggcacgagct ctgtgagact gaggtggcgg tcagccggag tgagtgttgg ggtcctgggg | 60 | |
| cacctgcctt acatggcttg tttatgaaca ttaaagggaa gaagttgaag cttgaggagc | 120 | |
| gaggatggca gtcaacaaag gcctcacctt gctggatgga gacctccctg agcaggagaa | 180 | |
| tgtgctgcag cgggtcctgc agctgccggt ggtgagtggc acctgcgaat gcttccagaa | 240 | |
| gacctacacc agcactaagg aagcccaccc cctggtggcc tctgtgtgca atgcctatga | 300 | |
| gaagggcgtg cagagcgcca gtagcttggc tgcctggagc atggagccgg tggtccgcag | 360 | |
| gctgtccacc cagttcacag ctgccaatga gctggcctgc cgaggcttgg accacctgga | 420 | |
| ggaaaagatc cccgccctcc agtacccccc tgaaaagatt gcttctgagc tgaaggacac | 480 | |
| catctccacc cgcctccgca gtgccagaaa cagcatcagc gttcccatcg cgagcacttc | 540 | |
| agacaaggtc ctgggggccg cttttggccgg gtgcgagctt gcctggggg tggccagaga | 600 | |
| cactgcggaa tttgctgcca acactcgagc tggccgactg gcttctggag gggccgactt | 660 | |
| ggccttgggc agcattgaga aggtggtgga gtacctcctc cctgcagaca aggaagagtc | 720 | |
| agcccctgct cctggacacc agcaagccca gaagtctccc aaggccaagc caagcctctt | 780 | |
| gagcaggggtt gggggctctga ccaacaccct ctctcgatac accgtgcaga ccatggcccg | 840 | |
| ggccctggag cagggccaca ccgtggccat gtggatccca ggcgtggtgc ccctgagcag | 900 | |
| cctggcccag tggggtgcct cagtggccat gcaggcggtg tccggcgga ggagcgaagt | 960 | |
| gcgggtaccc tggctgcaca gcctcgcagc cgcccaggag gaggatcatg aggaccagac | 1020 | |
| agacacggag ggagaggaca cggaggagga ggaagaattg gagactgagg agaacaagtt | 1080 | |
| cagtgaggta gcagccctgc caggccctcg aggcctcctg ggtggtgtgg cacatacctt | 1140 | |
| gcagaagacc ctccagacca ccatctcggc tgtgacatgg gcacctgcag ctgtgctggg | 1200 | |
| catggcaggg agggtgctgc acctcacacc agccccgct gtctcctcaa ccaaggggag | 1260 | |
| ggccatgtcc ctatcagatg ccctgaaggg cgttactgac aacgtggtgg acacagtggt | 1320 | |
| gcattacgtg ccgctcccca ggctgtcgct gatggagccc gagagcgaat tccgggacat | 1380 | |

| | |
|---|---|
| cgacaaccca ccagccgagg tcgagcgccg ggaggcggag cgcagagcgt ctggggcgcc | 1440 |
| gtccgccggc ccggagcccg ccccgcgtct cgcacagccc cgccgcagcc tgcgcagcgc | 1500 |
| gcagagcccc ggcgcgcccc ccggcccggg cctggaggac gaagtcgcca cgcccgcagc | 1560 |
| gccgcgcccg ggcttcccgg ccgtgccccg cgagaagcca agcgcaggg tcagcgacag | 1620 |
| cttcttccgg cccagcgtca tggagcccat cgtgggccgc acgcattaca gccagctgcg | 1680 |
| caagaagagc tgagtcgccg caccagccgc gcgccccgg gccggcgggt ttctctaaca | 1740 |
| aataaacaga acccgcactg cccaggcgag cgttgccact ttcaaagtgg tcccctgggg | 1800 |
| agctcagcct catcctgatg atgctgccaa ggcgcacttt ttattttat tttatttta | 1860 |
| tttttttttt agcatccttt tggggcttca ctctcagagc cagttttaa gggacaccag | 1920 |
| agccgcagcc tgctctgatt ctatggcttg gttgttacta aagagtaat tgcctaactt | 1980 |
| gattttcat ctctttaacc aaacttgtgg ccaaaagata tttgaccgtt tccaaaattc | 2040 |
| agattctgcc tctgcggata aatatttgcc acgaatgagt aactcctgtc accactctga | 2100 |
| aggtccagac agaaggtttt gacacattct tagcactgaa ctcctctgtg atctaggatg | 2160 |
| atctgttccc cctctgatga acatcctctg atgatcaagg ctcccagcag gctactttga | 2220 |
| agggaacaat cagatgcaaa agctcttggg tgtttattta aaatactagt gtcactttct | 2280 |
| gagtaccgc cgcttcacag gctgagtcca ggcctgtgtg cttttgtagag ccagctgctt | 2340 |
| gctcacagcc acatttccat ttgcatcatt actgccttca cctgcatagt cactcttttg | 2400 |
| atgctgggga accaaaatgg tgatgatata tagacttat gtatagccac agttcatccc | 2460 |
| caaccctagt cttcgaaatg ttaatatttg ataaatctag aaaatgcatt catacaatta | 2520 |
| cagaattcaa atattgcaaa aggatgtgtg tctttctccc cgagctcccc tgttcccctt | 2580 |
| cattgaaaac caccacggtg ccatctcttg tgtatgcagg gctatgcacc tgcaggcacg | 2640 |
| tgtgtatgca ctccccgctt gtgtttacac aagctgtggg gtgttacgca tgcctgcttt | 2700 |
| tttcacttaa taatacagct tggagagatt tttgtatcac attataaatc ccactcgctc | 2760 |
| tttttgatgg ccacataata actactgcat aatatggata cgccttattt gatttaacta | 2820 |
| gttccctaat gatggacttt taagttgttt ccttttttt tcttttttgc tactgcaaac | 2880 |
| gatgctataa taaatgtcct tatc | 2904 |

<210> SEQ ID NO 98
<211> LENGTH: 4626
<212> TYPE: DNA
<213> ORGANISM: Homo sapiens
<220> FEATURE:
<221> NAME/KEY: misc_feature
<223> OTHER INFORMATION: TPP II: Acc. No. M73047

<400> SEQUENCE: 98

| | |
|---|---|
| gaattcccct ccatcctgcg tccatggcca ccgctgcgac tgaggagccc ttcccttttc | 60 |
| acggtctcct gccgaagaag gagaccggag ccgcctcctt cctctgccgc tacccggagt | 120 |
| atgatgggcg gggggtgctc atcgcagtcc tggacacggg ggtcgacccg ggggctccgg | 180 |
| gcatgcaggt tacaactgat ggaaaaccaa aaatcgttga tatcattgat acaacaggaa | 240 |
| gtggcgatgt gaatactgct acagaagtag agccaaagga tggtgagatt gttggccttt | 300 |
| caggaagagt gcttaagatt cctgcaagct ggacaaatcc ctcaggcaaa tatcatattg | 360 |
| gcataaaaaa tggctatgac ttctatccta aggcactcaa ggaaaggata cagaagaac | 420 |
| ggaaggaaaa aatctgggac cctgttcaca gagtggccct tgcagaagcc tgtagaaaac | 480 |
| aggaagaatt tgatgttgcc aacaacggct cttctcaagc aaataaacta atcaaggagg | 540 |

```
aacttcaaag tcaagtggaa ttgctaaatt cttttgagaa gaaatacagc gatcctggcc    600
ctgtatatga ctgcttggta tggcatgatg gcgaagtctg gagagcctgc attgattcta    660
atgaagatgg ggacttgagt aaatctaccg tgttgagaaa ctacaaagaa gcccaagaat    720
atggctcttt tggcacagct gagatgttga attactccgt taatatatac gatgatagaa    780
acctgctctc cattgtgacc agtggaggag ctcatgggac acatgtagct agtatagctg    840
ctggacactt tccagaagaa cctgaacgga atggggtagc tcctggtgct caaattcttt    900
ccatcaagat tggtgataca agactaagca caatggaaac aggcacaggc ctcataagag    960
ctatgataga agttataaat cataagtgtg atcttgtcaa ctacagttac ggagaagcaa   1020
ctcactggcc aaattctggg agaatttgtg aagtaattaa tgaagcagta tggaagcata   1080
atataattta tgtttcaagt gctggaaata atggtccatg cctgtctaca gttggttgtc   1140
caggtggaac tacatcaagt gtgataggtt tggtgcttta tgtttctcct gatatgatgg   1200
ttgctgagta ttcactgaga gagaaattac ctgcaaatca atatacttgg tcttctagag   1260
gacctagtgc tgacggggcc cttggtgtga gtatcagtgc gccaggagga gccattgctt   1320
ctgttcctaa ctgacactg agagggacgc agctgatgaa tggaacatct atgtcttccc     1380
ccaatgcatg tggaggcatt gccctgatcc tttcaggtct gaaagctaat aacattgact   1440
acacagttca ttcagtcaga agagctctag aaaacactgc agtgaaggct gacaatatag   1500
aagtatttgc tcaaggacat ggtattattc aggttgataa agcctatgac tacctcgttc   1560
agaatacatc atttgctaat aaattaggtt ttactgttac tgttggaaat aaccgtggca   1620
tctacctccg agatcctgtt caggtggctg caccttcaga tcatggcgtt ggcattgaac   1680
ctgtatttcc ggagaacaca gaaaactctg aaaaaatatc ccttcagctt catttagctc   1740
tgacttcaaa ttcatcttgg gttcagtgtc ccagccattt ggaactcatg aatcaatgta   1800
gacacataaa catacgtgtg gatcccaggg gcttaagaga aggattgcat tatacagagg   1860
tatgtggcta tgatatagca tcccctaacg caggtccgct cttcagagtt ccgatcactg   1920
cagttatagc agcaaagta aatgaatcat cacattatga tctagccttt acagatgtac     1980
actttaaacc tggtcaaatt cgaaggcatt ttattgaggt tcctgagggt gcaacatggg   2040
ctgaagtgac agtgtgttcg tgttcttctg aggtgtcagc aaagtttgtt ctacatgcag   2100
tccagcttgt gaagcaaaga gcatatcgaa gccatgaatt ctataagttt tgttctcttc   2160
cagagaaagg aacactgact gaagcttttc ctgtcctagg tggaaaagca attgaatttt   2220
gcattgctcg ttggtgggca agtctcagtg atgtcaacat tgattatacc atttctttcc   2280
atgggatagt gtgtactgct cctcagttaa acattcatgc atcggaagga atcaaccgct   2340
ttgatgttca gtcctccttg aaatacgaag atctggctcc ctgcataact ttgaagaact   2400
gggtccaaac actgcgccca gtgagtgcaa aaacaaaacc tttaggatca agagatgttt   2460
tgccaaataa ccgtcaactt tatgagatgg tcctgacata taactttcat caacccaaga   2520
gtggggaagt aactccaagc tgcccactac tttgtgaact attatatgaa tctgaatttg   2580
acagccaact gtggattatt tttgaccaga acaaaagaca gatgggttca ggcgatgcct   2640
atccacatca gtattctttg aaactggaga aaggagatta caattcga ctacagattc       2700 gccatgagca aatcagtgat ttggaacgcc ttaaagacct tccatttatt gtttctcata   2760
gattgtctaa taccttgagc ttagatattc atgaaaatca tagttttgca cttctaggga   2820
agaagaaatc aagcaatttg acattaccac ccaaatataa ccagccattc tttgttactt   2880
ccttacctga tgataaaata cctaaagggg caggacctgg atgctatctt gcaggatcct   2940
```

| | |
|---|---:|
| taacattgtc aaagactgaa ctaggaaaga aagctgatgt aatccctgtt cattactact | 3000 |
| taatacctcc accaacaaag actaagaatg gcagcaaaga taaggaaaaa gattcagaaa | 3060 |
| aagagaaaga tttaaaagaa gagtttactg aagcattacg agatcttaaa attcagtgga | 3120 |
| tgacaaagct ggattctagt gacatttata acgaattgaa agaaacatat cctaattatc | 3180 |
| ttcctctgta cgttgcacga cttcatcaat tggatgctga aaaggaacga atgaaaagac | 3240 |
| ttaatgaaat tgttgatgcg gcaaatgctg ttatttctca tatagatcaa acagccctag | 3300 |
| cagtttatat tgcaatgaag actgatccca ggcctgatgc agctactata aaaaatgaca | 3360 |
| tggacaaaca aaaatccacc ctcgtagatg ccctttgtag gaaaggttgt gccctggcag | 3420 |
| accatcttct tcacacccag gctcaagacg gagccatttc cactgatgca gaaggaaagg | 3480 |
| aggaggaagg agaaagtcct ttggattctc tggcagaaac attttgggaa actactaaat | 3540 |
| ggactgatct ctttgacaat aaggttttga catttgcata taaacatgca ttagtaaata | 3600 |
| aaatgtatgg gagaggcctt aaatttgcaa ctaaacttgt ggaagaaaaa ccaacaaaag | 3660 |
| aaaactggaa aaattgtatt caactgatga agttacttgg atggacccat tgtgcatctt | 3720 |
| ttactgaaaa ctggctcccc atcatgtatc ctcccgatta ttgcgtattc taaaatagga | 3780 |
| aacaagactt taaattttaa aaaaggaagt tttatagtga atgggtataa aaacaaattt | 3840 |
| gtggcatttt tagtctaatg catgttttca tccactatcc agtactgatt attaaaatga | 3900 |
| catgtattta tcagagaatt cactgacgtg tggcttaata catgtaaatc tagacctctg | 3960 |
| acatcatggt gttttcttaa tgcctcacat tgctggcacg gggatgtgcc ctgcctgcca | 4020 |
| gcacctagga cttcgagttg ggttgcagct tatgacatgc atgataggtt ttggaaggta | 4080 |
| acttttaact gcaaacctat aaagtactat ttttattttt ataaatgaac agggttttaa | 4140 |
| cgtgctcaac tttaattttt ttcaattgta tgaaggcctt aaaaaagcta cattaagcgt | 4200 |
| agctaaaatt atttattgga ctaaaaacta acagaacttc atttccagaa ttttttttttt | 4260 |
| tttttttttt ttggcaaatg tttacattca attaagggga aaaagtagaa ccagcacaaa | 4320 |
| tgagtggcag ttgctggagc ataactgctt caataaatct tcatcttggg gtaattacag | 4380 |
| gcaagtcatt ttcacatcct cttgaggttc agagcatcag aatgaactct atgaatacat | 4440 |
| gtgtaagtgc cagacagctg aatctttatc aggtattgta aagatacaca tatgatatgt | 4500 |
| ttattaaaat tgaaataatg taaaacacat gaataaattt gcaaaccaa gatcacagta | 4560 |
| caccatatgc actctggtac cttaattttt ttttataaat aataaagtg aatattgaag | 4620 |
| cttctt | 4626 |

<210> SEQ ID NO 99
<211> LENGTH: 3224
<212> TYPE: DNA
<213> ORGANISM: Homo sapiens
<220> FEATURE:
<221> NAME/KEY: misc_feature
<223> OTHER INFORMATION: MTP: Acc. No. X59657

<400> SEQUENCE: 99

| | |
|---|---:|
| actccctcac tggctgccat tgaaagagtc cacttctcag tgactcctag ctgggcactg | 60 |
| gatgcagttg aggattgctg gtcaatatga ttccttcttgc tgtgcttttt ctctgcttca | 120 |
| tttcctcata ttcagcttct gttaaaggtc acacaactgg tctctcatta ataatgacc | 180 |
| ggctgtacaa gctcacgtac tccactgaag ttcttcttga tcgggcaaa ggaaaactgc | 240 |
| aagacagcgt gggctaccgc atttcctcca acgtggatgt ggccttacta tggaggaatc | 300 |

```
ctgatggtga tgatgaccag ttgatccaaa taacgatgaa ggatgtaaat gttgaaaatg    360
tgaatcagca gagaggagag aagagcatct tcaaaggaaa aagcccatct aaaataatgg    420
gaaaggaaaa cttggaagct ctgcaaagac ctacgctcct tcatctaatc catggaaagg    480
tcaaagagtt ctactcatat caaaatgagg cagtggccat agaaaatatc aagagaggtc    540
tggctagcct atttcagaca cagttaagct ctggaaccac caatgaggta gatatctctg    600
gaaattgtaa agtgacctac caggctcatc aagacaaagt gatcaaaatt aaggccttgg    660
attcatgcaa aatagcgagg tctggattta cgaccccaaa tcaggtcttg ggtgtcagtt    720
caaaagctac atctgtcacc acctataaga tagaagacac ctttgttata gctgtgcttg    780
ctgaagaaac acacaatttt ggactgaatt cctacaaaac cattaagggg aaaatagtat    840
cgaagcagaa attagagctg aagacaaccg aagcaggccc aagattgatg tctggaaagc    900
aggctgcagc cataatcaaa gcagttgatt caaagtacac ggccattccc attgtggggc    960
aggtcttcca gagccactgt aaaggatgtc cttctctctc ggagctctgg cggtccacca   1020
ggaaatacct gcagcctgac aacctttcca aggctgaggc tgtcagaaac ttcctggcct   1080
tcattcagca cctcaggact gcgaagaaag aagagatcct tcaaatacta agatggaaa    1140
ataaggaagt attacctcag ctggtggatg ctgtcacctc tgctcagacc tcagactcat   1200
tagaagccat tttggacttt ttggatttca aaagtgacag cagcattatc ctccaggaga   1260
ggtttctcta tgcctgtgga tttgcttctc atcccaatga agaactcctg agagccctca   1320
ttagtaagtt caaggttct attggtagca gtgacatcag agaaactgtt atgatcatca   1380
ctgggacact tgtcagaaag ttgtgtcaga atgaaggctg caaactcaaa gcagtagtgg   1440
aagctaagaa gttaatcctg ggaggacttg aaaaagcaga gaaaaagag gacaccagga   1500
tgtatctgct ggctttgaag aatgccctgc ttccagaagg catcccaagt cttctgaagt   1560
atgcagaagc aggagaaggg cccatcagcc acctggctac cactgctctc cagagatatg   1620
atctcccttt cataactgat gaggtgaaga agaccttaaa cagaatatac caccaaaacc   1680
gtaaagttca tgaaaagact gtgcgcactg ctgcagctgc tatcatttta aataacaatc   1740
catcctacat ggacgtcaag aacatcctgc tgtctattgg ggagcttccc caagaaatga   1800
ataaatacat gctcgccatt gttcaagaca tcctacgttt ggaaatgcct gcaagcaaaa   1860
ttgtccgtcg agttctgaag gaaatggtcg ctcacaatta tgaccgtttc tccaggagtg   1920
gatcttcttc tgcctacact ggctacatag aacgtagtcc ccgttcggca tctacttaca   1980
gcctagacat tctctactcg ggttctggca ttctaaggaa aagtaacctg aacatctttc   2040
agtacattgg gaaggctggt cttcacggta gccaggtggt tattgaagcc caaggactgg   2100
aagccttaat cgcagccacc cctgacgagg gggaggagaa ccttgactcc tatgctggta   2160
tgtcagccat cctctttgat gttcagctca gacctgtcac ctttttcaac ggatacagtg   2220
atttgatgtc caaaatgctg tcagcatctg gcgaccctat cagtgtggtg aaaggactta   2280
ttctgctaat agatcattct caggaacttc agttacaatc tggactaaaa gccaatatag   2340
aggtccaggg tggtctagct attgatattt caggtgcaat ggagtttagc ttgtggtatc   2400
gtgagtctaa aacccgagtg aaaaataggg tgactgtggt aataaccact gacatcacag   2460
tggactcctc ttttgtgaaa gctggcctgg aaaccagtac agaaacagaa gcaggcttgg   2520
agtttatctc cacagtgcag ttttctcagt acccattctt agtttgcatg cagatggaca   2580
aggatgaagc tccattcagg caatttgaga aaaagtacga aaggctgtcc acaggcagag   2640
gttatgtctc tcagaaaaga aagaaagcg tattagcagg atgtgaattc ccgctccatc   2700
```

| | |
|---|---|
| aagagaactc agagatgtgc aaagtggtgt ttgcccctca gccggatagt acttccagcg | 2760 |
| gatggttttg aaactgacct gtgatatttt acttgaattt gtctccccga aagggacaca | 2820 |
| atgtggcatg actaagtact tgctctctga gagcacagcg tttacatatt tacctgtatt | 2880 |
| taagattttt gtaaaaagct acaaaaaact gcagtttgat caaatttggg tatatgcagt | 2940 |
| atgctaccca cagcgtcatt ttgaatcatc atgtgacgct ttcaacaacg ttcttagttt | 3000 |
| acttatacct ctctcaaatc tcatttggta cagtcagaat agttattctc taagaggaaa | 3060 |
| ctagtgtttg ttaaaaacaa aaataaaaac aaaaccacac aaggagaacc caattttgtt | 3120 |
| tcaacaattt ttgatcaatg tatatgaagc tcttgatagg acttccttaa gcatgacggg | 3180 |
| aaaaccaaac acgttcccta atcaggaaaa aaaaaaaaaa aaaa | 3224 |

<210> SEQ ID NO 100
<211> LENGTH: 5856
<212> TYPE: DNA
<213> ORGANISM: Homo sapiens
<220> FEATURE:
<221> NAME/KEY: misc_feature
<223> OTHER INFORMATION: HisR: Acc. No. D14436

<400> SEQUENCE: 100

| | |
|---|---|
| gagctcatca ttttttatgg ctgcatagta ttccatggtg tatatgtgcc acattttctt | 60 |
| aatccagtct atcattgttg gacagttggg ttggttccaa gtctttgcta ctgtgaatag | 120 |
| tgcctcaata aacatatgtg tgcatgtgtc tttatagcag caagatttat agtcctttgg | 180 |
| gtatataccc agtaatggga tggctgggtc aaatggtatt tctagttcta catccctgag | 240 |
| gaatcgccac accgacttcc acaatggttg aactagttta cagtcccacc aaaagtgtaa | 300 |
| aaatgttcct atttctccac ttcctctcca gcatctgttg tttcctgact ttttaatgat | 360 |
| tgctattcta actggtgtga gatggtatct cattgtggtt ttgatttgca tttctctgat | 420 |
| ggccagtgat ggtgagcatt ttttcatgtg ttttttggat gcataaatgt cttcttttga | 480 |
| gaagtgtctg ttcatgtcct tcgcccactt tttgatgggg atgttttttt cttgtaaatt | 540 |
| tgtttgagtt cattgtagat tctggatatt agccctttgt cagatgagta ggttgtgaaa | 600 |
| attttctccc attttgtagg ttgcctgttc actctgatgg tagtttcttt tgctgtgcag | 660 |
| aaaatcttta gtttaattag atcccatttg tcaattttgg cttttgttgc cattgttttt | 720 |
| ggtgttttag acatgaagtc cttgcccatg cctatgtcct gaatggtaat gcctaggatt | 780 |
| tcttctgggg gttttatggt tttaggtcta atgtttaagt ctttaatcca tcttgaatta | 840 |
| atttttgtat aaggtgtaag aagggatcc agtttcagct ttctacatat ggctagccag | 900 |
| ttttcccagc actttttatt aaatagagaa tcctttcccc attgcttttc tcaggtttgt | 960 |
| caaagatcag atagttgtag atatgcaatg ctatttctga gggctctgtt ctgttccatt | 1020 |
| gatctatatc tctgttttgg taccagtacc atgctgtttt ggttactgtg gccttgtagt | 1080 |
| atagtttgaa gtcaggtagc atgatgcctc cagctttgtt cttttggctt aggattgact | 1140 |
| tggcgatgtg ggctcttttt ggttccatat gaactttaaa gtagtttttt ccaattctgt | 1200 |
| gaagaaagtc attggtagct tgatgggдат ggcattgaat ctatcaatta ccttgggcag | 1260 |
| tatggccatt tcaagatat tgatt cttcc tacccatgag catggaatgt tcttccatt | 1320 |
| gttttgtatcc tctttt att ccttgagcag tggtttgtag ttctcctcga agaggtcctt | 1380 |
| cacatccct gtaagttgga ttcctagta ttttatt ctc ttt gaagcaa ttgtgaatgg | 1440 |
| gagttcactc atgatt tggc tctctgttt g tctgttattg gтgттаттaga atgcttgtga | 1500 |
| ттттт gтаcа ттgатт tt gt atcctgagac ttt gctgaag ttgctt atca gcttaaggag | 1560 |

```
attttgggct gagacaatgg ggttttctag atatacaatc atgtcatctg caaacaggga    1620
caatttgact tcctctttc ctaattgagt acccttat tccttctcct gcctaattgc    1680
cctggccaga acttccaaca ctatgttgaa taggagtggt gagagagggc atccctgtct    1740
tgtgccagtt ttcaaaggga atgcttgcag tttttgccca ttcagtatga tactggctgt    1800
gggtttgtca tagatagctc ttattatttt gagatacgtc ccatgaatac ctaatttatt    1860
gagagttttt agcatgaagg gttgttgaat tttgtcaaag gccttttctg catctattga    1920
gataatcatg tggttttgt ctttggttct gtttacatgc tggattacat ttattgattt    1980
gcatatattg aaccagcctt gcatcccagg gatgaagtcc acttgatcac ccccaacagc    2040
atacaactcc agtctgatga acatcatgct actaagtggc cactcatcac ccaagtctct    2100
gaccttactt tttctctctt ttctcccagg gagtgagcca taactggcgg ctgctcttgc    2160
gccaatgagc ctccccaatt cctcctgcct cttagaagac aagatgtgtg agggcaacaa    2220
gaccactatg gccagccccc agctgatgcc cctggtggtg gtcctgagca ctatctgctt    2280
ggtcacagta gggctcaacc tgctggtgct gtatgccgta cggagtgagc ggaagctcca    2340
cactgtgggg aacctgtaca tcgtcagcct ctcggtggcg gacttgatcg tgggtgccgt    2400
cgtcatgcct atgaacatcc tctacctgct catgtccaag tggtcactgg gccgtcctct    2460
ctgcctcttt tggctttcca tggactatgt ggccagcaca gcgtccattt tcagtgtctt    2520
catcctgtgc attgatcgct accgctctgt ccagcagccc ctcaggtacc ttaagtatcg    2580
taccaagacc cgagcctcgg ccaccattct gggggcctgg tttctctctt ttctgtgggt    2640
tattcccatt ctaggctgga atcacttcat gcagcagacc tcggtgcgcc gagaggacaa    2700
gtgtgagaca gacttctatg atgtcacctg gttcaaggtc atgactgcca tcatcaactt    2760
ctacctgccc accttgctca tgctctggtt ctatgccaag atctacaagg ccgtacgaca    2820
acactgccag caccgggagc tcatcaatag gtccctccct tccttctcag aaattaagct    2880
gaggccagag aaccccaagg gggatgccaa gaaaccaggg aaggagtctc cctgggaggt    2940
tctgaaaagg aagccaaaag atgctggtgg tggatctgtc ttgaagtcac catcccaaac    3000
ccccaaggag atgaaatccc cagttgtctt cagccaagag gatgatagag aagtagacaa    3060
actctactgc tttccacttg atattgtgca catgcaggct gcggcagagg ggagtagcag    3120
ggactatgta gccgtcaacc ggagccatgg ccagctcaag acagatgagc agggcctgaa    3180
cacacatggg gccagcgaga tatcagagga tcagatgtta ggtgatagcc aatccttctc    3240
tcgaacggac tcagatacca ccacagagac agcaccaggc aaaggcaaat tgaggagtgg    3300
gtctaacaca ggcctggatt acatcaagtt tacttggaag aggctccgct cgcattcaag    3360
acagtatgta tctgggttgc acatgaaccg cgaaaggaag gccgccaaac agttgggttt    3420
tatcatggca gccttcatcc tctgctggct cccttatttc atcttcttca tggtcattgc    3480
cttctgcaag aactgttgca atgaacattt gcacatgttc accatctggc tgggctacat    3540
caactccaca ctgaacccc tcatctaccc cttgtgcaat gagaacttca agaagacatt    3600
caagagaatt ctgcatattc gctcctaagg gaggctctga ggggatgcaa caaaatgatc    3660
cttatgatgt ccaacaagga aatagaggac gaaggcctgt gtgttgccag gcaggcacct    3720
gggctttctg gaatccaaac cacagtctta ggggcttggt agtttggaaa gttcttaggc    3780
accatagaag aacagcagat ggcggtgatc agcagagaga ttgaactttg aggaggaagc    3840
agaatctttg caagaaagtc agacctgttt cttgtaactg ggttcaaaaa gaaaaaaata    3900
ataaaaataa aagagagaga gaatcagacc tgggtggaac tctcctgctc ctcaggaact    3960
```

```
atgggagcct cagactcatt gtaattcaag ctttccgagt caagtgattg acaactgaag      4020
agacacgtgg ctagggttcc actggagaat tgaaaaggac tcttgagccc tcctggaatg      4080
gagctgtata actgtgcaga gactttatcc atgccaatag ttgctgtccc cttccagggg      4140
tcaccttgag aggcatgaca gctgttccac agggggctatc ccttctcaga aaacttctct      4200
```

Note: line at 4200 in image reads: `tcaccttgag aggcatgaca gctgttccac agggctatc ccttctcaga aaacttctct`

```
tctgagcctc tttaacagct ttctccagaa ccagtgtctg aaccaccctg aaaattctgc      4260
cttattattt cttactcaaa catgtttaga gtggatagaa aattatgcag cttgcacacc      4320
catcatcttt aacccaaat ttcctttggc tattaaaaaa gtggtggcaa aaggcatcct       4380
caaaagaaag agaaatgaaa tattttgaa tggttgcacg ttaaaaatta aagaaggaa        4440 tgggggcaga atgccatatt tttgagggct gtactaggtt tatctcattt aagccccaca     4500
acaccccaca ggagggtaat tttctaactc tagtttgcag aggagcaaat tgaggttcag      4560
caaggtgaga gaggtaccca aggtcacata gctagttatg tgagaaagtt agagtacaga     4620
tcctctgggg tttcagctta ttgtagcata ttttctccga aaggcaaaaa tgtgcccttt      4680
tggccgggca tggtagctca agcctataat cccagcatgt tgagaggctg aggtgggcag     4740
atcatttgag gccaggagtt caagaccagt ctggccaata tggagaaacc ttgtctctac     4800
taaaaacaca aaaattatct gggcatggtg gggcatgcct gtagtcccac ttacttggga    4860
ggccgaggca cgagaatcgc ttgaacccgg gaggtggagg ttgccgtgag ccaagatcac     4920
gccactgcac tccagcctgg gcaacagagc aagactctgt ctcaaaaaaa aaaatacaat    4980
attttaacaa tgtgccctct taagtgtgca cagatacaca tacacggtat tcccaagagt    5040
ggtggcagct caaaatgata tgtttgagta gacgaacagc tgacatggag ttcccgtgca    5100
cctacggaag gggacgcttt gaaggaacca agtgcatttt tatctgtgag ttctgttgtg    5160
tttgtcaaaa agtcattgta atctttcata gccatacctg gtaagcaaaa actagtaaag   5220
acataggaac atgtagtttt acttggtgtt tatgttgcaa tctggttgtg atttatattt    5280
taaagcttgg tgctaaaacca caatatgtat agcacatgga gtgcctgtac aagctgatgt    5340
tttgtatttt gtgttcctct ttgcatgatc tgtcaaagtg atatattttt acctgcctaa   5400
aatatgatgt ttaaaagcat actctatgtg atttatttat ttctacctt ctgagtctct    5460 tggactaaga agatgttttg aaatgtacca tcaaatgtta acagagtttg atatgggctt   5520
tctctttggt ttctcatcac atttgtaaat gtcttttcaa aaggatttac tttttgtaaa    5580
aagcttcatt ctcactctgc tttgcatccc ccaaacttct tgttcaaaac ggggggagtt    5640
taggagactt taatcccggt ttcagaagct gcagctggtc tgtttccagg tcagaaacca    5700
ttgttcagaa gacctccctg tgagagagtt gctcctcagg gtccctcagg accaaagaac    5760
actcgaaaag agcacttcac acagacaagt ggctaagtgt ccattattta ccttgaacaa    5820
tcaaggcaac tagtggagag aactgattgt gagctc                              5856
```

<210> SEQ ID NO 101
<211> LENGTH: 2438
<212> TYPE: DNA
<213> ORGANISM: Homo sapiens
<220> FEATURE:
<221> NAME/KEY: misc_feature
<223> OTHER INFORMATION: CRP: Acc. No. M11880

<400> SEQUENCE: 101

```
aataaataac tcacattgat ttctctggtc tgaaataatt ttgcttcccc tcttcccgaa        60
gctctgacac ctgccccaac aagcaatgtt ggaaaattat ttacatagtg gcgcaaactc       120
```

```
ccttactgct ttggatataa atccaggcag gaggaggtag ctctaaggca agagatctag    180
gacttctagc ccctgaactt tcagccgaat acatcttttc caaaggagtg aattcaggcc    240
cttgtatcac tggcagcagg acgtgaccat ggagaagctg ttgtgtttct tggtcttgac    300
cagcctctct catgctttg gccagacagg taagggccac cccaggctat gggagagttt    360
tgatctgagg tatggggtg gggtctaaga ctgcatgaac agtctcaaaa aaaaaaaaa    420 aagactgtat gaacagaaca gtggagcatc cttcatggtg tgtgtgtgtg tgtgtgtgtg    480
tgtgtgtggt gtgtaactgg agaagggtc agtctgtttc tcaatcttaa attctatacg    540
taagtgaggg gatagatctg tgtgatctga gaaacctctc acatttgctt gttttctgg    600 ctcacagaca tgtcgaggaa ggcttttgtg tttcccaaag agtcggatac ttcctatgta    660
tccctcaaag caccgttaac gaagcctctc aaagccttca ctgtgtgcct ccacttctac    720
acggaactgt cctcgacccg tgggtacagt attttctcgt atgccaccaa gagacaagac    780
aatgagattc tcatattttg gtctaaggat ataggataca gttttacagt gggtgggtct    840
gaaatattat tcgaggttcc tgaagtcaca gtagctccag tacacatttg tacaagctgg    900
gagtccgcct cagggatcgt ggagttctgg tagatggga agcccagggt gaggaagagt    960
ctgaagaagg gatacactgt gggggcagaa gcaagcatca tcttgggca ggagcaggat   1020 tccttcggtg ggaactttga aggaagccag tccctagtgg gagacattgg aaatgtgaac   1080
atgtgggact ttgtgctgtc accagatgag attaacacca tctatcttgg cgggcccttc   1140
agtcctaatg tcctgaactg gcgggcactg aagtatgaag tgcaaggcga agtgttcacc   1200 aaacccagc tgtggccctg aggcccagct gtgggtcctg aaggtacctc ccggttttt   1260 acaccgcatg ggccccacgt ctctgtctct ggtacctccc gcttttttac actgcatggt   1320
tcccacgtct ctgtctctgg gcctttgttc cctatatgc attgaggcct gctccaccct   1380
cctcagcgcc tgagaatgga ggtaaagtgt ctggtctggg agctcgttaa ctatgctggg   1440
aaatggtcca aaagaatcag aatttgaggt gttttgttt cattttatt tcaagttgga   1500 cagatcttgg agataatttc ttacctcaca tagatgagaa aactaacacc cagaaaggag   1560
aaatgatgtt ataaaaaact cataaggcaa gagctgagaa ggaagcgctg atcttctatt   1620
taattcccca cccatgaccc ccagaaagca ggagcattgc ccacattcac agggctcttc   1680
agtatcagaa tcaggacact ggccaggtgt ctggtttggg tccagagtgc tcatcatcat   1740
gtcatagaac tgctgggccc aggtctcctg aaatgggaag cccagcaata ccacgcagtc   1800
cctccacttt ctcaaagcac actggaaagg ccattagaat tgccccagca gagcagatct   1860
gctttttttc cagagcaaaa tgaagcacta ggtataaata tgttgttact gccaagaact   1920
taaatgactg gttttttgttt gcttgcagtg cttcttaat tttatggctc ttctgggaaa   1980 ctcctccct tttccacacg aaccttgtgg ggctgtgaat tctttcttca tccccgcatt   2040
cccaatatac ccaggccaca agagtggacg tgaaccacag ggtgtcctgt cagaggagcc   2100
catctcccat ctccccagct ccctatctgg aggatagttg ataggtacg tgttcctagc   2160 aggaccaact acagtcttcc caaggattga gttatggact ttgggagtga gacatcttct   2220
tgctgctgga tttccaagct gagaggacgt gaacctggga ccaccagtag ccatcttgtt   2280
tgccacatgg agagagactg tgaggacaga agccaaactg gaagtggagg agccaaggga   2340
ttgacaaaca acagagcctt gaccacgtgg agtctctgaa tcagccttgt ctggaaccag   2400
atctacacct ggactgccca ggtctataag ccaataaa                          2438
```

<210> SEQ ID NO 102

```
<211> LENGTH: 1457
<212> TYPE: DNA
<213> ORGANISM: Homo sapiens
<220> FEATURE:
<221> NAME/KEY: misc_feature
<223> OTHER INFORMATION: CETP:  Acc. No. XM_008050

<400> SEQUENCE: 102
cctggccctg ctgggcaatg cccatgcctg ctccaaaggc acctcgcacg aggcaggcat      60
cgtgtgccgc atcaccaagc ctgccctcct ggtgttgaac cacgagactg ccaaggtgat     120
ccagaccgcc ttccagcgag ccagctaccc agatatcacg ggcgagaagg ccatgatgct     180
ccttggccaa gtcaagtatg ggttgcacaa catccagatc agccacttgt ccatcgccag     240
cagccaggtg gagctggtgg aagccaagtc cattgatgtc tccattcaga acgtgtctgt     300
ggtcttcaag gggaccctga gtatggcta caccactgcc tggtggctgg gtattgatca     360
gtccattgac ttcgagatcg actctgccat tgacctccag atcaacacac agctgacctg     420
tgactctggt agagtgcgga ccgatgcccc tgactgctac ctgtctttcc ataagctgct     480
cctgcatctc aaggggagc gagagcctgg gtggatcaag cagctgttca caaatttcat     540
ctccttcacc ctgaagctgg tcctgaaggg acagatctgc aaagagatca cgtcatctc     600
taacatcatg gccgattttg tccagacaag gctgccagc atcctttcag atggagacat     660
tggggtggac atttccctga caggtgatcc cgtcatcaca gcctcctacc tggagtccca     720
tcacaaggca gtgctggaga cctggggctt caacaccaac caggaaatct tccaagaggt     780
tgtcggcggc ttccccagcc aggcccaagt caccgtccac tgcctcaaga tgcccaagat     840
ctcctgccaa aacaagggag tcgtggtcaa ttcttcagtg atggtgaaat tcctctttcc     900
acgcccagac cagcaacatt ctgtagctta cactttgaa gaggatatcg tgactaccgt     960
ccaggcctcc tattctaaga aaagctctt cttaagcctc ttggatttcc agattacacc    1020
aaagactgtt tccaacttga ctgagagcag ctccgagtcc gtccagagct tcctgcagtc    1080
aatgatcacc gctgtgggca tccctgaggt catgtctcgg ctcgaggtag tgtttacagc    1140
cctcatgaac agcaaaggcg tgagcctctt cgacatcatc aaccctgaga ttatcactcg    1200
agatggcttc ctgctgctgc agatggactt tggcttccct gagcacctgc tggtggattt    1260
cctccagagc ttgagctaga agtctccaag gaggtcggga tggggcttgt agcagaaggc    1320
aagcaccagg ctcacagctg gaaccctggt gtctcctcca gcgtggtgga agttgggtta    1380
ggagtacgga gatggagatt ggctcccaac tcctccctat cctaaaggcc cactggcatt    1440
aaagtgctgt atccaag                                                   1457

<210> SEQ ID NO 103
<211> LENGTH: 2986
<212> TYPE: DNA
<213> ORGANISM: Homo sapiens
<220> FEATURE:
<221> NAME/KEY: misc_feature
<223> OTHER INFORMATION: ICAM:  Acc. No. J03132

<400> SEQUENCE: 103
gcgccccagt cgacgctgag ctcctctgct actcagagtt gcaacctcag cctcgctatg      60
gctcccagca gccccggcc cgcgctgccc gcactcctgg tcctgctcgg ggctctgttc     120
ccaggacctg gcaatgccca gacatctgtg tccccctcaa aagtcatcct gccccgggga    180
ggctccgtgc tggtgacatg cagcacctcc tgtgaccagc ccaagttgtt gggcatagag    240
acccgttgc ctaaaaagga gttgctcctg cctgggaaca accggaaggt gtatgaactg    300
```

```
agcaatgtgc aagaagatag ccaaccaatg tgctattcaa actgccctga tgggcagtca    360
acagctaaaa ccttcctcac cgtgtactgg actccagaac gggtggaact ggcacccctc    420
ccctcttggc agccagtggg caagaacctt accctacgct gccaggtgga gggtggggca    480 cccgggcca acctcaccgt ggtgctgctc cgtggggaga aggagctgaa acggagcca     540 gctgtggggg agcccgctga ggtcacgacc acggtgctgg tgaggagaga tcaccatgga    600
gccaatttct cgtgccgcac tgaactggac ctgcggcccc aagggctgga gctgtttgag    660
aacacctcgg cccctacca gctccagacc tttgtcctgc agcgactcc cccacaactt     720 gtcagccccc gggtcctaga ggtggacacg caggggaccg tggtctgttc cctggacggg    780
ctgttcccag tctcggaggc ccaggtccac ctggcactgg ggaccagag gttgaacccc     840 acagtcacct atggcaacga ctccttctcg gccaaggcct cagtcagtgt gaccgcagag    900
gacgagggca cccagcggct gacgtgtgca gtaatactgg ggaaccagag ccaggagaca    960
ctgcagacag tgaccatcta cagctttccg gcgcccaacg tgattctgac gaagccagag   1020
gtctcagaag ggaccgaggt gacagtgaag tgtgaggccc accctagagc caaggtgacg   1080
ctgaatgggt tccagcccca gccactgggc ccgaggcccc agctcctgct gaaggccacc   1140
ccagaggaca acgggcgcag cttctcctgc tctgcaaccc tggaggtggc cggccagctt   1200
atacacaaga accagacccg ggagcttcgt gtcctgtatg gccccgact ggacgagagg    1260 gattgtccgg gaaactggac gtggccagaa aattcccagc agactccaat gtgccaggct   1320
tgggggaacc cattgcccga gctcaagtgt ctaaaggatg gcactttccc actgcccatc   1380
ggggaatcag tgactgtcac tcgagatctt gagggcacct acctctgtcg ggccaggagc   1440
actcaagggg aggtcacccg cgaggtgacc gtgaatgtgc tctccccccg gtatgagatt   1500
gtcatcatca ctgtggtagc agccgcagtc ataatgggca ctgcaggcct cagcacgtac   1560
ctctataacc gccagcggaa gatcaagaaa tacagactac aacaggccca aaaagggacc   1620
cccatgaaac cgaacacaca agccacgcct ccctgaacct atcccgggac agggcctctt   1680
cctcggcctt cccatattgg tggcagtggt gccacactga acagagtgga agacatatgc   1740
catgcagcta cacctaccgg ccctgggacg ccggaggaca gggcattgtc ctcagtcaga   1800
tacaacagca tttggggcca tggtacctgc acacctaaaa cactaggcca cgcatctgat   1860
ctgtagtcac atgactaagc caagaggaag gagcaagact caagacatga ttgatggatg   1920
ttaaagtcta gcctgatgag aggggaagtg gtgggggaga catagcccca ccatgaggac   1980
atacaactgg gaaatactga acttgctgc ctattgggta tgctgaggcc cacagactta    2040
cagaagaagt ggccctccat agacatgtgt agcatcaaaa cacaaaggcc cacacttcct   2100
gacggatgcc agcttgggca ctgctgtcta ctgaccccaa cccttgatga tatgtattta   2160
ttcatttgtt attttaccag ctatttattg agtgtctttt atgtaggcta aatgaacata   2220
ggtctctggc ctcacggagc tcccagtcca tgtcacattc aaggtcacca ggtacagttg   2280
tacaggttgt acactgcagg agagtgcctg gcaaaaagat caaatggggc tgggacttct   2340
cattggccaa cctgccttc cccagaagga gtgatttttc tatcggcaca aaagcactat    2400
atggactggt aatggttcac aggttcagag attacccagt gaggccttat tcctcccttc   2460
cccccaaaac tgacaccttt gttagccacc tccccaccca catacatttc tgccagtgtt   2520
cacaatgaca ctcagcggtc atgtctggac atgagtgccc agggaatatg cccaagctat   2580
gccttgtcct cttgtcctgt ttgcatttca ctgggagctt gcactattgc agctccagtt   2640
tcctgcagtg atcagggtcc tgcaagcagt ggggaagggg gccaaggtat tggaggactc   2700
```

```
cctcccagct ttggaagggt catccgcgtg tgtgtgtgtg tgtatgtgta gacaagctct      2760
cgctctgtca cccaggctgg agtgcagtgg tgcaatcatg gttcactgca gtcttgacct      2820
tttgggctca agtgatcctc ccacctcagc ctcctgagta gctgggacca taggctcaca      2880
acaccacacc tggcaaattt gattttttt ttttttttca gagacggggt ctcgcaacat       2940
tgcccagact tcctttgtgt tagttaataa agctttctca actgcc                    2986
```

<210> SEQ ID NO 104
<211> LENGTH: 3634
<212> TYPE: DNA
<213> ORGANISM: Homo sapiens
<220> FEATURE:
<221> NAME/KEY: misc_feature
<223> OTHER INFORMATION: X02910

<400> SEQUENCE: 104

```
gaattccggg tgatttcact cccggctgtc caggcttgtc ctgctacccc acccagcctt        60
tcctgaggcc tcaagcctgc caccaagccc ccagctcctt ctccccgcag gacccaaaca       120
caggcctcag gactcaacac agcttttccc tccaacccgt tttctctccc tcaacggact       180
cagctttctg aagcccctcc cagttctagt tctatctttt tcctgcatcc tgtctggaag       240
ttagaaggaa acagaccaca gacctggtcc ccaaaagaaa tggaggcaat aggttttgag       300
gggcatgggg acggggttca gcctccaggg tcctacacac aaatcagtca gtggcccaga       360
agacccccct cggaatcgga gcaggagga tggggagtgt gaggggtatc cttgatgctt        420
gtgtgtcccc aactttccaa atccccgccc ccgcgatgga gaagaaaccg agacagaagg       480
tgcagggccc actaccgctt cctccagatg agctcatggg tttctccacc aaggaagttt       540
tccgctggtt gaatgattct ttccccgccc tcctctcgcc ccaggacat ataaaggcag        600 ttgttggcac acccagccag cagacgctcc ctcagcaagg acagcagagg accagctaag       660
agggagagaa gcaactacag accccccctg aaaacaaccc tcagacgcca catccctga       720 caagctgcca ggcaggttct cttcctctca catactgacc cacggcttca ccctctctcc       780
cctggaaagg acaccatgag cactgaaagc atgatccggg acgtgagct ggccgaggag       840 gcgctcccca agaagacagg ggggcccag ggctccaggc ggtgcttgtt cctcagcctc       900
ttctccttcc tgatcgtggc aggcgccacc acgctcttct gcctgctgca ctttggagtg       960
atcggccccc agagggaaga ggtgagtgcc tggccagcct tcatccactc tcccacccaa      1020
ggggaaatga gagacgcaag agagggagag agatgggatg ggtgaaagat gtgcgctgat      1080
agggagggat gagagagaaa aaaacatgga gaaagacggg gatgcagaaa gagatgtggc      1140
aagagatggg gaagagagag agagaaagat ggagagacag gatgtctggc acatggaagg      1200
tgctcactaa gtgtgtatgg agtgaatgaa tgaatgaatg aatgaacaag cagatatata      1260
aataagatat ggagacagat gtggggtgtg agaagagaga tggggaaga aacaagtgat       1320 atgaataaag atggtgagac agaaagagcg ggaaatatga cagctaagga gagagatggg      1380
ggagataagg agagaagaag ataggtgtc tggcacacag aagacactca gggaaagagc        1440
tgttgaatgc tggaaggtga atacacagat gaatggagag agaaaccag acacctcagg       1500 gctaagagcg caggccagac aggcagccag ctgttcctcc tttaagggtg actccctcga      1560
tgttaaccat tctccttctc cccaacagtt ccccaggac ctctctctaa tcagccctct       1620
ggcccaggca gtcagtaagt gtctccaaac ctctttccta attctgggtt tgggtttggg      1680
ggtagggtta gtaccggtat ggaagcagtg ggggaaattt aaagttttgg tcttggggga     1740
ggatggatgg aggtgaaagt aggggggtat tttctaggaa gtttaagggt ctcagctttt     1800
```

| | |
|---|---|
| tcttttctct ctcctcttca ggatcatctt ctcgaacccc gagtgacaag cctgtagccc | 1860 |
| atgttgtagg taagagctct gaggatgtgt cttggaactt ggagggctag gatttgggga | 1920 |
| ttgaagcccg gctgatggta ggcagaactt ggagacaatg tgagaaggac tcgctgagct | 1980 |
| caagggaagg gtggaggaac agcacaggcc ttagtgggat actcagaacg tcatggccag | 2040 |
| gtgggatgtg ggatgacaga cagagaggac aggaaccgga tgtggggtgg gcagagctcg | 2100 |
| agggccagga tgtggagagt gaaccgacat ggccacactg actctcctct ccctctctcc | 2160 |
| ctccctccag caaaccctca agctgagggg cagctccagt ggctgaaccg ccgggccaat | 2220 |
| gccctcctgg ccaatggcgt ggagctgaga gataaccagc tggtggtgcc atcagagggc | 2280 |
| ctgtacctca tctactccca ggtcctcttc aagggccaag gctgcccctc cacccatgtg | 2340 |
| ctcctcaccc acaccatcag ccgcatcgcc gtctcctacc agaccaaggt caacctcctc | 2400 |
| tctgccatca agagcccctg ccagaggag accccagagg gggctgaggc caagccctgg | 2460 |
| tatgagccca tctatctggg aggggtcttc cagctggaga agggtgaccg actcagcgct | 2520 |
| gagatcaatc ggcccgacta tctcgacttt gccgagtctg ggcaggtcta ctttgggatc | 2580 |
| attgccctgt gaggaggacg aacatccaac cttcccaaac gcctcccctg ccccaatccc | 2640 |
| tttattaccc cctccttcag acaccctcaa cctcttctgg ctcaaaaaga gaattggggg | 2700 |
| cttagggtcg gaacccaagc ttagaacttt aagcaacaag accaccactt cgaaacctgg | 2760 |
| gattcaggaa tgtgtggcct gcacagtgaa gtgctggcaa ccactaagaa ttcaaactgg | 2820 |
| ggcctccaga actcactggg gcctacagct ttgatccctg acatctggaa tctggagacc | 2880 |
| agggagcctt tggttctggc cagaatgctg caggacttga gaagacctca cctagaaatt | 2940 |
| gacacaagtg gaccttaggc cttcctctct ccagatgttt ccagacttcc ttgagacacg | 3000 |
| gagcccagcc ctccccatgg agccagctcc ctctatttat gtttgcactt gtgattattt | 3060 |
| attatttatt tattatttat ttatttacag atgaatgtat ttatttggga gaccggggta | 3120 |
| tcctggggga cccaatgtag gagctgcctt ggctcagaca tgttttccgt gaaaacggag | 3180 |
| ctgaacaata ggctgttccc atgtagcccc ctggcctctg tgccttcttt tgattatgtt | 3240 |
| ttttaaaata tttatctgat taagttgtct aaacaatgct gatttggtga ccaactgtca | 3300 |
| ctcattgctg agcctctgct ccccagggga gttgtgtctg taatcgccct actattcagt | 3360 |
| ggcgagaaat aaagtttgct tagaaaagaa acatggtctc cttcttggaa ttaattctgc | 3420 |
| atctgcctct tcttgtgggt gggaagaagc tccctaagtc ctctctccac aggctttaag | 3480 |
| atccctcgga cccagtccca tccttagact cctagggccc tggagaccct acataaacaa | 3540 |
| agcccaacag aatattcccc atcccccagg aaacaagagc ctgaacctaa ttacctctcc | 3600 |
| ctcagggcat gggaatttcc aactctggga attc | 3634 |

<210> SEQ ID NO 105
<211> LENGTH: 11233
<212> TYPE: DNA
<213> ORGANISM: Homo sapiens

<400> SEQUENCE: 105

| | |
|---|---|
| gaattccttc cgtagcttca ccagacacct aattggccaa gaaggtttga agacctgatg | 60 |
| tggttcttaa ttggggatgg ggaattaagg gctactgtat ctataggatt atcttttcac | 120 |
| ttgcatagac ctatttggtg tgttcagggc atagtgatac tataattgcc atatttaaca | 180 |
| gtttataaag ttcaagccca gcatattctt tgcctgttta atgatgtctt ggtatcagcc | 240 |
| ttttaatggt acttatcagc atagaaaatg gaaacaaaat aacttttaaa acagtagctc | 300 |

```
tcaagcttta gtgtgctcag aatgaccaga gaaccttgtg aaatatacag atttctgggt    360
ccagatctgg ggcaggacca ggaagtctgc atttcatctg cacccccacc ctactctgag    420
gcttatagtc ctgagaacat gctttgaaaa aggctgtccc aagggctcgc agacaggcta    480
ttgaccagct actctttctt gatgttctcc aggaaaaacc caacaaagga atgcctttca    540
ttgagtagta gcagcatagg agcaatagtt gctcctgaat tatggtgggt ttcccctctt    600
catcaatgtg ctttaagggt acagtttcat ttggtctatc taccatgttc tataaaaaca    660
tgaaaattca caggtaagtt tgagatacag aaaataacta aactgattct tctcacgaac    720
tctgatcact aggctgtggt tgatttagct ctctaaccaa caagtaattt gttcttttggc   780 atgagtaagg ggggaaaagg aggagtgggt aaaagcagct gataacagat ggcttgcgcc    840
catctaaaat gtggggagag aaataaagct gtcccaagag aactaaagct gagttctctc    900
gtcatatatc tgaagattca tatcaggggt ctaaacatgg tatgtcgggt agcttaattg    960
gaaactcctg gactgtgagt gtcacagact catggatggg ccaatcagtg ccacttttag   1020
tgtctgggct gcagcaaaat gagacaatag ctgtcattca caaacctttg gaattaaaaa   1080
aaccccgaaa tgacattggt gctttaaagt aaaataaagt cctgccttta agtccagcat   1140
atcactgttg tttctgagtt taaatattaa gaaccacatt tcgttaatga ttaaaacaac    1200
agtgattgat ttaggggctc agtgagcatt taatctgtcc tgacttcagg taccatgcta    1260
aaggagcaca atgcctgatg ctgcaggaga acattaggt aactatttaa tggagtttta    1320
attttctgtt attatttttta ataattaatt gtgattttga ctatttggaa gctacaggta    1380
tattttgtcc tccttttggg gtggtgttat tgccctgccc tgttttaatc agtggttctt    1440
agagaaagtg aactcaggag tgacttaaaa tgaaggaaga cggactttgg ctaaaattac    1500
aattaaataa tcaaatcatt ttcaaatata aagggagcat gcagatgatc tggcccaatc    1560
ctttcattct gcagatgaga aaactgagac tcataggaat gaaaagactt gcccaaagcc    1620
atacagcttg tttctgttgt ttggtgcatt aggccaaaag acctaggcct aatagatgga    1680
aaagatggca ggatgtcttg gccttgctct gacagttgct tctctgatct cagatatttc    1740
ccaccctttg taatctgtgt tccacacagg aagtagttct tgttttttaa atatcgaagg    1800
tgtataaacg taaagttttt atagatgagc cacccagggc caatatctgt ttaagtaaag    1860
acctaaatgc tttgcagaga cagtaaagtg tcatgtctgt cccagggaaa gaaatccagg    1920
acaggaaatg ctcagtcttc cagcactcct ctggctacct ggagctcagg ctatgagcct    1980
caacccctcc ctgaagcatt agctctggag cagaggctgt gatttacttc agagatctgg    2040
gcaagtccct ttaacctggt agtccttcct ttccttgttt gtaaaacaga gagatgaggc    2100
tgatagctcc ctcacagctc catcagaggc agtgtgtgaa attagttcct gtttgggaag    2160
gtttaaaagc caccacattc cacctcccotg ctaatatgat tactaaaatg tttttatatg    2220
aaagggccaa ttcctcatct cccctcttcc tttaaaaaca gaccaagggg catcttttct    2280
tgtctccctg tggcctaaaa ggttactgct tctgtggtta tctccttgga aagacagagt    2340
gtcaggactc ttaggtacac caaaaatgaa caaaaaaatc aacaacaacc ataacaccaa    2400
caaaaataac tgctgtgtcg gttcttaaga cggcttctga gctagaaaca gattttttcta   2460 actgtaaaaa acgtggcccc agcctgtctg caggccacct ctgtctttag gccttggggg    2520
gaggagggaa gtgagctcat ttactggggt ctacctcagg gtcatcacca aggtgttcta    2580
caaaacgcac tttaagaatg ttttggaagg aaattcacct tttaacagcc caagaggtat    2640
ctctctctgg cacacagttc tgcacacagc ctgtttctca acgtttggaa atcttttaac    2700
```

```
agtttatgga aggccacctt ttaaaccgat ccaacagctc ctttctccat aacctgattt    2760
tagaggtgtt tcattatctc taattactca gggtaaatgg tgattactca gtgttttaat    2820
catcagtttg ggcagcagtt acactaaact cagggaagcc cagactccca tgggtatttt    2880
tggaaggtac ggcgactagt cggtgcatgc tttctagtac ctccgcacgt ggtccccagg    2940
tgagccccag ccgcttccca gagctggagg cagcggcgtc ccagctccga cggcagctgc    3000
ggactcgggc gctgcctggg cttccgggac ccgggcctgc taggcgaggt cgggcggctg    3060
gaggggagga tgtgggcggg gctcccatcc ccagaaaggg aggcgagcga gggaggaggg    3120
aaggagggag gggccgccgg ggaagaggag gaggaaggaa agaaagaaag cgagggaggg    3180
aaagaggagg aaggaagatg cgagaaggca gaggaggagg gagggaggga aggagcgcgg    3240
agcccggccc ggaagctagg tgagtgtggc atccgagctg agggacgcga gcctgagacg    3300
ccgctgctgc tccggctgag tatctagctt gtctccccga tgggattccc gtccaagcta    3360
tctcgagcct gcagcgccac agtccccggc cctcgcccag gttcactgca accgttcaga    3420
ggtccccagg agctgctgct ggcgagcccg ctactgcagg gacctatggt gagcaaggct    3480
acctggtgag gggagacagg cagaggggt ctaggagcct ccttgggggg aagaagctgg    3540
tcacaggctg tgaccgaggc aaaaggtggc ctaattattt tccaatagtg gtgctggagg    3600
tggggatgct ggcgctgaaa gacctttaaa tatcggctac tgcccctgcc caggccttct    3660
ctgtccagca gtccctggga gattctcacc tttgggaagt gcggggcagg agagcagaaa    3720
caagagaagc ccttggtagg ggggtcgttg gaaaaactg tggggtcttg ggctgaacgc    3780
gttgcccacg ggctggaggt tgcgatcccc ggacggaaag cgcgggagga ggaaggagag    3840
aaccggctct gaggtccaga gagagtgagg gggcagagcg acggcgagat ggggagagaa    3900
cacctagctg gagcaggttc tgcggtagag agcgcagtcc tgctggcctc tggagagtgc    3960
gcgccgctac ggaggctgcg tcgaggggag tgtcacccaa tctggccccc agctggcggg    4020
gcgccctgag agcttgcgaa ctgcagttgc aggacgcgcc ttctccacga gctattttcg    4080
tcgacttgcg gaacccaagg aacctcgcct ctatcatttc acggtgtagg gtccctagag    4140
acgacagcca agatcccagg ggctcccagg acgcttgttc ctgcggtgtc gtgtcctatg    4200
gggagttcct ggcgggacga aaggcggacg cgcggctctt cctggccctc caggcccgga    4260
accgacggga aaggttcccg tgattcccga gtccctgcag gcttcttcca gcgggagttg    4320 gtccggggc cttagaggcc tccaagcact gctttggagg atggtttcca aggatcgcgg    4380
tttgtgagtt gaaggctttg tgagaggtta aaccccccaaa agatacatac ttggtaaact    4440
gaggctacct gtaaacacat ttcggcatta ggagaagatt cgagtaggga agtgaaggac    4500
aaccaccccg agttacattc ctttccccca ataaaagct ctggggatga aagttctttt    4560
ggcttttatc ttttcgattt aaaaatttga gaagaaaaat gtgactagag atgaatcctg    4620
gtgaatccga aattgaaaca caactccccc ttccccttcc tatcctctcg gttttagaac    4680
cgcgctctcc cgcccagga gattccttgg ggccgagggt tttccgggga acccgggcgc    4740
ccgccccttc tactgtccct ttgccccgcg ggcacagctt gcctccgtct gctttctcta    4800
cttctggacc tctcctcgcc gggcttttta aagggcttct gcgtctcaaa acaaaacaaa    4860
aaaacccttt gctcttccca acccctttcgc agcccgcccc agcggtggcg cgggaccagc    4920
aaaggcgaaa gccgcgcggc tcttgccggg cgcggacggt cgcgcagggg cgcccgcggc    4980
ctccgcaccc ggacctgagg tgttggtcga ctccgggcat ccacggtcgg gagggagggc    5040
tgagctgttc gatcctttac ttttcttcct caaagtctac ctgccaatgc ccctaagaag    5100
```

```
aaaaccaagt atgtgcgtgg agagtggggc ggcaggcaac ccgagttctt gagctccgga   5160
gcgacccaaa gcagcaactg ggaacagcct caggaaaggg aggtcgggtg gagtgggctt   5220
tggggcagga gtcatggggc ccgggccccg ggacgacct ggcgctcccg cccctgctga    5280
acgctgagtt gcgcctagtc gggttttcga agaggcctt gcgcagagcg acccacgcgc    5340
gcggcagcat cttcgattag tcaggacatc ccagtaactg cttgaactgt aggtaggtaa    5400
aattcttgaa ggagtatttg ctgcgtgcga ctctgctgct ggtgcaacgg aggaagggg    5460 tgggggaagg aagtggcggg ggaaggagtg tggtggtggt ttaaaaaata agggaagccg    5520
aggcgagaga gacgcagacg cagaggtcga gcgcaggccg aaagctgttc accgttttct    5580
cgactccggg gaacatggtg ggatttcctt tctgcgccgg gtcggagagtt gtaaaacctc   5640 ggccacatta agatctgaaa actgtgatgc gtcctttctg cagagacgcc tctttctgaa    5700
tctgcccgga gcttcgagcc ccggcgtctg tccctcagcc tggcatggct tcttcggggg    5760
tctgctttgc atggggagag gggccacgca gcggcggact aggtttgggg attctcggta    5820
atggacccgg agcaatgact aacagccgct ccctctcact ttcccacagc gatcaccctc    5880
taacaccctc cctcccattc ccggccccgc gcgtgacaag gtcggctgct ttcagccggg    5940
agctagatcg gtggcccggc tcttcggagc cttagcaggc gttcgccaag gggtgactgg    6000
ctgtcattgg gagcaatatt tggccttgag gagaccctgg ggaggaagtg gcggggagct    6060
cgtgtttgct tgtgtgtgtg tgggggggg ggtgtgtgta cacgcgcgtg ggcagggtcc    6120
ctctgcgctt tcctttttaa gtgcctctcg gtggtgaggc tttgggcggg tgagactttc    6180
ccgacctcgc tcccggcccc acttaagccg ggttcgagct gggagacgca gtcccttcag    6240
tgcgccccaa atcctctggc ttcaggtggc ccggcgcggg ggcccagcac gacgcaccgc    6300
gccgagaacc gggttctccg tgcgctgcgc cagtagccct gggagcgcgg cggccgcggg    6360
gcaccggccg agggctctgc cgagcgccgc cgggagctcc tcccgaccgg ctgaggctcg    6420
ggcggcgggc gcggaggttg gcctcgcctg gagggggcggg cccgcgaggg gcgggggggct  6480 gtggaggagg ggagggcgcg caggccctt cgccgcctgc cgcgggaggg gcctcggcgc    6540
tcacgtgact ccgaggggct ggaagaaaaa cagagcctgt ctgcggtgga gtctcattat    6600
attcaaatat tccttttagg agccattccg tagtgccatc ccgagcaacg cactgctgca    6660
gcttccctga gccttttccag caagtttgtt caagattggc tgtcaagaat catggactgt    6720
tattatatgc cttgttttct gtcagtgagt agacacctct tccttccccc tctccggaat    6780
tcactctgcc ctcaccaccc ctgctcgccg gctgtcccctt ccgtcggacc tcctttacaa    6840
tatccacact ctgctccctg gcagcactgt cgctcccttc ttggcccggc agccggggcg    6900
ctggaagcgt acgggttcct tttaaagtgc tgctagcgcg cactcgccct tcagcgttg    6960 caagaaaggg gagcgcgagg gagctaaaga gatgaaagcc cggggttgta ccttgagggc   7020
taaccactcc cttccctat ccaacttgtc tgggagagcc cccagtgtct ccgtggcgcg    7080
ttcccactct cttgtcaaaa ctcacagagg tctctccgga atcgtctctc acccttccc    7140 tggggatgag cgggcacgat caggcacttt tggctgaata tttcaaactc atcggccaca    7200
ataaaataag ccctcaagcc acccggttag ctcccagacc accttctcgg cttctggacc    7260
ctgtcgccct ctgtcttcgc ccagcccctg cctctcactt tccctccctc tggctctgaa    7320
ccaactggaa gttgtgaaag ttgggctctg agggtggagg aaaagggaga gaagctgaag    7380
gtctaaagtg gagagcaatg ccattttaat tctccctccc ccaccccttt tcaccccctc    7440
aatgttaact gtttatcctt caagaagcca cgctgagatc atggcccaga tagcagttag    7500
```

```
gacaaaaaaa gattaacagg atggaggcta tctgatttgg ggttatttga ctgtaaacaa    7560
gttagaccaa gtaattacag ggcaattctt actttcaggc cgtgcatggc tgcagctggt    7620
gggtgggcgg gtggtgtgag ggagaagaca caaacttgat ctttctgacc tgctttccat    7680
cttgcccctc catttctagc cctaaatgca tatgcagaca catctctatt tctccctatt    7740
tattggtgtt tgtttattct ttaaccttcc actcccctcc ccctccccag agacaccatg    7800
attcctggta accgaatgct gatggtcgtt ttattatgcc aagtcctgct aggaggcgcg    7860
agccatgcta gtttgatacc tgagacgggg aagaaaaaag tcgccgagat tcagggccac    7920
gcgggaggac gccgctcagg gcagagccat gagctcctgc gggacttcga ggcgacactt    7980
ctgcagatgt ttgggctgcg ccgccgcccg cagcctagca agagtgccgt cattccggac    8040
tacatgcggg atctttaccg gcttcagtct ggggaggagg aggaagagca gatccacagc    8100
actggtcttg agtatcctga gcgcccggcc agccgggcca acaccgtgag gagcttccac    8160
cacgaaggtc agtctcttcc cccagtctgc gtggggagg gctggtggga ctggctagag    8220
gggcagtgaa agccctgggg aagaagagtt cgggttacat caaacccag tccaggaggc    8280 tgaggaacag agctgcttac ctccaagaat ttgcagagct gccgccgaac ttatttttg     8340 gagacagagg gggaggtgtt caggggaagg ggaatgacag cactcagacg tgggctagcc    8400
ccagcggtgt gttttgcta tatcaaagcc ttttctgcta ggttttctgc ccgtttttt     8460 caaagcacct actgaattta atattacagc tgtgtgtttg tcgggtttat tcaatagggg    8520
ccttgtaatc cgatctgaat gtttcctagc ggatgtttct tttccaaagt aaatctgagt    8580
tattaatcca ccagcatcat tactgtgttg gaatttattt tccctctgt aacatgatca    8640 acaaggcatg ctctgtgttt ccaagatcgc tggggaaatg tttagtaaca tactcaatag    8700
tggaagaggg agagggtggt tgtctccatg tttcctcctg cctgtgctct gttggcccct    8760
ctttttcttt acaaccactt gtaaagaaaa ctgtggacac aaagccaagg tgggggttt     8820 aaaagaggag tctgattgtg gtgccataga ggagttgaca catagaaatt attagacata    8880
tcaaggaggc tggatatagt ttctgtcttt ggtgcttgag aaatgctagc tacattttgc    8940
tggtttgtta gctgccccac ttatctgctc cttcaaatta aggggtatgc ttattttccc    9000
ccagtaggtt tcccctgcat aagcagaatt caccattcat tgcccaaccc tgagctatct    9060
cttgactctt ccatctttga aaaagttca tatgcttttt cttttcccct tccttcctaa     9120
ctgtgcctag aacatctgga gaacatccca gggaccagtg aaaactctgc ttttcgtttc    9180
ctctttaacc tcagcagcat ccctgagaac gaggcgatct cctctgcaga gcttcggctc    9240
ttccgggagc aggtggacca gggccctgat tgggaaaggg gcttccaccg tataaacatt    9300
tatgaggtta tgaagccccc agcagaagtg gtgcctgggc acctcatcac acgactactg    9360
gacacgagac tggtccacca caatgtgaca cggtgggaaa cttttgatgt gagccctgcg    9420
gtccttcgct ggacccggga gaagcagcca aactatgggc tagccattga ggtgactcac    9480
ctccatcaga ctcggaccca ccagggccag catgtcagga ttagccgatc gttacctcaa    9540
gggagtggga attgggccca gctccggccc tcctggtca cctttggcca tgatggccgg     9600
ggccatgcct tgacccgacg ccggagggcc aagcgtagcc ctaagcatca ctcacagcgg    9660
gccaggaaga agaataagaa ctgccggcgc cactcgctct atgtggactt cagcgatgtg    9720
ggctggaatg actggattgt ggccccacca ggctaccagg ccttctactg ccatggggac    9780 tgccccttt cactggctga ccactcaac tcaaccaacc atgccattgt gcagaccctg     9840
gtcaattctg tcaattccag tatccccaaa gcctgttgtg tgcccactga actgagtgcc    9900
```

```
atctccatgc tgtacctgga tgagtatgat aaggtggtac tgaaaaatta tcaggagatg    9960
gtagtagagg gatgtgggtg ccgctgagat caggcagtcc ttgaggatag acagatatac   10020
acaccacaca cacacaccac atacaccaca cacacacgtt cccatccact cacccacaca   10080
ctacacagac tgcttcctta tagctggact tttatttaaa aaaaaaaaaa aaaaaatgga   10140
aaaaatccct aaacattcac cttgacctta tttatgactt tacgtgcaaa tgttttgacc   10200
atattgatca tatattttga caaaatatat ttataactac gtattaaaag aaaaaaataa   10260
aatgagtcat tattttaaag gtaaatcatg atttttttt ctccttaatc ctttctcttt    10320
tccttcgggc tcatctcttt tgaatgaggc ttttttctgt tcaggtgagt tggaggctgg   10380
atggaagtca aaaggtggta cctggaggtg gttaagttgt agggacagga agtaaactgt   10440
tggcagagag agatggtaat tgccagcatg aattgttttc tatttctatt taatgttaac   10500
aaggatgcag tatcctctcc catctggatg acacatgcct tggagaaaca ctgggatgaa   10560
aggagtgtag gtcagattaa agacttcatt tcaggcccct tgtacatctt ctgtttcact   10620
cacctgttga ggtgtatcac agctgagcgt gatgaggtct caaccctaga aaaatgatac   10680
ccacctctgc tttcatgata cctcagggta tctccagtta ttacaggtac caatgtgata   10740
tttccaaatc aaaactaatt tgtacactaa catcataatg tgtgtgtgaa ggcatgtttt   10800
taaacttatt ttttttttct ccaggtagga ctcttttgtt ttttcttttg tcttttttt   10860
tttgaaacaa gttctctctt tgttgcccca ggctggtctt gaactcctgg gctcaagcaa   10920
tcttctcatt tcggcctctt tgggattaca ggcatgcact gctattttgt cttttttttt   10980
tttttgtaac aaataatgta ccctaccttc aaaaagtttg atgactactg ttttaatatg   11040
ccacttgata gaatttccca ttgtttcttg acttttttccc ttgtcctctt ttcccaatgt   11100
gaaggccttc atcaagttta ggatcccaac agattgggct gggtggggggt tgacaatggg   11160
gtcagatact aaagggtcag aatttctaag caggcactgt gaaggtgtcc cactattata   11220
cagaaatctc gag                                                      11233
```

<210> SEQ ID NO 106  
<211> LENGTH: 1723  
<212> TYPE: DNA  
<213> ORGANISM: Homo sapiens  
<220> FEATURE:  
<221> NAME/KEY: misc_feature  
<223> OTHER INFORMATION: BB1=BAR1 Acc. No. NM_000684

<400> SEQUENCE: 106

```
tgctacccgc gcccgggctt ctggggtgtt ccccaaccac ggcccagccc tgccacaccc      60
cccgccccg gcctccgcag ctcggcatgg gcgcgggggt gctcgtcctg ggcgcctccg     120
agcccggtaa cctgtcgtcg gccgcaccgc tccccgacgg cgcggccacc gcggcgcggc     180
tgctggtgcc cgcgtcgccg cccgcctcgt tgctgcctcc cgccagcgaa agccccgagc     240
cgctgtctca gcagtggaca gcgggcatgg gtctgctgat ggcgctcatc gtgctgctca     300
tcgtggcggg caatgtgctg gtgatcgtgg ccatcgccaa gacgccgcgg ctgcagacgc     360
tcaccaacct cttcatcatg tccctggcca gcgccgacct ggtcatgggg ctgctggtgg     420
tgccgttcgg ggccaccatc gtggtgtggg gccgctggga gtacggctcc ttcttctgcg     480
agctgtggac ctcagtggac gtgctgtgcg tgacggccag catcgagacc ctgtgtgtca     540
ttgccctgga ccgctacctc gccatcacct cgccttccg ctaccagagc ctgctgacgc     600
gcgcgcgggc gcggggcctc gtgtgcaccg tgtgggccat ctcggccctg gtgtccttcc     660
```

```
tgcccatcct catgcactgg tggcgggcgg agagcgacga ggcgcgccgc tgctacaacg    720
accccaagtg ctgcgacttc gtcaccaacc gggcctacgc catcgcctcg tccgtagtct    780
ccttctacgt gcccctgtgc atcatggcct tcgtgtacct gcgggtgttc cgcgaggccc    840
agaagcaggt gaagaagatc gacagctgcg agcgccgttt cctcggcggc ccagcgcggc    900
cgccctcgcc ctcgcccctcg cccgtccccg cgcccgcgcc gcgcccggca ccccgcgcc    960
ccgccgccgc cgccgccacc gccccgctgg ccaacgggcg tgcgggtaag cggcggccct   1020
cgcgcctcgt ggcctacgc gagcagaagg cgctcaagac gctgggcatc atcatgggcg   1080
tcttcacgct ctgctggctg cccttcttcc tggccaacgt ggtgaaggcc ttccaccgcg   1140
agctggtgcc cgaccgcctc ttcgtcttct tcaactggct gggctacgcc aactcggcct   1200
tcaaccccat catctactgc cgcagccccg acttccgcaa ggccttccag ggactgctct   1260
gctgcgcgcg cagggctgcc cgccggcgcc acgcgaccca cggagaccgg ccgcgcgcct   1320
cgggctgtct ggcccggccc ggaccccgc catcgcccgg gccgcctcg acgacgacg     1380
acgacgatgt cgtcggggcc acgccgcccg cgcgcctgct ggagccctgg gccggctgca   1440
acggcggggc ggcggcggac agcgactcga gcctggacga gccgtgccgc cccggcttcg   1500
cctcggaatc caaggtgtag ggcccggcgc ggggcgcgga ctccgggcac ggcttcccag   1560
gggaacgagg agatctgtgt ttacttaaga ccgatagcag gtgaactcga agcccacaat   1620
cctcgtctga atcatccgag gcaaagagaa aagccacgga ccgttgcaca aaaaggaaag   1680
tttgggaagg gatgggagag tggcttgctg atgttccttg ttg                     1723

<210> SEQ ID NO 107
<211> LENGTH: 1145
<212> TYPE: DNA
<213> ORGANISM: Homo sapiens
<220> FEATURE:
<221> NAME/KEY: misc_feature
<223> OTHER INFORMATION: IL-6:  Acc. No. X04430

<400> SEQUENCE: 107
aggactggag atgtctgagg ctcattctgc cctcgagccc accgggaacg aaagagaagc     60
tctatctccc ctccaggagc ccagctatga actccttctc cacaagcgcc ttcggtccag    120
ttgccttctc cctggggctg ctcctggtgt tgcctgctgc cttccctgcc ccagtacccc    180
caggagaaga ttccaaagat gtagccgccc cacacagaca gccactcacc tcttcagaac    240
gaattgacaa acaaattcgg tacatcctcg acggcatctc agccctgaga aggagacat    300
gtaacaagag taacatgtgt gaaagcagca agaggcact ggcagaaaac aacctgaacc    360
ttccaaagat ggctgaaaaa gatggatgct ccaatctgg attcaatgag gagacttgcc    420
tggtgaaaat catcactggt cttttggagt ttgaggtata cctagagtac ctccagaaca    480
gatttgagag tagtgaggaa caagccgaga ctgtccagat gagtacaaaa gtcctgatcc    540
agttcctgca gaaaaaggca agaatctag atgcaataac caccctgac ccaaccacaa    600
atgccagcct gctgacgaag ctgcaggcac agaaccagtg ctgcaggac atgcaactc     660
atctcattct gcgcagcttt aaggagttcc tgcagtccag cctgagggct cttcggcaaa    720
tgtagcatgg gcacctcaga ttgttgttgt taatgggcat tccttcttct ggtcagaaac    780
ctgtccactg ggcacagaac ttatgttgtt ctctatggag aactaaaagt atgagcgtta    840
ggacactatt ttaattattt ttaatttatt aatatttaaa tatgtgaagc tgagttaatt    900
tatgtaagtc atattttata tttttaagaa gtaccacttg aaacattta tgtattagtt    960
ttgaaataat aatggaaagt ggctatgcag tttgaatatc ctttgtttca gagccagatc   1020
```

```
atttcttgga aagtgtaggc ttacctcaaa taaatggcta actttataca tattttaaa    1080 gaaatattta tattgtattt atataatgta taaatggttt ttataccaat aaatggcatt    1140
ttaaa                                                                 1145

<210> SEQ ID NO 108
<211> LENGTH: 2063
<212> TYPE: DNA
<213> ORGANISM: Homo sapiens
<220> FEATURE:
<221> NAME/KEY: misc_feature
<223> OTHER INFORMATION: U82535

<400> SEQUENCE: 108
tgccgggcgg taggcagcag caggctgaag ggatcatggt gcagtacgag ctgtgggccg      60
cgctgcctgg cgcctccggg gtcgccctgg cctgctgctt cgtggcggcg gccgtggccc     120
tgcgctggtc cgggcgccgg acggcgcggg gcgcggtggt ccgggcgcga cagaagcagc     180
gagcgggcct ggagaacatg gacagggcgg cgcagcgctt ccggctccag aacccagacc     240
tggactcaga ggcgctgcta gccctgcccc tgcctcagct ggtgcagaag ttacacagta     300
gagagctggc ccctgaggcc gtgctcttca cctatgtggg aaaggcctgg gaagtgaaca     360
aagggaccaa ctgtgtgacc tcctatctgg ctgactgtga gactcagctg tctcaggccc     420
caaggcaggg cctgctctat ggcgtccctg tgagcctcaa ggagtgcttc acctacaagg     480
gccaggactc cacgctgggc ttgagcctga atgaaggggt gccggcggag tgcgacagcg     540
tagtggtgca tgtgctgaag ctgcagggtg ccgtgccctt cgtgcacacc aatgttccac     600
agtccatgtt cagctatgac tgcagtaacc ccctctttgg ccagaccgtg aacccatgga     660
agtcctccaa aagcccaggg ggctcctcag ggggtgaagg ggccctcatc gggtctggag     720
gctcccccct gggcttaggc actgatatcg gaggcagcat ccgcttcccc tcctccttct     780
gcggcatctg cggcctcaag cccacaggga accgcctcag caagagtggc ctgaagggct     840
gtgtctatgg acaggaggca gtgcgtctct ccgtgggccc catggcccgg acgtggagaa     900
gcctggcact gtgcctgcga gccctgctgt gcgaggacat gttccgcttg gaccccactg     960
tgcctccctt gccttcaga aagaggtct acaccagctc tcagccctg cgtgtggggt    1020
```

```
actatgagac tgacaactat accatgccct ccccggccat gaggcgggcc gtgctggaga    1080
ccaaacagag ccttgaggct gcggggcaca cgctggttcc cttcttgcca agcaacatac    1140
cccatgctct ggagaccctg tcaacaggtg ggctcttcag tgatggtggc cacaccttcc    1200
tacagaactt caaaggtgat ttcgtggacc cctgcctggg ggacctggtc tcaattctga    1260
agcttcccca atggcttaaa ggactgctgg ccttcctggt gaagcctctg ctgccaaggc    1320
tgtcagcttt cctcagcaac atgaagtctc gttcggctgg aaaactctgg gaactgcagc    1380
acgagatcga ggtgtaccgc aaaaccgtga ttgcccagtg ggagcgctg gacctggatg    1440 tggtgctgac ccccatgctg gccctgctc tggacttgaa tgccccaggc agggccacag    1500
gggccgtcag ctacactatg ctgtacaact gcctggactt ccctgcaggg gtggtgcctg    1560
tcaccacggt gactgctgag gacgaggccc agatggaaca ttacaggggc tactttgggg    1620
atatctggga caagatgctg cagaaggca tgaagaagag tgtggggctg ccggtggccg    1680
tgcagtgtgt ggctctgccc tggcaagaag agttgtgtct gcggttcatg cgggaggtgg    1740
agcgactgat gaccctgaa aagcagtcat cctgatggct ctggctccag aggacctgag    1800
actcacactc tctgcagccc agcctagtca gggcacagct gccctgctgc cacagcaagg    1860
```

```
aaatgtcctg catggggcag aggcttccgt gtcctctccc ccaaccccct gcaagaagcg    1920
ccgactccct gagtctggac ctccatccct gctctggtcc cctctcttcg tcctgatccc    1980
tccaccccca tgtggcagcc catgggtatg acataggcca aggcccaact aacagtcaag    2040
aaacaaaaaa aaaaaaaaaa aaa                                           2063

<210> SEQ ID NO 109
<211> LENGTH: 2729
<212> TYPE: DNA
<213> ORGANISM: Homo sapiens
<220> FEATURE:
<221> NAME/KEY: misc_feature
<223> OTHER INFORMATION: ACAT-1: Acc. No. XM_031119

<400> SEQUENCE: 109
agcttagcag gcgacgttgc gggccctggg cgccaggaga gcttcccgga gtcgaccttc      60
ctgctggctg ctctgtgacc gcttcccggc tctgccctct tggccgaagt gcccgctgcc     120
gggcgcgggc ctcagacaat acaatggtgg gtgaagagaa gatgtctcta agaaaccggc     180
tgtcaaagtc cagggaaaat cctgaggaag atgaagacca gagaaaccct gcaaggagt     240 ccctagagac acctagtaat ggtcgaattg acataaaaca gttgatagca agaagataa     300 agttgacagc agaggcagag gaattgaagc cattttttat gaaggaagtt ggcagtcact     360
ttgatgattt tgtgaccaat ctcattgaaa agtcagcatc attagataat ggtgggtgcg     420
ctctcacaac cttttctgtt cttgaaggag agaaaaacaa ccatagagcg aaggatttga     480
gagcacctcc agaacaagga aagatttta ttgcaaggcg ctctctctta gatgaactgc     540
ttgaagtgga ccacatcaga acaatatatc acatgtttat tgccctcctc attctcttta     600
tcctcagcac acttgtagta gattacattg atgaaggaag gctggtgctt gagttcagcc     660
tcctgtctta tgcttttggc aaatttccta ccgttgtttg gacctggtgg atcatgttcc     720
tgtctacatt tcagttccc tattttctgt tcaacattg ggccactggc tatagcaaga     780
gttctcatcc gctgatccgt tctctcttcc atggctttct tttcatgatc ttccagattg     840
gagttctagg ttttggacca acatatgttg tgttagcata tactgcca ccagcttccc     900 ggttcatcat tatattcgag cagattcgtt ttgtaatgaa ggcccactca tttgtcagag     960
agaacgtgcc tcgggtacta aattcagcta aggagaaatc aagcactgtt ccaatacca    1020 cagtcaacca gtatttgtac ttcttatttg ctcctaccct tatctaccgt gacagctatc    1080
ccaggaatcc cactgtaaga tggggttatg tcgctatgaa gtttgcacag gtctttggtt    1140
gcttttctta tgtgtactac atctttgaaa ggctttgtgc ccccttgttt cggaatatca    1200
aacaggagcc cttcagcgct cgtgttctgg tcctatgtgt atttaactcc atcttgccag    1260
gtgtgctgat tctcttcctt actttttttg ccttttttgca ctgctggctc aatgcctttg    1320
ctgagatgtt acgctttggt gacaggatgt tctataagga ttggtggaac tccacgtcat    1380
actccaacta ttatagaacc tggaatgtgg tggtccatga ctggctatat tactatgctt    1440
acaaggactt tctctggttt ttctccaaga gattcaaatc tgctgccatg ttagctgtct    1500
ttgctgtatc tgctgtagta cacgaatatg ccttggctgt ttgcttgagc tttttctatc    1560
ccgtgctctt cgtgctcttc atgttctttg gaatggcttt caacttcatt gtcaatgata    1620
gtcggaaaaa gccgatttgg aatgttctga tgtggacttc tctttttcttg ggcaatggag    1680 tcttactctg cttttattct caagaatggt atgcacgtca gcactgtcct ctgaaaaatc    1740
ccacattttt ggattatgtc cggccacgtt cctggacttg tcgttacgtg ttttagaagc    1800
ttggactttg tttcctcctt gtcactgaag attgggtagc tccctgattt ggagccagct    1860
```

-continued

```
gtttccagtt gttactgaag ttatctgtgt tatttggacc actccaggct ttacagatga   1920
ctcactccat tcctaggtca cttgaagcca aactgttgga agttcactgg agtcttgtac   1980
acttaagcag agcagaactt tttttgtggg gctgggtggg gggagaagac cgactaacag   2040
ctgaagtaat gacagattgt tgctgggtca tatcagcttt atcccttggt aattatatct   2100
gttttgtttc ttgactctgt ccaatcagag aataaacatc atagtttctt ggccactgaa   2160
ttagccaaaa cacttaggaa gaaatcactt aaatacctct ggcttagaaa ttttttcatg   2220
cacactgttg gaatgtatgc taattgaaca tgcaattggg gaagaaaaaa tgtagaatga   2280
tttttgctat ttctagtaga aagaaaatgt ctgttttcca aagataatgt tatacatcct   2340
attttgtaat ttttttgaaa aaagttcaat gttcagtttt ccttagtttt taccttgttt   2400
tctctatagg tcatgatttc tgtgaagcaa aaagatgcct tttaccatga attcttgagt   2460
ttacatcaat aatattgtat attaagggga tcagaagtag gaaggaaaaa ataagagata   2520
gcagaggaaa aagaaaaaca tttcctctta aacttctga agtaatttgt aaaaaagatt   2580
tgtagagtca atcatgtgtt taaattattt tatcacaaac ttaacatgga agatattcct   2640 ttttaactt gtggtaactt ctttgaagtt atttagaaat atcctttgga acaattattt   2700
tattgtctaa taaatattga cttctcttg                                    2729
```

<210> SEQ ID NO 110
<211> LENGTH: 3779
<212> TYPE: DNA
<213> ORGANISM: Homo sapiens
<220> FEATURE:
<221> NAME/KEY: misc_feature
<223> OTHER INFORMATION: IBAT: Acc. No. NM_000452

<400> SEQUENCE: 110

```
ttctattgaa agggaaatgg gagaacaata tgtgttccta tggctcagtc cctataagat     60
tctgtactat tcagagttga ttttaagtgt cacttaactg aaattatcca acaaaccttc    120
atggcatgaa acattaacac agctctttt atatggcatg gttcctatgg ctcaatccct    180
ataagattct gtactagttc agagttgatt ttaaaagtca cttaactgaa attatccaac    240
aaaccctcga ggacattaaa cattaacgtg gctctttta tatggcatgg ttcattatca    300
tgccaataaa tgattaatcg taactctctg tcttgaccaa taattttgct ggacttttgt    360
gattcacaac gtgctctgtg ttgtaatgct acctcttgaa actgacatcc tagctttatt    420
gttttttatt acttccctaa ggtggctttc aaaagagaca ccaagtgaca tatttttagg    480 agggggtttaa aagtttgatg gggtagaagt aaacgttgct taactcaacc agcagcagag    540
ccagggccca gggaccagcg cttctgtgga cttggccttt ccagcagcag acccagcaat    600
gaatgatccg aacagctgtg tggacaatgc aacagtttgc tctggtgcat cctgtgtggt    660
acctgagagc aatttcaata acatcctaag tgtggtccta agtacggtgc tgaccatcct    720
gttggccttg gtgatgttct ccatgggatg caacgtggaa atcaagaaat ttctagggca    780
cataaagcgg ccgtggggca tttgtgttgg cttcctctgt cagtttggaa tcatgccct    840 cacaggattc atcctgtcgg tggcctttga catcctcccg ctccaggccg tagtggtgct    900
cattatagga tgctgccctg gaggaactgc ctccaatatc ttggcctatt gggtcgatgg    960
cgacatggac ctgagcgtca gcatgaccac atgctccaca ctgcttgccc tcggaatgat   1020
gccgctgtgc ctcctttatct ataccaaaat gtgggtcgac tctgggagca tcgtaattcc   1080
ctatgataac ataggtacat ctctggttgc tctcgttgtt cctgtttcca ttggaatgtt   1140
```

```
tgttaatcac aaatggcccc aaaaagcaaa gatcatactt aaaattgggt ccatcgcggg    1200
cgccatcctc attgtgctca tagctgtggt tggaggaata ttgtaccaaa gcgcctggat    1260
cattgctccc aaactgtgga ttataggaac aatatttcct gtggcgggtt actccctggg    1320
gtttcttctg gctagaattg ctggtctacc ctggtacagg tgccgaacgg ttgcttttga    1380
aacggggatg cagaacacgc agctatgttc caccatcgtt cagctctcct tcactcctga    1440
ggagctcaat gtcgtattca ccttcccgct catctacagc attttccagc tcgcctttgc    1500
cgcaatattc ttaggatttt atgtggcata caagaaatgt catggaaaaa acaaggcaga    1560
aattccagag agcaaagaaa atggaacgga gccagagtca tcgttttata aggcaaatgg    1620
aggatttcaa cctgacgaaa agtagacatc aagtggacaa acagacgag ttccaaatta    1680 cgttcttaaa ccgtaactat atttaattat ttgttttggt aggacagttg gcagaaaaga    1740
gttaaagtga aaattggaat tcattggaa ttcatgtatt ggtttcagta ccaagtgact    1800
ggtggcccaa ttctttaatg ggacaaatat tgtttcctat atatatgtat atgtttttata    1860 tatgtatgta tactcatata gatatattgt cattgaaata ttcccccaaa atattctcag    1920
actaaacctg acatagggaa caccgagaat gaaaacatcg ttaacaccaa aactgaattc    1980
ttatgcagaa tttcctagcc catagatgac aacctgagtt tctgtatgtt aaagtagatg    2040
taatgaatta ttattattac agtggtcacg attttcttca gtgtttatga ttataaaaat    2100
tgacatgaac atctttcact gacattttaa tcattatttt aaaagctttg caacctatat    2160
atttatataa ctttgtaata taacatgggc aaatatctga cttcagtatt tttaaaaagt    2220
tgccttctcc agtggcagtc caaaagcaga aatgagagga aattattaca aaatagaatt    2280
caataaccat attggatgca ggctcttaac tcagcaggga tatcgtacat ctattgctct    2340
acctcagggg tccagtgata cccactagat cttccaagga aaaacataat tctttcaaac    2400
ggtgtgtatt tggcaaagag ctcttcaaat ctgggagagg gacttcctca aggttttcct    2460
gtgtgcagtg gatccacata gctaatatga cagctagtca gttgacaggg accacccaca    2520
gtaagcacca tggtcaggga ggtggcagga ggtgcaaaga cagaagtatt gagagaaaca    2580
ccaagactct agtggaggaa ttaattcaat gggagatagt ataaaataca tagaaaacac    2640
aagtaacaga aacctggttg aaatgcttaa ctagagtcaa ttagatgtgc aggagtaagt    2700
agtataagaa gaatcaagtc cgagagtgat caggaaatga gtattaaaca gtatttgaaa    2760
cagagaacgt gtcccagggc ccaaaagtca gaagggcccc accagccagg aaagttgttt    2820
caatgctgta gtaggtgta gccaaggaa gccaggacta tctgatatac ggtagcaggg    2880
gtttacggct gccaggggaa aataactcat caagtgttgg actttcaatt ataagatcga    2940
atttaatttc ctttccctca ttctgcagca atcagaatac acaatcttaa ccactcggtc    3000
cttagtggtt ttgttccatt ttgcattggg tattttcact gcctcataga gtctatttca    3060
agtgtttggc tgaaagggct ttttgcattt gcatgttctg agttcagatt ctgctggtgc    3120
acccaagcat tatgggaaca ggaactcaac ttagctcttc cagtagaggg gtgagggatt    3180
ctgcttttca aattcataac attgatcttt ttatgcaaga tttccattta cagttgaata    3240
agtacttcat attttttccat cattagacaa atacaaaatg gactaaataa ttttaagaga    3300
tagtggaggc agcaggggt acagacttcc ttcttagaga gtgtcagaga atatgctccc    3360
aatggtggaa aggaagattt acagtctagc ggctaagtac ctcctacaca tttcccatca    3420
atcagaaaat agacaggtac actaaaggga cctgagaact cctcttgtaa tttcaacaca    3480
cccaaaatca agggcctgga tgccagcagc tgcagcaagc aggttttttcc tccctgttga    3540
```

| | |
|---|---|
| gcaagacagg tgaggcaaga taggacttgg ctttcttaca tgatgcggta acttgtgact | 3600 |
| tgagtctttt tccctaattt gctagtggga agaaaaatag ctgagctttc taaaatgata | 3660 |
| gctctctatt tttaaatgaa tttgaaaagt cgattaaatt atgtatttta ttgcctctga | 3720 |
| gtatcatatt aaatgaatat tttattttaa aggcttaaat aaatgaaaat gattttttgt | 3779 |

<210> SEQ ID NO 111
<211> LENGTH: 4067
<212> TYPE: DNA
<213> ORGANISM: Homo sapiens
<220> FEATURE:
<221> NAME/KEY: misc_feature
<223> OTHER INFORMATION: U28749

<400> SEQUENCE: 111

| | |
|---|---|
| cttgaatctt ggggcaggaa ctcagaaaac ttccagcccg ggcagcgcgc gcttggtgca | 60 |
| agactcagga gctagcagcc cgtccccctc cgactctccg gtgccgccgc tgcctgctcc | 120 |
| cgccacccta ggaggcgcgg tgccacccac tactctgtcc tctgcctgtg ctccgtgccc | 180 |
| gaccctatcc cggcggagtc tccccatcct cctttgcttt ccgactgccc aaggcacttt | 240 |
| caatctcaat ctcttctctc tctctctctc tctctctgtc tctctctctc tctctctctc | 300 |
| tctctctctc gcagggtggg gggaagagga ggaggaattc tttccccgcc taacatttca | 360 |
| agggacacaa ttcactccaa gtctcttccc tttccaagcc gcttccgaag tgctcccggt | 420 |
| gcccgcaact cctgatccca acccgcgaga ggagcctctg cgacctcaaa gcctctcttc | 480 |
| cttctccctc gcttccctcc tcctcttgct acctccacct ccaccgccac ctccacctcc | 540 |
| ggcacccacc caccgccgcc gccgccaccg gcagcgcctc ctcctctcct cctcctcctc | 600 |
| ccctcttctc tttttggcag ccgctggacg tccgtgttg atggtggcag cggcggcagc | 660 |
| ctaagcaaca gcagccctcg cagcccgcca gctcgcgctc gccccgccgg cgtccccagc | 720 |
| cctatcacct catctcccga aggtgctggg gcagctccgg ggcggtcgag gcgaagcggc | 780 |
| tgcagcggcg gtagcggcgg cgggaggcag gatgagcgca cgcggtgagg gcgcggggca | 840 |
| gccgtccact tcagcccagg gacaacctgc cgccccagcg cctcagaaga gaggacgcgg | 900 |
| ccgcccagg aagcagcagc aagaaccaac cggtgagccc tctcctaaga gacccagggg | 960 |
| aagacccaaa ggcagcaaaa acaagagtcc ctctaaagca gctcaaaaga agcagaagc | 1020 |
| cactggagaa aaacggccaa gaggcagacc taggaaatgg ccacaacaag ttgttcagaa | 1080 |
| gaagcctgct caggaggaaa ctgaagagac atcctcacaa gagtctgccg aagaggacta | 1140 |
| gggggcgcaa cgttcgattt ctacctcagc agcagttgga tcttttgaag ggagaagaca | 1200 |
| ctgcagtgac cacttattct gtattgccat ggtctttcca ctttcatctg gggtggggtg | 1260 |
| gggtggggtg ggggaggggg gggtggggtg gggagaaatc acataacctt aaaaaggact | 1320 |
| atattaatca ccttctttgt aatcccttca cagtcccagg tttagtgaaa actgctgta | 1380 |
| aacacagggg acacagctta caatgcaac ttttaattac tgtttctttt tttcttaacc | 1440 |
| tactaatagt ttgttgatct gataagcaag agtgggcggg tgagaaaaac cgaattgggt | 1500 |
| ttagtcaatc actgcactgc atgcaaacaa gaaacgtgtc acacttgtga cgtcgggcat | 1560 |
| tcatatagga agaacgcggt gtgtaacact gtgtacacct caaataccac cccaacccac | 1620 |
| tccctgtagt gaatcctctg tttagaacac caaagataag gactagatac tactttctct | 1680 |
| ttttcgtata atcttgtaga cacttacttg atgattttta acttttttatt tctaaatgag | 1740 |
| acgaaatgct gatgtatcct ttcattcagc taacaaacta gaaaaggtta tgttcatttt | 1800 |
| tcaaaaaggg aagtaagcaa acaaatattg ccaactcttc tatttatgga tatcacacat | 1860 |

```
atcagcagga gtaataaatt tactcacagc acttgttttc aggacaacac ttcattttca    1920
ggaaatctac ttcctacaga gccaaaatgc catttagcaa taaataacac ttgtcagcct    1980
cagagcattt aaggaaacta gacaagtaaa attatcctct ttgtaattta atgaaaaggt    2040
acaacagaat aatgcatgat gaactcacct aattatgagg tgggaggagc gaaatctaaa    2100
tttcttttgc tatagttata catcaattta aaaagcaaaa aaaaaaaggg gggggcaatc    2160
tctctctgtg tctttctctc tctctctccc tctccctctc tcttttcatg tgtatcagtt    2220
tccatgaaag acctgaatac cacttacctc aaattaagca tatgtgttac ttcaagtaat    2280
acgttttgac ataagatggt tgaccaaggt gcttttcttc ggcttgagtt caccatctct    2340
tcattcaaac tgcactttta gccagagatg caatatatcc ccactactca atactacctc    2400
tgaatgttac aacgaattta cagtctagta cttattacat gctgctatac acaagcaatg    2460
caagaaaaaa acttactggg taggtgattc taatcatctg cagttctttt tgtacactta    2520
attacagtta aagaagcaat ctccttactg tgtttcagca tgactatgta tttttctatg    2580 ttttttttaat taaaaatttt taaaatactt gtttcagctt ctctgctaga tttctacatt    2640
aacttgaaaa ttttttaacc aagtcgctcc taggttctta aggataattt tcctcaatca    2700
cactacacat cacacaagat ttgactgtaa tatttaaata ttaccctcca agtctgtacc    2760
tcaaatgaat tctttaagga gatggactaa ttgacttgca aagacctacc tccagacttc    2820
aaaaggaatg aacttgttac ttgcagcatt catttgtttt ttcaatgttt gaaatagttc    2880
aaactgcagc taaccctagt caaaactatt tttgtaaaag acatttgata gaaaggaaca    2940 cgttttttaca tacttttgca aaataagtaa ataataaata aaataaagcc aaccttcaaa    3000
gaacttgaag ctttgtaggt gagatgcaac aagccctgct tttgcataat gcaatcaaaa    3060
atatgtgttt ttaagattag ttgaatataa gaaaatgctt gacaaatatt ttcatgtatt    3120
ttacacaaat gtgattttg taatatgtct caaccagatt tattttaaac gcttcttatg    3180
tagagttttt atgcctttct ctcctagtga gtgtgctgac ttttttaacat ggtattatca    3240 actgggccag gaggtagttt ctcatgacgg cttttgtcag tatggctttt agtactgaag    3300
ccaaatgaaa ctcaaaacca tctctcttcc agctgcttca gggaggtagt ttcaaaggcc    3360
acatacctct ctgagactgg cagatcgctc actgttgtga atcaccaaag gagctatgga    3420
gagaattaaa actcaacatt actgttaact gtgcgttaaa taagcaaata aacagtggct    3480
cataaaaata aaagtcgcat tccatatctt tggatgggcc ttttagaaac ctcattggcc    3540
agctcataaa atggaagcaa ttgctcatgt tggccaaaca tggtgcaccg agtgatttcc    3600
atctctggta aagttacact tttatttcct gtatgttgta caatcaaaac acactactac    3660
ctcttaagtc ccagtatacc tcattttca tactgaaaaa aaaagcttgt ggccaatgga    3720
acagtaagaa catcataaaa tttttatata tatagtttat ttttgtggga gataaatttt    3780
ataggactgt tctttgctgt tgttggtcgc agctacataa gactggacat ttaacttttc    3840
taccatttct gcaagttagg tatgtttgca ggagaaaagt atcaagacgt ttaactgcag    3900
ttgactttct ccctgttcct ttgagtgtct tctaacttta ttctttgttc tttatgtaga    3960
attgctgtct atgattgtac tttgaatcgc ttgcttgttg aaaatatttc tctagtgtat    4020
tatcactgtc tgttctgcac aataaacata acagcctctg tgatccc                  4067
```

<210> SEQ ID NO 112
<211> LENGTH: 511
<212> TYPE: DNA
<213> ORGANISM: Homo sapiens

```
<220> FEATURE:
<221> NAME/KEY: misc_feature
<223> OTHER INFORMATION: NM_016362

<400> SEQUENCE: 112
gcaggcccac ctgtctgcaa cccagctgag gccatgccct ccccagggac cgtctgcagc        60
ctcctgctcc tcggcatgct ctggctggac ttggccatgg caggctccag cttcctgagc       120
cctgaacacc agagagtcca gcagagaaag gagtcgaaga agccaccagc caagctgcag       180
ccccgagctc tagcaggctg gctccgcccg gaagatggag gtcaagcaga aggggcagag       240
gatgaactgg aagtccggtt caacgccccc tttgatgttg aatcaagct gtcaggggtt        300 cagtaccagc agcacagcca ggccctgggg aagtttcttc aggacatcct ctgggaagag       360
gccaaagagg ccccagccga caagtgatcg cccacaagcc ttactcacct ctctctaagt       420
ttagaagcgc tcatctggct tttcgcttgc ttctgcagca actcccacga ctgttgtaca       480
agctcaggag gcgaataaat gttcaaactg t                                      511

<210> SEQ ID NO 113
<211> LENGTH: 2268
<212> TYPE: DNA
<213> ORGANISM: Homo sapiens
<220> FEATURE:
<221> NAME/KEY: misc_feature
<223> OTHER INFORMATION: S77410

<400> SEQUENCE: 113
accccaggca gcagcgagtg acaggacgtc tggaccggcg cgccgctagc agctctgccg        60
ggccgcggcg gtgatcgatg gggagcggct ggagcggacc cagcgagtga gggcgcacag       120
ccgggacgcc gaggcggcgg gcgggagacc cgcaccagcg cagccggccc tcggcgggac       180
gtgacgcagc gcccggggcg cgggtttgat atttgacaaa ttgatctaaa atggctgggt       240
ttttatctga ataactcact gatgccatcc cagaaagtcg gcaccaggtg tatttgatat       300
agtgtttgca acaaattcga cccaggtgat caaaatgatt ctcaactctt ctactgaaga       360
tggtattaaa agaatccaag atgattgtcc caaagctgga aggcataatt acatatttgt       420
catgattcct actttataca gtatcatctt tgtggtggga atatttggaa acagcttggt       480
ggtgatagtc atttactttt atatgaagct gaagactgtg gccagtgttt ttcttttgaa       540
tttagcactg gctgacttat gcttttact gactttgcca ctatgggctg tctacacagc        600
tatggaatac cgctggccct ttggcaatta cctatgtaag attgcttcag ccagcgtcag       660
tttcaacctg tacgctagtg tgtttctact cacgtgtctc agcattgatc gatacctggc       720
tattgttcac ccaatgaagt cccgccttcg acgcacaatg cttgtagcca aagtcacctg       780
catcatcatt tggctgctgg caggcttggc cagtttgcca gctataatcc atcgaaatgt       840 attttttcatt gagaacacca atattacagt ttgtgctttc cattatgagt cccaaaattc       900 aaccccttccg atagggctgg gcctgaccaa aaatatactg ggtttcctgt ttcctttttct      960 gatcattctt acaagttata ctcttatttg gaaggcccta agaaggctt atgaaattca      1020 gaagaacaaa ccaagaaatg atgatatttt taagataatt atggcaattg tgcttttctt      1080
tttcttttcc tggattcccc accaaatatt cactttctg gatgtattga ttcaactagg      1140
catcatacgt gactgtagaa ttgcagatat tgtggacacg gccatgccta tcaccatttg      1200
tatagcttat tttaacaatt gcctgaatcc tctttttat ggctttctgg ggaaaaaatt      1260
taaaagatat tttctccagc ttctaaaata tattcccca aaagccaaat cccactcaaa      1320
cctttcaaca aaaatgagca cgctttccta ccgcccctca gataatgtaa gctcatccac      1380
```

```
caagaagcct gcaccatgtt ttgaggttga gtgacatgtt cgaaacctgt ccataaagta    1440
attttgtgaa agaaggagca agagaacatt cctctgcagc acttcactac caaatgagca    1500
ttagctactt ttcagaattg aaggagaaaa tgcattatgt ggactgaacc gactttctca    1560
aagctctgaa caaaagcttt tctttccttt tgcaacaaga caaagcaaag ccacattttg    1620
cattagacag atgacggctg ctcgaagaac aatgtcagaa actcgatgaa tgtgttgatt    1680
tgagaaattt tactgacaga aatgcaatct ccctagcctg cttttgtcct gttatttttt    1740
atttccacat aaaggtattt agaatatatt aaatcgttag aggagcaaca ggagatgaga    1800
gttccagatt gttctgtcca gtttccaaag ggcagtaaag ttttcgtgcc ggttttcagc    1860
tattagcaac tgtgctacac ttgcacctgg tactgcacat tttgtacaaa gatatgctaa    1920
gcagtagtcg tcaagttgca gatctttttg tgaaattcaa cctgtgtctt ataggtttac    1980
actgccaaaa caatgcccgt aagatggctt atttgtataa tggtgttact aaagtcacat    2040
ataaaagtta aactacttgt aaaggtgctg cactggtccc aagtagtagt gtcctcctag    2100
tatattagtt tgatttaata tctgagaagt gtatatagtt tgtggtaaaa agattatata    2160
tcataaagta tgccttcctg tttaaaaaaa gtatatattc tacacatata tatatatgta    2220
tatctatatc tctaaactgc tgttaattga ttaaaatctg gcaaagtt                 2268
```

<210> SEQ ID NO 114
<211> LENGTH: 785
<212> TYPE: DNA
<213> ORGANISM: Homo sapiens
<220> FEATURE:
<221> NAME/KEY: misc_feature
<223> OTHER INFORMATION: XM_166457

<400> SEQUENCE: 114

```
gcgcgagccg cgccggcccc ggtcgggcct ccgaaaccat gaactttctg ctgtcttggg      60
tgcattggag ccttgccttg ctgctctacc tccaccatgc caagtggtcc caggctgcac     120
ccatggcaga aggaggaggg cagaatcatc acgaagtggt gaagttcatg gatgtctatc     180
agcgcagcta ctgccatcca atcgagaccc tggtggacat cttccaggag taccctgatg     240
agatcgagta catcttcaag ccatcctgtg tgcccctgat gcgatgcggg ggctgctgca     300
atgacgaggg cctggagtgt gtgcccactg aggagtccaa catcaccatg cagattatgc     360
ggatcaaacc tcaccaaggc cagcacatag gagagatgag cttcctacag cacaacaaat     420
gtgaatgcag accaaagaaa gatagagcaa gacaagaaaa aaaatcagtt cgaggaaagg     480
gaaaggggca aaaacgaaag cgcaagaaat cccggtataa gtcctggagc gtgtacgttg     540
gtgcccgctg ctgtctaatg ccctggagcc tccctggccc ccatccctgt gggccttgct     600
cagagcggag aaagcatttg tttgtacaag atccgcagac gtgtaaatgt tcctgcaaaa     660
acacagactc gcgttgcaag gcgaggcagc ttgagttaaa cgaacgtact tgcagatgtg     720
acaagccgag gcggtgagcc gggcaggagg aaggagcctc cctcagggtt tcgggaacca     780
gatct                                                                 785
```

<210> SEQ ID NO 115
<211> LENGTH: 8460
<212> TYPE: DNA
<213> ORGANISM: Homo sapiens
<220> FEATURE:
<221> NAME/KEY: misc_feature
<223> OTHER INFORMATION: U29344
<220> FEATURE:
<221> NAME/KEY: misc_feature
<222> LOCATION: (1)..(8460)
<223> OTHER INFORMATION: n can be a or c or g or t

<400> SEQUENCE: 115

| | | | | | |
|---|---|---|---|---|---|
| cggccgtcga | cacggcagcg | gccccggcct | ccctctccgc | cgcgcttcag | cctcccgctc | 60 |
| cgccgcgctc | cagcctcgct | ctccgccgcc | cgcaccgccg | cccgcgccct | caccagagca | 120 |
| gccatggagg | aggtggtgat | tgccggcatg | tccgggaagc | tgccagagtc | ggagaacttg | 180 |
| caggagttct | gggacaacct | catcggcggt | gtggacatgg | tcacggacga | tgaccgtcgc | 240 |
| tggaaggcgg | ggctctacgg | cctgcccgg | cggtccggca | agctgaagga | cctgtctagg | 300 |
| tttgatgcct | ccttcttcgg | agtccacccc | aagcaggcac | acacgatgga | ccctcagctg | 360 |
| cggctgctgc | tggaagtcac | ctatgaagcc | atcgtggacg | gaggcatcaa | cccagattca | 420 |
| ctccgaggaa | cacacactgg | cgtctgggtg | ggcgtgagcg | gctctgagac | ctcggaggcc | 480 |
| ctgagccgag | accccgagac | actcgtgggc | tacagcatgg | tgggctgcca | gcgagcgatg | 540 |
| atggccaacc | ggctctcctt | cttcttcgac | ttcagagggc | ccagcatcgc | actggacaca | 600 |
| gcctgctcct | ccagcctgat | ggccctgcag | aacgcctacc | aggccatcca | cagcgggcag | 660 |
| tgccctgccg | ccatcgtggg | gggcatcaat | gtcctgctga | agcccaacac | ctccgtgcag | 720 |
| ttcttgaggc | tggggatgct | cagccccgag | ggcacctgca | aggccttcga | cacagcgggg | 780 |
| aatgggtact | gccgctcgga | gggtgtggtg | ccgtcctgc | tgaccaagaa | gtccctggcc | 840 |
| cggcgggtgt | acgccaccat | cctgaacgcc | ggcaccaata | cagatggctt | caaggagcaa | 900 |
| ggcgtgacct | tcccctcagg | ggatatccag | gagcagctca | tccgctcgtt | gtaccagtcg | 960 |
| gccggagtgg | cccctgagtc | atttgaatac | atcgaagccc | acggcacagg | caccaaggtg | 1020 |
| ggcgaccccc | aggagctgaa | tggcatcacc | cgagccctgt | cgccaccccg | ccaggagccg | 1080 |
| ctgctcatcg | gctccaccaa | gtccaacatg | gggcacccgg | agccagcctc | ggggctggca | 1140 |
| gccctggcca | aggtgctgct | gtccctggag | cacgggctct | gggcccccaa | cctgcacttc | 1200 |
| catagcccca | accctgagat | cccagcgctg | ttggatgggc | ggctgcaggt | ggtggaccag | 1260 |
| cccctgcccg | tccgtggcgg | caacgtgggc | atcaactcct | ttggcttcgg | gggctccaac | 1320 |
| gtgcacatca | tcctgaggcc | caacacgcag | ccgccccccg | cacccgcccc | acatgccacc | 1380 |
| ctgccccgtc | tgctgcgggc | cagcggacgc | acccctgagg | ccgtgcagaa | gctgctggag | 1440 |
| cagggcctcc | ggcacagcca | ggacctggct | ttcctgagca | tgctgaacga | catcgcgctg | 1500 |
| tccccgacca | ccgccatgcc | cttccgtggc | tacgctgtgc | tgggtggtga | gcgcggtggc | 1560 |
| ccagaggtgc | agcaggtgcc | cgctggcgag | cgcccgctct | ggttcatctg | ctctgggatg | 1620 |
| ggcacacagt | ggcgcgggat | ggggctgagc | ctcatgcgcc | tggaccgctt | ccgagattcc | 1680 |
| atcctacgct | ccgatgaggc | tgtgaaccga | ttcggcctga | aggtgtcaca | gctgctgctg | 1740 |
| agcacagacg | agagcacctt | tgatgacatc | gtccattcgt | ttgtgagcct | gactgccatc | 1800 |
| cagataggcc | tcatagacct | gctgagctgc | atggggctga | ggcagatgg | catcgtcggc | 1860 |
| cactccctgg | ggaggtggc | ctgtggctac | gccgacggct | gcctgtccca | ggaggaggcc | 1920 |
| gtcctcgctg | cctactggag | gggacagtgc | atcaaagaag | cccatctccc | gccgggcgcc | 1980 |
| atggcagccg | tgggcttgtc | ctgggaggag | tgtaaacagc | gctgcccccc | ggcggtggtg | 2040 |
| cccgcctgcc | acaactccaa | ggacacagtc | accatctcgg | gacctcaggc | cccggtgttt | 2100 |
| gagttcgtgg | agcagctgag | gaaggagggt | gtgtttgcca | aggaggtgcg | gaccggcggt | 2160 |
| atggccttcc | actcctactt | catggaggcc | atcgcacccc | cactgctgca | ggagctcaag | 2220 |
| aaggtgatcc | gggagccgaa | gccacgttca | gcccgctggc | tcagcacctc | tatccccgag | 2280 |

```
gcccagtggc acagcagcct ggcacgcacg tcctccgccg agtacaatgt caacaacctg    2340
gtgagccctg tgctgttcca ggaggccctg tggcacgtgc ctgagcacgc ggtggtgctg    2400
gagatcgcgc cccacgccct gctgcaggct gtcctgaagc gtggcctgaa gccgagctgc    2460
accatcatcc ccctgatgaa gaaggatcac agggacaacc tggagttctt cctggccggc    2520
atccggaggc tgcacctctc aggcatcgac gccaaccccs atgccttgtt cccacctgtg    2580
gagttcccag ctccccgagg aactcccctc atctccccac tcatcaagtg ggaccacagc    2640
ctggcctggg acgtgccggc cgccgaggac ttccccaacg gttcaggttc ccctcagcc     2700 gccatctaca acatcgacac cagctccgag tctcctgacc actacctggt ggaccacacc    2760
ctcgacggtc gcgtcctctt ccccgccact ggctacctga gcatagtgtg gaagacgctg    2820
gcccgacccc tgggcctggg cgtcgagcag ctgcctgtgg tgtttgagga tgtggtgctg    2880
caccaggcca ccatcctgcc caagactggg acagtgtccc tggaggtacg gctcctggag    2940
gcctcccgtg ccttcgaggt gtcagagaac ggcaacctgg tagtgagtgg gaaggtgtac    3000
cagtgggatg accctgaccc caggctcttc gaccacccgg aaagccccac ccccaacccc    3060
acggagcccc tcttcctggc ccaggctgaa gtttacaagg agctgcgtct gcgtggctac    3120
gactacggcc ctcatttcca gggcatcctg gaggccagcc tggaaggtga ctcggggagg    3180
ctgctgtgga aggataactg ggtgagcttc atggacacca tgctgcagat gtccatcctg    3240
ggctcggcca agcacggcct gtacctgccc acccgtgtca ccgccatcca catcgaccct    3300
gccacccaca ggcagaagct gtacacactg caggacaagg cccaagtggc tgacgtggtg    3360
gtgagcaggt ggctgagggt cacagtggcc ggaggcgtcc acatctccgg gctccacact    3420
gagtcggccc cgcggcggca gcaggagcag caggtgccca tcctggagaa gttttgcttc    3480
acttcccaca cggaggaggg gtgcctgtct gagcgcgctg ccctgcagga ggagctgcaa    3540
ctgtgcaagg ggctggtgca ggcactgcag accaaggtga cccagcaggg gctgaagatg    3600
gtggtgcccg gactggatgg ggcccagatc ccccgggacc cctcacagca ggaactgccc    3660
cggctgttgt cggctgcctg caggcttcag ctcaacggga acctgcagct ggagctggcg    3720
caggtgctgg cccaggagag gcccaagctg ccagaggacc ctctgctcag cggcctcctg    3780
gactccccgg cactcaaggc ctgcctggac actgccgtgg agaacatgcc cagcctgaag    3840
atgaaggtgg tggaggtgct ggccggccac ggtcacctgt attcccgcat cccaggcctg    3900
ctcagccccc atccctgct gcagctgagc tacacggcca ccgaccgcca cccccaggcc    3960
ctggaggctg cccaggccga gctgcagcag cacgacgttg cccagggcca gtgggatccc    4020
gcagaccctg cccccagcgc cctgggcagc gccgacctcc tggtgtgcaa ctgtgctgtg    4080
gctgccctcg ggacccggc ctcagctctc agcaacatgg tggctgccct gagagaaggg    4140
ggctttctgc tcctgcacac actgctccgg gggcacccct cgggacatgt ggccttcctc    4200
acctccactg agccgcagta tggccagggc atcctgagcc aggacgcgtg ggagagcctc    4260
ttctccaggg tgtccgtgcg cctggtgggc ctgaagaagt ccttctacgg ctccacgctc    4320
ttcctgtgcc gccggcccac cccgcaggac agccccatct tcctgccggt ggacgatacc    4380
agcttccgct gggtggagtc tctgaagggc atcctggctg acgaagactc ttcccggcct    4440
gtgtggctga aggccatcaa ctgtgccacc tcggcgtgg tgggcttggt gaactgtctc    4500
cgccgagagc ccggcggaac gctccggtgt gtgctgctct ccaacctcag cagcacctcc    4560
cacgtcccgg aggtggaccc gggctccgca gaactgcaga aggtgttgca gggagacctg    4620
gtgatgaacg tctaccgcga cggggcctgg ggggctttcc gccacttcct gctggaggag    4680
```

```
gacaagcctg aggagccgac ggcacatgcc tttgtgagca ccctcacccg gggggacctg   4740
tcctccatcc gctgggtctg ctcctcgctg cgccatgccc agcccacctg ccctggcgcc   4800
cagctctgca cggtctacta cgcctccctc aacttccgcg acatcatgct ggccactggc   4860
aagctgtccc ctgatgccat cccagggaag tggacctccc aggacagcct gctaggtatg   4920
gagttctcgg gccgagacgc cagcggcaag cgtgtgatgg gactggtgcc tgccaagggc   4980
ctggccacct ctgtcctgct gtcaccggac ttcctctggg atgtgccttc caactggacg   5040
ctggaggagg cggcctcggt gcctgtcgtc tacagcacgg cctactacgc gctggtggtg   5100
cgtgggcggg tgcgccccgg ggagacgctg ctcatccact cgggctcggg cggcgtgggc   5160
caggccgcca tcgccatcgc cctcagtctg ggctgccgcg tcttcaccac cgtggggtcg   5220
gctgagaagc gggcgtacct ccaggccagg ttcccccagc tcgacagcac cagcttcgcc   5280
aactcccggg acacatcctt cgagcagcat gtgctgtggc acacgggcgg aagggcgtt   5340 gacctggtct tgaactcctt ggcggaagag aagctgcagg ccagcgtgag gtgcttggct   5400
acgcacggtc gcttcctgga aattggcaaa ttcgaccttt tcagaaccac cccgctcggc   5460
atggctatct tcctgaagaa cgtgacattc acggggtcc tactggatgc gttcttcaac    5520
gagagcagtg ctgactggcg ggaggtgtgg gcgcttgtgc aggccggcat ccgggatggg   5580
gtggtacggc ccctcaagtg cacggtgttc catggggccc aggtggagga cgccttccgc   5640
tacatggccc aagggaagca cattggcaaa gtcgtcgtgc aggtgcttgc ggaggagccg   5700
gaggcagtgc tgaagggggc caaacccaag ctgatgtcgg ccatctccaa gaccttctgc   5760
ccggcccaca agagctacat catcgctggt ggtctgggtg gcttcggcct ggagttggcg   5820
cagtggctga tacagcgtgg ggtgcagaag ctcgtgttga cttctcgctc cgggatccgg   5880
acaggctacc aggccaagca ggtccgccgg tggagggccc agggcgtaca ggtgcaggtg   5940
tccaccagca acatcagctc actggagggg cccggggcc tcattgccga ggcggcgcag    6000
cttgggcccg tgggcggcgt cttcaacctg gccgtggtct tgagagatgg cttgctggag   6060
aaccagaccc cagagttctt ccaggacgtc tgcaagccca agtacagcgg caccctgaac   6120
ctggacaggg tgacccgaga ggcgtgccct gagctggact actttgtggt cttctcctct   6180
gtgagctgcg ggcgtggcaa tgcgggacag agcaactacg gctttgccaa ttccgccatg   6240
gagcgtatct gtgagaaacg ccggcacgaa ggcctcccag gctggccgt gcagtggggc    6300 gccatcggcg acgtgggcat tttggtggag acgatgagca ccaacgacac gatcgtcagt   6360
ggcacgctgc cccaggccat ggcgtcctgc ctggaggtgc tggacctctt cctgaaccag   6420
ccccacatgg tcctgagcag ctttgtgctg gctgagaagg ctgcggccta tagggacagg   6480
gacagccagc gggacctggt ggaggccgtg gcacacatcc tgggcatccg cgacttggct   6540
gctgtcaacc tggacagctc actgcgggac ctgggcctgg actcgctcat gagcgtggag   6600
gtgcgccaga cgctggagcg tgagctcaac ctggtgctgt ccgtgcgcga ggtgcggcaa   6660
ctcacgctcc ggaaactgca ggagctgtcc tcaaaggcgg atgaggccag cgagctggca   6720
tgccccacgc ccaaggagga tggtctggcc cagcagcaga ctcagctgaa cctgcgctcc   6780
ctgctggtga acccgagggg ccccaccctg atgcggctca actccgtgca gagctcggag   6840
cggcccctgt tcctggtgca cccaatcgag ggctccacca ccgtgttcca cagcctggcc   6900
tcccggctca gcatccccac ctatggcctg cagtgcaccc gagctgcgcc ccttgacagc   6960
atccacagcc tggctgccta ctacatcgac tgcatcaggc aggtgcagcc cgagggcccc   7020
taccgcgtgg ccggctactc ctacggggcc tgcgtggcct ttgaaatgtg ctcccagctg   7080
```

```
caggcccagc agagcccagc ccccacccac aacagcctct tcctgttcga cggctcgccc    7140
acctacgtac tggcctacac ccagagctac cgggcaaagc tgaccccagg ctgtgaggct    7200
gaggctgaga cggaggccat atgcttcttc gtgcagcagt tcacggacat ggagcacaac    7260
agggtgctgg aggcgctgct gccgctgaag ggcctagagg agcgtgtggc agccgccgtg    7320
gacctgatca tcaagagcca ccagggcctg gaccgccagg agctgagctt tgcggcccgg    7380
tccttctact acaagctcgg tgccgctgag cagtacacac ccaaggccaa gtaccatggc    7440
aacgtgatgc tactgcgcgc caagacgggt ggcgcctacg gcgaggacct gggcgcggat    7500
tacaacctct cccaggtatg cgacgggaaa gtatccgtcc acgtcatcga gggtgaccac    7560
cgcacgctgc tggagggcag cggcctggag tccatcatca gcatcatcca cagctccctg    7620
gctgagccac gcgtgagcgt gcgggagggc taggcccgtg cccccgcctg ccaccggagg    7680
tcactccacc atccccaccc caccccaccc caccccgcc atgcaacggg attgaagggt    7740
cctgccggtg ggaccctgtc cggcccagtg ccactgcccc ccgaggctgc tagatgtagg    7800
tgttaggcat gtcccaccca cccgccgcct cccacggcac ctcggggaca ccagagctgc    7860
cgacttggag actcctggtc tgtgaagagc cggtggtgcc cgttcccgca ggaactgggc    7920
tgggcctcgt gcgccgtgg ggtctgcgct tggtctttct gtgcttggat ttgcatattt    7980
attgcattgc tggtagagac ccccaggcct gtccaccctg ccaagactcc tcaggcagcg    8040
tgtgggtccc gcactctgcc cccatttccc cgatgtcccc tgcgggcgcg ggcagccacc    8100
caagcctgct ggctgcggcc ccctctcggc caggcattgg ctcagccngc tgagtggggg    8160
gtcgtgggcc agtccccgag gagctgggcc cctgcacagg cacacagggc ccggccacac    8220
ccagcggccc cccgcacagc caccgtggg gtgctgccct tatcgcccgg cgccgggcac    8280
caactccatg tttggtgttt gtctgtgttt gtttttcaag aaatgattca aattgctgct    8340
tggattttga aatttactgt aactgtcagt gtacacgtct ggaccccgtt tcatttttac    8400
accaatttgg taaaaatgct gctctcagcc tcccacaatt aaaccgcatg tgatctcccc    8460
```

<210> SEQ ID NO 116  
<211> LENGTH: 959  
<212> TYPE: DNA  
<213> ORGANISM: Homo sapiens  
<220> FEATURE:  
<221> NAME/KEY: misc_feature  
<223> OTHER INFORMATION: NM_001639

<400> SEQUENCE: 116

```
gggcatgaat atcagacgct aggggacag ccactgtgtt gtctgctacc ctcatcctgg     60
tcactgcttc tgctataaca gccctaggcc aggaatatga acaagccgct gctttggatc    120
tctgtcctca ccagcctcct ggaagccttt gctcacacag acctcagtgg aaggtgttt    180 gtatttccta gagaatctgt tactgatcat gtaaacttga tcacaccgct ggagaagcct    240
ctacagaact ttaccttgtg ttttcgagcc tatagtgatc tctctcgtgc ctacagcctc    300
ttctcctaca atacccaagg cagggataat gagctactag tttataaaga aagagttgga    360
gagtatagtc tatacattgg aagacacaaa gttacatcca agttatcga aaagttcccg    420 gctccagtgc acatctgtgt gagctgggag tcctcatcag gtattgctga attttggatc    480
aatgggacac ctttggtgaa aaagggtctg cgacagggtt actttgtgga agctcagccc    540
aagattgtcc tggggcagga acaggattcc tatggggca agtttgatag agccagtcc    600 tttgtgggag agattgggga tttgtacatg tgggactctg tgctgccccc agaaaatatc    660
```

```
ctgtctgcct atcagggtac ccctctccct gccaatatcc tggactggca ggctctgaac    720
tatgaaatca gaggatatgt catcatcaaa cccttggtgt gggtctgagg tcttgactca    780
acgagagcac ttgaaaatga aatgactgtc taagagatct ggtcaaagca actggatact    840
agatcttaca tctgcagtct ttcttctttg aatttcctat ctgtatgtct gcctaattaa    900
aaaaatatat attgtattat gctacctgca aaaaaaaaaa aaaaaaaaa aaaaaaaaa     959
```

```
<210> SEQ ID NO 117
<211> LENGTH: 1471
<212> TYPE: DNA
<213> ORGANISM: Homo sapiens
<220> FEATURE:
<221> NAME/KEY: misc_feature
<223> OTHER INFORMATION: NM_000936

<400> SEQUENCE: 117
ggaactgcca cgatgctgcc actttggact ctttcactgc tgctgggagc agtagcagga     60
aaagaagttt gctacgaaag actcggctgc ttcagtgatg actccccatg gtcaggaatt    120
acggaaagac ccctccatat attgccttgg tctccaaaag atgtcaacac ccgcttcctc    180
ctatatacta atgagaaccc aaacaacttt caagaagttg ccgcagattc atcaagcatc    240
agtggctcca atttcaaaac aaatagaaaa actcgcttta ttattcatgg attcatagac    300
aagggagaag aaaactggct ggccaatgtg tgcaagaatc tgttcaaggt ggaaagtgtg    360
aactgtatct gtgtggactg gaaaggtggc tcccgaactg gatacacaca agcctcgcag    420
aacatcagga tcgtgggagc agaagtggca tattttgttg aatttcttca gtcggcgttc    480
ggttactcac cttccaacgt gcatgtcatt ggccacagcc tgggtgccca cgctgctggg    540
gaggctggaa ggagaaccaa tgggaccatt ggacgcatca cagggttgga cccagcagaa    600
ccttgctttc agggcacacc tgaattagtc cgattggacc ccagcgatgc caaatttgtg    660
gatgtaattc acacggatgg tgcccccata gtccccaatt tggggtttgg aatgagccaa    720
gtcgtgggcc acctagattt cttttccaaat ggaggagtgg aaatgcctgg atgtaaaaag    780
aacattctct ctcagattgt ggacatagac ggaatctggg aagggactcg agactttgcg    840
gcctgtaatc acttaagaag ctacaaatat tacactgata gcatcgtcaa ccctgatggc    900
tttgctggat tccctgtgc ctcttacaac gtcttcactg caaacaagtg tttcccttgt    960
ccaagtggag gctgcccaca gatgggtcac tatgctgata gatatcctgg aaaacaaat    1020 gatgtgggcc agaaattta tctagacact ggtgatgcca gtaattttgc acgttggagg    1080
tataaggtat ctgtcacact gtctggaaaa aaggttacag acacatact agtttctttg    1140 ttcggaaata aggaaactc taagcagtat gaaattttca agggcactct caaaccagat    1200
agtactcatt ccaatgaatt tgactcagat gtggatgttg gggacttgca gatggttaaa    1260
tttatttggt ataacaatgt gatcaaccca actttaccta gagtgggagc atccaagatt    1320
atagtggaga caaatgttgg aaaacagttc aacttctgta gtccagaaac cgtcagggag    1380
gaagttctgc tcacccctcac accgtgttag gagactactg ttatttgacc aatgaattga    1440
cttctaataa aatctagtgg tgatgcaaaa a                                   1471
```

```
<210> SEQ ID NO 118
<211> LENGTH: 7452
<212> TYPE: DNA
<213> ORGANISM: Homo sapiens
<220> FEATURE:
<221> NAME/KEY: misc_feature
<223> OTHER INFORMATION: U89344
```

-continued

```
<400> SEQUENCE: 118
atggtcttgc ttctttgtct atcttgtctg attttctcct gtctgacctt ttcctggtta      60
aaaatctggg agaaaatgac ggactccaag ccgatcacca agagtaaatc agaagcaaac     120
ctcatcccga gccaggagcc ctttccagcc tctgataact caggggagac accgcagaga     180
aatggggagg gccacactct gcacaaagac acccagccag gccgagccca gcctcccaca     240
aaggcccaaa gatccggtcg gcggagaaac tccctaccac cctcccgcca gaagccccca     300
agaaaccccc tttcttccag tgacgcagca ccctcccag agcttcaagc caacgggact      360
gggacacaag gtctggaggc cacagatacc aatggcctgt cctcctcagc caggccccag     420
ggcagcaagc tggtcccctc caaagaagac aagaagcagg caaacatcaa gaggcagctg     480
atgaccaact tcatcctggg ctcttttgat gactactcct ccgacgagga ctctgttgct     540
ggctcatctc gtgagtctac ccggaagggc agccgggcca gcttgggggc cctgtccctg     600
gaggcttatc tgaccacagg tgaagctgag acccgcgtcc ccactatgag gccgagcatg     660
tcgggactcc acctggtgaa gaggggacgg gaacacaaga agctggacct gcacagagac     720
tttaccgtgg cttctcccgc tgagtttgtc acacgctttg gggggatcg ggtcatcgag       780 aaggtgctta ttgccaacaa cgggattgcc gctgtgaagt gcatgcgctc catccgcagg     840
tgggcctatg agatgttccg caacgagcgg gccatccggt ttgttcgcat ggtgaccccc     900 gaggaccttα aggccaacgc agagtacatc aagatggcgg atcattacgg gcccgcccca     960
ggagggccca ataacaacaa ctatgccaac gtggagctga ttgtggacat tgccaagaga    1020
atcccgttgc aggcggtgtg ggctggctgg ggccatgctt tagaaaaccc taaacttccg    1080
gagctgctgt gcaagaatgg agttgctttc ttaggccctc ccaggttgag gccaatggtg    1140
ggtctaggag ataagatcgc ctccaccgtt gtcgcccaga cgctacaggt cccaaccctg    1200
cccaggagtg gaagcgccct gacagtggag tggacagaag atgatctgca gcagggaaaa    1260
agaatcagtg tcccagaaga tgtttatgac aagggttgcg tgaaagacgt agatgagggc    1320
ttggaggcag cagaaagaat tggttttcca ttgatgatca aagcttctga aggtggcgga    1380
gggaagggaa tccgggaaac tgagagtgcg gaggacttcc cgatcctttt cagacaagta    1440
cagagtgaga tcccaggctc gcccatcttt ctcatgaagc tggcccagca cgcccgtcac    1500
ctggaagttc agatcctcgc tgaccagtat gggaatgctg tgtctctgtt tggtcgcgac    1560
tgctccatcc agcggcggca tcagaagatc gttgaggaag caccggccac catcgcgccg    1620
ctggccatat tcgagttcat ggagcagtgt gccattcgcc tggccaagac cgtgggctat    1680
gtgagtgcag ggacagtgga atacctctat agtcaggatg gtagcttcca cttcttggag    1740
ctgaatcctc gcttgcaggt ggaacatccc tgcacagaaa tgattgctga cgttaatctg    1800
ccggccgccc agctacagat cgccatgggt gccccactgc accggctgaa agatatccgg    1860
cttctgtatg gagagtcacc ctgggggaga tccccaattt cttttgaaaa ctcagctcat    1920
ctcccctgcc cccgaggcca cgtcattgcc accagaatca ccagcgaaaa cccagacgag    1980
ggttttaagc cgagctccgg gactgtccag gaactgaatt tccggagcag caagaacgtc    2040
tggggttact tcacggtggc cgctactgga ggcctgcacg agtttgcgat tcccagtttt    2100
gggcactgct tctcctgggg agagaaccgg aaagaggcca tttcgaacat ggtggtggct    2160
ttgaaggaac tgtccctccg aggcgacttt aggactaccg tggaatacct cattaacctc    2220
ctggagaccg agagcttcca gaacaactac atcgacaccg gtggttgga ctacctcatt     2280 gctgagaaag tgcaaaagaa accgaatatc atgcttgggg tggtatgcgg ggcccttgaa    2340
```

```
cgtggagatg cgatgttcag aacgtgcatg acagatttct tacactccct ggaaaggggc    2400
caggtcctcc cagcggattc actactgaac ctcgtagatg tggaattaat ttacgagggt    2460
gtaaagtaca ttctaaaggt gacccggcag tctctgacca tgttcgttct catcatgaat    2520
ggctgccaca tcgagattga tgcccaccgg ctgaatgatg gggggctcct gctctcctac    2580
aatgggaaca gctacaccac ctacatgaag gaagaggttg acagttaccg taccatcggc    2640
aataagacgt gtgttttga gaggagaac gatcctacag tcctgagatc ccctcggct     2700 gggaagctga cacagatcac agtggaggat gggggccacg ttgaggctgg gagacgctac    2760
gctgagatgg aggtgatgaa gatgatcatg accctgaacg ttcaggaaag aggccgggtg    2820
aagtacatca gcgtccagg tgcggtgctg gaagcaggct gcgtggtggc caggctggag     2880
ctcgatgacc cttctaaagt ccacccggct gaaccgttca caggagaact ccctgcccag    2940
cagaacactg ccgacctcgg aaagaaactg cacagggtct tccacagcgt cctgggaagc    3000
ctcaccaacg tcatgagtgg cttttgtctg ccagagccgc tttttagcat aaagctgaag    3060
gagtgggtgc agaagctcat gatgaccctc cggcacccgt cactgctgct ggacgtgcag    3120
gagatcatga ccagtcgtgc aggccgcatc ccccccctg ttgagaagtc tgtccgcaag     3180
gtgatggccc agtatgccag caacatcacc tcggtgctgt gccagttccc cagccagcag    3240
atagccacca tcctggactg ccatgcagcc accctgcagc ggaaggctga tcgagaggtc    3300
ttcttcatca cacccagag catggtgcag ttggtccaga ggtaccgaag tggaatccgc     3360
ggtcatatga aaacagtggt gatcgatctc ttgagaagat acttgcgtgt tgagaccatt    3420
ttcggcaagg caagagatgc tgatgccaac tccagtggga tggtggggg cgtgaggagc     3480 ctgagcttta cctctgtgtg ggtggttttg tctccccag cccactacga caagtgtgtg     3540
ataaacctca gggaacagtt caagccagac atgtcccagg tgctggactg catcttctcc    3600
cacgcacagg tgaccaagaa gaaccagctg gtgatcatgt tgatcgatga gctgtgtggc    3660
ccagaccctt ccctgtcgga cgagctgatc tccatcctca acgagctcac tcagctgagc    3720
aaaagcgagc actgcaaagt ggccctcaga gcccggcaga tcctgatcgc ctcccccctcc    3780 tacgagctgc ggcataacca ggtggagtcc attttcctgt ctgccattga catgtacggc    3840
caccagttct gccccgagaa cctccagaaa ttaatacttt cggaaacaac catcttcgac    3900
gtcctgaata ctttcttcta tcacgcaaac aaagtcgtgt gcatggcgtc cttggaggtt    3960
tacgtggggg gggcttacat cgcctatgtg ttaaacagcc tgcagcaccg gcagctcccg    4020
gacggcacct gcgtggtaga attccagttc atgctgccgt cctcccaccc aaaccggatg    4080
accgtgccca tcagcatcac caaccctgac ctgctgaggc acacgacaga gctcttcatg    4140
gacagcggct tctcccccact gtgccagcgc atgggagcca tggtagcctt caggagattc    4200
gaggacttca ccagaaattt tgatgaagtc atctcttgct tcgccaacgt gccgaaagac    4260 cccccccctct tcagcgaggc ccgcacctcc ctatactccg aggatgactg caagagcctc    4320
agagaagagc ccatccacat tctgaatgtg tccatccagt gtgcggacca cctggaggat    4380
gaggcactgt tgccgatttt acgtacattc gtacagtcca agaaaaatat ccttgtggat    4440
tatggactcc gacgaatccc attcttgatt gcccaagaga agaatttcc caagtttttc    4500 acattcagag caagagatga gtttgcagaa gatcgcattt accgtcactt ggaacctgcc    4560
ctggctttcc agctggaact caaccggatg cgtaacttcg atctgaccgc cgtgccctgt    4620
gccaaccaca agatgcacct ttacctgggt gctgccaagg tggaaggaag gtatgaagtg    4680
acggaccata ggttcttcat ccgtgccatc atcaggcact ctgacctgat cacaaaggaa    4740
```

-continued

| | |
|---|---|
| gcctccttcg aatacctgca gaacgagggt gagcggctgc tcctggaggc catggacgag | 4800 |
| ctggaggtgg cgttcaataa caccaacgtg cgcaccgact gcaaccacat cttcctcaac | 4860 |
| ttcgtgccca ctgtcatcat ggaccccaac aagatcgagg agtccgtgcg ctacatggtt | 4920 |
| atgcgctacg gcagccggct gtggaaactc cgtgtgctac aggctgaggt caagatcaac | 4980 |
| atccgccaga ccaccaccgg cagtgccgtt cccatccgcc tgttcatcac caatgagtcg | 5040 |
| ggctactacc tggacatcag cctctacaaa gaagtgactg actccagatc tggaaatatc | 5100 |
| atgtttcact ccttcggcaa caagcaaggg ccccagcacg ggatgctgat caatactccc | 5160 |
| tacgtcacca aggatctgct ccaggccaag cgattccagg cccagaccct gggaaccacc | 5220 |
| tacatctatg acttcccgga aatgttcagg caggctctct ttaaactgtg gggctcccca | 5280 |
| gacaagtatc ccaaagacat cctgacatac actgaattag tgttggactc tcagggccag | 5340 |
| ctggtggaga tgaaccgact tcctggtgga aatgaggtgg gcatggtggc cttcaaaatg | 5400 |
| aggtttaaga cccaggagta cccggaagga cgggatgtga tcgtcatcgg caatgacatc | 5460 |
| accttcgca ttggatcctt tggccctgga gaggaccttc tgtacctgcg ggcatccgag | 5520 |
| atggcccggg cagaggcgat tcccaaaatt tacgtggcag ccaacagtgg cgcccgtatt | 5580 |
| ggcatggcag aggagatcaa acacatgttc cacgtggctt gggtggaccc agaagacccc | 5640 |
| cacaaaggat ttaaatacct gtacctgact ccccaagact acaccagaat cagctccctg | 5700 |
| aactccgtcc actgtaaaca catcgaggaa ggaggagagt ccagatacat gatcacggat | 5760 |
| atcatcggga aggatgatgg cttgggcgtg gagaatctga ggggctcagg catgattgct | 5820 |
| ggggagtcct ctctggctta cgaagagatc gtcaccatta gcttggtgac ctgccgagcc | 5880 |
| attgggattg gggcctactt ggtgaggctg ggccagcgag tgatccaggt ggagaattcc | 5940 |
| cacatcatcc tcacaggagc aagtgctctc aacaaggtcc tgggaagaga ggtctacaca | 6000 |
| tccaacaacc agctgggtgg cgttcagatc atgcattaca atggtgtctc ccacatcacc | 6060 |
| gtgccagatg actttgaggg ggtttatacc atcctggagt ggctgtccta tatgccaaag | 6120 |
| gataatcaca gccctgtccc tatcatcaca cccactgacc ccattgacag agaaattgaa | 6180 |
| ttcctcccat ccagagctcc ctacgacccc cggtggatgc ttgcaggaag gcctcaccca | 6240 |
| actctgaagg gaacgtggca gagcggattc tttgaccacg gcagtttcaa ggaaatcatg | 6300 |
| gcaccctggg cgcagaccgt ggtgacagga cgagcaaggc ttgggggat tcccgtggga | 6360 |
| gtgattgctg tggagacacg gactgtggag gtggcagtcc ctgcagaccc tgccaacctg | 6420 |
| gattctgagg ccaagataat tcagcaggca ggacaggtgg ggttcccaga ctcagcctac | 6480 |
| aaaaccgccc aggccatcaa ggacttcaac cgggagaagt tgcccctgat gatctttgcc | 6540 |
| aactggaggg ggttctccgg tggcatgaaa gacatgtatg accaggtgct gaagtttgga | 6600 |
| gcctacatcg tggacggcct tagacaatac aaacagccca tcctgatcta tatccgccct | 6660 |
| atgcgggagc tccggggagg ctcctgggtg gtcatagatg ccaccatcaa cccgctgtgc | 6720 |
| atagaaatgt atgcagacaa agagagcagg ggtggtgttc tggaaccaga ggggacagtg | 6780 |
| gagattaagt tccgaaagga agatctgata aagtccatga aaggatcga tccagcttac | 6840 |
| aagaagctca tggaacagct agggaacct gatctctccg acaaggaccg aaaggacctg | 6900 |
| gagggccggc taaaggctcg cgaggacctg ctgctcccca tctaccacca ggtggcggtg | 6960 |
| cagttcgccg acttccatga cacacccggc cggatgctgg agaagggcgt catatctgac | 7020 |
| atcctggagt ggaagaccgc acgcaccttc ctgtattggc gtctgcgccg cctcctcctg | 7080 |
| gaggaccagg tcaagcagga gatcctgcag gccagcgggg agctgagtca cgtgcatatc | 7140 |

-continued

| | |
|---|---|
| cagtccatgc tgcgtcgctg gttcgtggag acggaggggg ctgtcaaggc ctacttgtgg | 7200 |
| gacaacaacc aggtggttgt gcagtggctg aacagcact ggcaggcagg ggatggcccg | 7260 |
| cgctccacca tccgtgagaa catcacgtac ctgaagcacg actctgtcct caagaccatc | 7320 |
| cgaggcctgg ttgaagaaaa ccccgaggtg gccgtggact gtgtgatata cctgagccag | 7380 |
| cacatcagcc cagctgagcg ggcgcaggtc gttcacctgc tgtctaccat ggacagcccg | 7440 |
| gcctccacct ga | 7452 |

<210> SEQ ID NO 119
<211> LENGTH: 3259
<212> TYPE: DNA
<213> ORGANISM: Homo sapiens
<220> FEATURE:
<221> NAME/KEY: misc_feature
<223> OTHER INFORMATION: M31158

<400> SEQUENCE: 119

| | |
|---|---|
| gacgcgcgcc gggagccggc ggccgggcca gccggcgccg gggcccagtg cgccgcgctc | 60 |
| gcagccggta gcgcgccagc cgtaggcgtc gctcggcagc cgcggggccc taggcgtgcc | 120 |
| ggggagggg cgagggcggc caggcgcctg ccgccccgga ggcaggatga gcatcgagat | 180 |
| cccggcggga ctgacggagc tgctgcaggg cttcacggtg gaggtgctga ggcaccagcc | 240 |
| cgcggacctg ctggagttcg cgctgcagca cttcaccccgc ctgcagcagg agaacgagcg | 300 |
| caaaggcacc gcgcgcttcg gccatgaggg caggacctgg ggggacctgg gcgccgctgc | 360 |
| cgggggcggc accccagca aggggtcaa cttcgccgag gagcccatgc agtccgactc | 420 |
| cgaggacggg gaggaggagg aggcggcgcc cgcggacgca ggggcgttca atgctccagt | 480 |
| aataaaccga ttcacaaggc gtgcctcagt atgtgcagaa gcttataatc ctgatgaaga | 540 |
| agaagatgat gcagagtcca ggattataca tccaaaaact gatgatcaaa gaaataggtt | 600 |
| gcaagaggct tgcaaagaca tcctgctgtt taagaatctg gatccggagc agatgtctca | 660 |
| agtattagat gccatgtttg aaaaattggt caaagatggg gagcatgtaa ttgatcaagg | 720 |
| tgacgatggt gacaactttt atgtaattga tagaggcaca tttgatattt atgtgaaatg | 780 |
| tgatggtgtt ggaagatgtg ttggtaacta tgataatcgt gggagtttcg gcgaactggc | 840 |
| cttaatgtac aatacaccca gagcagctac aatcactgct acctctcctg gtgctctgtg | 900 |
| gggtttggac agggtaacct tcaggagaat aattgtgaaa acaatgcca aaaagagaaa | 960 |
| aatgtatgaa agctttattg agtcactgcc attccttaaa tctttggagt tttctgaacg | 1020 |
| cctgaaagta gtagatgtga taggcaccaa agtatacaac gatggagaac aaatcattgc | 1080 |
| tcagggagat tcggctgatt ctttttttcat tgtagaatct ggagaagtga aaattactat | 1140 |
| gaaaagaaag ggtaaatcag aagtggaaga gaatggtgca gtagaaatgc ctcgatgctc | 1200 |
| gcggggacag tactttggag agcttgcccct ggtaactaac aaacctcgag cagcttctgc | 1260 |
| ccacgccatt gggactgtca atgtttagc aatggatgtg caagcatttg aaaggcttct | 1320 |
| gggaccttgc atggaaatta tgaaaaggaa catcgctacc tatgaagaac agttagttgc | 1380 |
| cctgtttgga acgaacatgg atattgttga acccactgca tgaagcaaaa gtatggagca | 1440 |
| agacctgtag tgacaaaatt acacagtagt ggttagtcca ctgagaatgt gtttgtgtag | 1500 |
| atgccaagca ttttctgtga tttcaggttt tttcctttt ttacatttac aacgtatcaa | 1560 |
| taaacagtag tgatttaata gtcaataggc tttaacatca ctttctaaag agtagttcat | 1620 |
| aaaaaaatca acatactgat aaaatgactt tgtactccac aaaattatga ctgaaaggtt | 1680 |
| tattaaaatg attgtaatat atagaaagta tctgtgttta agaagataat taaaggatgt | 1740 |

```
tatcataggc tatatgtgtt ttacttattc agactgataa tcatattagt gactatcccc    1800
atgtaagagg gcacttggca attaaacatg ctacacagca tggcatcact ttttttata    1860 actcattaaa cacagtaaaa ttttaatcat ttttgttta aagttttcta gcttgataag    1920
ttatgtgctg ccttggccta ttggtgaaat ggtataaaat atcatatgca gttttaaaac    1980 ttttatatt tttgcaataa agtacatttt gactttgttg gcataatgtc agtaacatac    2040
atattccagt ggttttatgg acaggcaatt tagtcattat gataataagg aaaacagtgt    2100
tttagatgag agatcattaa tgcatttttc cctcatcaag catatatctg ctttttttta    2160
ttttgcaatt ctctgtattc tatgtcttta aaaatttgat cttgacattt aatgtcacaa    2220
agttttgttt ttttaaaaag tgatttaaac ttaagatccg acattttttg tattctttaa    2280
gattttacac ctaaaaaatc tctcctatcc caaaaataat gtgggatcct tatcagcatg    2340
cccacagttt atttctttgt tcttcactag gcctgcataa tacagtccta tgtagacatc    2400
tgttcccttg ggtttccgtt cttcttagg atggttgcca acccacaatc tcattgatca    2460
gcagccaata tgggtttgtt tggtttttt aattcttaaa aacatcctct agaggaatag    2520
aaacaaattt ttatgagcat aaccctatat aaagacaaaa tgaatttctg accttaccat    2580
atataccatt aggccttgcc attgctttaa tgtagactca tagttgaaat tagtgcagaa    2640
agaactcaga tgtactagat tttcattgtt cattgatatg ctcagtatgc tgccacataa    2700
gatgaattta attatattca accaaagcaa tatactctta catgatttct aggccccatg    2760
acccagtgtc tagagacatt aattctaacc agttgtttgc ttttaaatga gtgatttcat    2820
tttgggaaac aggtttcaaa tgaatatata tacatgggta aaattactct gtgctagtgt    2880
agtcttacta gagaatgttt atggtcccac ttgtatatga aaatgtggtt agaatgttaa    2940
ttggataatg tatatataag aagttaaagt atgtaaagta taacttcagc cacatttta    3000 gaacactgtt taacattttt gcaaaaccctt cttgtaggaa aagagagctc tctacatgaa    3060
gatgacttgt tttatatttc agatttttatt ttaaaagcca tgtctgttaa acaagaaaaa    3120
acacaaaaga actccagatt cctggttcat cattctgtat tcttactcac tttttcaagt    3180
tatctatttt gttgcataaa ctaattgtta actattcatg gaacagcaaa cgcctgttta    3240
ataaagaact ttgaccaag                                                 3259
```

<210> SEQ ID NO 120
<211> LENGTH: 3261
<212> TYPE: DNA
<213> ORGANISM: Homo sapiens
<220> FEATURE:
<221> NAME/KEY: misc_feature
<223> OTHER INFORMATION: XM_008512

<400> SEQUENCE: 120

```
gcccgggacc ccacggaggc ggggagacca ctcttctccc acacgagccc agctctccct      60
tcgagtagca accgccttca agctcacaag cacccgtggg cctgggtgt gcctgcgtct     120 agctggttgc acactgggcc acagaggatc cagcaaggat gaagaaatgg agcagcacag     180
acttgggggc agctgcggac ccactccaaa aggacacctg cccagacccc ctggatggag     240
accctaactc caggccacct ccagccaagc cccagctctc cacggccaag agccgcaccc     300
ggctctttgg gaagggtgac tcggaggagg ctttcccggt ggattgccct cacgaggaag     360
gtgagctgga ctcctgcccg accatcacag tcagccctgt tatcaccatc cagaggccag     420
gagacggctc caccggtgcc aggctgctgt cccaggactc tgtcgccgcc agcaccgaga     480
```

```
agaccctcag gctctatgat cgcaggagta tctttgaagc cgttgctcag aataactgcc    540
aggatctgga gagcctgctg ctcttcctgc agaagagcaa gaagcacctc acagacaacg    600
agttcaaaga ccctgagaca gggaagacct gtctgctgaa agccatgctc aacctgcatg    660
acggacagaa caccaccatc cccctgctcc tggagatcgc gcggcaaacg acagcctga    720 aggagcttgt caacgccagc tacacggaca gctactacaa gggccagaca gcactgcaca    780
tcgccatcga gagacgcaac atggcctgg tgaccctcct ggtggagaac ggagcagacg    840
tccaggctgc ggcccatggg gacttcttta agaaaaccaa agggcggcct ggattctact    900
tcggtgaact gccctgtcc ctggccgcgt gcaccaacca gctgggcatc gtgaagttcc    960
tgctgcagaa ctcctggcag acggccgaca tcagcgccag ggactcggtg gcaacacgg   1020 tgctgcacgc cctggtggag gtggccgaca cacggccga caacacgaag tttgtgacga   1080
gcatgtacaa tgagattctg atcctggggg ccaaactgca cccgacgctg aagctggagg   1140
agctcaccaa caagaaggga atgacgccgc tggctctggc agctgggacc gggaagatcg   1200
gggtcttggc ctatattctc cagcgggaga tccaggagcc cgagtgcagg cacctgtcca   1260
ggaagttcac cgagtgggcc tacgggcccg tgcactcctc gctgtacgac ctgtcctgca   1320
tcgacacctg cgagaagaac tcggtgctgg aggtgatcgc ctacagcagc agcgagaccc   1380
ctaatcgcca cgacatgctc ttggtggagc cgctgaaccg actcctgcag acaagtgggg   1440
acagattcgt caagcgcatc ttctacttca acttcctggt ctactgcctg tacatgatca   1500
tcttcaccat ggctgcctac tacaggcccg tggatggctt gcctccctt aagatggaaa   1560 aaattggaga ctatttccga gttactggag agatcctgtc tgtgttagga ggagtctact   1620 tcttttccg agggattcag tatttcctgc agaggcggcc gtcgatgaag accctgtttg   1680
tggacagcta cagtgagatg ctttctcttc tgcagtcact gttcatgctg ccaccgtgg   1740 tgctgtactt cagccaccttc aaggagtatg tggcttccat ggtattctcc ctggccttgg   1800
gctggaccaa catgctctac tacacccgcg gtttccagca gatgggcatc tatgccgtca   1860
tgatagagaa gatgatcctg agagacctgt gccgtttcat gtttgtctac atcgtcttct   1920
tgttcggttt ttccacagcg gtggtgacgc tgattaagga cgggaagaat gactccctgc   1980
cgtctgagtc cacgtcgcac aggtggcggg ggcctgcctg caggccccc gatagctcct   2040 acaacagcct gtactccacc tgcctggagc tgttcaagtt caccatcggc atgggcgacc   2100
tggagttcac tgagaactat gacttcaagg ctgtcttcat catcctgctg ctggcctatg   2160
taattctcac ctacatcctc ctgctcaaca tgctcatcgc cctcatgggt gagactgtca   2220
acaagatcgc acaggagagc aagaacatct ggaagctgca gagagccatc accatcctgg   2280
acacggagaa gagcttcctt aagtgcatga ggaaggcctt ccgctcaggc aagctgctgc   2340
aggtggggta cacacctgat ggcaaggacg actaccggtg gtgcttcagg gtggacgagg   2400
tgaactggac cacctggaac accaacgtgg gcatcatcaa cgaagacccg ggcaactgtg   2460
agggcgtcaa gcgcaccctg agcttctccc tgcggtcaag cagagtttca ggcagacact   2520
ggaagaactt tgccctggtc cccttttaa gagaggcaag tgctcgagat aggcagtctg   2580
ctcagcccga ggaagtttat ctgcgacagt tttcagggtc tctgaagcca gaggacgctg   2640
aggtcttcaa gagtcctgcc gcttccgggg agaagtgagg acgtcacgca gacagcactg   2700
tcaacactgg gccttaggag accccgttgc cacgggggc tgctgaggga acaccagtgc   2760
tctgtcagca gcctggcctg gtctgtgcct gcccagcatg ttcccaaatc tgtgctggac   2820
aagctgtggg aagcgttctt ggaagcatgg ggagtgatgt acatccaacc gtcactgtcc   2880
```

-continued

| | |
|---|---|
| ccaagtgaat ctcctaacag actttcaggt ttttactcac tttactaaac agtttggatg | 2940 |
| gtcagtctct actgggacat gttaggccct tgttttcttt gattttattc ttttttttga | 3000 |
| gacagaattt cactcttctc acccaggctg gaatgcagtg gcacaatttt ggctccctgc | 3060 |
| aacctccgcc tcctggattc cagcaattct cctgcctcgg cttcccaagt agctgggatt | 3120 |
| acaggcacgt gccaccatgt ctggctaatt ttttgtattt ttttaataga tatggggttt | 3180 |
| cgccatgttg gccaggctgg tctcgaactc ctgacctcag gtgatccgcc cacctcggcc | 3240 |
| tcccaaagtg ctgggattac a | 3261 |

<210> SEQ ID NO 121
<211> LENGTH: 4307
<212> TYPE: DNA
<213> ORGANISM: Homo sapiens
<220> FEATURE:
<221> NAME/KEY: misc_feature
<223> OTHER INFORMATION: NM_005099

<400> SEQUENCE: 121

| | |
|---|---|
| cacagacaca tatgcacgag agagacagag gaggaaagag acagagacaa aggcacagcg | 60 |
| gaagaaggca gagacagggc aggcacagaa gcggcccaga cagagtccta cagagggaga | 120 |
| ggccagagaa gctgcagaag acacaggcag ggagagacaa agatccagga aaggagggct | 180 |
| caggaggaga gtttggagaa gccagacccc tgggcacctc tcccaagccc aaggactaag | 240 |
| ttttctccat ttcctttaac ggtcctcagc ccttctgaaa actttgcctc tgaccttggc | 300 |
| aggagtccaa gccccaggc tacagagagg agctttccaa agctagggtg tggaggactt | 360 |
| ggtgccctag acggcctcag tccctcccag ctgcagtacc agtgccatgt cccagacagg | 420 |
| ctcgcatccc gggaggggct tggcaggcg ctggctgtgg ggagcccaac cctgcctcct | 480 |
| gctccccatt gtgccgctct cctggctggt gtggctgctt ctgctactgc tggcctctct | 540 |
| cctgccctca gccggctgg ccagccccct ccccgggag gaggagatcg tgtttccaga | 600 |
| gaagctcaac ggcagcgtcc tgcctggctc gggcacccct gccaggctgt tgtgccgctt | 660 |
| gcaggccttt ggggagacgc tgctactaga gctggcagag gactccggtg tgcaggtcga | 720 |
| ggggctgaca gtgcagtacc tgggccaggc gcctgagctg ctgggtggag cagagcctgg | 780 |
| cacctacctg actggcacca tcaatggaga tccggagtcg gtggcatctc tgcactggga | 840 |
| tgggggagcc ctgttaggcg tgttacaata tcgggggct gaactccacc tccagcccct | 900 |
| ggagggaggc acccctaact ctgctggggg acctggggct cacatcctac gccggaagag | 960 |
| tcctgccagc ggtcaaggtc ccatgtgcaa cgtcaaggct cctcttggaa gcccagccc | 1020 |
| cagaccccga agagccaagc gctttgcttc actgagtaga tttgtggaga cactggtggt | 1080 |
| ggcagatgac aagatggccg cattccacgg tgcgggcta aagcgctacc tgctaacagt | 1140 |
| gatggcagca gcagccaagg ccttcaagca cccaagcatc cgcaatcctg tcagcttggt | 1200 |
| ggtgactcgg ctagtgatcc tggggtcagg cgaggagggg cccaagtgg ggcccagtgc | 1260 |
| tgccagacc ctgcgcagct tctgtgcctg gcagcgggc ctcaacaccc ctgaggactc | 1320 |
| ggaccctgac cactttgaca cagccattct gtttacccgt caggacctgt gtggagtctc | 1380 |
| cacttgcgac acgctgggta tggctgatgt gggcaccgtc tgtgaccgg ctcggagctg | 1440 |
| tgccattgtg gaggatgatg gctccagtc agccttcact gctgctcatg aactgggtca | 1500 |
| tgtcttcaac atgctccatg acaactccaa gccatgcatc agtttgaatg gcctttgag | 1560 |
| cacctctcgc catgtcatgg cccctgtgat ggctcatgtg gatcctgagg agccctggtc | 1620 |
| cccctgcagt gcccgcttca tcactgactt cctggacaat ggctatgggc actgtctctt | 1680 |

```
agacaaacca gaggctccat tgcatctgcc tgtgactttc cctggcaagg actatgatgc   1740
tgaccgccag tgccagctga ccttcgggcc cgactcacgc cattgtccac agctgccgcc   1800
gccctgtgct gccctctggt gctctggcca cctcaatggc catgccatgt gccagaccaa   1860
acactcgccc tgggccgatg cacaccctg cgggcccgca caggcctgca tgggtggtcg    1920
ctgcctccac atggaccagc tccaggactt caatattcca caggctggtg ctggggtcc    1980
ttggggacca tggggtgact gctctcggac ctgtgggggt ggtgtccagt tctcctcccg   2040
agactgcacg aggcctgtcc cccggaatgg tggcaagtac tgtgagggcc gccgtacccg   2100
cttccgctcc tgcaacactg aggactgccc aactggctca gccctgacct ccgcgagga    2160
gcagtgtgct gcctacaacc accgcaccga cctcttcaag agcttcccag ggcccatgga   2220
ctgggttcct cgctacacag gcgtggcccc ccaggaccag tgcaaactca cctgccaggc   2280
ccgggcactg ggctactact atgtgctgga ccacgggtg gtagatggga cccctgttc    2340
cccggacagc tcctcggtct gtgtccaggg ccgatgcatc catgctggct gtgatcgcat   2400
cattggctcc aagaagaagt ttgacaagtg catggtgtgc ggaggggacg ttctggttg    2460
cagcaagcag tcaggctcct tcaggaaatt caggtacgga tacaacaatg tggtcactat   2520
ccccgcgggg gccacccaca ttcttgtccg gcagcaggga aaccctggcc accggagcat   2580
ctacttggcc ctgaagctgc cagatggctc ctatgccctc aatggtgaat acacgctgat   2640
gccctccccc acagatgtgg tactgcctgg ggcagtcagc ttgcgctaca gcggggccac   2700
tgcagcctca gagacactgt caggccatgg ccactggcc cagcctttga cactgcaagt    2760
cctagtggct ggcaaccccc aggacacacg cctccgatac agcttcttcg tgccccggcc   2820
gaccccttca acgccacgcc ccactcccca ggactggctg caccgaagag cacagattct   2880
ggagatcctt cggcggcgcc cctgggcggg caggaaataa cctcactatc ccggctgccc   2940
tttctgggca ccggggcctc ggacttagct gggagaaaga gagagcttct gttgctgcct   3000
catgctaaga ctcagtgggg aggggctgtg ggcgtgagac ctgcccctcc tctctgccct   3060
aatgcgcagg ctgccctgc cctggttccc tgccctggga ggcagtgatg ggttagtgga    3120
tggaaggggc tgacagacag ccctccatct aaactgcccc ctctgccctg cgggtcacag   3180
gagggagggg gaaggcaggg agggcctggg ccccagttgt atttatttag tatttattca   3240
cttttatttta gcaccaggga aggggacaag gactagggtc ctggggaacc tgaccctga    3300
cccctcatag ccctcaccct ggggctagga aatccagggt ggtggtgata ggtataagtg   3360
gtgtgtgtat gcgtgtgtgt gtgtgtgtga aaatgtgtgt gtgcttatgt atgaggtaca   3420
acctgttctg ctttcctctt cctgaatttt attttttggg aaaagaaaag tcaagggtag   3480
ggtgggcctt cagggagtga gggattatct ttttttttt tctttctttt ctttctttt    3540
ttttttttgag acagaatctc gctctgtcgc ccaggctgga gtgcaatggc acaatctcgg   3600
ctcactgcat cctccgcctc ccgggttcaa gtgattctca tgcctcagcc tcctgagtag   3660
ctgggattac aggctcctgc caccacgccc agctaatttt tgttttgttt tgtttggaga   3720
cagagtctcg ctattgtcac cagggctgga atgatttcag ctcactgcaa ccttcgccac   3780
ctgggttcca gcaattctcc tgcctcagcc tcccgagtag ctgagattat aggcacctac   3840
caccacgccc ggctaatttt tgtattttta gtagagacgg ggtttcacca tgttggccag   3900
gctggtctcg aactcctgac cttaggtgat ccactcgcct tcatctccca aagtgctggg   3960
attacaggcg tgagccaccg tgcctggcca cgcccaacta ttttttgtat ttttagtaga   4020
gacagggttt caccatgttg ccaggctgc tcttgaactc ctgacctcag gtaatcgacc    4080
```

| | |
|---|---|
| tgcctcggcc tcccaaagtg ctgggattac aggtgtgagc caccacgccc ggtacatatt | 4140 |
| ttttaaattg aattctacta tttatgtgat cctttggag tcagacagat gtggttgcat | 4200 |
| cctaactcca tgtctctgag cattagattt ctcatttgcc aataataata cctcccttag | 4260 |
| aagtttgttg tgaggattaa ataatgtaaa taaagaacta gcataac | 4307 |

<210> SEQ ID NO 122
<211> LENGTH: 1423
<212> TYPE: DNA
<213> ORGANISM: Homo sapiens
<220> FEATURE:
<221> NAME/KEY: misc_feature
<223> OTHER INFORMATION: U94320

<400> SEQUENCE: 122

| | |
|---|---|
| gaaaggctat cggtaacaac tgacctgcca caaagttaga agaaaggatt gattcaagaa | 60 |
| agactataat atggatttag agctcgacga gtattataac aagacacttg ccacagagaa | 120 |
| taatactgct gccactcgga attctgattt cccagtctgg gatgactata aaagcagtgt | 180 |
| agatgactta cagtattttc tgattgggct ctatacattt gtaagtcttc ttggctttat | 240 |
| ggggaatcta cttattttaa tggctctcat gaaaaagcgt aatcagaaga ctacggtaaa | 300 |
| cttcctcata ggcaatctgg cctttttctga tatcttggtt gtgctgtttt gctcaccttt | 360 |
| cacactgacg tctgtcttgc tggatcagtg gatgtttggc aaagtcatgt gccatattat | 420 |
| gcctttctt caatgtgtgt cagttttggt ttcaacttta attttaatat caattgccat | 480 |
| tgtcaggtat catatgataa acatcccat atctaataat ttaacagcaa accatggcta | 540 |
| cttctgata gctactgtct ggacactagg ttttgccatc tgttctcccc ttccagtgtt | 600 |
| tcacagtctt gtggaacttc aagaaacatt tggttcagca ttgctgagca gcaggtattt | 660 |
| atgtgttgag tcatggccat ctgattcata cagaattgcc tttactatct ctttattgct | 720 |
| agttcagtat attctgccct tagtttgtct tactgtaagt catacaagtg tctgcagaag | 780 |
| tataagctgt ggattgtcca acaaagaaaa cagacttgaa gaaaatgaga tgatcaactt | 840 |
| aactcttcat ccatccaaaa agagtgggcc tcaggtgaaa ctctctggca gccataaatg | 900 |
| gagttattca ttcatcaaaa aacacagaag aagatatagc aagaagacag catgtgtgtt | 960 |
| acctgctcca gaaagacctt tcaagagaa ccactccaga atacttccag aaaactttgg | 1020 |
| ctctgtaaga agtcagctct cttcatccag taagttcata ccaggggtcc ccacttgctt | 1080 |
| tgagataaaa cctgaagaaa attcagatgt tcatgaattg agagtaaaac gttctgttac | 1140 |
| aagaataaaa aagagatctc gaagtgtttt ctacagactg accatactga tattagtatt | 1200 |
| tgctgttagt tggatgccac tacaccttt ccatgtggta actgatttta atgacaatct | 1260 |
| tatttcaaat aggcatttca agttggtgta ttgcatttgt catttgttgg gcatgatgtc | 1320 |
| ctgttgtctt aatccaattc tatatgggtt tcttaataat gggattaaag ctgatttagt | 1380 |
| gtcccttata cactgtcttc atatgtaata attctcactg ttt | 1423 |

<210> SEQ ID NO 123
<211> LENGTH: 5078
<212> TYPE: DNA
<213> ORGANISM: Homo sapiens
<220> FEATURE:
<221> NAME/KEY: misc_feature
<223> OTHER INFORMATION: NM_002410

<400> SEQUENCE: 123

| | |
|---|---|
| taatactcct ttattccctg ttttaaaaat tttttaaat ttgatacaat aattatacat | 60 |

```
aataatggag taccatgtga gattcaatcc acatatacat tgtgaaatga tcaaattagg    120
atagttagca tgcacatcac ccccaaataa ttattacttt tgtggtgaga acacttaaaa    180
ttgtctcttt tagaaatata cgttattatt aaccatagtc acctcgctgt gcaatagaac    240
accagaactt attcctccta aatgtaactt tttacccatt gaccactccc tcctcacccc    300
cctctctcct ccccacccct ggtaaccact gttctgttat ctcctatgat agcaactttt    360
tagcttctgc atgtgagatt gtacggtagt tgcctttctg tgcctggatt atttcattta    420
gcataatgtc cttcgggtat atccctgttg ctgcaaaaga caggatttct ctctcttttt    480
ctggttgaat agtattccat tgtcagagaa tgttgtaaga ctaggaaagg aacactgcag    540
gctggagccc tggggaaatg gtctgaggca ggtggtggga ctagagctgg ggtctggcaa    600
acaggctggg tttgattgtc agcataatag agagcactca tgtgccagct gggtgggagg    660
agcagccgag tgaagaaggg gaagcctctc aggaagcatg tgcagggttt atggtaatga    720
gcagaccagc aggtacgtag tgggagaggg gtgtgatggg gcagaggaac ttacgttatg    780
atagtacaag acagaggttg agcctcattt taataggcat tgtggtgggt gttgaatagt    840 gatgaatgt atgggtctgg aatcaggctg cctggtcaag ggctctgaaa catgagtgtg    900
catcagaatc acctcgaggc ttgttaaagg ataggctgtg gaccacatct cctcagttgc    960
tgattcagtg ggtgtgggtg gggcctgaga attcacattt cccactggtg atgctgctgt    1020
tactgattgg gaccacattt ggggaacact ggtctagaat tgagaggttg gcaaaccttc    1080
tctgttaaga ggtagatagt aaatatttta ggccttctgg gctacaaaga gtatctgtta    1140
catatttttt attgcttttc atgacccatt aagcatatat atatcattct ctgccatata    1200
caaacaggct gttgggggag tgaggatgat gtagggaagg tggggcatgg tttaataacc    1260
cctgggccat gcctagatga tcagtcctct gccacatagc tggctgacct ttgccaagtt    1320 aatcacccttt tacctttatt ttctcatgtt tctaataaaa cagagacgat aatattcata    1380
cttcttacca tatagaactt ctgaggattc agtgagcaaa gccacaaaag atggtatgtc    1440
acaatatctg ggatatagct agaatttata atttattttt actctgttga taggcaatgg    1500
gaaaacagta agaggcagac caacagtgat ccagggctct gaaagctaat tgcttcaaga    1560
tcctgctacc attttctttt gggccgcttg caaagaagaa tcctttgact gaagcatgta    1620
tgtacactct gaagtacagc ctgggttagt ctcttataag ggatcggatc attgctcagc    1680
tctcccttga gtggcactta gaaaatggcg ctattcgtaa gctgactggt attgggccca    1740
ggactctggc tgaaggggtg ggcatgctgg taaccatttg caacctatgc tcaggtccta    1800
cttgttggga agccctgatt gagaagagtg gcctggtctg tgctggcatt agataggatc    1860
tggctgcatt aatattgaaa ctactctgcc ttttaatgtc tcattttgcc tcatggtggg    1920
agtgaaagtg agaaccacag aaaatctgcc tgccaggtgt tccacatttc ttgtgctaca    1980
gcatgcaagt gagcagtgag gtgtacccttt tcctcatgta gctgggaaag caataccctt    2040
gcttgtacct ctggcatatc ttctctgtgc tggtgcacct agagaggttg cctggtggcc    2100
ctgagagagc catctcatca ctaaacactg atggtgaaaa gctggccatg ctcaaataag    2160
atgtagcaat ctacctcttc tttgtctagt taccccaag ggggcatcca ctttcttgct    2220
cacctcacca gttgcatgtt ctagtccttg ccagaagcac ataataatga ctttgtaagc    2280
ttaagttaca ggcacacaaa agggcctgat ggtgatatga ctccacccctc cccgttttg    2340 ctgacattcc gccaaaatatc cttctgtctc ctccccacct tgcaaaacaa acttcctgtt    2400
ttgaatttgg tccaggctgg aacagcccca ccacacctgt taacacacgc agacgcacac    2460
```

```
ttcccccttc ataattgctt agcttcttgt tgcctagcca gatttcccct cagcttacag    2520
ttcctgaatc ataagatatt gaaccagcaa atttaagagt tgacatttta cttagaggta    2580
ttcaagtgaa acatggctt ctggtttatt ttgctgtatt gtgccatgac cacttggcta     2640
attcttctcc tccttcacat cagaatggaa gtgaggaaag gcaaccagct gacacaggag    2700
ccagagtgag accagcagac tctcacactc aacctacacc atgaatttgt gtctatcttc    2760
tacgcgttaa gagccaagga caggtgaagt tgccagagag caatggctct cttcactccg    2820
tggaagttgt cctctcagaa gctgggcttt ttcctggtga cttttggctt catttggggt    2880
atgatgcttc tgcactttac catccagcag cgaactcagc ctgaaagcag ctccatgctg    2940
cgcgagcaga tcctggacct cagcaaaagg tacatcaagg cactggcaga agaaaacagg    3000
aatgtggtgg atgggccata cgctggagtc atgacagctt atgatctgaa gaaaacccct    3060
gctgtgttat tagataacat tttgcagcgc attggcaagt tggagtcgaa ggtggacaat    3120
cttgttgtca atggcaccgg aacaaactca accaactcca ctacagctgt tcccagcttg    3180
gttgcacttg agaaaattaa tgtggcagat atcattaacg gagctcaaga aaaatgtgta    3240
ttgcctccta tggacggcta ccctcactgt gagggaaaga tcaagtggat gaaagacatg    3300
tggcgttcag atccctgcta cgcagactat ggagtggatg gatccacctg ctcttttttt    3360
atttacctca gtgaggttga aaattggtgt cctcatttac cttggagagc aaaaaatccc    3420
tacgaagaag ctgatcataa ttcattggcg gaaattcgta cagattttaa tattctctac    3480
agtatgatga aaaagcatga agaattccgg tggatgagac tacggatccg gcgaatggct    3540
gacgcatgga tccaagcaat caagtccctg gcagaaaagc agaaccttga aagagaaag     3600 cggaagaaag tcctcgttca cctgggactc ctgaccaagg aatctggatt taagattgca    3660
gagacagctt tcagtggtgg ccctcttggt gaattagttc aatggagtga tttaattaca    3720
tctctgtact tactgggcca tgacattagg atttcagctt cactggctga gctcaaggaa    3780
atcatgaaga aggttgtagg aaaccgatct ggctgcccaa ctgtaggaga cagaattgtt    3840
gagctcattt acattgatat tgtaggactt gctcaattca agaaaactct tggaccatcc    3900
tgggttcatt accagtgcat gctccgagtc cttgattcat ttggtactga acccgaattt    3960
aatcatgcaa attatgccca atcgaaaggc cacaagaccc cttggggaaa atggaatctg    4020
aaccctcagc agttttatac catgttccct cataccccag acaacagctt tctggggttt    4080
gtggttgagc agcacctgaa ctccagtgat atccaccaca ttaatgaaat caaaaggcag    4140
aaccagtccc ttgtgtatgg caaagtggat agcttctgga agaataagaa gatctacttg    4200
gacattattc acacatacat ggaagtgcat gcaactgttt atggctccag cacaaagaat    4260
attcccagtt acgtgaaaaa ccatggtatc ctcagtggac gggacctgca gttccttctt    4320
cgagaaacca gttgtttgt tggacttggg ttcccttacg agggcccagc tcccctggaa     4380
gctatcgcaa atggatgtgc ttttctgaat cccaagttca cccacccaa aagcagcaaa     4440 aacacagact ttttcattgg caagccaact ctgagagagc tgacatccca gcatccttac    4500
gctgaagttt tcatcgggcg gccacatgtg tggactgttg acctcaacaa tcaggaggaa    4560
gtagaggatg cagtgaaagc aatttttaaat cagaagattg agccatacat gccatatgaa    4620
tttacgtgcg aggggatgct acagagaatc aatgctttca ttgaaaaaca ggacttctgc    4680
catgggcaag tgatgtggcc accccctcagc gccctacagg tcaagcttgc tgagcccggg    4740
cagtcctgca gcaggtgtg ccaggagagc cagctcatct gcgagccttc tttcttccag     4800
cacctcaaca aggacaagga catgctgaag tacaaggtga cctgccaaag ctcagagctg    4860
```

```
gccaaggaca tcctggtgcc ctcctttgac cctaagaata agcactgtgt gtttcaaggt    4920
gacctcctgc tcttcagctg tgcaggcgcc cacccaggc accagagggt ctgcccctgc     4980
cgggacttca tcaagggcca ggtggctctc tgcaaagact gcctatagca gctacctgct    5040
cagccctgca ccatgctgct ggggaagaca gtggcccc                            5078
```

<210> SEQ ID NO 124
<211> LENGTH: 887
<212> TYPE: DNA
<213> ORGANISM: Homo sapiens
<220> FEATURE:
<221> NAME/KEY: misc_feature
<223> OTHER INFORMATION: X16863

<400> SEQUENCE: 124

```
tctttggtga cttgtccact ccagtgtggc atcatgtggc agctgctcct cccaactgct     60
ctgctacttc tagtttcagc tggcatgcgg actgaagatc tcccaaaggc tgtggtgttc    120
ctggagcctc aatggtacag cgtgcttgag aaggacagtg tgactctgaa gtgccaggga    180
gcctactccc ctgaggacaa ttccacacag tggtttcaca atgagagcct catctcaagc    240
caggcctcga gctacttcat tgacgctgcc acagtcaacg acagtggaga gtacaggtgc    300
cagacaaacc tctccaccct cagtgacccg gtgcagctag aagtccatat cggctggctg    360
ttgctccagg cccctcggtg ggtgttcaag gaggaagacc ctattcacct gaggtgtcac    420
agctggaaga acactgctct gcataaggtc acatatttac agaatggcaa agacaggaag    480
tattttcatc ataattctga cttccacatt ccaaaagcca cactcaaaga tagcggctcc    540
tacttctgca gggggcttgt tgggagtaaa aatgtgtctt cagagactgt gaacatcacc    600
atcactcaag gtttggcagt gtcaaccatc tcatcattct ctccacctgg gtaccaagtc    660
tctttctgct tggtgatggt actccttttt gcagtggaca caggactata tttctctgtg    720
aagacaaaca tttgaagctc aacaagagac tggaaggacc ataaacttaa atggagaaag    780
gaccctcaag acaaatgacc cccatcccat gggagtaata agagcagtgg cagcagcatc    840
tctgaacatt tctctggatt tgcaaccca tcatcctcag gcctctc                   887
```

<210> SEQ ID NO 125
<211> LENGTH: 1800
<212> TYPE: DNA
<213> ORGANISM: Homo sapiens
<220> FEATURE:
<221> NAME/KEY: misc_feature
<223> OTHER INFORMATION: XM_042961

<400> SEQUENCE: 125

```
cttctctgcc agaagatacc atttcaactt aacacagca tgatcgaaac atacaaccaa      60
acttctcccc gatctgcggc cactggactg cccatcagca tgaaaatttt tatgtattta    120
cttactgttt ttcttatcac ccagatgatt gggtcagcac tttttgctgt gtatcttcat    180
agaaggttgg acaagataga agatgaaagg aatcttcatg aagattttgt attcatgaaa    240
acgatacaga gatgcaacac aggagaaaga tccttatcct tactgaactg tgaggagatt    300
aaaagccagt ttgaaggctt tgtgaaggat ataatgttaa acaagagga gacgaagaaa    360 gaaaacagct ttgaaatgca aaaggtgat cagaatcctc aaattgcggc acatgtcata    420
agtgaggcca gcagtaaaac aacatctgtg ttacagtggg ctgaaaaagg atactacacc    480
atgagcaaca acttggtaac cctggaaaat gggaaacagc tgaccgttaa aagacaagga    540
ctctattata tctatgccca agtcaccttc tgttccaatc gggaagcttc gagtcaagct    600
```

```
ccatttatag ccagcctctg cctaaagtcc cccggtagat tcgagagaat cttactcaga      660
gctgcaaata cccacagttc cgccaaacct tgcgggcaac aatccattca cttgggagga      720
gtatttgaat tgcaaccagg tgcttcggtg tttgtcaatg tgactgatcc aagccaagtg      780
agccatggca ctggcttcac gtcctttggc ttactcaaac tctgaacagt gtcaccttgc      840
aggctgtggt ggagctgacg ctgggagtct tcataataca gcacagcggt taagcccacc      900
ccctgttaac tgcctattta taaccctagg atcctcctta tggagaacta tttattatac      960
actccaaggc atgtagaact gtaataagtg aattacaggt cacatgaaac caaaacgggc     1020
cctgctccat aagagcttat atatctgaag cagcaacccc actgatgcag acatccagag     1080
agtcctatga aaagacaagg ccattatgca caggttgaat tctgagtaaa cagcagataa     1140
cttgccaagt tcagttttgt ttctttgcgt gcagtgtctt tccatggata atgcatttga     1200
tttatcagtg aagatgcaga agggaaatgg ggagcctcag ctcacattca gttatggttg     1260
actctgggtt cctatggcct tgttggaggg ggccaggctc tagaacgtct aacacagtgg     1320
agaaccgaaa ccccccccc ccccccgcca ccctctcgga cagttattca ttctctttca     1380
atctctctct ctccatctct ctctttcagt ctctctctct caacctcttt cttccaatct     1440
ctctttctca atctctctgt ttcccttttgt cagtctcttc cctcccccag tctctcttct     1500
caatccccct ttctaacaca cacacacaca cacacacaca cacacacaca cacacacaca     1560
cacacacaga gtcaggccgt tgctagtcag ttctcttctt tccaccctgt ccctatctct     1620
accactatag atgagggtga ggagtaggga gtgcagccct gagcctgccc actcctcatt     1680
acgaaatgac tgtatttaaa ggaaatctat tgtatctacc tgcagtctcc attgtttcca     1740
gagtgaactt gtaattatct tgttatttat ttttttgaata ataaagacct cttaacatta     1800

<210> SEQ ID NO 126
<211> LENGTH: 1450
<212> TYPE: DNA
<213> ORGANISM: Homo sapiens
<220> FEATURE:
<221> NAME/KEY: misc_feature
<223> OTHER INFORMATION: J04101

<400> SEQUENCE: 126
ttgggaagaa agtcggattt cccccgtccc cttccccctg ttactaatcc tcattaaaaa       60
gaaaaacaac aataactgca aacttgctac catcccgtac gtcccccact cctggcacca      120
tgaaggcggc cgtcgatctc aagccgactc tcaccatcat caagacggaa aaagtcgatc      180
tggagctttt cccctccccg gatatggaat gtgcagatgt cccactatta actccaagca      240
gcaaagaaat gatgtctcaa gcattaaaag ctactttcag tggtttcact aaagaacagc      300
aacgactggg gatcccaaaa gaccccggc agtggacaga aacccatgtt cgggactggg      360
tgatgtgggc tgtgaatgaa ttcagcctga aggtgtagaa cttccagaag ttctgtatga      420
atggagcagc cctctgcgcc ctgggtaaag actgctttct cgagctggcc ccagactttg      480
ttggggacat cttatgggaa catctagaga tcctgcagaa agaggatgtg aaaccatatc      540
aagttaatgg agtcaaccca gcctatccag aatcccgcta tacctcggat tacttcatta      600
gctatggtat tgagcatgcc cagtgtgttc caccatcgga gttctcagag cccagcttca      660
tcacagagtc ctatcagacg ctccatccca tcagctcgga agagctcctc tccctcaagt      720
atgagaatga ctacccctcg gtcattctcc gagaccctct ccagacagac accttgcaga      780
atgactactt tgctatcaaa caagaagtcg tcaccccaga caacatgtgc atggggagga      840
```

| | |
|---|---|
| ccagtcgtgg taaactcggg ggccaggact cttttgaaag catagagagc tacgatagtt | 900 |
| gtgatcgcct cacccagtcc tggagcagcc agtcatcttt caacagcctg cagcgtgttc | 960 |
| cctcctatga cagcttcgac tcagaggact atccggctgc cctgcccaac cacaagccca | 1020 |
| agggcacctt caaggactat gtgcgggacc gtgctgacct caataaggac aagcctgtca | 1080 |
| ttcctgctgc tgccctagct ggctacacag gcagtggacc aatccagcta tggcagtttc | 1140 |
| ttctggaatt actcactgat aaatcctgtc agtcttttat cagctggaca ggagatggct | 1200 |
| gggaattcaa actttctgac ccagatgagg tggccaggag atggggaaag aggaaaaaca | 1260 |
| aacctaagat gaattatgag aaactgagcc gtggcctacg ctactattac gacaaaaaca | 1320 |
| tcatccacaa gacagcgggg aaacgctacg tgtaccgctt tgtgtgtgac ctgcagagcc | 1380 |
| tgctggggta caccectgag gagctgcacg ccatgctgga cgtcaagcca gatgccgacg | 1440 |
| agtgatggca | 1450 |

<210> SEQ ID NO 127
<211> LENGTH: 6069
<212> TYPE: DNA
<213> ORGANISM: Homo sapiens
<220> FEATURE:
<221> NAME/KEY: misc_feature
<223> OTHER INFORMATION: XM_047802

<400> SEQUENCE: 127

| | |
|---|---|
| gcagctgccg actgggdatg acggcgggca ggaggagacc gcagccgaag ggacacagac | 60 |
| acgccgcttc accagctcgc ctcaggctgc cccctgcat ttttgtttta attttacgg | 120 |
| cttttccc tctctttctt cccttcctcc tggtcccagc agagccaagg aaacccacaa | 180 |
| aataagaaag gaagtgggcc ccggagcttg aacctccac agccggcttg tccagcgcag | 240 |
| cgcggggcg ggaggctgcg cgcaccagtt gccagcccgg tgcgcggtac cttccttac | 300 |
| ttttcttgaa acagcgatcg tgcctgcatt tggtggtttt ttggtttttg ttttttcct | 360 |
| tttcccgtat ttgctgaatc tccactatcc gactttttt ttttaatctt tctttcccc | 420 |
| ccccccccac cccacctctt tctggagcac gaatccaaac attttcccaa gcaacaaaga | 480 |
| aaagttcgca cgctggcacc gcagccggaa caggctggcg ctgctgccgg gccccctcc | 540 |
| ctccgacact tgactcaatc ctgcaagcaa gtgtgtgtgt gtcccatcc ccgcccgt | 600 |
| taacttcata gcaaataaca ataccata aagtcccagt cgcgcagccc ctccccgcgg | 660 |
| gcagcgcact atgctgctcg ggtgggcgtc cctgctgctg tgcgcgttcc gcctgccccct | 720 |
| ggccgcggtc ggccccgccg cgacacctgc ccaggataaa gccgggcagc ctccgactgc | 780 |
| tgcagcagcc gccagccccc gccgcggca gggggaggag gtgcaggagc gagccgagcc | 840 |
| tcccggccac ccgcaccccc tggcgcagcg gcgcaggagc aaggggctgg tgcagaacat | 900 |
| cgaccaactc tactccggcg gcggcaaggt gggctacctc gtctacgcgg gcggccggag | 960 |
| gttcctcttg gacctggagc gagatggttc ggtgggcatt gctggcttcg tgcccgcagg | 1020 |
| aggcgggacg agtgcgccct ggcgccaccg gagccactgc ttctatcggg gcacagtgga | 1080 |
| cggtagtccc cgctctctgg ctgtcttttga cctctgtggg ggtctcgacg gcttcttcgc | 1140 |
| ggtcaagcac gcgcgctaca cctaaagccc actgctgcgc ggaccctggg cggaggaaga | 1200 |
| aaagggcgc gtgtacgggg atgggtccgc acgatcctg cacgtctaca cccgcgaggg | 1260 |
| cttcagcttc gagggcctgc cgcgcgcgcg cagctgcgaa accccgcgt ccacaccgga | 1320 |
| ggcccacgag catgctccgg cgcacagcaa cccgagcgga cgcgcagcac tggcctcgca | 1380 |
| gctcttggac cagtccgctc tctcgcccgc tgggggctca ggaccgcaga cgtggtggcg | 1440 |

```
gcggcggcgc cgctccatct cccgggcccg ccaggtggag ctgcttctgg tggctgacgc    1500
gtccatggcg cggttgtatg gccggggcct gcagcattac ctgctgaccc tggcctccat    1560
cgccaatagg ctgtacagcc atgctagcat cgagaaccac atccgcctgg ccgtggtgaa    1620
ggtggtggtg ctaggcgaca aggacaagag cctggaagtg agcaagaacg ctgccaccac    1680
actcaagaac ttttgcaagt ggcagcacca acacaaccag ctgggagatg accatgagga    1740
gcactacgat gcagctatcc tgtttactcg ggaggattta tgtgggcatc attcatgtga    1800
caccctggga atggcagacg ttgggaccat atgttctcca gagcgcagct gtgctgtgat    1860
tgaagacgat ggcctccacg cagccttcac tgtggctcac gaaatcggac atttacttgg    1920
cctctcccat gacgattcca aattctgtga agagacctttt ggttccacag aagataagcg    1980
cttaatgtct tccatcctta ccagcattga tgcatctaag ccctggtcca aatgcacttc    2040
agccaccatc acagaattcc tggatgatgg ccatggtaac tgtttgctgg acctaccacg    2100
aaagcagatc ctgggcccccg aagaactccc aggacagacc tacgatgcca cccagcagtg    2160
caacctgaca ttcgggcctg agtactccgt gtgtccccggc atggatgtct gtgctcgcct    2220
gtggtgtgct gtggtacgcc agggccagat ggtctgtctg accaagaagc tgcctgcggt    2280
ggaagggacg ccttgtggaa aggggagaat ctgcctgcag ggcaaatgtg tggacaaaac    2340
caagaaaaaa tattattcaa cgtcaagcca tggcaactgg ggatcttggg gatcctgggg    2400
ccagtgttct cgctcatgtg gaggaggagt gcagtttgcc tatcgtcact gtaataaccc    2460
tgctcccaga aacaacggac gctactcac agggaagagg gccatctacc gctcctgcag    2520
tctcatgccc tgcccaccca atggtaaatc atttcgtcat gaacagtgtg aggccaaaaa    2580
tggctatcag tctgatgcaa aaggagtcaa aacttttgtg gaatggggttc ccaaatatgc    2640 aggtgtcctg ccagcggatg tgtgcaagct gacctgcaga gccaagggca ctggctacta    2700
tgtggtattt tctccaaagg tgaccgatgg cactgaatgt aggctgtaca gtaattccgt    2760
ctgcgtccgg gggaagtgtg tgagaactgg ctgtgacggc atcattggct caaagctgca    2820
gtatgacaag tgcggagtat gtggaggaga caactccagc tgtacaaaga ttgttggaac    2880
ctttaataag aaaagtaagg gttacactga cgtggtgagg attcctgaag gggcaaccca    2940
cataaaagtt cgacagttca aagccaaaga ccagactaga ttcactgcct atttagccct    3000 gaaaagaaa acggtgagt accttatcaa tggaaagtac atgatctcca cttcagagac    3060
tatcattgac atcaatggaa cagtcatgaa ctatagcggt tggagccaca gggatgactt    3120
cctgcatggc atgggctact ctgccacgaa ggaaattcta atagtgcaga ttcttgcaac    3180
agaccccact aaaccattag atgtccgtta tagctttttt gttcccaaga agtccactcc    3240 aaaaagtaaac tctgtcacta gtcatggcag caataaagtg ggatcacaca cttcgcagcc    3300
gcagtgggtc acgggcccat ggctcgcctg ctctaggacc tgtgacacag ttggcacac    3360 cagaacggtg cagtgccagg atggaaaccg gaagttagca aaaggatgtc ctctctccca    3420 aaggcccttct gcgtttaagc aatgcttgtt gaagaaatgt tagcctgtgg ttatgatctt    3480
atgcacaaag ataactggag gattcagcac tgatgcagtc gtggtgaaca ggaggtctac    3540
ctaacgcaca gaaagtcatg cttcagtgac attgtcaaca ggagtccaat tatgggcaga    3600
atctgctctc tgtgaccaaa agaggatgtg cactgcttca cgtgacagtg gtgaccttgc    3660
aatatagaaa aacttgggag ttattgaaca tcccctgggc ttacaagaaa cactgatgaa    3720
tgtaaaatca ggggacattt gaagatggca gaactgtctc ccccttgtca cctacctctg    3780
atagaatgtc tttaatggta tcataatcat tttcacccat aatacacagt agcttcttct    3840
```

```
tactgtttgt aaatacattc tcccttggta tgtcacttta tatccsctgg ttctattaaa    3900
atatccatat atatttctat aaaaaaagtg tttgaccaaa gtaggtctgc agctatttca    3960
acttccttcc gtttccagaa agagctgtgg atattttact ggaaattaag aacttgctgc    4020
tgttttaata agatgtagta tattttctga ctacaggaga taaaatttca gtcaaaaaac    4080
cattttgaca gcaagtatct tctgagaaat tttgaaaagt aaatagatct cagtgtatct    4140
agtcacttaa atacatacac gggttcattt acttaaacct ttgactgcct gtattttttt    4200
caggtagcta gccaaattaa tgcataattt cagatgtaga agtagggttt gcgtgtgtgt    4260
gtgtgatcat actcaagagt ctaaaaacta gtttccttgt gttggaaatt taaaaggaaa    4320
aaaatcgtat ttcactgtgt tttcaattta tattttcaca actactttct ctctccagag    4380
ctttcatctg atatctcaca atgtatgata tacgtacaaa acacacagca agttttctat    4440
catgtccaac acattcaaca ctggtatacc tcctaccagc aagcctttaa aatgcatttg    4500
tgtttgctta tttgttttgt tcaagggttc agtaagacct acaatgtttt gtatttcttg    4560
acttatttta ttagaaacat aaagatcac ttggtagtta gccacattga gaagtggtta    4620
tcattgttaa tgtggttaat gccaaaaagt ggttaatatt aataagactg tttccacacc    4680
ataggcaata atttcttaat ttaaaaaatc taagtatatt cctattgtac taaatatttt    4740
tcccaactgg aaagcacttg attgtacccg taagtgtttg agtgatgaca tgtgatgatt    4800
ttcagaaagt tgttgttttt gttccatag cctgtttaag taggttgtaa gtttgaatag    4860
ttagacatgg aaattatttt ataagcacac acctaaagat atcttttttag atgataaaat    4920
gtacacccc ccatcaccaa cctcacaact tagaaaatct aagttgtttg atttctttgg    4980
gatttctttt gttgtgaaac actgcaaagc caattttttct ttataaaaat tcatagtaat    5040
cctgccaaat gtgccattg ttaaagattt gcatgtgaag atcttaggga accactgttt    5100
gagttctaca agctcatgag agtttatttt tattataaga tgttttttaat ataaaagaat    5160
tatgtaactg atcactatat tacatcattt cagtgggcca ggaaaataga tgtcttgctg    5220
ttttcagtat tttcttaaga aattgctttt aaaacaaata attgttttac aaaaccaata    5280
attatccttt gaattttcat agactgactt tgcttttgac gtagaaattt ttttttctcaa    5340
taaattatca ctttgagaaa tgaggcctgt acaaggctga taacctatat gtgatggaga    5400
tcacccaatg ccaagggcag aaagcaaacc tagttaaata ggtgagaaaa aaaataataa    5460
tcccagtgcc atttgtctgt gcaaagagaa ttaggagaga ggttaatgtt acttttttcc    5520
attttggaaa taatttttaat caagtaactc aaatgtgaca aaatttattt ttatttttg    5580
tggttatatt cccaacaaca ttaaaaaata ctcgaggcat aaatgtagtt gtctcctact    5640
ctgcttctct tactatactc atacattttt aatatggttt atcaatgatt catgtttccc    5700
tcaaatagtg atggtttaca cctgtcatgg aaacaatcct agagagctca gagcaattaa    5760
accactattc catgcttta agtagttttc tccacctttt tcttatgagt ctcactagat    5820
tgactgagga atgtatgtct aaattcctgg agaagatgat atggattgga aactgaaatt    5880
cagagaaatg gagtgttcaa tagataccac gaattgtgaa caaagggaaa attctataca    5940
actcaatcta agtcagtcca cttgtgacttc gtactgtctt tcacctttcc attgttgcat    6000
cttgaatttt ttaaaatgtc tagaattcag gatgctaggg gctacttctt taaaaaaaaa    6060
aaaaaaaaa                                                              6069
```

<210> SEQ ID NO 128
<211> LENGTH: 3318

<212> TYPE: DNA
<213> ORGANISM: Homo sapiens
<220> FEATURE:
<221> NAME/KEY: misc_feature
<223> OTHER INFORMATION: NM_002827

<400> SEQUENCE: 128

```
gtgatgcgta gttccggctg ccggttgaca tgaagaagca gcagcggcta gggcggcggt      60
agctgcaggg gtcggggatt gcagcgggcc tcggggctaa gagcgcgacg cggcctagag     120
cggcagacgg cgcagtgggc cgagaaggag gcgcagcagc cgccctggcc cgtcatggag     180
atggaaaagg agttcgagca gatcgacaag tccgggagct gggcggccat ttaccaggat     240
atccgacatg aagccagtga cttcccatgt agagtggcca agcttcctaa gaacaaaaac     300
cgaaataggt acagagacgt cagtcccttt gaccatagtc ggattaaaact acatcaagaa     360
gataatgact atatcaacgc tagtttgata aaaatggaag aagcccaaag gagttacatt     420
cttacccagg gccctttgcc taacacatgc ggtcactttt gggagatggt gtgggagcag     480
aaaagcaggg gtgtcgtcat gctcaacaga gtgatggaga aaggttcgtt aaaatgcgca     540
caatactggc cacaaaaaga agaaaaagag atgatctttg aagacacaaa tttgaaatta     600
acattgatct ctgaagatat caagtcatat tatacagtgc gacagctaga attggaaaac     660
cttacaaccc aagaaactcg agagatctta catttccact ataccacatg gcctgacttt     720
ggagtccctg aatcaccagc ctcattcttg aactttcttt tcaaagtccg agagtcaggg     780
tcactcagcc cggagcacgg gcccgttgtg gtgcactgca gtgcaggcat cggcaggtct     840
ggaaccttct gtctggctga tacctgcctc ttgctgatgg acaagaggaa agaccctttct     900
tccgttgata tcaagaaagt gctgttagaa atgaggaagt ttcggatggg gctgatccag     960
acagccgacc agctgcgctt ctcctacctg gctgtgatcg aaggtgccaa attcatcatg    1020
ggggactctt ccgtgcagga tcagtggaag gagctttccc acgaggacct ggagccccca    1080
cccgagcata tccccccacc tcccccggcca cccaaacgaa tcctggagcc acacaatggg    1140
aaatgcaggg agttcttccc aaatcaccag tgggtgaagg aagagaccca ggaggataaa    1200
gactgcccca tcaaggaaga aaaaggaagc cccttaaatg ccgcacccta cggcatcgaa    1260
agcatgagtc aagacactga agttagaagt cgggtcgtgg ggggaagtct tcgaggtgcc    1320
caggctgcct ccccagccaa aggggagccg tcactgcccg agaaggacga ggaccatgca    1380
ctgagttact ggaagcccctt cctggtcaac atgtgcgtgg ctacggtcct cacggccggc    1440
gcttacctct gctacaggtt cctgttcaac agcaacacat agcctgaccc tcctccactc    1500
cacctccacc cactgtccgc ctctgcccgc agagcccacg cccgactagc aggcatgccg    1560
cggtaggtaa gggccgccgg accgcgtaga gagccgggcc ccggacggac gttggttctg    1620
cactaaaacc catcttcccc ggatgtgtgt ctcaccctc atccttttac tttttgcccc    1680
ttccactttg agtaccaaat ccacaagcca ttttttgagg agagtgaaag agagtaccat    1740
gctggcggcg cagagggaag gggcctacac ccgtcttggg gctcgcccca cccagggctc    1800
cctcctggag catcccaggc gggcggcacg ccaacagccc ccccttgaa tctgcaggga    1860
gcaactctcc actccatatt tatttaaaca attttttccc caaaggcatc catagtgcac    1920
tagcattttc ttgaaccaat aatgtattaa aattttttga tgtcagcctt gcatcaaggg    1980
ctttatcaaa aagtacaata ataaatcctc aggtagtact gggaatggaa ggctttgcca    2040
tgggcctgct gcgtcagacc agtactggga aggaggacgg ttgtaagcag ttgttattta    2100
gtgatattgt gggtaacgtg agaagataga acaatgctat aatatataat gaacacgtgg    2160
```

-continued

| | |
|---|---|
| gtatttaata agaaacatga tgtgagatta ctttgtcccg cttattctcc tccctgttat | 2220 |
| ctgctagatc tagttctcaa tcactgctcc cccgtgtgta ttagaatgca tgtaaggtct | 2280 |
| tcttgtgtcc tgatgaaaaa tatgtgcttg aaatgagaaa ctttgatctc tgcttactaa | 2340 |
| tgtgccccat gtccaagtcc aacctgcctg tgcatgacct gatcattaca tggctgtggt | 2400 |
| tcctaagcct gttgctgaag tcattgtcgc tcagcaatag ggtgcagttt tccaggaata | 2460 |
| ggcatttgcc taattcctgg catgacactc tagtgacttc ctggtgaggc ccagcctgtc | 2520 |
| ctggtacagc agggtcttgc tgtaactcag acattccaag ggtatgggaa gccatattca | 2580 |
| cacctcacgc tctggacatg atttagggaa gcagggacac cccccgcccc ccacctttgg | 2640 |
| gatcagcctc cgccattcca agtcaacact cttcttgagc agaccgtgat ttggaagaga | 2700 |
| ggcacctgct ggaaaccaca cttcttgaaa cagcctgggt gacggtcctt taggcagcct | 2760 |
| gccgccgtct ctgtcccggt tcaccttgcc gagagaggcg cgtctgcccc accctcaaac | 2820 |
| cctgtggggc ctgatggtgc tcacgactct tcctgcaaag ggaactgaag acctccacat | 2880 |
| taagtggctt tttaacatga aaaacacggc agctgtagct cccgagctac tctcttgcca | 2940 |
| gcattttcac attttgcctt tctcgtggta gaagccagta cagagaaatt ctgtggtggg | 3000 |
| aacattcgag gtgtcaccct gcagagctat ggtgaggtgt ggataaggct taggtgccag | 3060 |
| gctgtaagca ttctgagctg ggcttgttgt ttttaagtcc tgtatatgta tgtagtagtt | 3120 |
| tgggtgtgta tatatagtag catttcaaaa tggacgtact ggtttaacct cctatccttg | 3180 |
| gagagcagct ggctctccac cttgttacac attatgttag agaggtagcg agctgctctg | 3240 |
| ctatatgcct taagccaata tttactcatc aggtcattat ttttttacaat ggccatggaa | 3300 |
| taaaccattt ttacaaaa | 3318 |

<210> SEQ ID NO 129
<211> LENGTH: 1973
<212> TYPE: DNA
<213> ORGANISM: Homo sapiens
<220> FEATURE:
<221> NAME/KEY: misc_feature
<223> OTHER INFORMATION: NM_002421

<400> SEQUENCE: 129

| | |
|---|---|
| gggatattgg agtagcaaga ggctgggaag ccatcactta ccttgcactg agaaagaaga | 60 |
| caaaggccag tatgcacagc tttcctccac tgctgctgct gctgttctgg ggtgtggtgt | 120 |
| ctcacagctt cccagcgact ctagaaacac aagagcaaga tgtggactta gtccagaaat | 180 |
| acctggaaaa atactacaac ctgaagaatg atgggaggca agttgaaaag cggagaaata | 240 |
| gtggcccagt ggttgaaaaa ttgaagcaaa tgcaggaatt cttgggctg aaagtgactg | 300 |
| ggaaaccaga tgctgaaacc ctgaaggtga tgaagcagcc cagatgtgga gtgcctgatg | 360 |
| tggctcagtt tgtcctcact gaggggaacc ctcgctggga gcaaacacat ctgacctaca | 420 |
| ggattgaaaa ttacacgcca gatttgccaa gagcagatgg ggaccatgcc attgagaaag | 480 |
| ccttccaact ctggagtaat gtcacacctc tgacattcac caaggtctct gagggtcaag | 540 |
| cagacatcat gatatctttt gtcagggagg atcatcggga caactctcct tttgatggac | 600 |
| ctggaggaaa tcttgctcat gcttttcaac caggcccagg tattggaggg atgctcatt | 660 |
| ttgatgaaga tgaaaggtgg accaacaatt tcagagagta caacttacat cgtgttgcgg | 720 |
| ctcatgaact cggccattct cttggactct cccattctac tgatatcggg gctttgatgt | 780 |
| accctagcta caccttcagt ggtgatgttc agctagctca ggatgacatt gatggcatcc | 840 |
| aagccatata tggacgttcc caaaatcctg tccagcccat cggcccacaa accccaaaag | 900 |

```
cgtgtgacag taagctaacc tttgatgcta taactacgat tcggggagaa gtgatgttct    960
ttaaagacag attctacatg cgcacaaatc ccttctaccc ggaagttgag ctcaatttca   1020
tttctgtttt ctggccacaa ctgccaaatg ggcttgaagc tgcttacgaa tttgccgaca   1080
gagatgaagt ccggtttttc aaagggaata agtactgggc tgttcaggga cagaatgtgc   1140
tacacggata ccccaaggac atctacagct cctttggctt ccctagaact gtgaagcata   1200
tcgatgctgc tctttctgag gaaaacactg gaaaaaccta cttctttgtt gctaacaaat   1260
actggaggta tgatgaatat aaacgatcta tggatccagg ttatcccaaa atgatagcac   1320
atgactttcc tggaattggc cacaaagttg atgcagtttt catgaaagat ggatttttct   1380
atttctttca tggaacaaga caatacaaat ttgatcctaa aacgaagaga attttgactc   1440
tccagaaagc taatagctgg ttcaactgca ggaaaaattg aacattacta atttgaatgg   1500
aaaacacatg gtgtgagtcc aaagaaggtg ttttcctgaa gaactgtcta ttttctcagt   1560
catttttaac ctctagagtc actgatacac agaatatata cttatttata cctcagtttg   1620
catatttttt tactatttag aatgtagccc tttttgtact gatataattt agttccacaa   1680
atggtgggta caaaaagtca agtttgtggc ttatggattc atataggcca gagttgcaaa   1740
gatcttttcc agagtatgca actctgacgt tgatcccaga gagcagcttc agtgacaaac   1800
atatcctttc aagacagaaa gagacaggag acatgagtct tgccggagg aaaagcagct   1860 caagaacaca tgtgcagtca ctggtgtcac cctggatagg caagggataa ctcttctaac   1920
acaaaataag tgttttatgt ttggaataaa gtcaaccttg tttctactgt ttt         1973
```

<210> SEQ ID NO 130
<211> LENGTH: 2279
<212> TYPE: DNA
<213> ORGANISM: Homo sapiens
<220> FEATURE:
<221> NAME/KEY: misc_feature
<223> OTHER INFORMATION: NM_001752

<400> SEQUENCE: 130

```
tgcctgctga gggtggagac ccacgagccg aggcctcctg cagtgttctg cacagcaaac     60
cgcacgctat ggctgacagc cgggatcccg ccagcgacca gatgcagcac tggaaggagc    120
agcgggccgc gcagaaagct gatgtcctga ccactggagc tggtaaccca gtaggagaca    180
aacttaatgt tattacagta gggccccgtg ggccccttct tgttcaggat gtggttttca    240
ctgatgaaat ggctcatttt gaccgagaga gaattcctga gagagttgtg catgctaaag    300
gagcaggggc ctttggctac tttgaggtca cacatgacat taccaaatac tccaaggcaa    360
aggtatttga gcatattgga aagaagactc ccatcgcagt tcggttctcc actgttgctg    420
gagaatcggg ttcagctgac acagttcggg accctcgtgg gtttgcagtg aaattttaca    480
cagaagatgt taactgggat ctcgttggaa ataacacccc cattttcttc atcagggatc    540
ccatattgtt tccatctttt atccacagcc aaaagagaaa tcctcagaca catctgaagg    600
atccggacat ggtctgggac ttctggagcc tacgtcctga gtctctgcat caggtttctt    660
tcttgttcag tgatcggggg attccagatg acatcgcca catgaatgga tatggatcac    720
atactttcaa gctggttaat gcaaatgggg aggcagttta ttgcaaattc cattataaga    780
ctgaccaggg catcaaaaac ctttctgttg aagatgcggc gagactttcc caggaagatc    840
ctgactatgg catccgggat ctttttaacg ccattgccac aggaaagtac ccctcctgga    900 cttttttacat ccaggtcatg acatttaatc aggcagaaac ttttccattt aatccattcg    960
```

```
atctcaccaa ggtttggcct cacaaggact accctctcat cccagttggt aaactggtct      1020
taaaccggaa tccagttaat tactttgctg aggttgaaca gatagccttc gacccaagca      1080
acatgccacc tggcattgag gccagtcctg acaaaatgct tcagggccgc cttttttgcct     1140
```

```
atctcaccaa ggtttggcct cacaaggact accctctcat cccagttggt aaactggtct      1020
taaaccggaa tccagttaat tactttgctg aggttgaaca gatagccttc gacccaagca      1080
acatgccacc tggcattgag gccagtcctg acaaaatgct tcagggccgc ctttttgcct      1140
atcctgacac tcaccgccat cgcctgggac ccaattatct tcatatacct gtgaactgtc      1200
cctaccgtgc tcgagtggcc aactaccagc gtgatggccc gatgtgcatg caggacaatc      1260
aggtggtgtc tccaaattac taccccaaca gcttгggtgc tccggaacaa cagccttctg      1320
ccctggagca cagcatccaa tattctggag aagtgcggag attcaacact gccaatgatg      1380
ataacgttac tcaggtgcgg gcattctatg tgaacgtgct gaatgaggaa cagaggaaac      1440
gtctgtgtga gaacattgcc ggccacctga aggatgcaca aattttcatc cagaagaaag      1500
cggtcaagaa cttcactgag gtccaccctg actacgggag ccacatccag gctcttctgg      1560
acaagtacaa tgctgagaag cctaagaatg cgattcacac ctttgtgcag tccggatctc      1620
acttggcggc aagggagaag gcaaatctgt gaggccgggg ccctgcacct gtgcagcgaa      1680
gcttagcgtt catccgtgta acccgctcat cactggatga agattctcct gtgctagatg      1740
tgcaaatgca agctagtggc ttcaaaatag agaatcccac tttctatagc agattgtgta      1800 acaatttaa tgctatttcc ccaggggaaa atgaaggtta ggatttaaca gtcatttaaa       1860 aaaaaattt gttttgacgg atgattggat tattcattta aaatgattag aaggcaagtt       1920
tctagctaga aatatgattt tatttgacaa aatttgttga aattatgtat gtttacatat      1980
cacctcatgg cctattatat taaaatatgg ctataaatat ataaaagaa aagataaaga       2040 tgatctactc agaaattttt atttttctaa ggttctcata ggaaaagtac atttaataca      2100
gcagtgtcat cagaagataa cttgagcacc gtcatggctt aatgtttatt cctgataata     2160
attgatcaaa ttcatttttt tcactggagt tacattaatg ttaattcagc actgatttca     2220
caacagatca atttgtaatt gcttacattt ttacaataaa taatctgtac gtaagaaca       2279
```

<210> SEQ ID NO 131
<211> LENGTH: 2438
<212> TYPE: DNA
<213> ORGANISM: Homo sapiens
<220> FEATURE:
<221> NAME/KEY: misc_feature
<223> OTHER INFORMATION: NM_016155

<400> SEQUENCE: 131

```
ccggcggggg cgccgcggag agcggagggc gccgggctgc ggaacgcgaa gcggagggcg        60
cgggaccctg cacgccgccc gcgggcccat gtgagcgcca tgcggcgccg cgcagcccgg       120
ggacccggcc cgccgccccc agggcccgga ctctcgcggt tgccgctgct gccgctgccg       180
ctgctgctgc tgctggcgct ggggacccgc ggggctgcg ccgcgcccgc acccgcgccg        240
cgcgccgagg acctcagcct gggagtggag tggctaagca ggttcggtta cctgcccccg       300
gctgacccca caacagggca gctgcagacg caagaggagc tgtctaaggc catcacagcc       360
atgcagcagt ttggtggcct ggaggccacc ggcatcctgg acgaggccac cctggccctg      420
atgaaaaccc cacgctgctc cctgccagac ctccctgtcc tgacccaggc tcgcaggaga      480
cgccaggctc cagcccccac caagtggaac aagaggaacc tgtcgtggag ggtccggacg      540
ttcccacggg actcaccact ggggcacgac acggtgcgtg cactcatgta ctacgccctc      600
aaggtctgga gcgacattgc gcccctgaac ttccacgagg tggcgggcag caccgccgac      660
atccagatcg acttctccaa ggccgaccat aacgacggct accccttcga cggccccggc      720
ggcaccgtgg cccacgcctt cttccccggc caccaccaca ccgccgggga cacccacttt      780
```

```
gacgatgacg aggcctggac cttccgctcc tcggatgccc acgggatgga cctgtttgca     840
gtggctgtcc acgagtttgg ccacgccatt gggttaagcc atgtggccgc tgcacactcc     900
atcatgcggc cgtactacca gggcccggtg ggtgacccgc tgcgctacgg gctcccctac     960
gaggacaagg tgcgcgtctg gcagctgtac ggtgtgcggg agtctgtgtc tcccacggcg    1020
cagcccgagg agcctcccct gctgccgagg cccccagaca accggtccag cgccccgccc    1080
aggaaggacg tgcccacag atgcagcact cactttgacg cggtggccca gatccgcggt     1140
gaagctttct tcttcaaagg caagtacttc tggcggctga cgcgggaccg gcacctggtg    1200
tccctgcagc cggcacagat gcaccgcttc tggcggggcc tgccgctgca cctggacagc    1260
gtggacgccg tgtacgagcg caccagcgac cacaagatcg tcttctttaa aggagacagg    1320
tactgggtgt tcaaggacaa taacgtagag gaaggatacc cgcgccccgt ctccgacttc    1380
agcctcccgc ctggcggcat cgacgctgcc ttctcctggg cccacaatga caggacttat    1440
ttctttaagg accagctgta ctggcgctac gatgaccaca cgaggcacat ggaccccggc    1500
taccccgccc agagccccct gtggaggggt gtccccagca cgctggacga cgccatgcgc    1560
tggtccgacg gtgcctccta cttcttccgt ggccaggagt actggaaagt gctggatggc    1620
gagctggagg tggcacccgg gtacccacag tccacggccc gggactggct ggtgtgtgga    1680
gactcacagg ccgatggatc tgtgctgcg ggcgtggacg cggcagaggg gccccgcgcc     1740
cctccaggac aacatgacca gagccgctcg gaggacggtt acgaggtctg ctcatgcacc    1800 tctgggcat cctctccccc gggggcccca ggccactgg tggctgccac catgctgctg      1860
ctgctgccgc cactgtcacc aggcgccctg tggacagcgg cccaggccct gacgctatga    1920
cacacagcgc gagcccatga gaggacgag cggtgggac agcctggcca cagagggcaa      1980
ggactgtgcc ggagtccctg ggggaggtgc tggcgcggga tgaggacggg ccaccctggc    2040
accggaaggc cagcagaggg cacggcccgc cagggctggg caggctcagg tggcaaggac    2100
ggagctgtcc cctagtgagg gactgtgttg actgacgagc cgaggggtgg ccgctccaga    2160
agggtgccca gtcaggccgc accgccgcca gcctcctccg gccctggagg gagcatctcg    2220
ggctgggggc ccaccctct ctgtgccggc gccaccaacc ccacccacac tgctgcctgg     2280
tgctcccgcc ggcccacagg gcctccgtcc ccaggtcccc agtggggcag ccctccccac    2340
agacgagccc cccacatggt gccgcggcac gtcccccctg tgacgcgttc cagaccaaca    2400
tgacctctcc ctgctttgta aaaaaaaaaa aaaaaaaa                            2438

<210> SEQ ID NO 132
<211> LENGTH: 1356
<212> TYPE: DNA
<213> ORGANISM: Homo sapiens
<220> FEATURE:
<221> NAME/KEY: misc_feature
<223> OTHER INFORMATION: U94332

<400> SEQUENCE: 132
gtatatataa cgtgatgagc gtacgggtgc ggagacgcac cggagcgctc gcccagccgc      60
cgyctccaag cccctgaggt ttccggggac cacaatgaac aagttgctgt gctgcgcgct     120
cgtgtttctg gacatctcca ttaagtggac cacccaggaa acgtttcctc caaagtacct     180
tcattatgac gaagaaacct ctcatcagct gttgtgtgac aaatgtcctc tggtaccta     240 cctaaaacaa cactgtacag caaagtggaa gaccgtgtgc gccccttgcc ctgaccacta    300
ctacacagac agctggcaca ccagtgacga gtgtctatac tgcagcccg tgtgcaagga     360
```

```
gctgcagtac gtcaagcagg agtgcaatcg cacccacaac cgcgtgtgcg aatgcaagga    420
agggcgctac cttgagatag agttctgctt gaaacatagg agctgccctc ctggatttgg    480
agtggtgcaa gctggaaccc cagagcgaaa tacagtttgc aaaagatgtc cagatgggtt    540
cttctcaaat gagacgtcat ctaaagcacc ctgtagaaaa cacacaaatt gcagtgtctt    600
tggtctcctg ctaactcaga aaggaaatgc aacacacgac aacatatgtt ccggaaacag    660
tgaatcaact caaaaatgtg gaatagatgt taccctgtgt gaggaggcat tcttcaggtt    720
tgctgttcct acaaagttta cgcctaactg gcttagtgtc ttggtagaca atttgcctgg    780
caccaaagta aacgcagaga gtgtagagag gataaaacgg caacacagct cacaagaaca    840
gactttccag ctgctgaagt tatggaaaca tcaaaacaaa gcccaagata tagtcaagaa    900
gatcatccaa gatattgacc tctgtgaaaa cagcgtgcag cggcacattg gacatgctaa    960
cctcaccttc gagcagcttc gtagcttgat ggaaagctta ccgggaaaga aagtgggagc   1020
agaagacatt gaaaaaacaa taaaggcatg caaacccagt gaccagatcc tgaagctgct   1080
cagtttgtgg cgaataaaaa atggcgacca agacaccttg aagggcctaa tgcacgcact   1140
aaagcactca aagacgtacc actttcccaa aactgtcact cagagtctaa agaagaccat   1200
caggttcctt cacagcttca caatgtacaa attgtatcag aagttattt tagaaatgat   1260 aggtaaccag gtccaatcag taaaaataag ctgcttataa ctggaaatgg ccattgagct   1320
gtttcctcac aattggcgag atcccatgga tgataa                             1356
```

OLIGONUCLEOTIDE-CONTAINING PHARMACOLOGICAL COMPOSITIONS AND THEIR USE

This application is a Continuation of U.S. patent application Ser. No. 10/191,997, "Oligonucleotide-Containing Pharmacological Compositions and Their Use", Roderic M. K. Dale, first author, filed Jul. 10, 2002 (abandoned), and claims the benefit of U.S. Provisional Application No. 60/303,820, filed on Jul. 10, 2001.

FIELD OF THE INVENTION

The present invention relates to compositions containing oligonucleotides, and particularly to oligonucleotide-containing compositions suitable for administration to humans and other mammals.

BACKGROUND OF THE INVENTION

Oligonucleotides, oligonucleotide analogs and other sequence-specific binding polymers designed to block translation of selected messenger RNA (the sense strand) are commonly called antisense oligonucleotides. Development of such oligonucleotides, for therapeutic applications entails selecting a target genetic sequence unique and critical to the pathogen or pathogenic state one wishes to treat. One then assembles an oligomer of genetic bases (adenine, cytosine, guanine, and thymine or uracil) complementary to that selected sequence. When such an antisense oligonucleotide binds to its targeted disease-causing sequence, it can inactivate that target and thereby alleviate the disease.

Antisense oligonucleotides offer the prospect of safe and effective therapeutics for a broad range of intractable diseases. Nonetheless, developing therapeutics that function by a true antisense mechanism presents a number of forbidding challenges. The oligonucleotides should achieve adequate efficacy at a concentration attainable within the cells of the patient. They should inhibit their selected target sequences without concomitant attack on any other sequences in the patient's pool of approximately 200 million bases of unique-sequence RNA. They should be stable in extracellular compartments and within cells. They must be deliverable into the cellular compartments containing their targeted sequences. They should be adequately soluble in aqueous solution. Finally, they should exhibit little or no toxicity at therapeutic concentrations.

First-generation antisense oligonucleotides comprised natural genetic material (Belikova et al. (1967) Tetrahedron Lett. 37, 3557-3562; Zamecnik et al. (1978) Proc. Natl. Acad. Sci. USA 75, 280-284; Summerton (1979) J. Theor. Biol. 78, 77-99) and often contained crosslinking agents for binding their targets irreversibly (Summerton et al. (1978) J. Mol. Biol. 122, 145-162). As the design challenges became more fully appreciated, a number of non-natural antisense structural types were developed in an effort to improve efficacy, stability and delivery. Of particular note are the early non-ionic DNA analogs including phosphotriester-linked DNA and methylphosphonate-linked DNA (Cohen (1989) Oligodeoxynucleotides: Antisense Inhibitors of Gene Expression, CRC Press, pp. 82-92). Other nucleic acid analogs of note include carbamate-linked DNA (Cohen (1989) Oligodeoxynucleotides Antisense Inhibitors of Gene Expression, CRC Press, pp. 97-117), phosphoroamidate-linked DNA (Froehler et al. (1988) Nucleic Acids Res. 16, 4831-4839) and 2'-O-methyl RNA (Shibahara et al. (1989) Nucleic Acids Res. 17, 239-252). These second generation oligonucleotides include oligonucleotides containing acyclic backbone moieties, including nylon (Weller et al. (1991) J. Org. Chem. 56, 6000-6006; Huang et al. (1991) J. Org. Chem. 56, 6007-6018), the exceptionally high-affinity peptide nucleic acids (PNA) (Egholm et al. (1992) J. Am. Chem. Soc. 114, 1895-1897) and related types (U.S. Pat. No. 5,217,866).

One approach to improving the potency of antisense oligonucleotides is to enhance the affinity or the efficiency with which the antisense oligonucleotides interact with their targets and induce RNase degradation of their target gene transcripts. The doses at which effects have been observed generally range from 10 to 30 mg/kg i.v. (Miragha et al. (2000) Antisense Nuc. Acid Drug Devel. 10, 453-461). Some clinical studies, however, have not demonstrated antisense activity at doses up to 30 mg/kg i.v. (Rudin et al. (2001) Clin. Cancer Res. 7, 1214-1220; Kushner et al. (2000) Curr. Oncol. Reports 2, 23-30), indicating that results vary based on the structure of the oligonucleotide administered. Typical dose-response curves for antisense oligonucleotides both in vivo and in vitro, often reveal that less than a factor of ten often separates the concentration producing antisense activity from the concentration producing no activity (Branch (1998) Trends Biochem. Sci. 23, 45-50). Since the ratio of antisense to non-antisense effects drops sharply outside a restricted concentration range, it remains challenging to identify common structural features for any antisense oligonucleotide that will enhance affinity and efficiency of the oligonucleotide for its target. Furthermore, no studies to date have identified common structural features of antisense oligonucleotides that would make them suitable for oral administration, thus necessitating intravenous administration (Chen et al. (2000) Antisense Nuc. Acid. Drug Develop. 10, 415-422). Identification of common structural modifications of antisense oligonucleotides that facilitate oral or topical administration would therefore also be advantageous.

Although each of these newer structural types provides one or more significant advantages over the first-generation oligonucleotides, none yet appear to provide the full combination of properties needed in antisense therapeutics for successful therapeutic applications.

SUMMARY OF THE INVENTION

The invention encompasses a composition suitable for administration in a mammal comprising a modified oligonucleotide of about seven to seventy-five nucleotides containing seven or more contiguous ribose groups linked by achiral 5' to 3' internucleoside phosphate linkages, wherein the modified oligonucleotide is complementary to a region of a gene associated with a pathological disorder. In some embodiments, the mammal is a human and the oligonucleotide is a ribonucleotide or deoxyribonucleotide. The modified oligonucleotide can be complementary to a region of the gene selected from the group consisting of the 5' UTR region, translational start site, the 3' UTR, and translational termination site.

In some embodiments, the gene is a gene selected from Table 1 and the pathological disorder is selected from the group consisting of abnormal appetite, hypertension, hypercholesteroremia, hyperlipidemia, erectile dysfunction, eczema, depression, anxiety, stress, inflammatory bowel syndrome, ulcerative colitis, Crohn's disease, renal stones, gall stones, constipation, migraine headache, seizure, multiple sclerosis, polymyositis, fibromyalgia, Parkinson's disease, ALS, chronic pain, pre-menstrual syndrome, sinusitis, colds, trauma, carpal tunnel syndrome, chronic fatigue syndrome, rosacea, arthritis, psoriasis, prostatitis, inflammation, heartburn, infection, poison ivy, colon cancer, malignant melanoma and malignant nasal polyps. In preferred embodiments, the modified oligonucleotide is selected from the group consisting of SEQ ID NO: 1-81

In some embodiments, the modified oligonucleotide is present in the composition at a concentration effective to reduce the expression of the gene when administered. When the composition is administered, the modified oligonucleotide is administered at a dose of less than 100 µg/kg, preferably less than 50 µg/kg, more preferably less than 5.0 µg/kg, even more preferably less than 0.50 µg/kg, yet even more preferably less than 0.050 µg/kg, and most preferably less than 0.0050 µg/kg. Furthermore, the modified oligonucleotide present in the composition may be suitable for oral administration.

The modified oligonucleotides present in the compositions of the invention preferably have a Tm of about 75-115° C. at a concentration of 1 mM and a length of 10 to 26 bases, or a Tm of 40° C. to 85° C. at a concentration of 1 pM and a length of 10 to 26 bases. In one embodiment, the ribose group has a modified 2' substituent selected from the group consisting of hydrogen, methoxy, propoxy, methoxy-ethoxy, flourine, chlorine, bromine and iodine. In another embodiment, the modified oligonucleotide is 3' or 5' end-blocked.

The compositions of the invention may be formulated as pharmaceutical compositions, nutritional or dietary supplement compositions, or as cosmetic compositions. In some embodiments, the compositions of the invention comprise two or more different modified oligonucleotides, while in other embodiments, three or more different modified oligonucleotides.

The invention also encompasses a method of treating a patient with a pathological disorder comprising administering one or more of the aforementioned modified oligonucleotides of the invention, wherein the modified oligonucleotides are about seven to seventy-five nucleotides, contain seven or more contiguous ribose groups linked by achiral 5' to 3' internucleoside phosphate linkages. Preferably, the modified oligonucleotide is complementary to a region of a gene associated with the pathological disorder. More preferably, the gene is selected from Table 1 and the aforementioned pathological disorders are selected from the group consisting of abnormal appetite, hypertension, hypercholesteroremia, hyperlipidemia, erectile dysfunction, eczema, depression, anxiety, stress, inflammatory bowel syndrome, ulcerative colitis, Crohn's disease, renal stones, gall stones, constipation, migraine headache, seizure, multiple sclerosis, polymyositis, fibromyalgia, Parkinson's disease, ALS, chronic pain, pre-menstrual syndrome, sinusitis, colds, trauma, carpal tunnel syndrome, chronic fatigue syndrome, rosacea, arthritis, psoriasis, prostatitis, inflammation, heart burn, infection, poison ivy, colon cancer, malignant melanoma and malignant nasal polyps.

As mentioned above, the invention includes a nutritional supplement comprising a modified oligonucleotide of about seven to seventy-file nucleotides containing seven or more contiguous ribose groups linked by achiral 5' to 3' internucleoside phosphate linkages. The invention also includes a method of supplementing the diet of an individual comprising administering this nutritional supplement, wherein administration of the nutritional supplement improves the health of the individual.

The invention further includes a cosmetic composition comprising a modified oligonucleotide of about seven to seventy-file nucleotides containing seven or more contiguous ribose groups linked by achiral 5' to 3' internucleoside phosphate linkages, wherein the modified oligonucleotide is complementary to a region of a gene associated with a skin disorder. The invention also includes a method of improving the appearance of the skin in an individual with a skin disorder comprising administering this cosmetic composition.

DETAILED DESCRIPTION

The present invention relates to compositions that comprise oligonucleotide molecules, and the use of such compositions to treat the symptoms of diseases/conditions such as acroparaesthia, allergic (psoric) conditions, allergic reactions, alopecia, amnesia, anaphrodisia, angina, arthritis, asthenopia, biliary sycosis, burns, cancerous conditions, such as colon cancer, malignant melanoma and malignant nasal polyps, carpal tunnel syndrome, colds, conjunctivitis, Crohn's disease, depression, depressive psychosis, dysthyroidism, epilepsy, erectile dysfunction, excessive appetite (i.e., appetite control and suppression, promotion of healthy weight loss while naturally satisfying the appetite), gingivitis, heart burn (i.e., relief of occasional heartburn or occasional acid indigestion), hemorrhage, hypertension (i.e. helps maintain cardiovascular function, and a healthy heart and circulatory system), high cholesterol (i.e., helps to maintain cholesterol levels that are already within the normal range), hyperthyroidism, infections, inflammatory disease, lack of willpower, laryngitis, leukopenia, liver disorders, mental disorders (i.e., reduces stress, frustration, muscle tension, anxiety, and occasional simple nervous tension; enhances resistance to stress), myopia, neurosis, neurological disorders such as multiple sclerosis and ALS, obesity, pain (i.e., relief of minor or temporary aches and pains), pancreatic disorders, poison ivy, premature senescence, pre-menstrual syndrome (i.e., treatment of common symptoms associated with the menstrual cycle such as edema, breast tenderness, headaches, skin problems, cramps and mild mood changes), prostatitis, psoriasis, rosacea, seborrhea, sinusitis, and trauma.

The Oligonucleotide

Generally

A double-stranded DNA molecule encoding a gene has both a sense and an antisense strand. The transcription of RNA uses the antisense strand to make an exact sequence copy of the sense strand (with the minor changes of employing uridine for thymidine, and an RNA backbone in lieu of a DNA backbone). Thus, the RNA formed in transcription has the same nucleotide sequence as the sense strand of the gene. The RNA transcript is processed in the cell to become mRNA, which may subsequently be used as a template to make protein.

The term "oligonucleotides" as used herein, refers to a molecule comprised of nucleotides (i.e., ribonucleotides, deoxyribonucleotides, or both). The term includes monomers and polymers of ribonucleotides and deoxyribonucleotides, or mixtures thereof, with the nucleotides being connected together via, for example 5' to 3' linkages, 5' to 2' linkages, etc. The nucleotides used in the oligonucleotides may be naturally occurring or may be synthetically produced analogues that are capable of forming base-pair relationships with naturally occurring base pairs. Examples of non-naturally occurring bases that are capable of forming base-pairing relationships include, but are not limited to, aza and deaza pyrimidine analogues, aza and deaza purine analogues, and other heterocyclic base analogues, wherein one or more of the carbon and nitrogen atoms of the purine and pyrimidine rings have been substituted by heteroatoms, e.g., oxygen, sulfur, selenium, phosphorus, etc.

The oligonucleotides of the present invention are at least five contiguous nucleotides in length. For example, the oligonucleotide can be five to seventy-five nucleotides in length. The oligonucleotide can also be at least ten sequential nucleotides and alternatively, at least fifteen sequential nucleotides in length. In one embodiment, the oligonucleotide is twelve to twenty-six nucleotides in length. The oligonucleotide sequence can be derived from any of the genes listed in Table 1 (SEQ ID NO: 82-132). Examples of suitable antisense oligonucleotide sequences for the compositions of the present invention are described in Table 1 below.

TABLE 1

Representative antisense oligonucleotides

| Oligo Name(s) | Gene Target (Accession #) | Nucleic Acid Sequence | SEQ ID |
|---|---|---|---|
| Asm | PDE-4 phosphodiesterase 4 (U50158) (SEQ ID NO: 82) | CGTGTCAGGAGAAC | 1 |
| Ace1, Ace12 | angiotensin I converting enzyme (J04144.1) (SEQ ID NO: 83) | CATGACGCGGTGCG | 2 |
| Acid-2 | ATP4A H + /K + ATPase alpha (NM_000704) (SEQ ID NO: 84) | GGCAGTCGTCCCTCTA | 3 |
| Acid B2 | ATP4B H + /K + ATPase beta (NM_000705) (SEQ ID NO: 85) | AACGTTTCACTTCTCA | 4 |
| cd18-1 | Cd-18 (M15395) (SEQ ID NO: 86) | TTGCTACCAGTCT | 5 |
| COX2 CX2 | cyclooxygenase 2 (M90100) (SEQ ID NO: 87) | TCTACAGTTCAGTCGA | 6 |
| Mg44 | HMGCoA reductase 3-hydroxy-3-methylglutaryl-coenzyme A reductase (NM_000859) (SEQ ID NO: 88) | TGACAACATTGTAGCTAC, AGCTACAGAATCCTTGGA, GTCGGGCTATTCAGGC | 7 8 9 |
| P65-2M 65 | NfkappaB p65 (nm_021975) (SEQ ID NO: 89) | GAACAGTTCGTCCATG | 10 |
| IL-501 | IL-5 (NM_000879) (SEQ ID NO: 90) | CCTCATGGCTCTGAA | 11 |
| LO5 | lipoxygenase 5 (J03571) (SEQ ID NO: 91) | GGAGGGCATGGCGCGG | 12 |
| MPB-19 | SRD5A2 steroid 5-alpha-reductase-2 (M74047) (SEQ ID NO: 92) | CCTGCATCGCGCCGTG | 13 |
| NEP-1 CALLA | neutral endopeptidase (NM_000902) (SEQ ID NO: 93) | GACTTGCCCATCACCT | 14 |
| NPY-1 | Neuropeptide Y (K01911) (SEQ ID NO: 94) | ACCTAGCATGGTGGCT | 15 |
| D5 PDE5.1 | phosphodiesterase 5 (SEG-AB001615) (SEQ ID NO: 95) | CGCTCCATGGTTGGC | 16 |
| D7 | phosphodiesterase 7A (L12052) (SEQ ID NO: 96) | CTTCCATTGAATACGC | 17 |

TABLE 1-continued

Representative antisense oligonucleotides

| Oligo Name(s) | Gene Target (Accession #) | Nucleic Acid Sequence | SEQ ID |
|---|---|---|---|
| Per | Perilipin (AB005293) (SEQ ID NO: 97) | ACTGCCATCCTCGCTC | 18 |
| TTP TTPII | tripeptidyl peptidase II (M73047) (SEQ ID NO: 98) | CGGTGGCCATGGACGC, AAGTTCATGGTTTCGGA | 19 20 |
| MTP | Microsomal triglyceride protein (X59657) (SEQ ID NO: 99) | GAATCATATTTGACCAGCA | 21 |
| HisR1 | Histamine receptor 1 (D14436) (SEQ ID NO: 100) | GGCTCATTGGCGCAAG, AGAGCCTCCCTTAGGA | 22 23 |
| CRP | C-reactive protein (M11880) (SEQ ID NO: 101) | CATGGTCACGTCCTGC | 24 |
| CETP | Cholesteryl ester transfer protein (XM_008050) (SEQ ID NO: 102) | ATGGTTATCAGGCAGTGG, CATGGTTATCAGGCAGTGG, CTGAAGAATTGACCAC | 25 26 27 |
| ICAM | ICAM-1 (J03132) (SEQ ID NO: 103) | CATAGCGAGGCTGAGG | 28 |
| TNF-α | Tumor necrosis factor-alpha (X02910) (SEQ ID NO: 104) | GTGCTCATGGTGTCC | 29 |
| BMP-4 | Bone morphogenic protein-4 (U43842) (SEQ ID NO: 105) | CGACCATCAGCATTC | 30 |
| BAR-1, BB1 | beta adrenergic receptor-1 (NM_000684) (SEQ ID NO: 106) | GCCCATGCCGAGCTGC | 31 |
| IL-6 | Interleukin-6 (X04430) (SEQ ID NO: 107) | AGGAGTTCATAGCTGG | 32 |
| FAAH, FA$_2$H | fatty acid amid hydrolase (U82535) (SEQ ID NO: 108) | GCACCATGATCCCTTC | 33 |
| ACAT-1 | sterol-O-acyl-transferase (XM_031119) (SEQ ID NO: 109) | CTTCACCCACCATTGT | 34 |
| IBAT | ileal sodium dependent bile acid transporter (NM_000452) (SEQ ID NO: 110) | CATTCATTGCTGGGTCTG | 35 |
| HMGIC | High mobility group phosphor-protein isoform C (U28749) (SEQ ID NO: 111) | CGTGCGCTCATCCTG, AACGTTGCGCCCCTA | 36 37 |
| Ghre | Ghrelin (NM_016362) (SEQ ID NO: 112) | TGCAGACAGGTGGGCC, GCATGGCCTCAGCTGGG, TGGGCGATCACTTGTC | 38 39 40 |
| AAT1R | angiotensin II receptor (S77410) (SEQ ID NO: 113) | CATTTTGATCACCTGGGT, CGAACATGTCACTCAA | 41 42 |

TABLE 1-continued

Representative antisense oligonucleotides

| Oligo Name(s) | Gene Target (Accession #) | Nucleic Acid Sequence | SEQ ID |
|---|---|---|---|
| VEGF | vascular endothelial growth factor (XM_166457) (SEQ ID NO: 114) | AAGTTCATGGTTTCGGA, TCACCGCCTCGGCTTGT | 43 44 |
| FAS | fatty acid synthase (U29344) (SEQ ID NO: 115) | CCTCCTCCATGGCTG, GCCTAGCCCTCCCGC | 45 46 |
| AmP | amyloid P (NM_001639) (SEQ ID NO: 116) | GCAGCGGCTTGTTCAT, GAGTCAAGACCTCAG | 47 48 |
| PanLip | pancreatic lipase (NM_000936) (SEQ ID NO: 117) | GTGGCAGCATCGTGGC, CCTAACACGGTGTGAG | 49 50 |
| ACC2 | Acetyl-CoA carboxylase (U893444) (SEQ ID NO: 118) | GAAGCAAGACCATTCAG, TCAGGTGGAGGCCGGGC | 51 52 |
| PKARIIbeta | cAMP dependent protein kinase subunit RII-beta (M31158) (SEQ ID NO: 119) | TGCTCATCCTGCCTCC, GCTTCATGCAGTGGGT | 53 54 |
| VR1R | vanilloid receptor subtype 1 (XM_008512) (SEQ ID NO: 120) | TCTTCATCCTTGCTGG, CTCACTTCTCCCCGGA | 55 56 |
| ADAMTS | disintegrin-like and metalloprotease with thrombospodin type 1 motif 4 (NM_005099) (SEQ ID NO: 121) | GGGACATGGCACTGGT, TTATTTCCTGCCCGCC | 57 58 |
| NPY-Y5R | neuropeptide Y5 receptor (U94320) (SEQ ID NO: 122) | TGTGGCAGGTCAGTTG, ATCCATATTATAGTCT, TATTACATATGAAGAC | 59 60 61 |
| GNTV | mannosyl (alpha-1,6)glycoprotein beta-1,6-N-acetyl glucosaminyl tranferase (NM_002410) (SEQ ID NO: 123) | AGCCATTGCTCTCTGG, TGCTATAGGCAGTCTT | 62 63 |
| FCRG3 | FC-gamma receptor III-1 (X16863) (SEQ ID NO: 124) | TGCCACATGATGCCAC, GTTGAGCTTCAAATGT | 64 65 |
| CD40L | tumor necrosis factor (ligand) superfamily, member 5 (XM_042961) (SEQ ID NO: 125) | TCGATCATGCTGTGTT, AGGTGACACTGTTCAG | 66 67 |
| ETS-1 | erythorblastosis virus oncogene homolog 1 (J04101) (SEQ ID NO: 126) | ACGGCCGCCTTCATGG, GCCATCACTCGTCGGC | 68 69 |
| ADAMTS-5 | disintegrin-like metalloprotease with throbospondin type, motif 5 (XM_047802) (SEQ ID NO: 127) | CCGAGCAGCATAGTGC, TCATAACCACAGGCTA | 70 71 |
| PTP-1B | protein tyrosine phosphatase, non-receptor type 1 (NM_002827) (SEQ ID NO: 128) | CATGACGGGCCAGGGC, GGGTCAGGCTATGTGT | 72 73 |

TABLE 1-continued

Representative antisense oligonucleotides

| Oligo Name(s) | Gene Target (Accession #) | Nucleic Acid Sequence | SEQ ID |
|---|---|---|---|
| MMP-1 | matrix metalloproteinase 1 (NM_002421) (SEQ ID NO: 129) | GCATACTGGCCTTTGTC, TCAATTTTTCCTGCAGT | 74 75 |
| Cat | catalase (NM_001752) (SEQ ID NO: 130) | GCCATAGCGTGCGGTT, CCCGGCCTCACAGATT | 76 77 |
| MMP-17 | matrix metalloprotinase 17 (NM_016155) (SEQ ID NO: 131) | CATGGCGCTCACATGGG, TGTCATAGCGTCAGGGC | 78 79 |
| OPG | osteoprotegerin (U94332) (SEQ ID NO: 132) | TCATTGTGGTCCCCGG, TCCAGTTATAAGCAGC | 80 |
| Nu-3 | | 3'5'-dibutyl-diphospho-thymidine | |

In one embodiment, the oligonucleotide composition of the present invention comprises at least about two oligonucleotides of differing sequence. In another embodiment, the oligonucleotide composition of the present invention comprises at least about three, four, five, six, seven, eight, nine, or ten oligonucleotides of differing sequences. Although Table 1 depicts the sequences as oligonucleotides containing only deoxyribonucleotide residues, it is to be understood that the present invention also includes the embodiments wherein the oligonucleotides are composed of ribonucleotide residues (e.g., by substituting uridine for thymidine, and ribosyl substituents for deoxyribosyl substituents). Moreover, it is to be understood that the present invention also includes the embodiments in which the oligonucleotides are composed of only deoxyribonucleotide residues, of only ribonucleotide residues, or of mixtures of deoxyribonucleotide and ribonucleotide residues.

The oligonucleotides in the present invention display greater than or equal to 80 percent sequence identity to a nucleotide sequence selected from the group of SEQ ID NO: 1-81 (see Table 1). Also preferred, the oligonucleotides display greater than or equal to 85 percent sequence identity to a nucleotide sequence selected from the group of SEQ ID NO: 1-81. Still preferred, the oligonucleotides display 90 percent sequence identity and still more preferred, the oligonucleotides display 95 percent sequence identity. Most preferably, the oligonucleotides of the present invention are selected such that their nucleotide sequence is complementary to the sense strand of a gene.

The degree of similarity between two sequences can be determined using methods well known to the art (e.g., computer programs including Fasta (Oxford Molecular Group Inc.) and BLAST (www.ncbi.nlm.nih.gov) (Altschul et al. (1997) Nucleic Acid Res. 25, 3389-3402). These methods can be employed to take into account gaps in the sequences due to deletions or insertions. Homology or sequence identity at the nucleotide or amino acid sequence level determined by BLAST (Basic Local Alignment Search Tool) analysis uses the algorithm employed by the programs blastp, blastn, blastx, tblastn and tblastx (Altschul et al. (1997) Nucleic Acids Res. 25, 3389-3402 and Karlin et al. (1990) Proc. Natl. Acad. Sci. USA 87, 2264-2268, both fully incorporated by reference) which are tailored for sequence similarity searching. The approach used by the BLAST program is to first consider similar segments, with gaps (non-contiguous) and without gaps (contiguous), between a query sequence and a database sequence, then to evaluate the statistical significance of all matches that are identified and finally to summarize only those matches which satisfy a preselected threshold of significance.

For a discussion of basic issues in similarity searching of sequence databases, see Altschul et al. (1994) Nature Genetics 6, 119-129 which is fully incorporated by reference. The search parameters for histogram, descriptions, alignments, expect (i.e., the statistical significance threshold for reporting matches against database sequences), cutoff, matrix and filter (low complexity) are at the default settings. The default scoring matrix used by blastp, blastx, tblastn, and tblastx is the BLOSUM62 matrix (Henikoff et al. (1992) Proc. Natl. Acad. Sci. USA 89, 10915-10919, fully incorporated by reference), recommended for query sequences over 85 nucleotides or amino acids in length.

For blastn, the scoring matrix is set by the ratios of M (i.e., the reward score for a pair of matching residues) to N (i.e., the penalty score for mismatching residues), wherein the default values for M and N are +5 and −4, respectively. Four blastn parameters were adjusted as follows: Q=10 (gap creation penalty); R=10 (gap extension penalty); wink=1 (generates word hits at every winkth position along the query); and gapw=16 (sets the window width within which gapped alignments are generated). The equivalent Blastp parameter settings were Q=9; R=2; wink=1; and gapw=32. A Bestfit comparison between sequences, available in the GCG package version 10.0, uses DNA parameters GAP=50 (gap creation penalty) and LEN=3 (gap extension penalty) and the equivalent settings in protein comparisons are GAP=8 and LEN=2.

In a related vein, the oligonucleotides described herein have a Guanine:Cytosine (GC content) greater than 35 percent. The GC content is preferably greater than 40 percent and most preferably, greater than 45 percent.

The Modified Oligonucleotide

The oligonucleotides that may be employed in accordance with the present invention may be modified. An oligonucleotide that comprises at least one modification has one or more chemical modifications at the molecular level of the natural molecular structures of all or any of the nucleic acid bases, sugar moieties, internucleoside phosphate linkages, as well as molecules having added substituents, such as diamines, cholesteryl or other lipophilic groups, or a combination of modifications at these sites. For example, oligonucleotides can be end-blocked, protonated, exhibit substantial acid resistance, substantial nuclease resistance, and contain achiral internucleoside phosphate linkages and modified ribose or deoxyribose substituents.

The term "end-blocked" as used herein refers to a nucleic acid with a chemical modification at the molecular level that prevents the degradation of selected nucleotides, e.g., by exonuclease action. This chemical modification is positioned such that it protects the integral portion of the nucleic acid, for example the portion of an RNA or DNA that is chemically similar to the gene involved in the physiological condition. An end block may be a 3' end block, a 5' end block, or both. For example, a 3' end block may be at the 3'-most position of the molecule, or it may be internal to the 3' ends, provided it is 3' of the integral sequences of the nucleic acid.

The term "protonated compound" refers to a molecule of the invention that, when dissolved in water having a pH of 7 causes the pH of the solution to fall. Generally, compounds are protonated by adding protons to the reactive sites on the molecule, although other modifications of the molecule are possible, and are intended to be encompassed by this term. Such protonation can be accomplished, for example by incubating the compound in the presence of a strong acid, most preferably one with a volatile conjugate base. The term "protonation" and "acidification" as used interchangeably herein refers to the process by which protons (or positively charged hydrogen ions) are added to proton acceptor sites on a compound of the invention. The proton acceptor sites include the substituted or unsubstituted phosphates of the central group, as well as any additional proton acceptor sites on either the central group or the end blocking groups. As the pH of the solution is decreased, the number of these acceptor sites which are protonated increases, resulting in a more highly protonated compound.

Many nucleic acid backbones are not stable at low pH (e.g., pH 1-3) and experience depurination, although a number of backbones are relatively stable at pH 4-5. One aspect of the present invention reflects the recognition that certain modifications, including 2'-halide, 2'-O-alkyl, 3'-O-alkyl, and 2'-O-alkyl-n(O-alkyl) nucleic acid molecules are stable at the desired pH of 2 to 1. These modifications enhance the ability of the oligonucleotides of the pharmacological compositions of the present invention to affect a condition in vivo. Thus, the composition of the present invention may include nucleic acid molecules that are substantially acid resistant. The compositions of the present invention may also include nucleic acid molecules that are nuclease resistant. This includes nucleic acid molecules completely derivatized by 2'-O-methylphosphodiesters, 2'-O-alkyl, 2'-O-alkyl-n(O-alkyl), 2'-fluoro, 2'-deoxy-erythropentofuranosyl, chimeric linkages, and any other backbone modifications, as well as other modifications, which render the nucleic acid molecules substantially resistant to endogenous nuclease activity. Additional suitable methods of rendering nucleic acid molecules nuclease resistant include, but are not limited to, covalently modifying the purine or pyrimidine bases that comprise the nucleic acid. For example, bases may be methylated, hydroxymethylated, or otherwise substituted (e.g., glycosylated) such that the nucleic acid molecules comprising the modified bases are rendered substantially nuclease resistant. Nuclease resistance also aids the oligonucleotides of the compositions of the present invention in retaining their effect in vivo.

Preferably, the oligonucleotides of the of the present invention remain relatively unchanged chemically upon administration to a subject and retain their activity in acidic conditions (pH less than 6.0) or in the presence of an endonuclease or exonuclease (e.g., in an in vivo setting).

The term "substantially acid resistant" as used herein refers to nucleic acid molecules that are resistant to acid degradation as compared to unmodified nucleic acid molecules. Typically, the relative acid resistance of a nucleic acid will be measured by comparing the percent degradation of a resistant nucleic acid with the percent degradation of its unmodified counterpart (i.e., a corresponding nucleic acid of the same length and sequence having a "normal" backbone and bases). A nucleic acid that is acid resistant is preferably at least one and a half times more resistant to acid degradation, more preferably at least two times more resistant, even more preferably at least five times more resistant, and most preferably at least ten times more resistant than their unmodified counterpart.

Although certain acid resistant nucleic acid molecules exhibit marked acid stability and endonuclease resistance, they are sensitive to 3' exonucleases. In order to enhance the exonuclease resistance of 2'-O-alkyl substituted nucleic acid molecules, the 3' or 5' and 3' ends of the nucleic acid are preferably attached to a chemical moiety that provides an exonuclease blocking function. For example, one or more phosphorothioate nucleotides can be placed at either end of the RNA or DNA. Additionally, one or more inverted bases can be placed on either end of the RNA or DNA, or one or more alkyl or alcohol (e.g., butanol-substituted) nucleotides or chemical groups can be placed on one or both ends. Accordingly, a preferred embodiment of the present invention is a nucleic acid comprising a nucleic acid having the following structure: A-B-C, wherein "B" is a 2'-O-alkyl or 2'-O-alkyl-n(O-alkyl) substituted RNA between about 1 and about 98 bases in length, and "A" and "C" are respective 5' and 3' end blocking groups (e.g., one or more phosphorothioate nucleotides (but typically fewer than six), inverted base linkages, or alkyl, alkenyl, alkynyl, O-alkyl, and O-alkyl-n (O-alkyl) groups or substituted nucleotides). A partial list of blocking groups includes inverted bases, dideoxynucleotides, methylphosphates, alkyl groups, aryl groups, cordycepin, cytosine arabanoside, 2'-methoxy, ethoxy nucleotides, phosphoramidates, a peptide linkage, dinitrophenyl group, 2'- or 3'-O-methyl bases with phosphorothioate linkages, 3'-O-methyl bases, fluorescein, cholesterol, biotin, acridine, rhodamine, psoralen, glyceryl, methyl phosphonates, butanol, butyl, hexanol, and 3'-O-alkyls. An enzyme-resistant butanol preferably has the structure $OH—CH_2CH_2CH_2CH_2$ (4-hydroxybutyl), which is also referred to as a C4 spacer.

The term "substantially nuclease resistant" refers to nucleic acid molecules that are resistant to nuclease degradation, as compared to naturally occurring or unmodified nucleic acid molecules. Modified oligonucleotides of the invention are at least 1.25 times more resistant to nuclease degradation than an unmodified nucleic acid having the same sequence and number of nucleotides, more preferably at least 2 times more resistant, even more preferably at least 5 times more resistant, and most preferably at least 10 times more resistant than their unmodified counterpart. Such substantially nuclease resistant nucleic acid molecules include, but are not limited to, nucleic acid molecules with modified backbones such as ethylphosphotriesters, 2'-O-methylphosphorothioates, 2'-O-methyl-p-ethoxy ribonucleotides, 2'-O-alkyls, 2'-O-alkyl-n(O-alkyl), 2'-fluoros, 2'-deoxy-erythropentofuranosyls, 2'-O-methyl ribonucleosides, 3'-O-methylribonucleotides, inverted bases (e.g., inverted T's), or chimeric versions of these backbones.

The modified oligonucleotide includes RNA or DNA comprising modifications to the sugar moieties such as 2'-substituted or 3'-substituted ribonucleotides, or deoxyribonucleotide monomers, any of which are connected together via internucleoside linkages. Modified RNA or DNA may also be comprised of PNA or morpholino modified backbones where specificity of the sequence is maintained.

The ribose groups and the internucleoside linkages link the bases in a nucleic acid and are referred to as the nucleic acid backbone. A modified backbone includes modifications to the chemical linkage between nucleotides, as well as other modifications that may be used to enhance stability and affinity, such as modifications to the sugar structure. For example, an L-anomer of deoxyribose may be used, where the base is inverted with respect to the natural D-anomer. In one embodiment, the 2'-OH of the sugar group may be altered to 2'-halogen, 2'-O-alkyl or 2'-O-alkyl-n(O-alkyl), which provides resistance to degradation without compromising affinity. Other suitable modified backbones include the following types of internucleotide linkages: 2'-O-methyl-phosphodiesters, 2'-O-alkyl, 2'-O-ethyl, 2'-O-propyl, 2'-O-butyl, 2'-O-alkyl-n(O-alkyl), 2'-methoxyethoxy, 2'-fluoro, 2'-deoxy-erythropentofuranosyl, 3'-O-methyl, p-isopropyl oligonucleotides, 2'-O($CH_2CH_2O)_xCH_3$, and/or butyne linkages. An oligonucleotide may have combinations of such modified backbones, may be completely modified, or may comprise all or some linkages being phosphodiester linkages.

Preferred internucleoside linkages on the modified oligonucleotide are achiral. The term "achiral" as used herein, refers to a molecule that is superimposable with its mirror image, whereas the term "chiral" refers to a molecule that is not superimposable with its mirror image. Oligonucleotides containing achiral 5' to 3' internucleoside phosphate linkages have internucleotide linkages which are achiral (i.e., no stereochemistry). The achiral oligonucleotides preferably contain at least about three to eight contiguous achiral internucleoside linkages, more preferably, nine to ten contiguous achiral internucleoside linkages, even more preferably, eleven to twelve contiguous achiral internucleoside linkages, and most preferably, is completely comprised of achiral internucleoside linkages through the entire contiguous sequence. In another embodiment, the achiral internucleoside linkages are interspersed with chiral internucleoside linkages (e.g., two contiguous achiral linkages followed by one chiral linkage followed by two contiguous achiral linkages; three contiguous achiral linkages followed by one chiral linkage; four contiguous achiral linkages followed by two achiral linkages, etc.). Examples of achiral internucleoside linkages include, but are not limited to, phosphodiester and diphosphorothioate linkages. Achiral RNA and DNA linkages in the backbone are routinely generated during automated synthesis of oligonucleotides if the final structure is a symmetrical molecule (i.e., a phosphate with the same atom attached to both sides).

The internucleoside phosphate linkages can be phosphodiester, or 3' to 3', 5' to 2' or 5' to 5' linkages, and combinations of such similar linkages (to produce mixed backbone modified RNA or DNA). The modifications can be internal (single or repeated) or at the end(s) of the RNA or DNA molecule. These modifications can include additions to the nucleic acid molecule, such as cholesteryl, diamine compounds with varying numbers of carbon residues between amino groups and terminal ribose, and deoxyribose or phosphate modifications which cleave or cross-link to the opposite chains or to associated enzymes or other proteins. Electrophilic groups such as ribose-dialdehyde could covalently link with an epsilon amino group of the lysyl-residue of such a protein. A nucleophilic group such as n-ethylmaleimide tethered to an RNA or DNA could covalently attach to the 5' end of an mRNA or to another electrophilic site.

Suitable oligonucleotides for the present invention can be determined by evaluating the Delta G or Gibbs Free energy of oligonucleotide binding to the complementary RNA strand at 37° C. and the Tm. The Gibbs Free energy and Tm are measured from the part of the target gene that corresponds to the RNA oligonucleotide that is added. These values can be calculated using the program found on ftp://rna.chem.rochester.edu and are described in Matthews et al. (1999) J. Mol. Biol. 288, 911-940 and Matthews et al. (1999) RNA 5, 1458-1469.

Accordingly, a composition comprising an oligonucleotide, (i) wherein said oligonucleotide is at least 10 nucleotides in length, (ii) the Gibbs Free energy of the binding of said oligonucleotide/RNA target duplex at 37° C. is −15 kCal, (iii) said oligonucleotide is complementary to a region within the target gene selected from the group consisting of 5' UTR, translational start site and translational termination site and (iv) wherein said target gene is a gene as listed in Table 1. The Gibbs free energy is measured between that part of the target gene that corresponds to the oligonucleotide, that part typically being the 5'UTR, translational start site or the translational termination site.

In a preferred embodiment, the Gibbs Free energy of the binding of said oligonucleotide/RNA target duplex at 37° C. is $\leq$−20 kCal. Also preferred, the Gibbs Free energy is $\leq$−25 kCal. For 12-14 mer oligonucleotides, the Gibbs Free energy is preferably $\leq$−15 kCal, for 15-17 mer oligonucleotides, the Gibbs Free energy is preferably $\leq$−20 kCal, for 18-20 mer oligonucleotides, the Gibbs Free energy is preferably $\leq$−25 kCal, for 21-23 mer oligonucleotides, the Gibbs Free energy is $\leq$−30 kCal, and for 24-26 mer oligonucleotides, the Gibbs Free energy is $\leq$35 kCal.

Further described in the present invention is a composition comprising an oligonucleotide, (i) wherein said oligonucleotide is at least 10 nucleotides in length, (ii) the Tm of said oligonucleotide to a target gene is about 65-90° C., (iii) said oligonucleotide is complementary to a region within the target gene selected from the group consisting of 5' UTR, translational start site an termination site, and (iv) wherein said target gene is selected from a gene as listed in Table 1. Preferably, the oligonucleotide has a Tm of about 75-90° C. Still preferred, the oligonucleotide has a Tm of about 85-90° C. Still preferred, the Tm of said oligonucleotide to a target gene at 1M monovalent cation concentration is about 65-90° C. The Gibbs free energy is measured between that part of the target gene that corresponds to the oligonucleotide, that part typically being the 5' UTR, translational start site or the translational termination site.

Nutritional Supplements

As used herein, the term "nutritional supplement" refers to a composition that is intended to supplement the diet. A nutritional supplement includes any dietary substance used in mammals to supplement the diet by increasing total dietary intake; or a concentrate, metabolite, constituent, extract, etc. Nutritional supplement includes any product that is intended for ingestion in tablet, capsule, powder, soft-gel, gel-cap, or liquid form. As used herein, the term "nutritional supplement" is used synomously with the term "dietary supplement" and "nutraceutical" throughout the specification.

The present invention provides a composition which is useful as a nutritional supplement to maintain or improve the an individual's health. Preferred indications for dietary supplements include, hut are not limited to, maintenance of cardiovascular function and a healthy circulatory system, maintenance of cholesterol levels that are already within the normal range, reduction of stress and frustration, relief of occasional simple nervous tension, relief of nervousness due to common everyday overwork and fatigue, alleviation of restlessness, reduction in nervous irritability, relief from anxiety, relief of muscle tension, enhancement of resistance to stress, promotion of emotional balance and a positive outlook, relief of sour stomach or upset stomach, relief of occasional heartburn or occasional acid indigestion, appetite suppression, promotion of healthy weight loss while naturally satisfying the appetite, appetite control, relief of minor or temporary aches and pains, treatment of common symptoms associated with the menstrual cycle, treatment of mild mood changes, cramps, and edema associated with the menstrual cycle, maintenance of a normal, healthy attitude during premenstrual syndrome, diminish the normal symptoms of premenstrual syndrome and maintenance of hormonal balance and alleviation of minor pre-menstrual syndrome symptoms such as cramping, breast tenderness, minor mood changes, headaches, bloating and skin problems.

The nutritional supplement composition of the present invention include compositions with a single oligonucleotide and/or a combination of about two or more oligonucleotides. The use of the nutritional supplement compositions of the present invention can be used to treat any of the aforementioned indications. These agents may be combined in an oral dosage with other well known nutritional supplements and/or non-flavonoid antioxidants (e.g., selenium, vitamin E (tocopherol, particularly alpha-tocopherol), vitamin C (ascorbic acid) and coenzyme Q10). Dietary fiber supplements may also be used in the composition.

Other additives may be incorporated in the nutritional supplement of the present invention. Such additives include minerals, (e.g., boron, etc. and trace metals such as zinc, magnesium, manganese, chromium, molybdenum, copper, iron, calcium, and potassium; and other micronutrients such as thiamine, riboflavin, niacin, pantothenic acid, pyridoxine, choline, biotin, inositol, para-aminobenzoic acid, vitamin D, vitamin K, vitamin A). In another embodiment of the invention a dietary fiber supplement such as oat bran or other natural fiber source may also be added to the composition.

Typically the nutritional supplement will further include a pharmaceutically acceptable carrier such as lactose, glucose, sucrose, corn starch, potato starch, cellulose acetate, ethyl cellulose, etc. Diluents and other additives such as one or more pharmaceutically acceptable binding agents, fillers, supports, thickening agents, taste-improving agents, coloring agents, preservatives, stabilizers, regulators, emulsifiers or mixtures thereof may be used depending on the form of the composition employed.

In addition to providing the aforementioned compositions, the invention also includes a method for orally administering the nutritional supplement composition in dosages effective to aid in the maintenance and improvement of an individual's health. The supplement is preferably administered orally. Suitable forms for the nutritional supplement composition for oral administration include tablets, capsules, lozenges, syrups, granules, solutions and suspensions which contain unit doses of the supplement for administration once or several times a day. The nutritional supplement composition of the invention will typically be administered orally as a liquid, tablet or a capsule. Tablets, gel tabs, capsules, liquid and sustained release formulations can be formulated and prepared according to manufacturing techniques well known in the pharmaceutical industry and in a variety of dosage forms.

In one embodiment, the nutritional supplement is a sports drink comprising one or more modified antisense oligonucleotides capable of hybridizing to one or more of the genes listed in Table 1. In a preferred embodiment, the sport drink comprises the modified oligonucleotides Asm (SEQ ID NO: 1), Pde5 (SEQ ID NO: 16), FAAH (SEQ ID NO: 23), CX2 (SEQ ID NO: 6), CRP (SEQ ID NO: 24), LO5 (SEQ ID NO: 12), P65 (SEQ ID NO: 10), CD18 (SEQ ID NO: 5).

Therapeutic Oligonucleotide Compositions

In a related vein, the present invention includes a pharmaceutical composition comprising at least about one oligonucleotide, wherein said oligonucleotide comprises (i) at least about ten contiguous nucleotides in length, (ii) at least about three to eight contiguous achiral internucleoside linkages, (iii) further comprising a pharmaceutically suitable excipient. In alternative embodiments, other oligonucleotides, described herein, are used in the inventive compositions. In some embodiments, the therapeutic composition can be a pharmaceutical or homeopathic composition.

As used herein, the term "pharmaceutical composition" refers to a therapeutic composition that is used to treat a particular disease or pathological disorder that is suitable for parenteral, oral or topical administration in humans.

The compositions containing the modified oligonucleotides of the invention in an admixture with a pharmaceutically acceptable carrier can be prepared according to known techniques. The carrier may take a wide variety of forms depending on the form of preparation desired for administration, e.g., intravenous, oral, topical, aerosol (for topical or inhalation therapy), suppository, parenteral, or spinal injection. The excipient may contain any number of carriers. In the case of homeopathic pharmaceuticals the carriers would preferably be homeopathic carriers, e.g. homeopathic agents that may increase the efficacy of the homeopathic composition or help to alleviate symptoms associated with a physiological condition. In addition, the composition may contain stabilizers, preservatives, and other ingredients, preferably in amounts from about 0.5 to 2.0 percent by weight, provided they do not adversely affect the ability of the pharmacological composition to treat the physiological condition. It is well within the skill of one in the art to determine an appropriate mode of administration and to select an appropriate delivery system.

Administration of the composition will introduce the modified oligonucleotides to the individual in a diluted amount. Exemplary ranges of dosage for oral or topical administration are between about 0.001 mg and 10 mg per day, and preferably between about 0.010 mg and 1.0 mg per day of oligonucleotide in the composition. When orally administered, it is preferred that one dosage unit be administered one to four times per day until relief is achieved or until the symptoms disappear or are satisfactorily attenuated. Normally, a patient is instructed to orally take two to three dosage units per day. The dosage unit may be placed under the tongue of the patient or simply swallowed for such oral administration.

The pharmaceutical compositions of the present invention may be formulated for administration to humans and animals in liquid form, or in tablets, pills, granules, powders, or in ointments, creams, injectables, or suppositories. Ointments and creams are impregnated with a low liquid potency or, sometimes, mother tinctures and are generally prescribed as specific remedies. Liquid compositions may be supplied in amber glass dropper bottles to protect them from light.

In preparing the compositions in oral dosage form, any of the usual pharmaceutical media may be employed, such as, for example, water, glycols, oils, alcohols, flavoring agents, preservatives, coloring agents and the like in the case of oral liquid preparations (such as, for example, suspensions, elixirs, and solutions); or carriers such as starches, sugars, diluents, granulating agents, lubricants, binders, disintegrating agents and the like in the case of oral solid preparations (such as, for example, powders, capsules and tablets). For homeopathic preparations for example, RNA can be dissolved in a liquid 1 part by weight to produce a ten volumes of liquid attenuation labeled 1×. To produce lower dilutions 1 ml of the 1× attenuation is used (mixed thoroughly) with 9 ml of diluent to produce 2×. This process is repeated until the desired attenuation is achieved.

For administration by injection, preparations may comprise an aqueous solution of a water soluble, or solubilized, and pharmacologically acceptable form of the nucleic acid in an appropriate liquid, e.g., water or saline solution. Injectable suspensions may also be prepared using appropriate liquid carriers, suspending agents, agents for adjusting the isotonicity, preserving agents, and the like. Actual methods for preparing administrable pharmacological compositions and adjustments necessary for administration to subjects will be known or apparent to those skilled in the art.

For topical administration, the carrier may take a wide variety of forms depending on the preparation, which may be a cream, dressing, gel, lotion, ointment, or liquid. A surfactant can be included in the composition to provide deeper penetration of the ingredients. Although natural surfactants are preferred, others such as isopropyl myristate can be used. In one embodiment, the composition is a cosmetic composition for topical administration to the skin. As used herein, the term "cosmetic composition" refers to a composition that is applied topically to the skin to improve the appearance of the skin.

Aerosols are prepared by dissolving or suspending the nucleic acid in a propellant such as ethyl alcohol or in propellant and solvent phases. The pharmaceutical compositions for topical or aerosol form will generally contain from about 0.001 percent by weight (of the nucleic acid) to about 40 percent by weight, preferably about 0.02 percent to about 10 percent by weight, and more preferably about 0.05 percent to about 5 percent by weight depending on the particular form employed. Suppositories are prepared by mixing the nucleic acid with a lipid vehicle such as theobroma oil, cacao butter, glycerin, gelatin, or polyoxyethylene glycols.

The compositions of the invention may also include plant or herbal extracts. For example, topical compositions may include Paraguay tea, Kola and Guarana which provide a source of methylxanthines, saponius, tannins and glycosides which have been shown to reduce swelling and redness. The extract of Paraguay tea is known as "Mate extract" and is described in the International Cosmetic Ingredient Dictionary, 5th Edition. Mate extract is commercially available in combination with extracts of Kola and Guarana that is sold by Cosmetic Ingredient Resources (Stamford, Conn.) under the "QUENCHT" trademark. Suitable herbs which can be used also include *Symphytum officinale, Moschus moscheferous, Pripalia geniculata, Plantago asiatica, Causticum, Helianthemum canadense, Ornithogalum umbellatum, Clematis crispa, Impatiens pallida, Prunus cerasus*, arnica, etc.

The nucleic acid molecule(s) may be combined with a lipid, cationic lipid, or anionic lipid and the active agent delivered via a nucleic acid/lipid emulsion, or a liposomal suspension. The use of cationic, anionic, and/or neutral lipid compositions or liposomes is generally described in International Publications WO90/14074, WO91/16024, WO91/17424, and U.S. Pat. No. 4,897,355, all herein incorporated by reference. By assembling nucleic acid molecules into lipid-associated structures, the nucleic acid molecules may exhibit an increased half-life in vivo. Examples of suitable anionic lipids for use with RNA or DNA include, but are not limited to, cardiolipin, dimyristoyl, dipalmitoyl, or dioleoyl phosphatidyl choline or phosphatidyl glycerol, palmitoyloleoyl phosphatidyl choline or phosphatidyl glycerol, phosphatidic acid, lysophosphatidic acid, phosphatidyl serine, phosphatidyl inositol, and anionic forms of cholesterol.

Making an Oligonucleotide Composition

The invention includes a method for making an oligonucleotide composition comprising (i) selecting an oligonucleotide that is adjacent to or overlaps a target region of a gene, (ii) determining the Gibbs Free energy value associated with said oligonucleotide in reference to said target gene, (iii) assessing Tm in reference to said target gene, and (iv) performing a sequence database search to determine if said oligonucleotide overlaps the 5' UTR, the translational start sequence, or the translational termination site of an mRNA of a gene different from the target gene.

The oligonucleotide of the present invention can be directed to a translational start site, a 5' UTR or a termination site. Preferably, the oligonucleotide is adjacent to or overlaps the translational start site of the gene by at least about one base. Still preferred, the oligonucleotide overlaps the translational start site by at least about two bases. Still more preferred, the oligonucleotide overlaps the translational start site by at least about three bases.

It is generally preferable to design an RNA or DNA that has the same or similar base sequence as the portion of the complement of a gene that encodes the 5' end of an RNA. However, a nucleic acid may also have, for example, a same or similar base sequence as other regions of the gene, such as the region encoding a translation start site or the 3' untranslated region. In another example, a nucleic acid may be designed to reflect the region around a splice donor or splice acceptor site, either with or without the intervening intron. Of particular interest are nucleic acid molecules whose sequences comprise all or a fragment of the sequence of the complement of a gene that is over-expressed in individuals exhibiting the disease or condition. The identification of overexpression of a gene can be through molecular means, e.g., detection of expression in affected tissue using conventional molecular techniques (e.g., Sambrook et al. (1989) Molecular Cloning: A Laboratory Manual, Cold Spring Harbor Laboratory Press). Overexpression of a gene may also be detected using array technology, or inferred from the results of protein assays, such as ELISA.

Making a Homeopathic Oligonucleotide Composition

A method of making a homeopathic composition comprising (i) triturating solid RNA in a 1/9 ratio with lactose to produce a 1× solid and (ii) repeating the process until the desired attenuation is achieved, is described in the present invention. In a related vein, a method of making a homeopathic composition comprising (i) dissolving 1 part RNA by weight in liquid to produce ten volumes of liquid attenuation labeled 1× and optionally (ii) mixing 1 ml of the 1× attenuation with 9 ml of diluent to produce a lower concentration, is also addressed.

In another embodiment, the invention includes homeopathic compositions containing modified oligonucleotides. In one embodiment, tablets for homeopathic use are preferably produced as placebo tablets that are then medicated by dripping or spraying liquid potencies onto the tablets in such a manner as to ensure a coefficient of impregnation of almost 100 percent. The placebo tablets are preferably formed by compression. Pills or granules are preferably spherical in shape, of about 4 millimeters diameter and 3 to 5 centigrams in weight. They are preferably prepared (form pure lactose) and medicated in the same manner as tablets. For example, solid RNA can be triturated (i.e., ground up) in a 1/9 ratio with lactose (1 gram of RNA+9 grams of lactose) to produce a 1× solid. The process is repeated (1 gram of that material plus 9 grams of lactose) until the desired attenuation is achieved.

For homeopathic compositions, the excipient may contain any number of carriers, and preferably homeopathic carriers, e.g., homeopathic agents that may increase the efficacy of the homeopathic composition or help to alleviate symptoms associated with a physiological condition. For example, RNA can be dissolved in a liquid 1 part by weight to produce a ten volumes of liquid attenuation labeled 1×. To produce lower dilutions 1 ml of the 1× attenuation is used (mixed thoroughly) with 9 ml of diluent to produce 2×. This process is repeated until the desired attenuation is achieved. A homeopathic carrier solution such as that described in U.S. Pat. No. 5,603,915 may be used for increasing the efficacy of the homeopathic agent. This carrier solution is sequentially subjected to an alternating current electrical treatment and a direct current electrical treatment, after which additional ingredients such as seawater, brain hormones, and biologically active enzymes are added. The electrical treatment of the carrier, along with the addition of homeopathically active substances, can be used to increase the efficacy of the homeopathic composition. Alternatively, an electromagnetic carrier, such as described in U.S. Pat. No. 5,830,140 may be employed.

Methods of Treatment

The invention includes a method of treating a disorder comprising administering an oligonucleotide to a patient in a therapeutically effective amount. As used herein, the term "therapeutically effective" amount is meant to refer to an amount of a pharmacological composition that is non-toxic and is the lowest amount necessary to provide a desired physiological effect. Preferably, the oligonucletide compositions of the present invention are administered at concentrations at or below 100 μg per kg of body weight. Also preferred, the concentration is at or below 10 μg per kg of body weight, still preferred, the concentration is at or below 1 μg per kg of body weight, and still more preferred, the concentration is at or below 0.1 μg per kg of body weight. Furthermore, for homeopathic use, the oligonucleotide compositions of the present invention can be combined with any homeopathic drug and still elicit a therapeutic effect.

Preferably, the oligonucleotide comprises at least one modification according to the present invention. A preferred modification is the incorporation of at least about three to eight contiguous achiral internucleoside phosphate linkages into the oligonucleotide backbone. More preferably the oligonucleotide incorporates at least nine to ten continuous achiral internucleoside phosphate linkages, even more preferably, eleven to fifteen achiral internucleoside phosphate linkages, and most preferably, the entire oligonucleotide contains achiral internucleoside phosphate linkages. Also preferred, the oligonucleotide is 3' end-blocked, comprises at least 10 contiguous nucleotides greater than or equal to 80 percent identical to a nucleotide sequence selected from SEQ ID NO: 1-81. Also preferred, the oligonucleotide is at least 85 percent identical to a nucleotide sequence selected from the group of SEQ ID NO: 1-81. Still preferred, the oligonucleotide is at least 90 percent identical and more preferred, at least 95 percent identical. Most preferably, the oligonucleotide comprises a sequence from SEQ ID NO: 1-81.

The methods of the present invention can be used to treat disorders including, but not limited to, acroparaesthsia, allergic (psoric) conditions, allergic reactions, alopecia, amnesia, anaphrodisia, angina, arthritis, asthenopia, biliary sycosis, burns, cancerous conditions, such as colon cancer, malignant melanoma and malignant nasal polyps, carpal tunnel syndrome, colds, conjunctivitis, Crohn's disease, depression, depressive psychosis, dysthyroidism, epilepsy, erectile dysfunction, excessive appetite (i.e., appetite control and suppression, promotion of healthy weight loss while naturally satisfying the appetite), gingivitis, heart burn (i.e., relief of occasional heartburn or occasional acid indigestion), hemorrhage, hypertension (i.e., helps maintain cardiovascular function, and a healthy heart and circulatory system), high cholesterol (i.e., helps to maintain cholesterol levels that are already within the normal range), hyperthyroidism, infections, inflammatory disease, lack of willpower, laryngitis, leukopenia, liver disorders, mental disorders (i.e., reduces stress, frustration, muscle tension, anxiety, and occasional simple nervous tension; enhances resistance to stress), myopia, neurosis, neurological disorders such as multiple sclerosis and ALS, obesity, pain (i.e., relief of minor or temporary aches and pains), pancreatic disorders, poison ivy, premature senescence, pre-menstrual syndrome (i.e., treatment of common symptoms associated with the menstrual cycle such as edema, breast tenderness, headaches, skin problems, cramps and mild mood changes), prostatitis, psoriasis, rosacea, seborrhea, sinusitis, and trauma.

Table 2 lists the oligonucleotides, or combinations of oligonucleotides that are preferably employed in remedies for the treatment of various symptoms and conditions. In Table 2, the use of a combination of oligonucleotides is denoted by a "/" (for example, "A/B/C" denotes the combined use of oligonucleotides A, B and C); where two or more different combinations are preferred, each such combination is presented on a separate line. The oligonucleotides are usually used in a 1:1:1 ratio, but this can vary. For example, a combination of 4×, 5×, and 6× solutions may be used, which deviates from 1:1:1.

TABLE 2

| Indication or Condition | Oligonucleotide Combination |
| --- | --- |
| Arthritis | Asm/X2/P65-2M |
|  | Asm/X2/P65-2M/LO5-38 |
| Carpal Tunnel Syndrome | Asm |
|  | Asm/X2/P65-2M |
| Chronic Fatigue/Fibromyalgia | Asm/D5/X2 |
| Colds | Asm |
| Crohn's Disease | X2/P65-2M |
| Depression | Asm/D5 |
| Erectile Dysfunction (ED) | Asm/D5 |
| Heartburn | Acid-2/B2 |
| High Cholesterol Hyperlipidemia | Mg44 |
|  | Mg44/Asm/D5 |
| Hypertension | Ace1 |
|  | Ace1/Nep-1 |
| Inflammation | Asm/X2 |
|  | Asm/X2/P65-2M |
|  | Asm/X2/P65-2M/LO5-38 |
| Pain | Asm/X2 |
|  | Asm/X2/P65-2M |
| Pre-Menstrual Syndrome (PMS) | Asm/D5/X2 |
| Psoriasis | Asm/D5/P65-2M |
| Rosacea | Asm |
|  | Asm/D5 |
| Prostatitis | MBP |
| Stress | Asm/D5 |
| Trauma | Asm |
|  | Asm/X2/P65-2M |
| Ulcerative colitis | X2/P65-2M/LO5-38 |
| Weight Management | TTP |

The compositions of the present invention are formulated to contain a "nutritionally effective" or "allopathically effective" or "homeopathically effective" amount of one or more nucleic acid molecules. As used herein, the term "nutritionally effective" amount is meant to refer to an amount of a oligonucleotide composition that is non-toxic and greater than the minimum amount necessary to maintain a desired physiological effect. As used herein, the term "allopathically effective" amount is meant to refer to an amount of a oligonucleotide composition that is non-toxic and greater than the minimum amount necessary to produce a desired physiological effect.

As used herein, the term "homeopathically effective" amount is meant to refer to an amount of a oligonucleotide composition that is non-toxic and is the lowest amount necessary to provide a desired physiological effect. A homeopathic effect, in accordance with the present invention, is achieved by a dose of modified nucleic acid that will be effective in treating (i.e., relieving, ameliorating, or preventing) symptoms of a particular condition or disease. Such treatment may be prophylactic in nature (i.e., completely or partially preventing the future occurrence of a symptom) and/or it may be therapeutic in nature (i.e., providing a partial or complete cessation or amelioration of a symptom). The method of treating of the present invention covers any treatment of symptoms of a disorder in a mammal, particularly a human, and includes:

(a) preventing symptoms of a disorder from occurring in a subject that may be predisposed to a condition but has not yet been diagnosed as having it;

(b) inhibiting symptoms of a disorder (i.e., arresting its development); or (c) relieving symptoms of a disorder (i.e., ameliorating and/or causing regression of the condition); and/or (d) maintaining homeostasis (i.e., the normal balance of RNA or DNA in a subject).

One of ordinary skill will appreciate that, from a medical practitioner's or patient's perspective, virtually any alleviation or prevention of an undesirable symptom would be desirable. Homeopathic compositions typically employ substantially less nucleic acid than is employed in allopathic compositions. Exemplary dosages to be employed in accordance with the present invention, are described in Table 3 below.

| Homeopathic RNA/DNA Concentration | |
|---|---|
| Dilution/Potency | µg/kg |
| 2× | 50 |
| 3× | 5 |
| 4× | 0.5 |
| 5× | 0.05 |
| 6× | 0.005 |

When used in the therapeutic treatment of disease, an appropriate dosage of one or more therapeutic compositions of the invention may be determined by any of several well-established methodologies. Additionally, dosages may also be altered depending upon factors such as the severity of infection, and the size or species of the host.

Preferably, animals are treated using compositions of the present invention having agents with compositions containing nucleic acid molecules having a sequence appropriate for the particular animal. Targeted species include, but are not limited to birds, fish, and mammals (especially pigs, goats, sheep, cows, dogs, horses, cats, and most preferably, humans).

Having now generally described the invention, the same will be more readily understood through reference to the following examples, which are provided by way of illustration, and are not intended to be limiting of the present invention, unless specified. The effectiveness of the RNA oligonucleotide compositions according to the preferred embodiments of the present invention is demonstrated in the Examples below.

Example 1

Individuals with cancers were typically administered a composition containing oligonucleotides complementary to cyclo-oxygenase 2 and NFκB p65 at concentrations of 3 to 30 $A_{260}$/RNA/ml (1.0-10 µg/kg). Some individuals were additionally administered oligonucleotides complementary to lipoxygenase 5. After approximately one to two months of therapy, the effect of the composition was then evaluated on individuals who completed the study (see Table 4). Treatment efficacy was evaluated by each patient and confirmed by the treating physician. A scaled score of 1 to 10 was used to evaluate treatment efficacy over a period of one to two months where a score=10 represented no improvement and a score=1 represented total alleviation of symptoms.

Example 2

Individuals with excessive appetite were orally administered an oligonucleotide composition containing RNA oligonucleotides complementary to the tripeptidyl gene. RNA oligonucleotide concentrations were typically 0.3 to 3.0 $A_{260}$/RNA/ml and given in dosages (0.1-1.0 µg/kg) of 0.5 ml twice daily). The effect of the composition was then evaluated after approximately one to two months of therapy (see Table 5). Treatment efficacy was evaluated by each patient and confirmed by the treating physician. A scaled score of 1 to 10 was used to evaluate treatment efficacy where a score=10 represented a voracious appetite and a score=1 represented the absence of hunger and the ability to lose weight.

Example 3

Individuals diagnosed with arthritis were orally administered oligonucleotide compositions with RNA oligonucleotides complementary to phosphodiesterase 4 and NFκB p65. Some people were additionally given compositions further containing RNA oligonucleotides complementary to other genes. RNA oligonucleotide concentrations were typically between the range of 0.3 to 300 $A_{260}$/RNA/ml and given in dosages (0.1-100 µg/kg) of 0.5 ml twice daily. The effect of the composition was then evaluated after approximately one to two months of therapy (see Table 6). Treatment efficacy was evaluated by each patient and confirmed by the treating physician. A scaled score of 1 to 10 was used to evaluate treatment efficacy where a score=10 represented severe arthritis characterized by inability to freely move affected joints, restricted movement, pain and inflammation and a score=1 represented reduced inflammation, restoration of movement and the absence of pain.

Example 4

Individuals with elevated blood pressure were orally administered oligonucleotide compositions with RNA oligonucleotides complementary to CE and/or neutral endopeptidase genes. Some individuals were additionally given compositions with RNA oligonucleotides complementary to other genes. Concentrations were typically 3.0 to 30 $A_{260}$/RNA/ml and given in dosages (1.0-10 µg/kg) of 0.5 ml twice daily. The effect of the composition was evaluated after approximately one to two months of therapy (see Table 7). Treatment efficacy was determined by measuring changes in blood pressure where a decrease in blood pressure below 160/89 was assessed as a successful treatment because blood pressure above this level has been associated with stroke, heart disease and kidney failure.

Example 5

Individuals with elevated cholesterol were orally administered oligonucleotide compositions containing RNA oligonucleotides complementary to the 3-hydroxy-3-methylglutaryl-coenzyme A reductase gene. Some individuals were also given oligonucleotide compositions further containing RNA oligonucleotides complementary to other genes such as phosphodiesterase 4 and phosphodiesterase 5. RNA oligonucleotide concentrations were typically 3.0 to 30 $A_{260}$/RNA/ml and given in dosages (1.0-10 µg/kg) of 0.5 ml twice daily. The effect of the composition on serum cholesterol was evaluated after approximately one to two months of therapy (see Table 8). Treatment efficacy was determined by measuring changes in serum cholesterol where a one-point drop corresponded to a two percent reduction in the probability of heart disease and a twenty-five-point drop corresponded to a fifty percent reduction in the probability of heart disease.

In addition, the effect of compositions containing RNA oligonucleotide with eight or more contiguous achiral internucleoside phosphate linkages on cholesterol levels was also assessed. In a representative individual, oligonucleotide compositions containing achiral RNA oligonucleotides complementary to 3-hydroxy-3-methylglutaryl-coenzyme A reductase, phosphodiesterase 4 and phosphodiesterase 5 were given orally in combination at a concentration of 3.0 $A_{260}$/RNA/ml at dosages of 0.5 ml, twice daily. The achiral RNA oligonucleotides produced a decrease of 46 mg/mL in serum cholesterol. The achiral 2'methoxy-RNA supplements resulted in a 31 mg/mL decrease in serum cholesterol levels. Chiral RNA or DNA did not effect cholesterol levels.

Example 6

Individuals with emotional distress were orally administered an oligonucleotide composition containing RNA oligonucleotides complementary to the phosphodiesterase 4 and phosphodiesterase 5 genes. RNA oligonucleotide concentrations were typically 0.3 to 3.0 $A_{260}$/RNA/ml and were given in dosages (0.1-1.0 µg/kg) of 0.5 ml two to six times per day. The effect of the composition was evaluated after approximately one to two months of therapy (see Table 9). A scaled score of 1 to 10 was used to evaluate treatment efficacy where a score=10 represented a severely depressed patient with suicidal tendencies and a score=1 represented a emotionally stable patient.

Example 7

Individuals with various gastrointestinal disorders were orally administered oligonucleotide compositions with RNA oligonucleotides complementary to the phosphodiesterase 4 and/or cyclooxygenase 2 genes. Some individuals were given compositions additionally containing RNA oligonucleotides complementary to other genes such as phosphodiesterase 5 and NFκB p65. Oligonucleotide concentrations were typically 0.3 to 3.0 $A_{260}$/RNA/ml and given in 0.5 ml dosages (0.1-1.0 µg/kg) twice per day. The effect of the composition was evaluated after approximately one to two months of therapy (see Table 10). A scaled score of 1 to 10 was used to evaluate treatment efficacy where a score=10 represented a patient with above normal bowel movement frequency and the presence of blood in the feces and a score=1 represented a patient with normal frequency of bowel movements and the absence of blood in the feces.

Example 8

Individuals with various types of inflammation were orally or topically (as indicated) administered oligonucleotide compositions containing oligonucleotides complementary to the phosphodiesterase 4 or interleukin 5 genes. Some individuals were given compositions additionally containing RNA oligonucleotides complementary to other genes such as cyclooxygenase 2 and NFκB p65. RNA oligonucleotide concentrations were typically 0.03 to 300 $A_{260}$/RNA/ml given in doses (0.01-100 µg/kg) of 0.5 ml twice per day. The effect of the composition was then evaluated (see Table 11). A scaled score of 1 to 10 was used to evaluate treatment efficacy after approximately one to two months of therapy, where a score=10 represented presence of debilitating inflammation with severe pain and a score=1 represented the absence of inflammation and pain.

Example 9

Individuals suffering from migraine headaches were orally administered oligonucleotide compositions containing RNA oligonucleotides complementary to the phosphodiesterase 4, phosphodiesterase 5 cyclooxygenase 2 and 3-hydroxy-3-methylglutaryl-coenzyme A reductase genes. Oligonucleotide concentrations were typically 3.0 to 30 $A_{260}$/RNA/ml taken in dosages (1.0-10 µg/kg) of 0.5 ml two to four times per day. The effect of the composition was evaluated after approximately one to two months of therapy (see Table 12). A scaled score of 1 to 10 was used to evaluate treatment efficacy where a score=10 represented severe debilitating headache pain including facial pain accompanied by nausea and sensitivity to light and a score=1 represented the absence of these conditions.

Example 10

Individuals with various neurological disorders were orally administered oligonucleotide compositions containing RNA oligonucleotides complementary to the phosphodiesterase 4, cyclooxygenase 2 and p65 genes. Some individuals were given compositions containing additional RNA oligonucleotides complementary to other genes such as lipoxygenase 5. Oligonucleotide concentrations were typically 3.0 to 30 $A_{260}$/RNA/ml taken in dosages (1-10 µg/kg) of 0.5 ml two to four times per day. The effect of the compositions was evaluated after approximately one to two months of therapy (see Table 13). A scaled score of 1 to 10 was used to evaluate treatment efficacy where a score=10 represented a patient with a debilitating form of the indicated neurological disorder (i.e., amyotrophic lateral sclerosis, multiple sclerosis, alzheimer's disease, parkinson's disease) and a score=1 represented a patient with no symptoms or mild symptoms associated with the indicated neurological disorder.

Example 11

Individuals suffering from various types of pain were orally administered oligonucleotide compositions containing RNA oligonucleotides complementary to phosphodiesterase 4 and/or cyclooxygenase 2. Some individuals were given compositions containing additional RNA oligonucleotides complementary to other genes such as phosphodiesterase 5 and p65. Oligonucleotide concentrations were typically 0.3 to 3.0 $A_{260}$/RNA/ml and taken in dosages (0.1-10 µg/kg) of 0.5 ml two to four times a day. The effect of the composition was evaluated after approximately one to two months of therapy (see Table 14). A scaled score of 1 to 10 was used to evaluate treatment efficacy where a score=10 represented a patient with severe pain requiring treatment with a subscription analgesic and a score=1 represented a patient with the absence of pain.

Example 12

Female individuals diagnosed with pre-menstrual syndrome were orally administered oligonucleotide compositions containing RNA oligonucleotides complementary to the phosphodiesterase 4 gene. Some individuals were given compositions containing additional RNA oligonucleotides complementary to other genes such as phosphodiesterase 5 and cyclooxygenase 2. RNA oligonucleotide concentrations were typically 0.03 to 3.0 $A_{260}$/RNA/ml taken in doses (0.01-1.0 µg/kg) of 0.5 ml two to four times per day. The effect of the composition was evaluated after approximately one to two months of therapy (see Table 15). A scaled score of 1 to 10 was used to evaluate treatment efficacy where a score=10 represented a patient with cramps, bloating, irritability, nausea and vomiting and a score=1 represented a patient with the absence of these conditions.

Example 13

Male individuals diagnosed with prostatitis were orally administered oligonucleotide compositions containing RNA oligonucleotides complementary to the steroid 5-alpha-reductase-2 gene. Some individuals were given compositions containing additional RNA oligonucleotides complementary to other genes such as phosphodiesterase 4 and p65 (Super 8+composition=Asm, X2, D5, P65, cd-18, IL-5, LO5 and ICAM). Oligonucleotide concentrations were typically 3.0 $A_{260}$/RNA/ml taken in doses (1.0 µg/kg) of 0.5 ml two to four times per day. The effect of the composition was evaluated after approximately one to two months of therapy (see Table 16). A scaled score of 1 to 10 was used to evaluate treatment efficacy where a score=10 represented a patient with urgent need to urinate three to five times per night and a score=1 represented a patient who slept through the night without urinating.

Example 14

Individuals suffering from cold and sinusitis symptoms were administered (intranasal) oligonucleotide compositions containing RNA oligonucleotides complementary to phosphodiesterase 4 and a DNA monomer, Nu 3. Some individuals were given compositions containing additional RNA oligonucleotides complementary to other gene targets such as cyclooxygenase 2 and NFκB p65. RNA and DNA concentrations were typically 0.3 to 30 $A_{260}$/RNA/ml (0.1-10 µg/kg). Treatment efficacy was evaluated after approximately one to two months of therapy (see Table 17). A scaled score of 1 to 10 was used to evaluate treatment efficacy where a score=10 represented a patient with sneezing, stuffy nose and watery eyes and a score=1 represented a patient with the absence of these conditions.

Example 15

Individuals with various types of trauma were orally or topically (as indicated) administered oligonucleotide compositions containing RNA oligonucleotides complementary to phosphodiesterase 4. Some individuals were given compositions containing additional RNA oligonucleotides complementary to other genes such as cyclooxygenase 2 and NFκB p65. Oligonucleotide concentrations ranged from 0.3 to 3.0 $A_{260}$/RNA/ml and taken in 0.5 ml doses (0.1-1.0 µg/kg) two to four times per day. The effect of the composition was evaluated after approximately one to two months of therapy (see Table 18). A scaled score of 1 to 10 was used to evaluate treatment efficacy where a score=10 represented a patient with severe inflammation and pain associated with the indicated trauma and a score=1 represented a patient with no inflammation or pain.

Example 16

Individuals diagnosed with carpal tunnel syndrome were orally administered oligonucleotide compositions containing RNA oligonucleotides complementary to the phosphodiesterase 4 gene. Some individuals were given compositions containing additional RNA oligonucleotides complementary to other genes such as cyclooxygenase 2, NFκB p65 and other gene targets. Oligonucleotide concentrations were typically 0.03 to 300 $A_{260}$/RNA/ml taken in doses (0.01-100 µg/kg) of 0.5 ml two to four times per day. The effect of the composition was evaluated after approximately one to two months of therapy (see Table 19). A scaled score of 1 to 10 was used to evaluate treatment efficacy where a score=10 represented a patient with pain, tingling and numbness in the wrist area necessitating the use of a wrist brace and a score=1 represented a patient with the absence of these conditions and who did not require the assistance of a wrist brace.

Example 17

Individuals diagnosed with chronic fatigue syndrome or fibromyalgia were orally administered oligonucleotide compositions containing RNA oligonucleotides complementary to the phosphodiesterase 4 gene. Some individuals were given compositions containing additional RNA oligonucleotides complementary to other genes such as cyclooxygenase 2 and p65. Oligonucleotide concentrations were typically 3.0 to 30 $A_{260}$/RNA/ml taken in doses (1.0-10 µg/kg) of 0.5 ml two to four times per day. The effect of the composition was evaluated after approximately one to two months of therapy (see Table 20). A scaled score of 1 to 10 was used to evaluate treatment efficacy where a score=10 represented a patient who complained of being chronically exhaustion accompanied by minor aches and pain and a score=1 represented a patient who did not complain of any such symptom.

Example 18

Individuals suffering from eczema and atopic dermatitis were orally or topically (as indicated) administered oligonucleotide compositions containing RNA oligonucleotides complementary to the phosphodiesterase 4 gene. Some individuals were given compositions containing additional RNA oligonucleotides complementary to other genes such as cyclooxygenase 2 and p65 and other gene targets. Oligonucleotide concentrations were typically 0.3 to 3.0 $A_{260}$/RNA/ml taken in doses (0.1-1.0 g/kg) of 0.5 m two to four times per day. The effect of the composition was evaluated after approximately one to two months of therapy (see Table 21). A scaled score of 1 to 10 was used to evaluate treatment efficacy where a score=10 represented patient with itching, inflamed skin and minor bleeding, and a score=1 represented a patient with normal skin.

Example 19

Male individuals suffering from erectile dysfunction were orally administered compositions containing RNA oligonucleotides complementary to the phosphodiesterase 4 gene. Some individuals were given compositions containing additional RNA oligonucleotides complementary to other genes such as phosphodiesterase-5. Oligonucleotide concentrations were typically 3.0 to 3.0 $A_{260}$/RNA/ml taken in doses (1.0-10 µg/kg) of 0.5 ml two to four times per day. The effect of the composition was evaluated after approximately one to two months of therapy (see Table 22). A scaled score of 1 to 10 was used to evaluate treatment efficacy where a score=10 represented a patient who could not obtain or maintain an erection and a score=1 represented a patient who was able to obtain and maintain an erection.

Example 20

Individuals suffering from acid reflux were orally administered compositions containing RNA oligonucleotides complementary to the ATP4A gene. Some individuals were given compositions containing additional RNA oligonucleotides complementary to other genes such as ATP4B. Oligonucleotide concentrations were typically 3.0 to 30 $A_{260}$/RNA/ml taken in doses (1.0-10 µg/kg) of 0.5 ml two to four times per day. The effect of the composition was evaluated after approximately one to two months of therapy (see Table 23). A scaled score of 1 to 10 was used to evaluate treatment efficacy where a score=10 represented a patient with heartburn requiring treatment with excessive amounts of antacid medication and a score=1 represented a patient with no heartburn.

Example 21

Individuals suffering from poison ivy were orally or topically (as indicated) administered compositions containing RNA oligonucleotides complementary to the phosphodiesterase 4 gene. Oligonucleotide concentrations were typically 0.3 to 300 $A_{260}$/RNA/ml taken in doses 0.1-100 µg/kg) of 0.5 ml two to four times per day. The effect of the composition was evaluated after approximately one to two months of therapy (see Table 24). A scaled score of 1 to 10 was used to evaluate treatment efficacy where a score=10 represented a patient with poison ivy covering up to ninety-five percent of the entire body with dermal discharge and secondary inflammation restricting eye openings and a score=1 represented a patient without these symptoms.

Example 22

Individuals with psoriasis were orally or topically administered compositions containing RNA oligonucleotides complementary to the phosphodiesterase 4 gene. Some individuals were given compositions containing additional RNA oligonucleotides complementary to other genes such as phosphodiesterase-5 and p65. Oligonucleotide concentrations were typically 0.3 to 300 $A_{260}$/RNA/ml taken in doses of 0.5 ml (0.1-100 µg/kg) two to four times per day. The effect of the composition was evaluated after approximately one to two months of therapy (see Table 25). A scaled score of 1 to 10 was used to evaluate treatment efficacy where a score=10 represented a patient with thick silvery-colored scaly patches of skin with dermal discharge and bleeding and a score=1 represented a patient with normal skin.

Example 23

Ten individuals with rosacea were orally or topically administered compositions containing RNA oligonucleotides complementary to the phosphodiesterase 4 gene. Some individuals were given compositions containing additional RNA oligonucleotides complementary to other genes such as cyclooxygenase 2 and p65. Oligonucleotide concentrations were typically 0.3 to 300 $A_{260}$/RNA/ml taken in doses (0.1-100 µg/kg) of 0.5 ml two to four times per day. The effect of the composition was evaluated after approximately one to two months of therapy (see Table 26). A scaled score of 1 to 10 was used to evaluate treatment efficacy where a score=10 represented a patient with red, inflamed facial skin with pimples (e.g., acne) and a score represented a patient normal skin.

TABLE 4

Cancer Therapy

| | sex | age | condition | oligonucleotides | Severity before | Severity after |
|---|---|---|---|---|---|---|
| 1 | m | 38 | Skin cancer | X2/65 | 7-8 | 1-2 |
| 2 | m | 72 | Skin cancer | X2/65/LO5-38 | 7-8 | stable |
| 3 | f | 52 | Malignant nasal polyps | X2/65/LO5-38/Mg44 | 10 | 1 |
| 4 | f | 47 | Malignant melanoma | X2/65/LO5-38/Mg44 | 10 | stable |
| 5 | f | 56 | Breast cancer | X2/65/LO5-38 | 10 | stable |

TABLE 5

Appetite Control

| | sex | age | condition | oligonucleotide | Efficacy |
|---|---|---|---|---|---|
| 1 | f | 37 | appetite control | Ttp | 7 |
| 2 | f | 52 | appetite control | Ttp | 10 |
| 3 | f | 65 | appetite control | Ttp | 5 |
| 4 | f | 46 | appetite control | Ttp | 8 |
| 5 | f | 44 | appetite control | Ttp | 7 |
| 6 | f | 63 | appetite control | Ttp | 8 |
| 7 | f | 48 | appetite control | Ttp | 6 |
| 8 | f | 59 | appetite control | Ttp | 7 |
| 9 | m | 40 | appetite control | Ttp | 7 |
| 10 | f | 40 | appetite control | Ttp | 8 |
| 11 | f | 54 | appetite control | Ttp | 8 |
| 12 | f | 52 | appetite control | Ttp | 7 |
| 13 | f | 58 | appetite control | Ttp | 7 |
| 14 | f | 41 | Appetite control | Ttp | 8 |
| 15 | f | 39 | Appetite control | Ttp | 8 |
| 16 | f | 54 | Appetite control | Ttp | 7 |

TABLE 6

Arthritis Treatment

| | sex | age | condition | oligonucleotide | Severity before | Severity after |
|---|---|---|---|---|---|---|
| 1 | m | 50 | Arthritis (back) | Asm/X2/65 | 5 | 1 |
| 2 | f | 60 | Arthritis (general) | Asm/X2/65 | 6 | 1 |
| 3 | f | 63 | Rheumatoid Arthritis | Asm/X2/65/LO5-38/CRP | 10 | 5 |
| 4 | f | 66 | Arthritis (general) | Asm/X2/65/D5 | 7 | 1 |

TABLE 6-continued

Arthritis Treatment

| | sex | age | condition | oligonucleotide | Severity before | Severity after |
|---|---|---|---|---|---|---|
| 5 | m | 50 | Arthritis (hands) | Asm/65 | 10 | 2 |
| 6 | f | 28 | Arthritis (knee) | Asm/X2/65 | 7 | 1-2 |
| 7 | f | 74 | Arthritis (knee) | Asm/X2/65 | 8 | 2-3 |
| 8 | f | 82 | Arthritis (general) | Asm/X2/65/LO5-38 | 8 | 2 |
| 9 | m | 65 | Arthritis (back/hand) | Asm/X2/65 | 6 | 2 |
| 10 | f | 63 | Arthritis (knee) | Asm/X2/65/LO5-38/CRP | 10 | 3-4 |
| 11 | f | 55 | Arthritis (back/hands) | Asm/X2/65 | 7 | 1 |
| 12 | m | 48 | Arthritis (general) | Asm/X2/65 | 6 | 1 |
| 13 | m | 46 | Arthritis (general) | Asm/X2/65 | 5 | 1 |
| 14 | f | 90 | Arthritis (hand) | Asm/X2/65 | 9-10 | 1 |
| 15 | m | 53 | Arthritis (fingers) | Asm/X2/65 | 8 | 1 |
| 16 | f | 28 | Arthritis (neck) | Asm/X2/65 | 7-8 | 1 |
| 17 | f | 49 | Arthritis (hands) | 65 | 5-6 | 1 |
| 18 | f | 51 | Arthritis (shoulder) | Asm/X2/65 | 5 | 1 |
| 19 | m | 77 | Arthritis (knee) | Asm/X2/65/LO5-38/CRP/D5 | 10 | 3-4 |
| 20 | m | 52 | Arthritis (knee) | Asm/X2/65/LO5-38/D7/CRP | 7 | 3-4 |
| 21 | f | 53 | Arthritis (back) | Asm/X2/65/LO5-38/CRP | 7 | 4 |
| 22 | f | 64 | Arthritis (thumbs) | Asm/X2/65/LO5-38/CRP | 7 | 3 |
| 23 | f | 47 | Arthritis (general) | Asm/X2/65 | 8-9 | 2 |
| 24 | f | 74 | Arthritis (general) | Asm/X2/65/LO5-38/Mg44 | 10 | 1 |
| 25 | m | 65 | Arthritis (back) | Asm/X2/65 | 9 | 2-3 |
| 26 | f | 61 | Arthritis (knees) | Asm/X2/65 | 8-9 | 2 |

TABLE 7

Blood Pressure

| | sex | age | Condition | oligonucleotides | Blood Pressure before | Blood Pressure after |
|---|---|---|---|---|---|---|
| 1 | f | 74 | Untreated hypertension | CE/NEP-1/Asm/D5 | 190/100 | 165/75 |
| 2 | f | 56 | Untreated hypertension | CE/NEP-1/Asm/D5 | 190/100 | 160/80 |
| 3 | f | 62 | Hypertension despite treatment with Zestril, Atenolol & Furosemide | CE/NEP-1/Asm/D5 | 200/90 | 170/75 |
| 4 | f | 63 | Hypertension despite treatment with Atenolol & Prinivil | CE/NEP-1/Asm/D5 | 170/70 | 150/70 |
| 5 | m | 65 | Hypertension despite treatment with Atenolol | CE/NEP-1/Asm/D5 | 190/98 | 150/80 |
| 6 | f | 55 | Untreated Hypertension | CE | 190/100 | 160/100 |
| 7 | m | 76 | Hypertension | NEP-1 | 170/69 | 158/74 |
| 8 | m | 36 | Untreated Hypertension | NEP-1 | 214/144 | 160/80 |

TABLE 8

Elevated Cholesterol

| | sex | age | Condition | oligonucleotides | Cholesterol Level before | Cholesterol Level after |
|---|---|---|---|---|---|---|
| 1 | f | | Hyperlipidemia | Mg44/Asm/D5 | 244 | 125 |
| 2 | f | | Hyperlipidemia | Mg44/Asm/D5 | 220 | <150 |
| 3 | m | | Hyperlipidemia | Mg44 | 265 | 177 |
| 4 | f | | Hyperlipidemia | Mg44 | 212 | 205 |
| 5 | m | | Hyperlipidemia | Mg44/Asm/D5 | 207 | 168 |
| 6 | f | | Hyperlipidemia | Mg44/Asm/D5 | 229 | 163 |
| 7 | f | | Hyperlipidemia | Mg44/Asm/D5 | 300 | 184 |
| 8 | m | | Hyperlipidemia (shifted from Zocor) | Mg44/Asm/D5/MTP | 213 | <150 |
| 9 | m | | Hyperlipidemia (shifted from Zocor) | Mg44/Asm/D5 | <150 | <150 |
| 10 | m | | Hyperlipidemia | Mg44/Asm/D5 | 201 | 164 |

TABLE 9

Emotional Distress

| | sex | age | condition | oligonucleotides | Severity before | Severity after |
|---|---|---|---|---|---|---|
| 1 | f | 39 | Stress | Asm/D5 | 9 | 1-2 |
| 2 | f | 46 | Stress | Asm/D5 | 8 | 2 |
| 3 | f | 52 | Depression | Asm/D5 | 10 | 1-2 |
| 4 | f | 29 | Stress/depression | Asm/D5 | 10 | 3 |
| 5 | m | 56 | Severe depression | Asm/D5 | 10 | 2 |
| 6 | f | 47 | Spousal abuse | Asm/D5 | 8-9 | 1-2 |
| 7 | f | 57 | stress | Asm/D5 | 10 | 1-2 |
| 8 | f | 40 | stress | Asm/D5 | 9 | 3 |
| 9 | f | 52 | Severe depression | Asm/D5 | 10 | 1 |
| 10 | f | 26 | stress | Asm/D5 | 8-9 | 1 |
| 11 | f | 36 | stress | Asm/D5 | 4-5 | 1 |
| 12 | f | 62 | Severe depression | Asm/D5 | 10 | 1 |
| 13 | m | 31 | stress | Asm/D5 | 8-9 | 1 |
| 14 | f | 52 | Stress/anxiety | Asm/D5 | 9-10 | 2-3 |
| 15 | f | 56 | Mild stress | Asm/D5 | 6 | 1 |
| 16 | f | 51 | mood swings | Asm/D5 | 7 | 1 |
| 17 | m | 47 | High stress | Asm/D5 | 10 | 2-3 |
| 18 | f | 56 | Spousal abuse | Asm/D5 | 10 | 5 |
| 19 | m | 56 | Stress | Asm/D5 | 7 | 2 |
| 20 | f | 63 | Depression | Asm/D5 | 10 | 1-2 |
| 21 | m | 51 | SAD | Asm/D5 | 10 | 1-2 |
| 22 | f | 35 | Suicidal | Asm/D5 | 10 | 1-2 |
| 23 | f | 38 | Severe depression | Asm/D5 | 10 | 1-3 |
| 24 | f | 63 | Severe depression | Asm/D5 | 10 | 1-2 |
| 25 | f | 45 | Depression | Asm/D5 | 8-9 | 1-2 |
| 26 | f | 31 | depression | Asm/D5 | 8 | 1-2 |
| 27 | f | 34 | stress | Asm/D5 | 9 | 2 |
| 28 | m | 63 | anxiety | Asm/D5 | 9 | 1 |
| 29 | m | 32 | Stress/anxiety | Asm/D5 | 10 | 1 |
| 30 | f | 60 | Severe depression | Asm/D5 | 10 | 1-2 |
| 31 | f | 25 | OCD/stress | Asm/D5 | 10 | 3 |
| 32 | m | 41 | agoraphobic | Asm/D5 | 10 | 3-4 |
| 33 | f | 42 | Severe anxiety | Asm/D5 | 10 | 1 |
| 34 | f | 36 | depression | Asm/D5 | 9-10 | 1-2 |
| 35 | m | 59 | Spousal abuse | Asm/D5 | 10 | 2 |
| 36 | f | 52 | Depression | Asm/D5 | 8 | 2 |
| 37 | f | 31 | stress | Asm/D5 | 9 | 1 |
| 38 | f | 63 | stress | Asm/D5 | 8 | 1 |
| 39 | m | 55 | Anxiety/stress | Asm/D5 | 7 | 4 |
| 40 | f | 45 | stress | Asm/D5 | 4 | 1 |
| 41 | f | 42 | stress | Asm/D5 | 10 | 1 |
| 42 | f | 38 | Severe depression | Asm/D5 | 10 | 1-2 |
| 43 | m | 50 | Mild stress | Asm/D5 | 4 | 1 |
| 44 | f | 33 | Mild stress | Asm/D5 | 5 | 1 |
| 45 | f | 42 | depression | Asm/D5 | 8 | 1 |
| 46 | f | 65 | depression | Asm/D5 | 9 | 2-3 |
| 47 | f | 63 | Stress/anxiety | Asm/D5 | 10 | 2-3 |
| 48 | f | 44 | Stress/anxiety | Asm/D5 | 9-10 | 1-2 |

TABLE 9-continued

Emotional Distress

|  | sex | age | condition | oligonucleotides | Severity before | Severity after |
|---|---|---|---|---|---|---|
| 49 | f | 34 | stress | Asm/D5 | 9 | 2 |
| 50 | f | 50 | Mild stress | Asm/D5 | 7 | 1 |
| 51 | m | 65 | depression | Asm/D5 | 9-10 | 1-2 |
| 52 | f | 38 | stress | Asm/D5 | 8 | 1 |
| 53 | f | 32 | Stress/anxiety | Asm/D5 | 9 | 2-3 |
| 54 | f | 40 | stress | Asm/D5 | 8-9 | 1-2 |
| 55 | f | 54 | stress | Asm/D5 | 7-8 | 1 |
| 56 | f | 33 | anxiety | Asm/D5 | 8 | 1 |
| 57 | f | 54 | Stress/depression | Asm/D5 | 9 | 2-3 |
| 58 | f | 41 | stress | Asm/D5 | 10 | 1-2 |
| 59 | m | 15 | Panic attacks | Asm/D5 | 10 | 1 |
| 60 | f | 44 | stress | Asm/D5 | 6 | 1 |
| 61 | f | 41 | stress | Asm/D5 | 9 | 1 |
| 62 | m | 40 | stress | Asm/D5 | 7-8 | 1-2 |
| 63 | f | 13 | Mood swings | Asm/D5 | 8-9 | 1-2 |
| 64 | f | 15 | Mood swings | Asm/D5 | 7-8 | 1 |
| 65 | f | 22 | stress | Asm/D5 | 10 | 1 |
| 66 | f | 51 | anxiety | Asm/D5 | 9 | 1 |
| 67 | m | 54 | Depression | Asm/D5 | 8 | 2 |
| 68 | f | 54 | depression | Asm/D5 | 8-9 | 3 |
| 69 | f | 51 | depression | Asm/D5 | 10 | 1-2 |
| 70 | f | 51 | stress | Asm/D5 | 5 | 1 |
| 71 | f | 56 | stress | Asm/D5 | 10 | 1-2 |
| 72 | f | 58 | depression | Asm/D5 | 8 | 2 |
| 73 | f | 39 | Mild stress | Asm/D5 | 5 | 1 |
| 74 | m | 24 | anxiety | Asm/D5 | 6 | 1 |
| 75 | m | 29 | stress | Asm/D5 | 8 | 4 |
| 76 | f | 43 | anxiety | Asm/D5 | 5 | 1 |
| 77 | m | 21 | Panic attacks | Asm/D5 | 10 | 1 |
| 78 | m | 66 | stress | Asm/D5 | 7-8 | 1-2 |
| 79 | f | 45 | Stress/anxiety | Asm/D5 | 7 | 1 |
| 80 | f | 74 | stress | Asm/D5 | 8-9 | 2 |
| 81 | f | 50 | Mild anxiety | Asm/D5 | 4 | 1 |
| 82 | f | 18 | Severe depression | Asm/D5 | 10 | 1 |
| 83 | f | 53 | stress | Asm/D5 | 9 | 3 |
| 84 | f | 32 | stress | Asm/D5 | 7 | 3 |
| 85 | f | 25 | stress | Asm/D5 | 8 | 1-2 |
| 86 | m | 47 | Severe depression | Asm/D5 | 9 | 1-2 |
| 87 | f | 38 | stress | Asm/D5 | 7 | 2 |
| 88 | m | 52 | stress | Asm/D5 | 5 | 1 |
| 89 | f | 14 | Panic attacks | Asm/D5 | 10 | 1-2 |
| 90 | m | 65 | anxiety | Asm/D5 | 8 | 1 |
| 91 | m | 39 | stress | Asm/D5 | 9 | 2 |
| 92 | m | 11 | stress | Asm/D5 | 7 | 1-2 |
| 93 | f | 31 | Severe depression | Asm/D5 | 10 | 3 |
| 94 | m | 67 | depression | Asm/D5 | 7 | 3 |
| 95 | f | 58 | stress | Asm/D5 | 7 | 2 |
| 96 | m | 67 | stress | Asm/D5 | 9 | 2 |
| 97 | f | 12 | ADD | Asm/D5 | 8 | 1 |
| 98 | f | 58 | stress | Asm/D5 | 9-10 | 2-3 |
| 99 | f | 30 | stress | Asm/D5 | 7 | 1 |
| 100 | m | 45 | stress | Asm/D5 | 6 | 1 |
| 101 | m | 13 | ADD | Asm/D5 | 9-10 | 2-3 |

TABLE 10

Gastrointestinal Disorders

|  | sex | age | condition | oligonucleotides | Elimination/day b/f | Elimination/day after | Severity b/f | Severity after |
|---|---|---|---|---|---|---|---|---|
| 1 | f | 46 | IBS | Asm/X2/65 | 11 | 2 | 10 | 3 |
| 2 | m | 40 | Ulcerative colitis | Asm/X2/65 | 5 | 2 | 7 | 1 |
| 3 | f | 40 | IBS | Asm/X2/65 | 20 | 1-2 | 10 | 1 |
| 4 | f | 38 | Ulcerative colitis | Asm/X2/65 | 10-20 | 1 | 10 | 3 |
| 5 | f | 31 | Crohn's | X2/65 | 22 | 1 | 10 | 1 |
| 6 | f | 34 | Crohn's | X2/65 | 8-10 | 1-2 | 7 | 2 |
| 7 | f | 33 | IBS | Asm/X2/65 | 20 | 1-2 | 8 | 1 |
| 8 | m | 50 | IBS | Asm/X2/65 | 5 | 1-2 | 5 | 1 |
| 9 | f | 22 | Chronic constipation | Asm/X2/65 | 0 | 1-2 | 10 | 2 |
| 10 | f | 26 | Crohn's | X2/65 | 19-20 | 1 | 10 | 1 |
| 11 | f | 57 | Ulcerative colitis | Asm/X2/65 | 5-6 | 1 | 6 | 2 |
| 12 | f | 42 | IBS | Asm/X2/65 | 12 | 1 | 9 | 1 |
| 14 | f | 8 | IBS | Asm/65 (testing + X2) | 8 | 3-4 | 10 | 3 |
| 16 | f | 47 | IBS | Asm/X2/65 | 8 | 1-2 | 9 | 1 |
| 17 | f | 55 | IBS | Asm/X2/65 | 10 | 1 | 10 | 1 |
| 18 | m | 67 | IBS | Asm/X2/65 | 6-7 | 1-2 | 6 | 1 |
| 19 | f | 36 | IBS | Asm/X2/65 | 4 | 1 | 7-8 | 1 |
| 20 | m | 31 | Gall bladder | Asm/D5/Mg44 | nd | nd | 10 | 1 |
| 21 | m | 56 | Kidney stones | Mg44 | nd | nd | 10 | 1 |
| 22 | f | 37 | Gall bladder attack | Asm/X2/65/Mg44 | nd | nd | 4 | 1 |
| 23 | f | 57 | Gall bladder attack | Asm/D5/Mg44 | nd | nd | 7-8 | 1 |
| 25 | f | 54 | IBS | Super 8 | 5 | 1-2 | 5 | 1 |
| 26 | f | 7 | IBS | Super 8 | nd | nd | 8 | 2 |
| 27 | f | 38 | Ulcerative colitis | Super 8 | 3 | 1-2 | 4-5 | 1 |

TABLE 11

Inflammation

|  | sex | age | condition | oligonucleotides | Severity before | Severity after |
|---|---|---|---|---|---|---|
| 1 | f | 39 | Post surgical | Asm/X2/65/cd18-1 | 10 | 4 |
| 2 | f | 64 | Post surgical | Asm | 10 | 2 |
| 3 | m | 55 | Asthma/emphysema | Asm/X2/65 | 9 | 7 |
| 4 | f | 33 | asthma | Asm/X2/65 | 10 | 1-2 |
| 5 | f | 40 | asthma | Asm | 10 | 1 |
| 6 | f | 40 | Bee sting | Asm | 10 | 1 |
| 7 | m | 5 | Bee sting | Asm/topical | 10 | 1 |
| 8 | f | 44 | Black fly bite | IL-501 | 10 | 1 |
| 9 | f | 8 | Black fly bite | IL-501 | 10 | 1 |
| 10 | f | 6 | Black fly bite | IL-501 | 10 | 1 |
| 11 | f | 63 | Hair implants | Asm | 10 | 1 |
| 12 | m | 66 | gout | Asm | 8 | 2 |
| 13 | m | 51 | gout | Asm | 10 | 1 |
| 14 | m | 45 | gout | Asm | 10 | 1 |
| 15 | f | 56 | Polymyalgia rheumatica | Asm/X2/65/D7/CRP | 10 | 3 |
| 16 | f | 31 | Multiple sclerosis | Asm/X2/65 | 9-10 | 2 |
| 17 | f | 67 | polymyositis | Asm/X2/65/D7/CRP | 8-9 | 3-4 |
| 18 | m | 32 | Swollen joints | Asm | 9 | 1-2 |
| 19 | f | 65 | Inner ear inflammation | Asm | 7 | 1 |
| 20 | m | 26 | hemorrhoids | Asm | 10 | 5 |
| 21 | f | 41 | hemorrhoids | Asm | 10 | 1 |
| 22 | f | 75 | shingles | Asm/D7 | 10 | 3 |
| 23 | m | 48 | Sore muscles | Asm | 7 | 1 |
| 24 | f | 36 | Varicose veins | Asm | 7 | 7 |
| 25 | f | 74 | Swollen ankle | Asm/X2/65 | 10 | 2 |
| 26 | f | 41 | Swollen ankle | Asm | 10 | 1 |
| 27 | f | 63 | Swollen knee | Asm/X2/65/cd18-1 | 10 | 2 |
| 28 | f | 45 | Ganglion cyst | Asm/X2/65 | 7 | 1 |

TABLE 11-continued

Inflammation

| | sex | age | condition | oligonucleotides | Severity before | Severity after |
|---|---|---|---|---|---|---|
| 29 | f | 73 | sciatica | Asm | 10 | 1 |
| 30 | m | 25 | sciatica | Asm | 10 | 1 |
| 31 | m | 54 | sciatica | Asm/X2/65 | 10 | 6 |
| 32 | m | 47 | sciatica | Asm/X2/65 | 10 | 1 |
| 33 | f | 44 | sciatica | Asm | 10 | 1 |
| 34 | f | 46 | Itchy ears | Asm | 6 | 1 |
| 35 | m | 59 | cellulitis | Asm/Nu-3 | 10 | 3-4 |
| 36 | f | 22 | Stomach inflammation | Asm/X2/65 | 9 | 2 |
| 37 | f | 44 | Pinched nerve | Asm/X2/65 | 10 | 1 |
| 38 | f | 44 | Pinched nerve | Asm/X2/65 | 10 | 1 |
| 39 | m | 46 | Hockey/tennis elbow | Asm/X2/65 | 9 | 1 |
| 40 | m | 40 | Hockey/tennis elbow | Asm/X2/65 | 10 | 1 |
| 41 | m | 16 | Pitcher's arm | Asm | 10 | 1 |
| 42 | f | 58 | Heel spur | Asm | 7 | 1 |
| 43 | f | 46 | Multiple sclerosis | Asm/X2/65 | 8 | 2 |
| 44 | f | 63 | hemorrhoids | Asm/Nu-3 | 10 | 3 |
| 45 | m | 64 | bursitis | Asm/X2/65/LO5-38 | 9 | 1-2 |
| 46 | f | 25 | Interstitial cystitis | Asm/X2/65/LO5-38 | 10 | 2 |
| 47 | m | 67 | Inflamed hands | Asm/D5/X2/65/IL-501 | 10 | 5 |
| 48 | f | 30 | Morning sickness | Asm/D5 | 10 | 7 |
| 49 | f | 12 | Inflamed tonsils | Asm | 10 | 1-2 |
| 50 | f | 33 | Inflamed cat scratch | Asm/topical | 6 | 1 |
| 51 | f | 38 | Allergies | Asm | 10 | 3 |
| 52 | f | 42 | Insect bite | IL-501/topical | 9 | 1 |
| 53 | f | 10 | Severe wasp bites | Asm/topical | 10 | 1 |
| 54 | f | 45 | Black fly bites | IL-501/topical | 9 | 1 |
| 55 | f | 62 | Wasp bite | Asm | 8 | 1 |
| 56 | f | 7 | Ear piercing | Asm | 8 | 1 |
| 57 | f | 9 | Ear piercing | Asm | 8 | 1 |
| 58 | m | 37 | Pinched nerve | Asm/X2/65 | 9-10 | 1 |
| 59 | f | 7 | "goose egg" on forehead | Asm/topical | 8 | 1 |
| 60 | m | 12 | Knee injury | Asm/topical | 6 | 1 |
| 61 | f | 43 | sciatica | Asm/topical | 9-10 | 1 |
| 62 | f | 45 | Pulled muscle (knee) | Asm/topical | 6 | 1 |
| 63 | m | 43 | Degenerative hip | Asm/topical | 5 | 1-2 |
| 64 | m | 65 | Chronic cough | D7 | 10 | 4 |
| 65 | m | 38 | Extreme autoimmune graft rejection/sinusitis/Erosive Peptic Esophagitis | Asm/X2/65/D7/LO5-38/ICAM/cd-18-1/IL6/HisR1 | 10 | 3 |
| 66 | f | 10 | Seasonal allergies | Asm | 7-8 | 1 |
| 67 | f | 42 | Interstitial cystitis | Asm/X2/65 | 9 | 1 |
| 68 | f | 34 | Chronic allergies | Asm/X2/65/D5 | 8 | 2 |
| 69 | f | 44 | Seasonal allergies/cough | IL-501 | 6 | 1 |
| 70 | f | 61 | Seasonal allergies/cough | IL-501 | 6 | 1 |

TABLE 12

Migraines

| | sex | age | Condition | oligonucleotides | Severity before | Severity after |
|---|---|---|---|---|---|---|
| 1 | f | 42 | migraine | Asm/D5/X2/Mg44 | 10 | 1 |
| 2 | f | 51 | migraine | Asm/D5/X2/Mg44 | 9 | 1-2 |
| 3 | f | 28 | migraine | Asm/D5/X2/Mg44 | 10 | 1 |
| 4 | f | 36 | migraine | Asm/D5/X2/Mg44 | 10 | 2 |
| 5 | f | 46 | migraine | Asm/D5/X2/Mg44 | 10 | 1 |
| 6 | f | 51 | migraine | Asm/D5/X2/Mg44 | 9 | 1 |
| 7 | f | 39 | migraine | Asm/D5/X2/Mg44 | 8 | 1 |
| 8 | f | 30 | migraine | Asm/D5/X2/Mg44 | 9 | 1 |
| 9 | f | 58 | Migraine | Asm/D5/X2/Mg44 | 9 | 1 |
| 10 | f | 57 | Migraine | Asm/D5/X2/Mg44 | 10 | 1 |
| 11 | f | 21 | migraine | Asm/D5/X2/Mg44 | 9 | 2-3 |

TABLE 13

Neurological Disorders

| | sex | age | Condition | oligonucleotides | Severity before | Severity after |
|---|---|---|---|---|---|---|
| 1 | f | 56 | polymyalgia | Asm/X2/65/D7/CRP | 10 | 3 |
| 2 | f | 31 | multiple sclerosis | Asm/X2/65 | 9-10 | 2 |
| 3 | f | 67 | polymyositis | Asm/X2/65/D7/CRP | 8-9 | 3-4 |
| 4 | f | 46 | multiple sclerosis | Asm/X2/65 | 8 | 2 |

TABLE 14

Pain

| | sex | age | Condition | oligonucleotides | Severity before | Severity after |
|---|---|---|---|---|---|---|
| 1 | f | 74 | Back | Asm/X2/65/LO5-38/Mg44 | 10 | 5 |
| 2 | m | 54 | back | Asm/X2/65 | 9 | 2 |
| 3 | f | 37 | shoulder | Asm/X2 | 6-7 | 1 |
| 4 | f | 41 | ankle | X2 | 5 | 1 |
| 5 | f | 61 | knee | X2 | 8 | 3 |
| 6 | f | 41 | ovarian | Asm/X2 | 8-9 | 3 |
| 7 | f | 61 | headache | Asm/X2 | 8 | 1 |
| 8 | f | 54 | headache | Asm/X2/65 | 8 | 5 |
| 9 | m | 26 | headache | Asm/X2 | 9 | 1 |
| 10 | f | 65 | headache | Asm/X2/65 | 8 | 1 |
| 11 | f | 36 | headache | Asm/X2 | 7 | 1 |
| 12 | f | 39 | headache | Asm/X2/D5 | 6 | 1 |
| 13 | f | 62 | headache | Asm/X2/D5 | 10 | 1-2 |
| 14 | f | 46 | knee | Asm/X2/D5 | 6 | 2 |
| 15 | f | 31 | knee | Asm/X2/65 | 7 | 1 |
| 16 | f | 62 | knee | Asm/X2/65 | 7 | 2 |
| 17 | f | 61 | knee | Asm/X2 | 8 | 3 |
| 18 | f | 37 | knee | Asm/X2 | 9 | 1-2 |
| 19 | f | 39 | Surgical pain | Asm/X2/65 | 10 | 4 |
| 20 | m | 56 | Cancer pain | X2 | 10 | 6 |
| 21 | m | 30 | stitches | Asm/X2 | 10 | 1-2 |
| 22 | m | 20 | Tooth extraction | Asm/X2 | 10 | 1 |
| 23 | f | 53 | Tooth extraction | Asm/X2 | 9 | 1-2 |
| 24 | f | 30 | Tooth extraction | Asm/X2 | 10 | 1 |
| 25 | f | 45 | Tooth extraction | Asm/X2 | 8 | 1-2 |
| 26 | f | 74 | Rib soreness | Asm/X2/LO5-38/Mg44 | 10 | 1 |
| 27 | f | 48 | shoulder | Asm/X2/65 | 8 | 1 |
| 28 | f | 43 | headache | X2 | 8-9 | 1-2 |
| 29 | m | 38 | headache | X2 | 7 | 1-2 |
| 30 | f | 76 | Tooth extraction | Asm/X2/65 | 8 | 1-2 |
| 31 | m | 23 | Wisdom tooth pain | Asm/X2/65 | 9 | 2-3 |
| 32 | f | 42 | headaches | Asm/D5/X2 | 7 | 1 |
| 33 | f | 47 | Neck pain | Super 8 | 7 | 1 |
| 34 | f | 31 | Headaches | Asm/D5/X2 | 10 | 3 |
| 35 | f | 59 | Teeth pain | Super 8 | 6 | 1 |
| 36 | f | 31 | Knee pain | Super 8 | 6 | 1 |
| 37 | m | 10 | Ankle pain | Asm/65 | 5 | 1 |
| 38 | f | 13 | Tooth extraction | Asm/X2/65 | 7 | 1 |

TABLE 14-continued

Pain

| | sex | age | Condition | oligonucleotides | Severity before | Severity after |
|---|---|---|---|---|---|---|
| 39 | m | 65 | thyroidectomy | Super 8 | 10 | 1 |
| 40 | f | 46 | Surgical pain | Super 8 | 9 | 1 |

TABLE 15

Premenstrual Syndrome

| | sex | age | Condition | oligonucleotides | Severity before | Severity after |
|---|---|---|---|---|---|---|
| 1 | f | 41 | PMS | Asm/D5/X2 | 10 | 1-2 |
| 2 | f | 34 | PMS | Asm/D5/X2 | 10 | 1 |
| 3 | f | 37 | PMS | Asm/D5/X2 | 10 | 1 |
| 4 | f | 53 | PMS | Asm | 10 | 1 |
| 5 | f | 13 | PMS | Asm/D5/X2 | 10 | 1 |
| 6 | f | 15 | PMS | Asm/D5/X2 | 10 | 1 |
| 7 | f | 47 | PMS | Asm/D5/X2 | 10 | 9 |
| 8 | f | 44 | PMS | Asm | 10 | 1 |
| 9 | f | 20 | PMS | Asm/D5/X2 | 10 | 1 |

TABLE 16

Prostatitis

| | sex | age | Condition | oligonucleotides | Severity before | Severity after |
|---|---|---|---|---|---|---|
| 1 | m | 63 | BPH | MPB/Asm/X2/65 | 10 | 1 |
| 2 | m | 77 | BPH | Asm/D5/X2 | 3 | 1 |
| 3 | m | 45 | Inflamed prostate | Asm/D5/X2 | 4 | 1 |
| 4 | m | 69 | BPH | MPB/Asm/X2/65 | 7 | 1-2 |

TABLE 17

Sinus

| | sex | age | Condition | oligonucleotides | Severity before | Severity after |
|---|---|---|---|---|---|---|
| 1 | m | 8 | Sinus/cold | Asm/Nu-3 nasal | 5 | 1-2 |
| 2 | f | 60 | Sinus/cold | Asm/Nu-3 nasal | 7 | 2 |
| 3 | f | 42 | Sinus/cold | Asm/Nu-3 nasal | 8 | 1 |
| 4 | f | 41 | Sinus/cold | Asm/Nu-3 nasal | 6 | 4 |
| 5 | m | 55 | Sinus/cold | Asm/Nu-3 nasal | 6 | 1 |
| 6 | f | 47 | Sinus/cold | Asm/Nu-3 nasal | 7 | 1-2 |
| 7 | f | 40 | Sinus/cold | Asm/Nu-3 nasal | 5 | 1-2 |
| 8 | f | 35 | Sinus/cold | Asm/Nu-3 nasal | 7 | 1 |
| 9 | f | 12 | Sinus/cold | Asm/Nu-3 nasal | 5 | 1 |
| 10 | f | 34 | Sinus/cold | Asm/Nu-3 nasal | 9 | 1 |
| 11 | m | 17 | Sinus/cold | Asm/Nu-3 nasal | 7 | 2 |
| 12 | m | 15 | Sinus/cold | Asm/Nu-3 nasal | 6 | 2 |
| 13 | m | 70 | Sinus/cold | Asm/Nu-3 nasal | 5 | 1 |
| 14 | f | 53 | Sinus/cold | Asm/Nu-3/CRP | 7 | 3 |
| 15 | m | 77 | Sinus/cold | Asm/Nu-3 nasal | 8 | 3 |
| 16 | f | 37 | Sinus/cold | Asm/Nu-3 nasal | 8 | 2 |
| 17 | f | 55 | Sinus/cold | Asm/Nu-3 nasal | 9 | 2 |
| 18 | m | 17 | Sinus/cold | Asm/Nu-3 nasal | 7 | 1 |
| 19 | f | 62 | Sinus/cold | Asm/Nu-3 nasal | 7 | 1 |
| 20 | m | 43 | Sinus/cold | Asm/Nu-3 nasal | 9 | 1 |
| 21 | f | 41 | Sinus/cold | Asm/Nu-3 nasal | 6 | 1 |
| 22 | f | 58 | Sinus/cold | Asm/Nu-3 nasal | 6 | 1 |
| 23 | f | 34 | Sinus/cold | Asm/Nu-3 nasal | 8 | 1 |
| 24 | f | 61 | Sinus/cold | Asm/Nu-3 nasal | 6 | 2 |
| 25 | f | 19 | Sinus/cold | Asm/Nu-3 nasal | 8 | 1 |

TABLE 17-continued

Sinus

| | sex | age | Condition | oligonucleotides | Severity before | Severity after |
|---|---|---|---|---|---|---|
| 26 | f | 50 | Sinus/cold | Asm/Nu-3 nasal | 6 | 1 |
| 27 | m | 36 | Sinus/cold | Asm/Nu-3 nasal | 7 | 6 |
| 28 | f | 48 | Sinus/cold | Asm/Nu-3 nasal | 8 | 2 |
| 29 | f | 60 | Sinus/cold | Asm/Nu-3 nasal | 7 | 1 |
| 30 | m | 40 | Sinus/cold | Asm/Nu-3 nasal | 8 | 1 |
| 31 | f | 45 | Sinus/cold | Asm/Nu-3 nasal | 8 | 1 |
| 32 | f | 32 | Sinus/cold | Asm/Nu-3 nasal | 6 | 1 |
| 33 | f | 48 | Sinus/cold | Asm/Nu-3 nasal | 9 | 2-3 |
| 34 | f | 37 | Sinus/cold | Asm/Nu-3 nasal | 7 | 2 |
| 35 | f | 49 | Sinus/cold | Asm/Nu-3 nasal | 7 | 1-2 |
| 36 | m | 30 | Sinus/cold | Asm/Nu-3 nasal | 8-9 | 1 |
| 37 | m | 52 | Sinus/cold | Asm/Nu-3 nasal | 7 | 3 |
| 38 | f | 67 | Sinus/cold | Asm/Nu-3 nasal | 8 | 1 |
| 39 | m | 53 | Sinus/cold | Asm/Nu-3 nasal | 7 | 1 |
| 40 | f | 12 | Sinus/cold | Asm/Nu-3 nasal | 9 | 2-3 |
| 41 | f | 8 | Sinus/cold | Asm/Nu-3 nasal | 5 | 1 |
| 42 | f | 25 | Sinus/cold | Asm/Nu-3 nasal | 7 | 1 |
| 43 | f | 42 | Sinus/cold | Asm/Nu-3 nasal | 9 | 1-2 |
| 44 | f | 54 | Sinus/cold | Asm/Nu-3 nasal | 9 | 2-3 |
| 45 | f | 42 | Sinus/cold | Asm/Nu-3 nasal | 7 | 2 |
| 46 | f | 45 | Sinus/cold | Asm/Nu-3 nasal | 6 | 1 |
| 47 | m | 47 | Sinus/cold | Asm/Nu-3 nasal | 7 | 1 |
| 48 | f | 60 | Sinus/cold | Asm/Nu-3 nasal | 8 | 1 |
| 49 | f | 34 | Sinus/cold | Asm/Nu-3 nasal | 9 | 2 |
| 50 | f | 37 | Sinus/cold | Asm/Nu-3 nasal | 9 | 2-3 |
| 51 | f | 49 | Sinus/cold | Asm/Nu-3 nasal | 7 | 1 |
| 52 | f | 39 | Sinus/cold | Asm/Nu-3 nasal | 9 | 1 |
| 53 | f | 51 | Sinus/cold | Asm/Nu-3 nasal | 10 | 1-2 |

TABLE 18

Trauma

| | sex | age | Condition | oligonucleotides | Severity before | Severity after |
|---|---|---|---|---|---|---|
| 1 | f | 41 | Broke femur | Asm | 10 | 1 |
| 2 | f | 54 | Torn ligament | Asm | 7 | 1 |
| 3 | m | 57 | Compound fracture/leg | Asm/X2/65 | 10 | 4 |
| 4 | f | 72 | Sprained ankle | Asm/X2/65 | 6 | 1 |
| 5 | f | 47 | Root canal | Asm/X2/65 | 7 | 2 |
| 6 | f | 28 | Neck surgery | Asm/X2/65 | 9 | 1 |
| 7 | f | 47 | Torn rotator cup | Asm/X2/65/LO5-38 | 7 | 2-3 |
| 8 | f | 28 | Fractured ankle | Asm/X2/65 | 10 | 1 |
| 9 | m | 48 | Hyperextended elbow | Asm/X2/65/D7 | 7 | 2 |
| 10 | m | 19 | Motorcycle back injury | Asm/X2/65 | 9 | 2 |
| 11 | f | 64 | Fractured tibia | Asm/X2/65/LO5-38 | 10 | 3 |
| 12 | f | 41 | Cellulitis from impaled object | Asm/X2/65/D7 | 10 | 3-4 |
| 13 | f | 74 | Broken ribs | Asm/X2/65/LO5-38/Mg44 | 10 | 1 |
| 14 | f | 36 | Lumpectomy pain | Asm/topical | 10 | 1 |
| 15 | f | 37 | Torn miniscus | Asm/topical | 10 | 1 |
| 16 | m | 43 | Two broken arms | Asm | 10 | 2-3 |
| 17 | m | 1 | Finger slammed in door | Asm | 9 | 1 |
| 18 | f | 48 | Hysterectomy scar | Asm/topical | 7 | 1 |
| 19 | f | 45 | Broken toe | Asm/topical | 10 | 1-2 |
| 20 | f | 37 | Shoulder injury | Asm/X2 | 6 | 1 |
| 21 | f | 59 | Fluid on knee | Super 8 | 7 | 1 |
| 22 | f | 33 | Broken collarbone | Super 8 | 9 | 2 |
| 23 | m | 12 | Sprained finger | Asm/65 | 8 | 1 |
| 24 | f | 43 | Broken foot | Super 8/Mg44 | 9 | 1 |

TABLE 19

Carpal tunnel

| | sex | age | Condition | oligonucleotides | Severity before | Severity after |
|---|---|---|---|---|---|---|
| 1 | m | 36 | Carpal tunnel | Asm | 9 | 1 |
| 2 | f | 42 | Carpal tunnel | Asm | 10 | 1 |
| 3 | f | 56 | Carpal tunnel | Asm | 9 | 1 |
| 4 | m | 75 | Carpal tunnel | Asm | 8 | 1-2 |
| 5 | m | 55 | Carpal tunnel | Asm/X2/65 | 8 | 1 |
| 6 | m | 21 | Carpal tunnel | Asm | 9 | 2 |
| 7 | m | 56 | Carpal tunnel | Asm/X2/65 | 10 | 1-2 |
| 8 | f | 63 | Carpal tunnel | Asm | 10 | 2-3 |
| 9 | f | 45 | Carpal tunnel | Super 8 | 7 | 2 |

TABLE 20

Chronic Fatigue/Fibromyalgia

| | sex | age | Condition | oligonucleotides | Severity before | Severity after |
|---|---|---|---|---|---|---|
| 1 | f | 62 | CFS | Asm/D5/X2 | 9 | 1 |
| 2 | f | 60 | Fibromyalgia | Asm/D5/X2 | 10 | 1 |
| 3 | f | 56 | CFS | Asm/D5/X2 | 9 | 1 |
| 4 | m | 36 | CFS | Asm/D5/X2 | 8 | 1-2 |
| 5 | m | 69 | CFS | Asm/D5/X2 | 8 | 1 |
| 6 | m | 51 | CFS | Asm/D5/X2 | 9 | 2 |
| 7 | m | 38 | CFS | Asm/D5/X2 | 10 | 1-2 |
| 8 | f | 40 | Fibromyalgia | Asm/D5/X2 | 10 | 2-3 |

TABLE 21

Eczema/Atopic Dermatitis

| | sex | age | Condition | oligonucleotides | Severity before | Severity after |
|---|---|---|---|---|---|---|
| 1 | f | 63 | Foot rash | Asm | 8 | 1 |
| 2 | f | 49 | hives | Asm/X2/65/D7 | 10 | 1-2 |
| 3 | f | 13 | Severe leg rashes | Asm | 10 | 3-4 |
| 4 | m | 36 | eczema | Asm/X2/65 | 7-8 | 3-4 |
| 5 | f | 41 | Non-specific rash | Asm | 8 | 1 |
| 6 | m | 11 | eczema | Asm | 10 | 1-2 |
| 7 | f | 51 | rash | Asm/X2 | 5 | 1 |
| 8 | m | 48 | rash | Asm | 6-7 | 1-2 |
| 9 | f | 30 | Atopic dermatitis | Asm | 9 | 1 |
| 10 | f | 26 | Face rash | Asm | 7 | 1 |
| 11 | m | 42 | Severe rash | Asm/X2/65/D7 | 10 | 1 |
| 12 | f | 8 | Rash | Asm | 4 | 1 |
| 13 | f | 12 | eczema | Asm | 6 | 1 |
| 14 | m | 67 | Severely inflamed fingers | Asm/X2/65/IL-501 | 10 | 3-4 |
| 15 | f | 52 | rash | Asm | 6 | 1 |
| 16 | f | 42 | Severe hives | Asm/X2/65 | 10 | 1 |
| 17 | f | 14 | Chronic eczema | Asm | 7 | 1 |
| 18 | m | 64 | eczema | Asm/X2/65 | 8 | 1 |
| 19 | f | 63 | Non-specific itching | Asm | 7-8 | 1 |
| 20 | f | 58 | Contact dermatitis | Asm/topical | 8 | 1 |
| 21 | m | 47 | Itchy scar | Asm/topical | 5 | 1 |
| 22 | f | 37 | Severe contact dermatitis | Asm/topical | 7 | 2 |
| 23 | m | 36 | Severe atopic dermatitis | Asm | 10 | 1 |
| 24 | m | 1 | Severe diaper rash | Asm/topical | 10 | 1 |
| 25 | f | 40 | Eczema | Asm | 6 | 1-2 |
| 26 | f | 35 | Itchy/scaly patches on feet | Asm | 7-8 | 1 |
| 27 | m | 17 | Atopic dermatitis | Asm | 7 | 1 |
| 28 | f | 19 | Severe razor burn | Asm/topical | 10 | 1 |

TABLE 21-continued

Eczema/Atopic Dermatitis

| | sex | age | Condition | oligonucleotides | Severity before | Severity after |
|---|---|---|---|---|---|---|
| 29 | m | 24 | Severe razor burn | Asm/topical | 10 | 1 |
| 30 | f | 40 | Inflamed hands | Asm/topical | 7 | 1 |
| 31 | m | 19 | split, cracked cuticles | cd18-1 | 7 | 1 |
| 32 | f | 51 | Split lips | cd18-1 | 5 | 1 |
| 33 | f | 30 | Dry, cracked skin on hands | cd18-1/topical | 8 | 1 |
| 34 | f | 60 | rash | Super 8 | 9 | 1 |
| 35 | f | 38 | Spider bite | Super 8 | 10 | 2-3 |
| 36 | f | 15 | rash | Super 8 | 5 | 1 |

TABLE 22

Erectile Dysfunction

| | sex | age | Condition | oligonucleotides | Severity before | Severity after |
|---|---|---|---|---|---|---|
| 1 | m | 65 | ED/blood pressure med. | D5 | 10 | 1 |
| 2 | m | 69 | ED/blood pressure med. | Asm/D5 | 9 | 2-3 |
| 3 | m | 52 | ED | Asm/D5 | 10 | 1 |

TABLE 23

Heartburn/Acid Reflux

| | sex | age | Condition | oligonucleotides | Severity before | Severity after |
|---|---|---|---|---|---|---|
| 1 | f | 63 | heartburn | Acid-2/Acid B2 | 10 | 1 |
| 2 | f | 49 | heartburn | Acid-2/Acid B2 | 10 | 1 |
| 3 | f | 22 | Heartburn | Acid-2/Acid B2 | 10 | 1 |
| 4 | f | 42 | Heartburn | Acid-2 | 7-8 | 1 |
| 5 | f | 41 | Heartburn | Acid-2/Acid B2 | 9-10 | 1 |
| 6 | f | 70 | Heartburn | Acid-2/Acid B2 | 5 | 1 |
| 7 | f | 47 | heartburn | Acid-2/Acid B2 | 8 | 1 |
| 8 | f | 41 | Heartburn | Acid-2/Acid B2 | 10 | 1 |
| 9 | f | 19 | heartburn | Acid-2/Acid B2 | 7 | 1 |
| 10 | m | 77 | heartburn | Acid-2/Acid B2 | 10 | 1 |
| 11 | f | 52 | heartburn | Acid-2/Acid B2 | 10 | 1 |
| 12 | f | 21 | Heartburn | Acid-2/Acid B2 | 10 | 1 |
| 13 | f | 41 | heartburn | Acid-2/Acid B2 | 10 | 1 |
| 14 | f | 46 | heartburn | Acid-2/Acid B2 | 10 | 1 |
| 15 | f | 63 | heartburn | Acid-2/Acid B2 | 10 | 1 |
| 16 | f | 62 | heartburn | Acid-2/Acid B2 | 10 | 1 |

TABLE 24

Poison Ivy

| | sex | age | Condition | oligonucleotides | Severity before | Severity after |
|---|---|---|---|---|---|---|
| 1 | m | 10 | Poison ivy | Asm | 7 | 1 |
| 2 | f | 43 | Poison ivy | Asm | 7 | 1 |
| 3 | f | 63 | Poison ivy | Asm | 10 | 1 |
| 4 | f | 42 | Poison ivy | Asm | 6 | 1 |
| 5 | m | 3 | Poison ivy | Asm | 6 | 1 |
| 6 | m | 47 | Poison ivy | Asm | 10 | 1 |
| 7 | f | 53 | Poison ivy | Asm | 10 | 1 |
| 8 | m | 21 | Poison ivy | Asm/topical | 8-9 | 1 |
| 9 | f | 12 | Poison ivy | Asm/topical | 10 | 1 |
| 10 | f | 56 | Poison ivy | Asm/topical | 9 | 1 |
| 11 | f | 40 | Poison ivy | Asm/topical | 7-8 | 1 |

TABLE 24-continued

Poison Ivy

| | sex | age | Condition | oligonucleotides | Severity before | Severity after |
|---|---|---|---|---|---|---|
| 12 | f | 49 | Poison ivy | Asm | 10 | 1 |
| 13 | m | 17 | Poison ivy | Asm | 7 | 1 |
| 14 | f | 65 | Poison ivy | Asm | 5-6 | 1 |

TABLE 25

Psoriasis

| | sex | age | Condition | oligonucleotides | Severity before | Severity after |
|---|---|---|---|---|---|---|
| 1 | m | 59 | stress induced psoriasis | Asm/D5/X2 | 10 | 3 |
| 2 | f | 77 | psoriasis | Asm/D5/65 | 5 | 1 |
| 3 | f | 34 | psoriasis | Asm/D5/65 | 9-10 | 1 |
| 4 | m | 27 | psoriasis | Asm/D5/65 | 7 | 1 |
| 5 | f | 41 | psoriasis | Asm/D5/65 | 7 | 2-3 |
| 6 | f | 19 | psoriasis | Asm/D5/65 | 9 | 1 |
| 7 | f | 6 | psoriasis | Asm | 6 | 1 |
| 8 | f | 75 | psoriasis | Asm | 4 | 1 |
| 9 | m | 47 | Severe psoriasis | Asm | 10 | 2-3 |
| 10 | m | 36 | psoriasis | Asm/D5/65 | 5 | 1 |
| 11 | f | 24 | psoriasis | Asm/D5/65 | 9 | 1 |

TABLE 26

Rosacea

| | sex | age | Condition | oligonucleotides | Severity before | Severity after |
|---|---|---|---|---|---|---|
| 1 | f | 40 | Rosacea | Asm | 6 | 1-2 |
| 2 | f | 38 | Rosacea | Asm | 4 | 1 |
| 3 | f | 58 | Rosacea | Asm | 7 | 1 |
| 4 | f | 40 | Rosacea | Asm | 8 | 1 |
| 5 | f | 40 | Rosacea | Asm | 8-9 | 1 |
| 6 | f | 36 | Rosacea | Asm | 6 | 3 |
| 7 | f | 48 | Rosacea | Asm/X2/65 | 6-7 | 1 |
| 8 | f | 32 | Rosacea | Asm | 6 | 1 |

TABLE 27

Average of Results

| Condition | # cases | pre-treatment average | post-treatment average |
|---|---|---|---|
| elevated cholesterol | 10 | 230 | 166 |
| hypertension | 8 | 190/96 | 159/79 |
| inflammatory bowel | 12 | 10 toilet trips | 1-2 toilet trips |
| crohn's disease | 3 | 17 toilet trips | 1-2 toilet trips |
| ulcerative colitis | 5 | 8 toilet trips | 1-2 toilet trips |
| acid reflux/heartburn | 16 | 9.2 | 1.0 |
| emotional distress | 127 | 8.2 | 1.4 |
| PMS | 9 | 10.0 | 1.0 |
| inflammation | 70 | 9.0 | 1.7 |
| pain | 40 | 8.8 | 2.0 |
| infection | 78 | 7.1 | 1.6 |
| migraine | 14 | 9.4 | 1.3 |
| neurological disorders | 9 | 9.0 | 3.0 |
| poison ivy | 14 | 8.0 | 1.0 |
| prostatitis | 5 | 6.6 | 1.2 |
| psoriasis | 14 | 7.1 | 1.5 |
| rocacea | 10 | 6.3 | 1.1 |
| trauma | 25 | 8.7 | 1.7 |
| sinus/cold | 53 | 7.3 | 1.6 |
| erectile dysfunction | 5 | 9.0 | 1.5 |
| eczema/rash | 36 | 8.5 | 1.4 |
| fibromyalgia | 7 | 10.0 | 1.8 |
| chronic fatigue | 9 | 9.5 | 1.2 |
| carpal tunnel syndrome | 9 | 8.9 | 1.3 |
| arthritis | 30 | 7.6 | 2.0 |
| appetite | 16 | 9.5 | 2.3 |

Example 24

For animal studies, animals with different indications were provided with oligonucleotide compositions containing RNA oligonucleotides complementary to the phosphodiesterase 4, phosphodiesterase 5 genes or as indicated in FIG. 24. Some animals were additionally given compositions containing additional RNA oligonucleotides complementary to other genes such as cyclooxygenase 2 and p65. Oligonucleotide concentrations were typically 0.3 to 300 $A_{260}$/RNA/ml taken in doses (0.1-100 µg/kg) of 0.5 ml two to four times per day. The effect of the composition was then evaluated (see Table 27). Treatment efficacy was evaluated by an attending veterinarian.

TABLE 27

Animal studies

| animal | Condition | oligonucleotides | Severity before | Severity after |
|---|---|---|---|---|
| dog | skin allergy | Asm | 8 | 2 |
| dog | inflammatory bowel disease | Asm, CX2, P65 | 7 | 2 |
| horse | nervous and agitated | Asm, D5 | 8 | 2 |

Example 24

The following is the method for selecting nucleic acid sequences from a known gene sequence for the design of oligonucleotides. Preferred choices are sequences that either are adjacent to, or overlap the start site, followed by sequences that are in the 5' un-translated region, followed by sequences immediately adjacent to or overlapping the termination signal. This method is very effective and when combined with, achiral RNA, it produces oligonucleotides that display therapeutic efficacy consistently.

For example, achiral RNA oligonucleotides (10-30 bases in length), or achiral 2'-methoxy oligonucleotides (10-30 bases in length), or achiral 2'-methoxy oligonucleotides (10-30 bases in length) with (a) 3' or 3' & 5' acid stable end-blocks located in the 5' UTR, or (b) immediately adjacent to or more preferably overlapping at least one of the three bases of the start site and extending either 5' or 3' of the start site, or (c) immediately adjacent to or overlapping one of the three bases of the termination signal and extending 3' or 5' of the termination site that are ten to thirty contiguous bases in length and complementary to a RNA or DNA and that have the following binding characteristics:

(d) ΔG of the oligonucleotide binding the complementary RNA strand at 37° C.

(i) $(G_{37}°) \leq -15$ KCal or less (more negative=more stable) for 10 to 14 mer, (ii) $(G_{37}°) \leq -20$ KCal or less (more negative=more stable) for 15 to 17 mer, (iii) $(G_{37}°) \leq -25$ KCal or less (more negative=more stable) for 18 to 20 mer, (iv) $(G_{37}°) \leq -30$ KCal or less (more negative=more stable) for 21 to 23 mer, (v) $(G_{37}°) \leq -35$ KCal or less (more negative=more stable) for 24 to 30 mer, (e) the ΔG of any hairpin structure the oligonucleotide could assume is $\geq -3.0$, (f) the Tm any hairpin that could form is at least 10° C. lower than the Tm of the oligonucleotide binding to the target RNA or DNA, (g) a melting temperature for the oligonucleotide binding to the target RNA is 45° C. by the percent GC method at 1.0 M salt For composition parameters, the percent G+C of the oligonucleotide to be used is >35 percent and are administered so that each specific RNA is at a concentration (1.0 g/100 ml), or lower in doses not to exceed 100 µg/kg per RNA, or more preferably 10 µg/kg, or more preferably 1 µg/kg, or still more preferably <1 µg/kg. Sequences are then screened to be sure they do not overlap the same regions in other known genes by conducting BLAST searches against the entire GenBank list of human sequences.

Factors contributing to the selective inhibition of gene expression in vivo by the modified oligonucleotides of the invention include the influence of chirality on melting temperature. 2'-O-methyl modified RNA oligonucleotides with achiral linkages resemble backbone linkages that very closely resemble normal unmodified nucleic acids. Typically, oligonucleotides synthesized using phosphoramidite based synthesis of phosphorothioates produces mixed isomers present at each modified phosphorothioate linkage. A measurable result of the presence of these mixed isomers is a decrease in melting temperature of the phosphorothioate oligonucleotide in a primer target duplex as compared to an unmodified oligonucleotide in the same duplex. The melting temperature of a 2'-O-methyl RNA oligonucleotide, however, is not substantially lowered relative to an unmodified oligonucleotide. Thus, the melting temperatures for 2'-O-methyl RNA oligonucleotides closely resemble those for unmodified RNA because the presence of the 2'-O-methyl group does not result in the generation of isomers.

While the invention has been described and illustrated herein by references to various specific materials, procedures and examples, it is understood that the invention is not restricted to the particular combinations of material and procedures selected for that purpose. Numerous variations of such details can be implied as will be appreciated by those skilled in the art. It is intended that the specification and examples be considered as exemplary, only, with the true scope and spirit of the invention being indicated by the following claims. All references, patents and patent applications referred to in this application are herein incorporated by reference in their entirety.

---

We claim:

1. A composition suitable for administration in a mammal suffering from a pathological disorder or disease comprising at least two modified oligonucleotides,
wherein a first and a second modified oligonucleotide each comprises about seven to seventy-five nucleotides containing seven or more contiguous ribose groups linked by achiral 5' to 3' internucleotide phosphate linkages,
wherein at least one ribose group of at least one of said modified oligonucleotides has a modified 2' substituent, wherein the 5' and 3' ends of at least one of said modified oligonucleotides are blocked,
wherein said first modified oligonucleotide is SEQ ID NO: 1, wherein said second modified oligonucleotide is SEQ ID NO: 16, and
wherein said first modified oligonucleotide is complementary to a region of a first gene associated with said pathological disorder or disease and said second modified oligonucleotide is complementary to a region of a second gene associated with said pathological disorder or disease,
wherein said pathological disorder is selected from the group consisting of abnormal appetite, hypertension, hypercholesterolemia, hyperlipidemia, erectile dysfunction, eczema, depression, anxiety, stress, inflammatory bowel syndrome, ulcerative colitis, Crohn's disease, renal stones, gall stones, constipation, migraine headache, seizure, multiple sclerosis, polymyositis, fibromyalgia, Parkinson's disease, ALS, chronic pain, pre-menstrual syndrome, chronic allergies, sinusitis, colds, trauma, carpal tunnel syndrome, chronic fatigue syndrome, rosacea, arthritis, psoriasis, prostatitis, inflammation, heartburn, infection, and poison ivy.

2. The composition of claim 1 wherein said composition further contains a pharmaceutically acceptable excipient.

3. The composition of claim 1 wherein said composition further contains a cosmetically acceptable excipient.

4. A nutritional supplement comprising
two or more modified oligonucleotides each comprising about seven to seventy-file nucleotides containing seven or more contiguous ribose groups linked by achiral 5' to 3' internucleoside phosphate linkages,
wherein at least one ribose group of at least one of said modified oligonucleotides has a modified 2' substituent,
wherein the 5' and 3' ends of at least one of said modified oligonucleotides are blocked, wherein said first modified oligonucleotide is SEQ ID NO: 1,
wherein said second modified oligonucleotide is SEQ ID NO: 16,
wherein each of said two or more modified oligonucleotides is complementary to a region of a gene associated with said pathological disorder or disease, and
wherein said pathological disorders are selected from the group consisting of: stress, migraine headache, minor or temporary pain, prostatitis, premenstrual syndrome, menstrual cramping, bloating, nausea, irritability, nervous tension, anxiety, and lack of control of appetite.

5. The nutritional supplement of claim 4 further comprising one or more nutritional supplements selected from the group consisting of selenium, vitamin E, vitamin C and coenzyme Q10.

6. The composition of claim 1 or nutritional supplement of claim 4 wherein one or more of said modified oligonucleotides is present at a concentration effective to reduce the expression of its gene.

7. The composition of claim 1 or nutritional supplement of claim 4 wherein said modified oligonucleotides are suitable for oral administration.

8. The composition of claim 1, or nutritional supplement of claim 4, wherein said first and second modified oligonucleotides are complementary to a region of said gene selected from the group consisting of the 5' UTR region, translational start site and transitional termination site.

9. The composition of claim 1 or nutritional supplement of claim 4, wherein said 2' substituent is selected from the group consisting of methoxy, propoxy, methoxy-ethoxy, fluorine, chlorine, bromine and iodine.

10. The composition of claim 1 or nutritional supplement of claim 4 wherein said composition further contains an excipient suitable for oral consumption.

11. The composition of claim 1 or the nutritional supplement of claim 4, wherein said mammal is a human.

12. The composition of claim 1 or the nutritional supplement of claim 4, wherein said 5' and 3' ends comprise a butanol.

* * * * *